US012781225B2

(12) United States Patent
Bogorad et al.

(10) Patent No.: US 12,781,225 B2
(45) Date of Patent: Nov. 3, 2026

(54) OLIGONUCLEOTIDE-MEDIATED KNOCKDOWN OF DUX4

(71) Applicant: Soufflé Therapeutics, Inc., Watertown, MA (US)

(72) Inventors: Roman Bogorad, Newton, MA (US); Timofey Zatsepin, Brookline, MA (US); Vadim Dudkin, Wellesley, MA (US)

(73) Assignee: Soufflé Therapeutics, Inc., Watertown, MA (US)

( * ) Notice: Subject to any disclaimer, the term of this patent is extended or adjusted under 35 U.S.C. 154(b) by 0 days.

(21) Appl. No.: 19/410,976

(22) Filed: Dec. 5, 2025

(65) Prior Publication Data

US 2026/0159835 A1 Jun. 11, 2026

Related U.S. Application Data

(60) Provisional application No. 63/728,473, filed on Dec. 5, 2024.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/321* (2013.01); *C12N 2310/322* (2013.01)

(58) Field of Classification Search
None
See application file for complete search history.

(56) References Cited

U.S. PATENT DOCUMENTS 5,138,045 A 8/1992 Cook et al.
5,212,295 A 5/1993 Cook
5,218,105 A 6/1993 Cook et al.
5,223,618 A 6/1993 Cook et al.
5,378,825 A 1/1995 Cook et al.
5,386,023 A 1/1995 Sanghvi et al.
5,457,191 A 10/1995 Cook et al.
5,459,255 A 10/1995 Cook et al.
5,506,351 A 4/1996 McGee
5,521,302 A 5/1996 Cook
5,539,082 A 7/1996 Nielsen et al.
5,541,307 A 7/1996 Cook et al.
5,554,746 A 9/1996 Ravikumar et al.
5,571,902 A 11/1996 Ravikumar et al.
5,578,718 A 11/1996 Cook et al.
5,587,361 A 12/1996 Cook et al.
5,587,469 A 12/1996 Cook et al.
5,587,470 A 12/1996 Cook et al.
5,599,797 A 2/1997 Cook et al.
5,602,240 A 2/1997 De Mesmaeker et al.
5,608,046 A 3/1997 Cook et al.
5,610,289 A 3/1997 Cook et al.
6,262,241 B1 7/2001 Cook et al.
9,988,628 B2 6/2018 Belayew et al.
10,385,338 B2 8/2019 Dumonceaux et al.
10,537,560 B2 1/2020 Cacace et al.
10,538,763 B2 1/2020 Rigo et al.
10,828,377 B2 11/2020 Mano et al.
10,907,157 B2 2/2021 Belayew et al.
11,332,733 B2 5/2022 Seth et al.
11,485,743 B2 11/2022 Mainolfi et al.
11,518,995 B2 12/2022 Chen et al.
11,525,137 B2 12/2022 Malecova et al.
11,555,190 B2 1/2023 Malecova et al.
11,674,140 B2 6/2023 Lek et al.
11,806,343 B2 11/2023 Rickard et al.
11,844,843 B2 12/2023 Subramanian et al.
11,898,143 B2 2/2024 Belayew et al.
11,912,779 B2 2/2024 Malecova et al.
11,963,975 B2 4/2024 Jones et al.
11,969,475 B2 4/2024 Subramanian et al.
11,999,955 B2 6/2024 Malecova et al.
12,049,629 B2 7/2024 Malecova et al.
12,071,485 B2 8/2024 Malecova et al.
12,084,658 B2 9/2024 Harper et al.
12,104,156 B2 10/2024 Malecova et al.
12,157,774 B2 12/2024 Malecova et al.
12,227,549 B2 2/2025 Fotin-Mleczek et al.
12,365,704 B2 7/2025 Doppalapudi et al.
12,383,534 B2 8/2025 Kyba et al.
12,428,487 B2 9/2025 Subramanian et al.
12,458,668 B2 11/2025 Tapscott et al.
12,478,657 B2 11/2025 Ko
12,486,328 B2 12/2025 Malecova et al.
12,497,615 B2 12/2025 Darimont et al.

(Continued)

FOREIGN PATENT DOCUMENTS

AU 2017258945 A1 1/2018
AU 2022201820 A1 4/2022

(Continued)

OTHER PUBLICATIONS

Kluchnikov et al. Molecular Therapy Nucleic Acids, vol. 36, pp. 1-14 (Year: 2025).*
Ahmad Dar et al. Scientific Reports 6:20031, pp. 1-8 (Year: 2016).*
He et al. Scientific Reports 7:44836, pp. 1-13 (Year: 2017).*
Abramova T., et al., "Novel oligonucleotide analogues based on morpholino nucleoside subunits-antisense technologies: new chemical possibilities," Indian journal of chemistry, vol. 48B, Organic including medicinal 48.12 (Dec 2009): 1721-1726.
Allen et al., "Targeting DUX4 mRNA with anti-TfR NANOBODY® oligonucleotide conjugates," [Poster P4.19, 2025 IRC Abstract Book] 32nd Annual FSHD Society International Research Congress, Amsterdam, Netherlands, (Jun. 12-13, 2025), 118 pages.
Anzalone, Vince, "2024 Summer Series of R&D WebinarsPart 1—Muscle Programs" [PowerPoint Presentation] Arrowhead Pharmaceuticals. [Accessed on May 23, 2024, publicly available at URL: https://ir.arrowheadpharma.com/events/event-details/2024-summer-series-rd-webinar-muscular-aro-dux4-and-aro-dm1], 58 pages.

(Continued)

*Primary Examiner* — Brian Whiteman
(74) *Attorney, Agent, or Firm* — COOLEY LLP; John Rearick; Gang Wang

(57) ABSTRACT

Provided herein are oligonucleotides for inhibiting the expression of Double Homeobox 4 (DUX4) and methods of using the oligonucleotides for reducing DUX4 expression in a subject.

30 Claims, No Drawings

Specification includes a Sequence Listing.

(56) References Cited

U.S. PATENT DOCUMENTS 12,529,056 B2 1/2026 Malecova et al.
12,624,396 B2 5/2026 Van Der Maarel et al.
2004/0265833 A1 12/2004 Lofton-Day et al.
2008/0064029 A1 3/2008 Lofton-Day et al.
2011/0159487 A1 6/2011 Hare et al.
2014/0242093 A1 8/2014 Tapscott et al.
2014/0296181 A1 10/2014 Arnold et al.
2015/0299807 A1 10/2015 Ross et al.
2015/0301067 A1 10/2015 Miller et al.
2016/0201132 A1 7/2016 Hayardeny et al.
2017/0009230 A1 1/2017 Agrawal et al.
2017/0306403 A1 10/2017 Jones et al.
2018/0045727 A1 2/2018 Spetzler et al.
2018/0050043 A1 2/2018 Sverdrup
2018/0237775 A1 8/2018 Dumonceaux et al.
2018/0245154 A1 8/2018 Tsalik et al.
2018/0256729 A1 9/2018 Seth et al.
2019/0105311 A1 4/2019 Cacace et al.
2019/0177794 A1 6/2019 Huang et al.
2019/0388547 A1 12/2019 Weeden et al.
2020/0087723 A1 3/2020 Halpern et al.
2020/0109402 A1 4/2020 Lee et al.
2020/0109406 A1 4/2020 Miller et al.
2020/0248179 A1 8/2020 Harper
2020/0261589 A1 8/2020 Galy et al.
2020/0297696 A1 9/2020 Sverdrup et al.
2020/0325237 A1 10/2020 Darimont et al.
2021/0010091 A1 1/2021 Kuiper et al.
2021/0017513 A1 1/2021 Seth et al.
2021/0052631 A1 2/2021 Prakash et al.
2021/0196723 A1 7/2021 Rickard et al.
2021/0198739 A1 7/2021 Van Der Maarel et al.
2021/0261680 A1 8/2021 Subramanian et al.
2021/0301290 A1* 9/2021 Malecova ............... A61P 21/00
2022/0049226 A1 2/2022 Schrepfer et al.
2022/0079951 A1 3/2022 Meyers et al.
2022/0098252 A1 3/2022 Gabellini et al.
2022/0106592 A1 4/2022 Harper et al.
2022/0117942 A1 4/2022 Attwell et al.
2022/0143221 A1 5/2022 Danos et al.
2022/0162672 A1 5/2022 Makarov et al.
2022/0202845 A1 6/2022 Bradley et al.
2022/0213505 A1 7/2022 Mingozzi et al.
2022/0226318 A1 7/2022 De Maeyer et al.
2022/0226340 A1 7/2022 De Maeyer et al.
2022/0228140 A1 7/2022 Kumagai et al.
2022/0241263 A1 8/2022 Alimzhanov et al.
2022/0267732 A1 8/2022 Cowan et al.
2022/0364086 A1 11/2022 Koizumi et al.
2022/0401539 A1 12/2022 Delattre et al.
2022/0411821 A1 12/2022 Wang et al.
2023/0025289 A1 1/2023 Schrepfer et al.
2023/0052017 A1 2/2023 Loke et al.
2023/0088865 A1 3/2023 Subramanian et al.
2023/0093080 A1 3/2023 Ji et al.
2023/0174958 A1 6/2023 Jones et al.
2023/0181621 A1 6/2023 Boletta et al.
2023/0193205 A1 6/2023 Ichim et al.
2023/0220473 A1 7/2023 Chen
2023/0250407 A1 8/2023 Jones et al.
2023/0257743 A1 8/2023 Cacace et al.
2023/0265430 A1 8/2023 Ding et al.
2023/0271953 A1 8/2023 Loke et al.
2023/0272065 A1 8/2023 Subramanian et al.
2023/0287420 A1 9/2023 Malecova et al.
2023/0293581 A1 9/2023 Schrepfer et al.
2023/0323456 A1 10/2023 Yamagata et al.
2023/0340469 A1 10/2023 Nelles
2023/0348906 A1 11/2023 Daugherty et al.
2023/0416737 A1 12/2023 Ding et al.
2024/0010988 A1 1/2024 Schrepfer et al.
2024/0018479 A1 1/2024 Emerson et al.
2024/0018594 A1 1/2024 Chen et al.
2024/0026356 A1 1/2024 Harper et al.
2024/0060140 A1 2/2024 Rosenzweig et al.
2024/0093191 A1 3/2024 Saad et al.
2024/0102083 A1 3/2024 Booth et al.
2024/0110184 A1 4/2024 Brown et al.
2024/0124600 A1 4/2024 Malecova et al.
2024/0132610 A1 4/2024 Malecova et al.
2024/0141346 A1 5/2024 Place et al.
2024/0141359 A1 5/2024 Emerson, Jr. et al.
2024/0181086 A1 6/2024 Quijano et al.
2024/0182561 A1 6/2024 Stitt et al.
2024/0192197 A1 6/2024 Jiang et al.
2024/0216482 A1 7/2024 Tsoa et al.
2024/0216530 A1 7/2024 Quijano et al.
2024/0247259 A1 7/2024 Shen et al.
2024/0252642 A1 8/2024 Schrepfer
2024/0254555 A1 8/2024 Keating et al.
2024/0271134 A1 8/2024 Saleh et al.
2024/0277776 A1 8/2024 Conway et al.
2024/0280590 A1 8/2024 Chamberlain et al.
2024/0285638 A1 8/2024 Harper et al.
2024/0317814 A1 9/2024 Richard et al.
2024/0318201 A1 9/2024 Harper et al.
2024/0327926 A1 10/2024 Otto et al.
2024/0336915 A1 10/2024 Valas et al.
2024/0352459 A1 10/2024 Emerson et al.
2024/0358761 A1 10/2024 Schrepfer
2024/0360455 A1 10/2024 Nair et al.
2024/0382605 A1 11/2024 Seth et al.
2024/0391969 A1 11/2024 Wang et al.
2024/0400707 A1 12/2024 Malecova et al.
2024/0401037 A1 12/2024 Belayew et al.
2024/0401061 A1* 12/2024 Kubli ........................ A61P 9/00
2024/0425820 A1 12/2024 Schrepfer
2025/0009904 A1 1/2025 Savva et al.
2025/0011775 A1 1/2025 Briggs et al.
2025/0019697 A1 1/2025 Harper
2025/0025569 A1 1/2025 Williams et al.
2025/0025570 A1 1/2025 Hsia et al.
2025/0051393 A1 2/2025 Qian et al.
2025/0051780 A1 2/2025 Qian et al.
2025/0084408 A1 3/2025 Byrne et al.
2025/0092376 A1 3/2025 Holm et al.
2025/0101382 A1 3/2025 Murry et al.
2025/0122529 A1 4/2025 Matias et al.
2025/0127820 A1 4/2025 Schrepfer
2025/0127912 A1 4/2025 Saleh et al.
2025/0129346 A1 4/2025 Dowdle et al.
2025/0163418 A1 5/2025 Zhang
2025/0177447 A1 6/2025 Kinder et al.
2025/0222039 A1 7/2025 Li et al.
2025/0223564 A1 7/2025 Schrepfer et al.
2025/0223598 A1 7/2025 Thompson
2025/0230470 A1 7/2025 Tham
2025/0249052 A1 8/2025 Fielden et al.
2025/0270340 A1 8/2025 Subramanian et al.
2025/0295814 A1 9/2025 Sper et al.
2025/0297251 A1 9/2025 Daugherty et al.
2025/0302876 A1 10/2025 Agarwal et al.
2025/0302953 A1 10/2025 Fry et al.
2025/0302979 A1 10/2025 Marks et al.
2025/0313555 A1 10/2025 Ozes et al.
2025/0313861 A1 10/2025 Fry et al.
2025/0333476 A1 10/2025 Johnson et al.
2025/0339531 A1 11/2025 Tapscott et al.
2025/0382582 A1 12/2025 Clarke et al.
2026/0009003 A1 1/2026 Sun et al.
2026/0034230 A1 2/2026 Zhang et al.

FOREIGN PATENT DOCUMENTS

CA 2528853 A1 6/2007
CN 113416785 A 9/2021
CN 113462763 A 10/2021
CN 114317753 A 4/2022
CN 113005200 B 7/2023
CN 116440286 A 7/2023
CN 116790758 A 9/2023
CN 117305457 A 12/2023
CN 117327789 A 1/2024
CN 117363720 A 1/2024

(56) References Cited

FOREIGN PATENT DOCUMENTS

| | | | | |
|---|---|---|---|---|
| CN | 117384853 A | | 1/2024 | |
| CN | 117672361 A | | 3/2024 | |
| CN | 114317741 B | | 7/2024 | |
| CN | 118702797 A | | 9/2024 | |
| CN | 118830516 A | | 10/2024 | |
| CN | 119351338 A | | 1/2025 | |
| CN | 115747336 B | | 9/2025 | |
| CN | 120591341 A | | 9/2025 | |
| CN | 120865375 A | | 10/2025 | |
| CN | 121065340 A | | 12/2025 | |
| CN | 117384852 B | | 1/2026 | |
| EP | 2426203 A2 | | 3/2012 | |
| JP | 2022055361 A | | 4/2022 | |
| RU | 2808833 | | 12/2023 | |
| WO | WO-2015143062 A1 | | 9/2015 | |
| WO | WO-2016115490 A1 | | 7/2016 | |
| WO | WO-2017054086 A1 | | 4/2017 | |
| WO | WO-2017065000 A1 | | 4/2017 | |
| WO | WO-2018073787 A3 | | 6/2018 | |
| WO | WO-2021037978 A1 | | 3/2021 | |
| WO | WO-2021188390 A1 | | 9/2021 | |
| WO | WO-2022051332 A1 | | 3/2022 | |
| WO | WO-2022147207 A1 | | 7/2022 | |
| WO | WO-2023283629 A1 | | 1/2023 | |
| WO | WO-2023288289 A2 | * | 1/2023 | ........... C12N 15/113 |
| WO | WO-2023019203 A1 | | 2/2023 | |
| WO | WO-2023036874 A1 | | 3/2023 | |
| WO | WO-2023056388 A1 | | 4/2023 | |
| WO | WO-2023168202 A2 | | 9/2023 | |
| WO | WO-2023183313 A1 | | 9/2023 | |
| WO | WO-2023185946 A1 | | 10/2023 | |
| WO | WO-2024011135 A2 | | 1/2024 | |
| WO | WO-2024012420 A1 | | 1/2024 | |
| WO | WO-2024044282 A1 | | 2/2024 | |
| WO | WO-2024081411 A1 | | 4/2024 | |
| WO | WO-2024086633 A1 | | 4/2024 | |
| WO | WO-2024102965 A1 | | 5/2024 | |
| WO | WO-2024112809 A2 | | 5/2024 | |
| WO | WO-2024124088 A1 | | 6/2024 | |
| WO | WO-2024125592 A1 | | 6/2024 | |
| WO | WO-2024129931 A1 | | 6/2024 | |
| WO | WO-2024149282 A1 | | 7/2024 | |
| WO | WO-2024151737 A2 | | 7/2024 | |
| WO | WO-2024163952 A3 | | 9/2024 | |
| WO | WO-2024192263 A2 | | 9/2024 | |
| WO | WO-2024204724 A1 | | 10/2024 | |
| WO | WO-2024229302 A1 | | 11/2024 | |
| WO | WO-2024238584 A1 | | 11/2024 | |
| WO | WO-2024220947 A3 | | 12/2024 | |
| WO | WO-2024229211 A3 | | 12/2024 | |
| WO | WO-2024255846 A1 | | 12/2024 | |
| WO | WO-2024220598 A9 | | 1/2025 | |
| WO | WO-2024226860 A3 | | 1/2025 | |
| WO | WO-2024243236 A3 | | 1/2025 | |
| WO | WO-2025019732 A1 | | 1/2025 | |
| WO | WO-2025019820 A1 | | 1/2025 | |
| WO | WO-2025021034 A1 | | 1/2025 | |
| WO | WO-2025026925 A1 | | 2/2025 | |
| WO | WO-2025054202 A1 | | 3/2025 | |
| WO | WO-2025061158 A1 | | 3/2025 | |
| WO | WO-2025081023 A1 | | 4/2025 | |
| WO | WO-2025085878 A1 | | 4/2025 | |
| WO | WO-2025101068 A1 | | 5/2025 | |
| WO | WO-2025108237 A1 | | 5/2025 | |
| WO | WO-2025137547 A8 | | 7/2025 | |
| WO | WO-2025137637 A3 | | 7/2025 | |
| WO | WO-2025140565 A1 | | 7/2025 | |
| WO | WO-2025160275 A1 | | 7/2025 | |
| WO | WO-2025212838 A1 | | 10/2025 | |
| WO | WO-2025212961 A1 | | 10/2025 | |
| WO | WO-2025230941 A1 | | 11/2025 | |
| WO | WO-2025230947 A1 | | 11/2025 | |
| WO | WO-2025235563 A1 | | 11/2025 | |
| WO | WO-2025250883 A1 | | 12/2025 | |
| WO | WO-2025252100 A1 | | 12/2025 | |
| WO | WO-2025255283 A1 | | 12/2025 | |
| WO | WO-2025257347 A1 | | 12/2025 | |
| WO | WO-2025259503 A1 | | 12/2025 | |
| WO | WO-2025259607 A1 | | 12/2025 | |
| WO | WO-2025259743 A1 | | 12/2025 | |
| WO | WO-2025260007 A1 | | 12/2025 | |
| WO | WO-2026006334 A1 | | 1/2026 | |
| WO | WO-2026026811 A1 | | 2/2026 | |
| WO | WO-2026030242 A1 | | 2/2026 | |
| WO | WO-2026122993 A2 | | 6/2026 | |

OTHER PUBLICATIONS

Avidity Biosciences, "Transforming Facioscapulohumeral Muscular Dystrophy (FSHD) AOC 1020 FORTITUDETM Phase 1/2 Initial Data," [PowerPoint slides]. Investorroom. [Accessed on Jun. 12, 2024, publicly available at URL: https://filecache.investorroom.com/mr5ir_aviditybiosciences/228/download/FINAL%20Avidity%20FSHD%20AOC%201020%20Data%20Webcast%20Deck%206.12.24.pdf], 47 pages.

Avidity Biosciences, "Delivering for People Living with Facioscapulohumeral Muscular Dystrophy (FSHD)," [PowerPoint slides]. Investorroom. [Accessed on Jun. 9, 2025, publicly available at URL: https://filecache.investorroom.com/mr5ir_aviditybiosciences/262/06-09-25%20Del-brax%20Topline%20Webcast%20Deck%20for%20website.pdf], 38 pages.

Bakewell, J., et al., "DUX4-rearranged B-ALL: deciphering a biological and clinical conundrum: Acute Lymphoblastic Leukemia," Epub Sep. 12, 2025; published Dec 2025; 39(12):2835-2847.

Beaucage, S. L., "Oligodeoxyribonucleotides synthesis: Phosphoramidite approach," Methods Mol Biol., 1993:20:33-61.

Beigelman L., et al. "Chemical Modification of Hammerhead Ribozymes: Catalytic Activity and Nuclease Resistance (*)," Journal of biological chemistry 270.43, Oct. 1995, 25702-25708.

Berge et al., "Pharmaceutical salts," J Pharm Sci. Jan. 1977; 6(1):1-19.

Bouwman et al. "The prospects of targeting DUX4 in facioscapulohumeral muscular dystrophy," Current Opinion in Neurology, Oct. 2020, 33(5):635-640.

Bouwman et al. "Systemic delivery of a DUX4-targeting antisense oligonucleotide to treat facioscapulohumeral muscular dystrophy," Molecular Therapy Nucleic Acids, Sep. 27, 2021; 26:813-27. eCollection Dec 3, 2021.

Campbell., et al., "BET bromodomain inhibitors and agonists of the beta-2 adrenergic receptor identified in screens for compounds that inhibit DUX4 expression in FSHD muscle cells," Skelet Muscle, Sep. 4, 2017;7(1):16.

Chau et al., "Relationship of DUX4 and target gene expression in FSHD myocytes," Hum Mutat., Apr. 2021; 42(4): 421-433.

Chen L., et al., "Single-cell spatial transcriptomics reveals a dystrophic trajectory following a developmental bifurcation of myoblast cell fates in facioscapulohumeral muscular dystrophy," Genome Res, Jun. 25, 2024; 34(5):665-679.

Clinical Trial Protocol No. ARODUX4-1001, "A Phase 1/2a Dose-Escalating Study to Evaluate the Safety, Tolerability, Pharmacokinetics, and Pharmacodynamics of ARO-DUX4 in Adult Patients with Facioscapulohumeral Muscular Dystrophy Type 1," [clinical trial protocol], amendment 4, Clinical trials in the European Union—EMA. "ARO-DUX4 for injection protocol No. ARODUX4-1001 protocol synopsis," (posted date Aug. 19, 2024) [Retrieval date unknown, publicly available at URL: https://euclinicaltrials.eu/ctis-public/view/2023-509748-89-00?lang=en.], 11 pages.

Earnshaw D.J., et al.,"Modified oligoribonucleotides as site-specific probes of RNA structure and function," Biopolymers: Original Research on Biomolecules 48.1, Aug. 18, 1998, vol. 48, pp. 39-55.

Fox., et al., "SIX transcription factors are necessary for the activation of DUX4 expression in facioscapulohumeral muscular dystrophy," Skelet Muscle, Dec 3, 2024;14(1):30, 18 pages.

Gait., et al., "Applications of Chemically synthesized RNA in RNA: Protein Interactions," Ed. Smith (1998), 1-36.

Gall., et al. "Therapeutic Strategies Targeting DUX4 in FSHD," Journal of Clinical Medicine. (Sep. 7, 2020);9(9):2886, 20 pages.

(56) References Cited

OTHER PUBLICATIONS

Gallo., et al., “2’-C-Methyluridine phosphoramidite: a new building block for the preparation of RNA analogues carrying the 2’-hydroxyl group,” Tetrahedron, May 2001. 57, 5707-5713.
Gao M., et al., “Human-specific activation of the DUX4-SLC34A2 axis by herpesviruses suppresses antiviral innate immunity,” mBio. Dec 10, 2025;16(12):e0255425, 17 pages.
Geng L., “Double homeobox 4 activates germline genes, endogenous retroelements and immune modulators: Implications for facioscapulohumeral muscular dystrophy,” [dissertation] Doctor of Philosophy, University of Washington, 2011, [Retrieval date unknown, publicly available at URL: https://digital.lib.washington.edu/researchworks/items/9392f6d8-374e-4ed0-8564-cbf14e420c75.], 188 pages.
Geng L.N., et al., “DUX4 activates germline genes, retroelements, and immune mediators: implications for facioscapulohumeral dystrophy,” Dev Cell. Jan. 17, 2012;22(1):38-51.
Griffey R.H., et al., “2’-O-aminopropyl ribonucleotides: a zwitterionic modification that enhances the exonuclease resistance and biological activity of antisense oligonucleotides,” Journal of medicinal chemistry, Dec 20, 1996;39(26):5100-9.
Gros M., et al., “Identification of Serum Interleukin 6 Levels as a Disease Severity Biomarker in Facioscapulohumeral Muscular Dystrophy,” Journal of Neuromuscular Diseases. 2022;9(1):83-93.
Hayakawa Y, et al., “Facile synthesis of oligodeoxyribonucleotides via the phosphoramidite method without nucleoside base protection,” J Am Chem Soc, Jun. 1998;120:12395-401.
Himeda et al., “FSHD Therapeutic Strategies: What Will It Take to Get to Clinic?” Journal of Personalized Medicine (May 25, 2022), 12, 865, 19 pages.
Jacobs J. W., “Losmapimod, a p38α/β MAPK Inhibitor for the Potential Treatment of Patients with FSHD,” [PowerPoint Presentation] Fulcrum Therapeutics (Jun. 23, 2024) [Retrieval date Jun. 23, 2024, publicly available at URL: https://www.fulcrumtx.com/wp-content/uploads/JJacobs-Losmapimod-and-FSHD-New-Directions-2024-06-23-Final.pdf], 26 pages.
Statland, Jeffrey, “Topline Results from FORTITUDETM, a Randomized Phase 1/2 Trial Evaluating AOC 1020 (Del-brax) in Adults with FSHD” Topline Results from FORTITUDETM, a Randomized Phase 1/2 Trial Evaluating AOC 1020 (Del-brax) in Adults with FSHDTopline Results from FORTITUDETM, a Randomized Phase 1/2 Trial Evaluating AOC 1020 (Del-brax) in Adults with FSHD, [PowerPoint slides]. Avidity Biosciences. (Jun. 12-13, 2017), [Retrieval date Jun. 20, 2025, publicly available at URL: https://www.aviditybiosciences.com/sites/default/files/2025-06/IRC%20Jun%202025_FORTITUDE%20FINAL.pdf], 23 pages.
Karpeisky A., et al., “Highly efficient synthesis of 2’-O-amino nucleosides and their incorporation in hammerhead ribozymes,” Tetrahedron letters 39.10, Mar. 1998, 1131-1134.
Koizumi M., 2’-O,4’-C-ethylene-bridged nucleic acids (ENA) as next-generation antisense and antigene agents, Biological and Pharmaceutical Bulletin, Apr. 2004;27(4):453-6.
Kong., et al., “Engineered FSHD mutations results in D4Z4 heterochromatin disruption and feedforward DUX4 network activation,” iScience, Feb. 29, 2024;27(4):109357, 26 pages.
Kools J., “Facioscapulohumeral muscular dystrophy (FSHD) disease progression and losmapimod efficacy assessed by reachable workspace in both arms,” [Powerpoint Presentation] Fulcrum Therapeutics, (Jun. 14, 2024) [Retrieval date unknown, publicly available at URL: https://www.fulcrumtx.com/wp-content/uploads/Facioscapulohumeral-Muscular-Dystrophy-FSHD-Disease-Progression-by-RWS-average-of-the-two-arms-for-FSHD-IRC-May-23_final-post-MLR-002.pdf], 18 pages.
Lemmers R.J., et al., “A unifying genetic model for facioscapulohumeral muscular dystrophy,” Science, Sep. 24, 2010;329(5999):1650-3.
Lim., et al., “Genetic Approaches for the Treatment of Facioscapulohumeral Muscular Dystrophy,” Front Pharmacol. Mar. 12, 2021;12:642858, 13 pages.
Loakes D.,“Survey and summary: The applications of universal DNA base analogues,” Nucleic Acids Research, Jun. 15, 2001;29(12):2437-47.
Malecova B., et al., “Targeted tissue delivery of RNA therapeutics using antibody-oligonucleotide conjugates (AOCs),” Nucleic acids research, Jul. 7, 2023;51(12):5901-5910.
Malecova., et al., “AOC 1020: An Antibody Oligonucleotide Conjugate (AOC) in Development for the Treatment of FSHD,” [Poster], Poster No. WMS LSVP.08, 27th International Hybrid Annual Congress of the World Muscle Society, Avidity Biosciences, Inc (2022) [Retrieval date unknown, publicly available at https://www.aviditybiosciences.com/sites/default/files/2025-04/63086_Avidity_BM-FSHD-AOC-1020-WMS_Poster-36x42in-05FB_FINAL-LSVP.08.pdf], 1 page.
Malecova., et al., “DUX4 siRNA Optimization for the Development of an Antibody-Oligonucleotide Conjugate (AOCTM) for the Treatment of FSHD,” [Poster Session]. Muscular Dystrophy Association (MDA) Clinical & Scientific Conference, Nashville, Tennessee, United States, Avidity Biosciences, Inc (2022), 3 pages.
Martinez J., et al., “Single-stranded antisense siRNAs guide target RNA cleavage in RNAi,” Cell, Sep. 6, 2002;110(5):563-74.
Mocciaro E., et al., “DUX4 Role in Normal Physiology and in FSHD Muscular Dystrophy,” Cells, Nov. 26, 2021;10(12):3322, 25 pages.
Mocciaro., et al., “WDR5 is required for DUX4 expression and its pathological effects in FSHD muscular dystrophy,” Nucleic Acids Research, Jun. 9, 2023;51(10):5144-5161.
Picariello et al., “The FORCE Platform Achieves Robust and Durable DUX4 Suppression and Improves Muscle Function in a Facioscapulohumeral Muscular Dystrophy Mouse Model,” (Oct. 12, 2024), [Retrieval date unknown, publicly available at URL: https://www.dyne-tx.com/wp-content/uploads/Picariello_FSHD_WMS_2024.pdf], 1 page.
Pineda JMB., et al., “DUX4 is a common driver of immune evasion and immunotherapy failure in metastatic cancers,” Elife, Jun. 3, 2024;12:RP89017, 26 pages.
Ponce R.K.M., “Molecular and therapeutic advancements in Capicua (CIC)-rearranged sarcoma,” Frontiers in Cell and Developmental Biology, May 31, 2024;12:1416697, 11 pages.
Ronco L., et al., “A Biomarker of Aberrant DUX4 Activity to Evaluate Losmapimod Treatment Effect in FSHD Phase 2 Trials,” [Poster], Poster No. P.231, (Oct. 1, 2020), [Retrieval date unknown, publicly available at URL: https://www.fulcrumtx.com/wp-content/uploads/A-Biomarker-of-Aberrant-DUX4-Activity-to-Evaluate-Losmapimod-Treatment-Effect-in-FSHD-Phase-2-Trials.pdf], 1 page.
Roy S., et al., “Synthesis of DNA/RNA and their analogs via phosphoramidite and H-phosphonate chemistries,” Molecules, Nov. 18, 2013;18(11):14268-84.
Scaringe S.A., “RNA oligonucleotide synthesis via 5’-silyl-2’-orthoester chemistry,” Methods, Mar. 2001;23(3):206-17.
Schwarz D.S., et al., “Evidence that siRNAs function as guides, not primers, in the *Drosophila* and human RNAi pathways,” Molecular cell, Sep. 2002;10(3):537-48.
Shao Y., et al., “Rational design and rapid screening of antisense oligonucleotides for prokaryotic gene modulation,” Nucleic acids research, Oct. 2006;34(19):5660-9.
Smith, A. A., “DUX4 expression in development versus disease: DUX4 expression in spermatogenesis, placentation, cancer and FSHD,” (Feb. 12, 2024), [Retrieval date unknown, publicly available at URL: https://digital.lib.washington.edu/researchworks/items/793d3d01-6880-4182-a053-e40ded135892], 66 pages.
Statland., et al., “Interim Results from FORTITUDE TM, a Randomized Phase 1/2 Trial Evaluating AOC 1020 in Adults with FSHD,” [Poster], Neuromuscular Study Group Annual Scientific Meeting, Avidity Biosciences, Inc, (2024), [Retrieval date unknown, publicly available at URL: https://www.aviditybiosciences.com/sites/default/files/2025-04/Final-NMSG-2024-FORTITUDE-Poster-16SEP24.pdf.],1 page.
Summerton J.E., “Morpholino, siRNA, and S-DNA compared: impact of structure and mechanism of action on off-target effects and sequence specificity,” Current topics in medicinal chemistry. 2007;7(7):651-60.

(56) References Cited

OTHER PUBLICATIONS

Sutliff, et al., "Characterization of a promising DUX4-Regulated Circulating biomarker for FSHD," [Poster] International Research Conference, (Jun. 13, 2025), [Retrieval date Jun. 2025, publicly available at URL: https://www.aviditybiosciences.com/sites/default/files/2025-06/TapscottFSHDIRC2025%20Poste%20Final.pdf], 1 page.
Sutliff N.A., et al., "Identification of KHDC1L, a DUX4-regulated protein, as a novel plasma biomarker in facioscapulohumeral muscular dystrophy," Hum Mol Genet, Feb. 9, 2026;35(2): ddaf183, 9 pages.
Tawil R., et al., "Facioscapulohumeral muscular dystrophy. Muscle & Nerve: Official Journal of the American Association of Electrodiagnostic Medicine," Jul. 2006;34(1):1-15.
Tihaya M.S., et al., "Facioscapulohumeral muscular dystrophy: the road to targeted therapies," Nature Review Neurology, Feb. 2023;19(2):91-108.
Usman N., et al., Exploiting the chemical synthesis of RNA. Trends in biochemical sciences. Sep. 1992;17(9):334-9.
Van Den Heuvel, et al., "Single-cell RNA sequencing in facioscapulohumeral muscular dystrophy disease etiology and development," Human molecular genetics. Apr. 1, 2019;28(7):1064-1075.
Van Dyke., et al., "Development of an RNAi Therapeutic, ARO DUX4, for the Treatment of FSHD" [Powerpoint Presentation] arrowhead pharmaceuticals, 28th Annual FSHD Society International Research Congress, Amsterdam, Netherlands, (Jun. 25, 2021), 11 pages.
Vangipurapu R. et al., GENBANK, Accession No. NM_001306068.3, "*Homo sapiens* double homeobox 4 (DUX4), MRNA," (Record created Nov. 12, 2019), [Retrieval date Feb. 11, 2026, publicly available at URL: https://www.ncbi.nlm.nih.gov/nuccore/NM_001306068.3.], 4 pages.
Verma et al., "Modified Oligonucleotides: Synthesis and Strategy for Users," Annual Review of Biochemistry, Jul. 1998, 67(1), pp. 99-134.
Wallace., et al., "Targeting DUX4 mRNA with anti-TfR NANOBODY® antisense oligonucleotide conjugates," [Poster] 21st Annual Meeting of the Oligonucleotide Therapeutics Society (OTS), Budapest, Hungary, Mirecule RNA Therapeutics, (Oct. 19-22, 2025), 1 page.
Wang., et al., "Current Therapeutic Approaches in FSHD," J Neuromuscul Dis. 2021;8(3):441-451.
Yoshida T., et al., "Evaluation of off-target effects of gapmer antisense oligonucleotides using human cells," Genes Cells. Dec 2019;24(12):827-835.
Zanotti S., "DYNE-302 Leads to Functional Improvement and Resolves Muscle Transcriptomic Changes in Mouse Models of FSHD," [Powerpoint Presentation], FSHD International Research Conference, 2025, Dyne Therapeutics, (Jun. 13, 2025), [Retrieval date Jun. 2025, publicly available at URL: http://www.dyne-tx.com/wp-content/uploads/Zanotti_FSHD-IRC_June_2025.pdf], 17 pages.
Zhang A., et al., "DUX4 reduction and muscle function improvement by subcutaneous delivery of gapmer antisense oligonucleotides," Molecular therapy. Nucleic acids. Dec 8, 2025;37(1):102791, 24 pages.
Genbank, Accession No. FJ439133.1 "*Homo sapiens* clone lambda42 DUX4 (DUX4) genes, complete cds," [sequence database entry], National Center for Biotechnology Information (NCBI), submitted Apr. 23, 2009. [Accessed Apr. 27, 2026, publicly available at URL: https://www.ncbi.nlm.nih.gov/nuccore/FJ439133], 5 pages.
PCT Application No. PCT/US2025/058469, International Search Report and Written Opinion mailed Jun. 3, 2026, Applicant Soufflé Therapeutics, Inc et al.; 23 pages.

* cited by examiner

OLIGONUCLEOTIDE-MEDIATED KNOCKDOWN OF DUX4

CROSS REFERENCE TO RELATED APPLICATIONS

This application claims the benefit of U.S. Provisional Application No. 63/728,473 filed on Dec. 5, 2024, the entirety of which is incorporated herein by reference.

INCORPORATION BY REFERENCE OF SEQUENCE LISTING

The present application is being filed along with a Sequence Listing in electronic format. The Sequence Listing is provided as a file entitled 360770-0003_SeqList_ST26.xml, created Dec. 4, 2025, which is 19,950,082 bytes in size. The information in the electronic format of the Sequence Listing is incorporated herein by reference in its entirety.

BACKGROUND

Facioscapulohumeral muscular dystrophy (FSHD) is a genetic disease affecting approximately 1 in 8,000 to 22,000 individuals worldwide, making it one of the most prevalent forms of muscular dystrophy. This autosomal dominant myopathy is characterized by progressive muscle weakness and atrophy, primarily impacting muscles in the face, shoulder girdle, and upper arms. As the condition progresses, additional muscle groups can be affected, such as the ankle dorsiflexors and proximal leg muscles, potentially leading to wheelchair dependence for around 20% of patients. Beyond muscular weakness, FSHD can also manifest with extra-muscular symptoms, including hearing loss, retinal vasculopathy, and cardiac conduction defects. FSHD has two distinct types: FSHD1 and FSHD2. The root cause in both types is the de-repression of a specific genetic region known as the D4Z4 macrosatellite repeat array, located on chromosome 4: FSHD1 (95% of cases)—a contraction of the D4Z4 repeat array to less than 10 units; FSHD2 (5% of cases)—mutations in genes involved in regulating the D4Z4 array. Despite the different genetic mechanisms, both FSHD1 and FSHD2 result in a loss of methylation in the D4Z4 region, leading to the same clinical presentation. The de-repression of the D4Z4 array leads to the aberrant expression of the DUX4 gene in skeletal muscle. This gene encodes a transcription factor normally active during early embryonic development but silenced in adult tissues, except for specific isoforms in the testis and thymus. The increased expression of DUX4 in adult muscle is highly toxic, causing a cascade of cellular problems that contribute to muscle degeneration: oxidative stress, dysregulated transcript quality control, protein aggregation, inflammation, impaired myogenesis, and muscle atrophy.

Due to the critical role of DUX4 in FSHD pathogenesis, it has become the primary target for therapeutic development. Various oligonucleotide therapies targeting DUX4 have shown promising results in preclinical studies. While significant progress has been made in understanding FSHD, further research is necessary to fully comprehend its complex nature and address the remaining unanswered questions. Overall, there is an unmet medical need for patients with FSHD that can be addressed by siRNA therapeutics.

SUMMARY

In some embodiments, the present disclosure provides an oligonucleotide for inhibiting expression of DUX4, wherein the oligonucleotide comprises an antisense strand comprising at least 14 contiguous nucleotides substantially complementary to a sequence of nucleotides encoding DUX4, with no more than 4 mismatched nucleotides.

In some embodiments, the present disclosure provides a pharmaceutical composition comprising an oligonucleotide described herein, or a pharmaceutically acceptable salt thereof, and a pharmaceutically acceptable carrier or excipient.

In some embodiments, the present disclosure provides methods of using provided oligonucleotides. In some embodiments, the present disclosure provides a method for inhibiting DUX4 expression or treating a DUX4 related disorder in a subject, the method comprising administering an effective amount of an oligonucleotide described herein, or a pharmaceutically acceptable salt thereof, or a pharmaceutical composition comprising an oligonucleotide described herein to the subject.

DETAILED DESCRIPTION

Provided herein are oligonucleotides for inhibiting the expression of Double Homeobox 4 ("DUX4"). In some embodiments, the oligonucleotide comprises an antisense strand substantially complementary to a sequence encoding DUX4. In some embodiments, the antisense strand comprises at least 14 contiguous nucleotides (for example, 14, 15, 16, 17, 18, 19, 20, 21, 22, 23, 24, 25, 26, 27, 28, 29, 30, 31, 32, 33, 34, 35, 36, 37, 38, 39, or 40 contiguous nucleotides) substantially complementary to the sequence of nucleotides encoding DUX4, with no more than 4 mismatched nucleotides.

The term "antisense strand" refers to an oligonucleotide having a nucleotide sequence substantially complementary to a target sequence in a transcript, e.g., an mRNA encoding DUX4. In embodiments wherein the oligonucleotide is an RNAi agent, the term antisense strand may be used interchangeably with the term "guide strand". In some embodiments, an antisense strand disclosed herein is 14, 15, 16, 17, 18, 19, 20, 21, 22, 23, 24, 25, 26, 27, 28, 29, or 30 nucleotides in length.

The term "sense strand" refers to an oligonucleotide having a nucleotide sequence substantially complementary to an antisense strand, e.g., the antisense strand of an RNAi agent herein. The term "sense strand" may be used interchangeably with the term "passenger strand." In some embodiments, a sense strand disclosed herein is 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length. For example, each of the sense strands in Tables 1A-1F is 19 nucleotides in length and substantially complementary to the corresponding antisense strand shown in the same row.

As used herein, and unless otherwise indicated, the term "complementary," when used to describe a first nucleotide sequence in relation to a second nucleotide sequence, refers to the ability of an oligonucleotide comprising the first nucleotide sequence to hybridize and form a duplex structure under certain conditions with an oligonucleotide comprising the second nucleotide sequence, as will be understood by the skilled person. In some embodiments, a duplex structure disclosed herein is 12, 13, 14, 15, 16, 17, 18, 19, 20, 21, 22, 23, 24, 25, 26, 27, 28, 29, or 30 base pairs in length.

The terms "complementary," "completely complementary" and "substantially complementary" herein can be used with respect to the base matching between the antisense strand of an oligonucleotide, e.g., an RNAi agent, and a target sequence, or between the sense strand and the antisense strand of an RNAi agent, as will be understood from the context of their use. Complementary sequences, e.g., between an antisense strand and a target sequence in a target transcript, or between the sense and antisense strand of an siRNA, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "completely complementary" with respect to each other when there are 0 mismatched base pairs upon hybridization of the two sequences. However, where a first sequence is referred to as "substantially complementary" with respect to a second sequence herein, the two sequences can be completely complementary, or they can form one or more, but generally not more than 5, 4, 3, 2, or 1 mismatched base pairs upon hybridization for a duplex up to 30 base pairs, while retaining the ability to hybridize under the conditions most relevant to their ultimate application, e.g., inhibition of gene expression via a RNA-induced silencing complex (RISC) pathway. However, where two oligonucleotides are designed to form, upon hybridization, one or more single stranded overhangs, such overhangs shall not be regarded as mismatches with regard to the determination of complementarity. For example, an siRNA comprising one oligonucleotide 21 nucleotides in length and another oligonucleotide 19 nucleotides in length, wherein the longer oligonucleotide comprises a sequence of 19 nucleotides that is fully complementary to the shorter oligonucleotide, can yet be referred to as "completely complementary" for the purposes described herein.

"Complementary" sequences, as used herein, can also include, or be formed entirely from, non-Watson-Crick base pairs or base pairs formed from non-natural and modified nucleotides, in so far as the above requirements with respect to their ability to hybridize are fulfilled. Such non-Watson-Crick base pairs include, but are not limited to, G:U Wobble or Hoogsteen base pairing.

If an RNA strand contains one or more thymidines ("T"s) in the sequence, the thymidines ("T"s) represent uridines ("U"s). For example, the nucleotide "T", as used in the unmodified siRNAs sense and antisense strands in Table 1A, for example, SEQ ID Nos: 1-15, 22-36, 43-128, 130-143, 152-315, 322-467, 471-475, 481-487, 489-511, 513, 516-524, 527-856, 868-975, 977-1113, 1115-1133, 1135-1161, and 1163-1212, represents RNA uridine, and the corresponding RNA sense and antisense strands are listed in Table 1F.

In some embodiments, the present disclosure provides an oligonucleotide or RNAi agent, as described herein, or a pharmaceutically acceptable salt thereof. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in, J. PHARMACEUTICAL SCIENCES, 1977, (66); 1-19, incorporated herein by reference. Pharmaceutically acceptable salts of the nucleic acids and analogues thereof of this disclosure include those derived from suitable inorganic and organic acids and bases. Salts derived from appropriate bases include alkali metal, alkaline earth metal, ammonium and $N^+(C_{1-4}alkyl)_4$ salts. In some embodiments, a pharmaceutically acceptable salt is the sodium salt. In some embodiments, a pharmaceutically acceptable salt is the potassium salt.

In some embodiments, the oligonucleotide comprises an antisense strand comprising at least 14 contiguous nucleotides (for example, 14, 15, 16, 17, 18, 19, 20, 21, 22, 23, 24, 25, 26, 27, 28, 29, 30, 31, 32, 33, 34, 35, 36, 37, 38, 39, or 40 contiguous nucleotides) substantially complementary to a sequence of nucleotides within a transcript encoding DUX4. In some embodiments, the antisense strand has no more than 5 mismatched nucleotides to the sequence of nucleotides within the transcript encoding DUX4. In some embodiments, the antisense strand has no more than 4 mismatched nucleotides to the sequence of nucleotides within the transcript encoding DUX4. In some embodiments, the antisense strand has no more than 3 mismatched nucleotides to the sequence of nucleotides within the transcript encoding DUX4. In some embodiments, the antisense strand has no more than 2 mismatched nucleotides to the sequence of nucleotides within the transcript encoding DUX4. In some embodiments, the antisense strand has no more than 1 mismatched nucleotides to the sequence of nucleotides within the transcript encoding DUX4. In some embodiments, the antisense strand is completely complementary to the sequence of nucleotides within the transcript encoding DUX4 (e.g., 0 mismatches).

The DUX4 gene encodes a transcription factor that is normally involved in zygotic genome activation during the four-cell stage of early embryonic development. Afterward, DUX4 is epigenetically silenced in all adult tissues apart from the limited expression of unrelated DUX4 isoforms in the testis and thymus. Following transcription of the DUX4 gene, stochastic, low-level DUX4 protein expression occurs in the myofiber nuclei of the skeletal muscle. Inappropriate DUX4 protein expression in adult skeletal muscle is highly toxic and causes Facioscapulohumeral muscular dystrophy (FSHD). DUX4 is a transcription factor comprising a single protein. Exemplary sequences of DUX4 may be found for example at NCBI RefSeq ID NM_001306068.3 (SEQ ID NO: 2425). In some embodiments, DUX4 is encoded by a nucleotide sequence corresponding to the transcript having the NCBI RefSeq ID NM_001306068.3 (SEQ ID NO: 2425).

In some embodiments, the sequence of nucleotides encoding DUX4 comprises a nucleotide sequence having at least 75% nucleotide sequence identity to SEQ ID NO: 2425. In some embodiments, the sequence of nucleotides encoding DUX4 comprises a nucleotide sequence having at least 80% nucleotide sequence identity to SEQ ID NO: 2425. In some embodiments, the sequence of nucleotides encoding DUX4 comprises a nucleotide sequence having at least 85% nucleotide sequence identity to SEQ ID NO: 2425. In some embodiments, the sequence of nucleotides encoding DUX4 comprises a nucleotide sequence having at least 90% nucleotide sequence identity to SEQ ID NO: 2425. In some embodiments, the sequence of nucleotides encoding DUX4 comprises a nucleotide sequence having at least 95% nucleotide sequence identity to SEQ ID NO: 2425. In some embodiments, the sequence of nucleotides encoding DUX4 comprises a nucleotide sequence having at least 99% nucleotide sequence identity to SEQ ID NO: 2425.

In some embodiments, the antisense strand is substantially complementary to a sequence of nucleotides corresponding to an untranslated region of the DUX4 transcript. In some embodiments, the antisense strand is substantially complementary to the sequence of nucleotides corresponding to an untranslated region of the DUX4 transcript with no more than 5, 4, 3, 2, 1, or 0 mismatches. In some embodiments, the antisense strand is completely complementary to the sequence of nucleotides corresponding to an untranslated region of the DUX4 transcript.

RNAi Agents

In some embodiments, the oligonucleotide is an RNAi agent or RNAi trigger for inhibiting expression of DUX4. As used herein, an "RNAi agent" or "RNAi trigger" refers to an oligonucleotide molecule capable of inducing RNA interference (RNAi), which mediates the targeted cleavage of an RNA transcript via an RNA-induced silencing complex (RISC) pathway. The RNAi agents disclosed herein include but are not limited to: short (or small) interfering RNAs (siRNAs), double stranded RNAs (dsRNA), micro RNAs (miRNAs), short hairpin RNAs (shRNA), and dicer substrates (e.g., DsiRNAs).

In some embodiments, the RNAi agent is a double stranded RNA molecule comprising an antisense strand and a sense strand that are complementary to one another and hybridize to form a duplex or double stranded region. One strand of the RNAi agent, the antisense strand or guide strand, includes a region of complementarity to a target sequence in DUX4. The other strand, the sense strand or passenger strand, includes a region that is complementary to the antisense strand, such that the two strands hybridize and form a duplex structure when combined under suitable conditions. In some embodiments, the double stranded RNA molecule may be formed by base pairing between two separate molecules of RNA (e.g., an antisense strand and a sense strand). In some embodiments, the double stranded RNA molecule is a self-complementary molecule formed by intramolecular base pairing between two separate regions of a single RNA molecule (e.g., an antisense region linked to a sense strand through an unpaired RNA linker forming a loop or hairpin loop).

Where the two strands are part of a self-complementary molecule, the connecting RNA chain is referred to as a "hairpin loop." A hairpin loop can comprise at least one unpaired nucleotide. In some embodiments, the hairpin loop can comprise at least 4, at least 5, at least 6, at least 7, at least 8, at least 9, at least 10, at least 20, at least 23 or more unpaired nucleotides or nucleotides not directed to the target site of the dsRNA. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides. In some embodiments, the hairpin loop can contain 1-4 oligoethyne glycols, including ethylene glycol, di ethylene glycol, triethylene glycol, tetraethylene glycol, hexaethylene glycol, or any combination thereof.

Where the two substantially complementary strands of a double stranded RNA molecule comprise separate RNA molecules, those molecules need not, but can be covalently connected. In certain embodiments, where the two strands are connected covalently by means other than an uninterrupted chain of nucleotides between the 3'-end of one strand and the 5'-end of the respective other strand forming the duplex structure, the connecting structure is referred to as a "linker" (though it is noted that certain other structures defined elsewhere herein can also be referred to as a "linker"). The RNA strands may have the same or a different number of nucleotides. The maximum number of base pairs is the number of nucleotides in the shortest strand of the double stranded RNA molecule minus any overhangs that are present in the duplex.

In some embodiments, the RNAi agent is an siRNA.

In some embodiments, the RNAi agent is a shRNA.

In some embodiments, the RNAi agent is a dicer substrate (e.g., a Dicer-substrate siRNA).

In some embodiments, the sense and antisense strands of the dsRNA are each independently about 15 to about 30 nucleotides in length, or about 25 to about 30 nucleotides in length, e.g., each strand is independently between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length.

In some embodiments, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length.

An RNAi agent as described herein can further include one or more single-stranded nucleotide overhangs, e.g., an overhang of 1, 2, 3, or 4 nucleotides. RNAi agent having at least one nucleotide overhang can have unexpectedly superior inhibitory properties relative to their blunt-ended counterparts. A nucleotide overhang can comprise or consist of a nucleotide/nucleoside analog, including a deoxynucleotide, an inverted deoxynucleotide or an inverted abasic nucleotide. The overhang(s) can be on the sense strand, the antisense strand or any combination thereof. Furthermore, the nucleotide(s) of an overhang can be present on the 5'-end, 3'-end or both ends of either an antisense or sense strand of the RNAi agent. In certain embodiments, longer, extended overhangs are possible.

In some embodiments, the antisense strand is 21 nucleotides in length, and the sense strand is 19 nucleotides in length. In some embodiments, the antisense strand is 19 nucleotides in length, and the sense strand is 19 nucleotides in length.

The oligonucleotides disclosed herein may be unmodified or modified (e.g., chemically modified or conjugated). A modified oligonucleotide as disclosed herein comprises an identical nucleobase sequence as compared to a corresponding unmodified oligonucleotide, but further comprises one or more modifications as disclosed herein.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides from any one of the antisense strand sequences of Tables 1A-1F. In some embodiments, the antisense strand differs by no more than 3 nucleotides from any one of the antisense strand sequences of Tables 1A-1F. In some embodiments, the antisense strand differs by no more than 2 nucleotides from any one of the antisense strand sequences of Tables 1A-1F. In some embodiments, the antisense strand differs by no more than 1 nucleotide from any one of the antisense strand sequences of Tables 1A-1F. In some embodiments, the antisense strand comprises any one of the antisense strand sequences of Tables 1A-1F. In some embodiments, the antisense strand consists of any one of the antisense strand sequences of Tables 1A-1F.

In some embodiments, the present disclosure provides oligonucleotides for inhibiting expression of DUX4, wherein the oligonucleotide comprises an antisense strand substantially complementary to a sequence encoding DUX4. In some embodiments, the oligonucleotide targets a sequence corresponding to positions selected from Table 4.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides from the nucleotide sequence of any one of SEQ ID NOs: 607-1212 or 1819-2424. In some embodiments, the antisense strand differs by no more than 3 nucleotides from the nucleotide sequence of any one of SEQ ID NOs: 607-1212 or 1819-2424. In some embodiments, the antisense strand differs by no more than 2 nucleotides from the nucleotide sequence of any one of SEQ ID NOs: 607-1212 or 1819-2424. In some embodiments, the antisense strand differs by no more than 1 nucleotide from the nucleotide sequence of any one of SEQ ID NOs: 607-1212 or 1819-2424. In some embodiments, the antisense strand comprises the nucleotide sequence of any one of SEQ ID NOs: 607-1212 or 1819-2424. In some embodiments, the antisense strand consists of the nucleotide sequence of any one of SEQ ID NOs: 607-1212 or 1819-2424. In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides from the nucleotide sequence of any one of SEQ ID NOs: 2437-2447. In some embodiments, the antisense strand differs by no more than 3 nucleotides from the nucleotide sequence of any one of SEQ ID NOs: 2437-2447. In some embodiments, the antisense strand differs by no more than 2 nucleotides from the nucleotide sequence of any one of SEQ ID NOs: 2437-2447. In some embodiments, the antisense strand differs by no more than 1 nucleotide from the nucleotide sequence of any one of SEQ ID NOs: 2437-2447. In some embodiments, the antisense strand comprises the nucleotide sequence of any one of SEQ ID NOs: 2437-2447. In some embodiments, the antisense strand consists of the nucleotide sequence of any one of SEQ ID NOs: 2437-2447.

In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 607-1212 or 1819-2424. In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 607-1212 or 1819-2424. In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 2437-2447. In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 2437-2447.

In some embodiments, the antisense strand consists of a nucleotide sequence having the nucleotide sequence of any one of SEQ ID NOs: 607-1212 or 1819-2424. In some embodiments, the antisense strand consists of a nucleotide sequence having the nucleotide sequence of any one of SEQ ID NOs: 2437-2447.

In some embodiments, the sense strand comprises a nucleotide sequence comprising at least 15 contiguous nucleotides (for example, 15, 16, 17, 18, or 19 contiguous nucleotides) differing by no more than 4 nucleotides from any one of the sense strand sequences of Tables 1A-1F. In some embodiments, the sense strand differs by no more than 3 nucleotides from any one of the sense strand sequences of Tables 1A-1F. In some embodiments, the sense strand differs by no more than 2 nucleotides from any one of the sense strand sequences of Tables 1A-1F. In some embodiments, the sense strand differs by no more than 1 nucleotide from any one of the sense strand sequences of Tables 1A-1F. In some embodiments, the sense strand comprises a sequence of any one of the sense strands of Tables 1A-1F. In some embodiments, the sense strand consists of a sequence of any one of the sense strands of Tables 1A-1F.

In some embodiments, the sense strand comprises a nucleotide sequence comprising at least 15 contiguous nucleotides (for example, 15, 16, 17, 18, or 19 contiguous nucleotides) differing by no more than 4 nucleotides from the nucleotide sequence of any one of SEQ ID NOs: 1-606 or 1213-1818. In some embodiments, the sense strand differs by no more than 3 nucleotides from the nucleotide sequence of any one of SEQ ID NOs: 1-606 or 1213-1818. In some embodiments, the sense strand differs by no more than 2 nucleotides from the nucleotide sequence of any one of SEQ ID NOs: 1-606 or 1213-1818. In some embodiments, the sense strand differs by no more than 1 nucleotide from the nucleotide sequence of any one of SEQ ID NOs: 1-606 or 1213-1818. In some embodiments, the sense strand comprises the nucleotide sequence of any one of SEQ ID NOs: 1-606 or 1213-1818. In some embodiments, the sense strand consists of the nucleotide sequence of any one of SEQ ID NOs: 1-606 or 1213-1818. In some embodiments, the sense strand comprises a nucleotide sequence comprising at least 15 contiguous nucleotides (for example, 15, 16, 17, 18, or 19 contiguous nucleotides) differing by no more than 4 nucleotides from the nucleotide sequence of any one of SEQ ID NOs: 2426-2436. In some embodiments, the sense strand differs by no more than 3 nucleotides from the nucleotide sequence of any one of SEQ ID NOs: 2426-2436. In some embodiments, the sense strand differs by no more than 2 nucleotides from the nucleotide sequence of any one of SEQ ID NOs: 2426-2436. In some embodiments, the sense strand differs by no more than 1 nucleotide from the nucleotide sequence of any one of SEQ ID NOs: 2426-2436. In some embodiments, the sense strand comprises the nucleotide sequence of any one of SEQ ID NOs: 2426-2436. In some embodiments, the sense strand consists of the nucleotide sequence of any one of SEQ ID NOs: 2426-2436.

In some embodiments, the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 1-606 or 1213-1818. In some embodiments, the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 1-606 or 1213-1818. In some embodiments, the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 2426-2436. In some embodiments, the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 2426-2436.

In some embodiments, the sense strand consists of a nucleotide sequence having the nucleotide sequence of any one of SEQ ID NOs: 1-606 or 1213-1818. In some embodiments, the sense strand consists of a nucleotide sequence having the nucleotide sequence of any one of SEQ ID NOs: 2426-2436.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides from the nucleotide sequence of any one of SEQ ID NOs: 607-1212 or 1819-2424, and the sense strand comprises a nucleotide sequence at least 15 contiguous nucleotides (for example, 15, 16, 17, 18, or 19 contiguous nucleotides) differing by no more than 4 nucleotides from the nucleotide sequence of any one of SEQ ID NOs: 1-606 or 1213-1818. In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides from the nucleotide sequence of any one of SEQ ID NOs: 2437-2447, and the sense strand comprises a nucleotide sequence at least 15 contiguous nucleotides (for example, 15, 16, 17, 18, or 19 contiguous nucleotides) differing by no more than 4 nucleotides from the nucleotide sequence of any one of SEQ ID NOs: 2426-2436.

In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 607-1212 or 1819-2424, and the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 1-606 or 1213-1818. In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 2437-2447, and the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to a portion of the nucleotide sequence of any one of SEQ ID NOs: 2426-2436.

In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 607-1212 or 1819-2424, and the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 1-606 or 1213-1818. In some embodiments, the antisense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 2437-2447, and the sense strand comprises a nucleotide sequence having at least 90% nucleotide sequence identity (for example, at least 90%, 91%, 92%, 93%, 94%, 95%, 96%, 97%, 98%, 99%, or 100% nucleotide sequence identity) to the nucleotide sequence of any one of SEQ ID NOs: 2426-2436

In some embodiments, the antisense strand consists of a nucleotide sequence of any one of SEQ ID NOs: 607-1212 or 1819-2424, and the sense strand consists of a nucleotide sequence of any one of SEQ ID Nos: 1-606 or 1213-1818. In some embodiments, the antisense strand consists of a nucleotide sequence of any one of SEQ ID NOs: 2437-2447, and the sense strand consists of a nucleotide sequence of any one of SEQ ID Nos: 2426-2436.

In some embodiments, the oligonucleotide of the present disclosure targets a sequence of nucleotides corresponding to any one of positions 11-29, 13-31, 61-79, 67-85, 109-127, 115-133, 124-142, 125-143, 131-149, 133-151, 163-181, 164-182, 165-183, 187-205, 188-206, 203-221, 204-222, 277-295, 292-310, 299-317, 300-318, 301-319, 307-325, 315-333, 316-334, 339-357, 347-365, 348-366, 349-367, 404-422, 412-430, 420-438, 532-550, 533-551, 619-637, 620-638, 621-639, 708-726, 747-765, 748-766, 749-767, 779-797, 781-799, 852-870, 1036-1054, 1100-1118, 1101-1119, 1107-1125, 1109-1127, 1115-1133, 1131-1149, 1132-1150, 1140-1158, 1141-1159, 1147-1165, 1148-1166, 1149-1167, 1163-1181, 1171-1189, 1428-1446, 1619-1637, 1628-1646, 1629-1647, 1635-1653, 1636-1654, 1637-1655, 1638-1656, 1639-1657, 1651-1669, 1652-1670, 1653-1671, 1654-1672, 1655-1673, 1656-1674, 27-45, 28-46, 251-269, 252-270, 317-335, 355-373, 363-381, 437-455, 452-470, 453-471, 547-565, 548-566, 549-567, 565-583, 579-597, 581-599, 588-606, 627-645, 652-670, 659-677, 668-686, 692-710, 715-733, 717-735, 732-750, 733-751, 813-831, 827-845, 843-861, 845-863, 877-895, 892-910, 893-911, 939-957, 956-974, 989-1007, 1028-1046, 1067-1085, 1083-1101, 1084-1102, 1085-1103, 1212-1230, 1213-1231, 1235-1253, 1251-1269, 1260-1278, 1261-1279, 1267-1285, 1268-1286, 1269-1287, 1274-1292, 1279-1297, 1284-1302, 1288-1306, 1389-1407, 1390-1408, 1421-1439, 1427-1445, 1612-1630, or 1613-1631 of SEQ ID NO: 2425 (NM_001306068.3).

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from an antisense strand selected from Table 1C, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from a sense strand selected from Table 1C. In some embodiments, the antisense strand comprises a nucleotide sequence differing by no more than 4 nucleotides (for example, 1, 2, 3, or 4 nucleotides) from an antisense strand selected from Table 1C, and the sense strand comprises a nucleotide sequence differing by no more than 4 nucleotides (for example, 1, 2, 3, or 4 nucleotides) from a sense strand selected from Table 1C. In some embodiments, the antisense strand comprises an antisense strand selected from Table 1C, and the sense strand comprises a sense strand selected from Table 1C. In some embodiments, the antisense strand consists of an antisense strand selected from Table 1C, and the sense strand consists of a sense strand selected from Table 1C.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1821, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1215. In some embodiments, the antisense strand comprises a nucleotide sequence differing by no more than 4 nucleotides (for example, 1, 2, 3, or 4 nucleotides) from SEQ ID NO: 1821, and the sense strand comprises a nucleotide sequence differing by no more than 4 nucleotides (for example, 1, 2, 3, or 4 nucleotides) from SEQ ID NO: 1215. In some embodiments, the antisense strand comprises the nucleotide sequence SEQ ID NO: 1821, and the sense strand comprises the nucleotide sequence SEQ ID NO: 1215. In some embodiments, the antisense strand consists of the nucleotide sequence SEQ ID NO: 1821, and the sense strand consists of the nucleotide sequence SEQ ID NO: 1215.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1823, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1217. In some embodiments, the antisense strand comprises a nucleotide sequence differing by no more than 4 nucleotides (for example, 1, 2, 3, or 4 nucleotides) from SEQ ID NO: 1823, and the sense strand comprises a nucleotide sequence differing by no more than 4 nucleotides (for example, 1, 2, 3, or 4 nucleotides) from SEQ ID NO: 1217. In some embodiments, the antisense strand comprises the nucleotide sequence SEQ ID NO: 1823, and the sense strand comprises the nucleotide sequence SEQ ID NO: 1217. In some embodiments, the antisense strand consists of the nucleotide sequence SEQ ID NO: 1823, and the sense strand consists of the nucleotide sequence SEQ ID NO: 1217.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1846, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1240. In some embodiments, the antisense strand comprises a nucleotide sequence differing by no more than 4 nucleotides (for example, 1, 2, 3, or 4 nucleotides) from SEQ ID NO: 1846, and the sense strand comprises a nucleotide sequence differing by no more than 4 nucleotides (for example, 1, 2, 3, or 4 nucleotides) from SEQ ID NO: 1240. In some embodiments, the antisense strand comprises the nucleotide sequence SEQ ID NO: 1846, and the sense strand comprises the nucleotide sequence SEQ ID NO: 1240. In some embodiments, the antisense strand consists of the nucleotide sequence SEQ ID NO: 1846, and the sense strand consists of the nucleotide sequence SEQ ID NO: 1240.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1852, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1246. In some embodiments, the antisense strand comprises a nucleotide sequence differing by no more than 4 nucleotides (for example, 1, 2, 3, or 4 nucleotides) from SEQ ID NO: 1852, and the sense strand comprises a nucleotide sequence differing by no more than 4 nucleotides (for example, 1, 2, 3, or 4 nucleotides) from SEQ ID NO: 1246. In some embodiments, the antisense strand comprises the nucleotide sequence SEQ ID NO: 1852, and the sense strand comprises the nucleotide sequence SEQ ID NO: 1246. In some embodiments, the antisense strand consists of the nucleotide sequence SEQ ID NO: 1852, and the sense strand consists of the nucleotide sequence SEQ ID NO: 1246.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1870, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1264. In some embodiments, the antisense strand comprises a nucleotide sequence differing by no more than 4 nucleotides (for example, 1, 2, 3, or 4 nucleotides) from SEQ ID NO: 1870, and the sense strand comprises a nucleotide sequence differing by no more than 4 nucleotides (for example, 1, 2, 3, or 4 nucleotides) from SEQ ID NO: 1264. In some embodiments, the antisense strand comprises the nucleotide sequence SEQ ID NO: 1870, and the sense strand comprises the nucleotide sequence SEQ ID NO: 1264. In some embodiments, the antisense strand consists of the nucleotide sequence SEQ ID NO: 1870, and the sense strand consists of the nucleotide sequence SEQ ID NO: 1264.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1876, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1270. In some embodiments, the antisense strand comprises a nucleotide sequence differing by no more than 4 nucleotides (for example, 1, 2, 3, or 4 nucleotides) from SEQ ID NO: 1876, and the sense strand comprises a nucleotide sequence differing by no more than 4 nucleotides (for example, 1, 2, 3, or 4 nucleotides) from SEQ ID NO: 1270. In some embodiments, the antisense strand comprises the nucleotide sequence SEQ ID NO: 1876, and the sense strand comprises the nucleotide sequence SEQ ID NO: 1270. In some embodiments, the antisense strand consists of the nucleotide sequence SEQ ID NO: 1876, and the sense strand consists of the nucleotide sequence SEQ ID NO: 1270.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1878, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1272. In some embodiments, the antisense strand comprises a nucleotide sequence differing by no more than 4 nucleotides (for example, 1, 2, 3, or 4 nucleotides) from SEQ ID NO: 1878, and the sense strand comprises a nucleotide sequence differing by no more than 4 nucleotides (for example, 1, 2, 3, or 4 nucleotides) from SEQ ID NO: 1272. In some embodiments, the antisense strand comprises the nucleotide sequence SEQ ID NO: 1878, and the sense strand comprises the nucleotide sequence SEQ ID NO: 1272. In some embodiments, the antisense strand consists of the nucleotide sequence SEQ ID NO: 1878, and the sense strand consists of the nucleotide sequence SEQ ID NO: 1272.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1879, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1273. In some embodiments, the antisense strand comprises a nucleotide sequence differing by no more than 4 nucleotides (for example, 1, 2, 3, or 4 nucleotides) from SEQ ID NO: 1879, and the sense strand comprises a nucleotide sequence differing by no more than 4 nucleotides (for example, 1, 2, 3, or 4 nucleotides) from SEQ ID NO: 1273. In some embodiments, the antisense strand comprises the nucleotide sequence SEQ ID NO: 1879, and the sense strand comprises the nucleotide sequence SEQ ID NO: 1273. In some embodiments, the antisense strand consists of the nucleotide sequence SEQ ID NO: 1879, and the sense strand consists of the nucleotide sequence SEQ ID NO: 1273.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1884, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1278. In some embodiments, the antisense strand comprises a nucleotide sequence differing by no more than 4 nucleotides (for example, 1, 2, 3, or 4 nucleotides) from SEQ ID NO: 1884, and the sense strand comprises a nucleotide sequence differing by no more than 4 nucleotides (for example, 1, 2, 3, or 4 nucleotides) from SEQ ID NO: 1278. In some embodiments, the antisense strand comprises the nucleotide sequence SEQ ID NO: 1884, and the sense strand comprises the nucleotide sequence SEQ ID NO: 1278. In some embodiments, the antisense strand consists of the nucleotide sequence SEQ ID NO: 1884, and the sense strand consists of the nucleotide sequence SEQ ID NO: 1278.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1886, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1280. In some embodiments, the antisense strand comprises a nucleotide sequence differing by no more than 4 nucleotides (for example, 1, 2, 3, or 4 nucleotides) from SEQ ID NO: 1886, and the sense strand comprises a nucleotide sequence differing by no more than 4 nucleotides (for example, 1, 2, 3, or 4 nucleotides) from SEQ ID NO: 1280. In some embodiments, the antisense strand comprises the nucleotide sequence SEQ ID NO: 1886, and the sense strand comprises the nucleotide sequence SEQ ID NO: 1280. In some embodiments, the antisense strand consists of the nucleotide sequence SEQ ID NO: 1886, and the sense strand consists of the nucleotide sequence SEQ ID NO: 1280.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1903, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1297. In some embodiments, the antisense strand comprises a nucleotide sequence differing by no more than 4 nucleotides (for example, 1, 2, 3, or 4 nucleotides) from SEQ ID NO: 1903, and the sense strand comprises a nucleotide sequence differing by no more than 4 nucleotides (for example, 1, 2, 3, or 4 nucleotides) from SEQ ID NO: 1297. In some embodiments, the antisense strand comprises the nucleotide sequence SEQ ID NO: 1903, and the sense strand comprises the nucleotide sequence SEQ ID NO: 1297. In some embodiments, the antisense strand consists of the nucleotide sequence SEQ ID NO: 1903, and the sense strand consists of the nucleotide sequence SEQ ID NO: 1297.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1904, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1298. In some embodiments, the antisense strand comprises a nucleotide sequence differing by no more than 4 nucleotides (for example, 1, 2, 3, or 4 nucleotides) from SEQ ID NO: 1904, and the sense strand comprises a nucleotide sequence differing by no more than 4 nucleotides (for example, 1, 2, 3, or 4 nucleotides) from SEQ ID NO: 1298. In some embodiments, the antisense strand comprises the nucleotide sequence SEQ ID NO: 1904, and the sense strand comprises the nucleotide sequence SEQ ID NO: 1298. In some embodiments, the antisense strand consists of the nucleotide sequence SEQ ID NO: 1904, and the sense strand consists of the nucleotide sequence SEQ ID NO: 1298.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1905, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1299. In some embodiments, the antisense strand comprises a nucleotide sequence differing by no more than 4 nucleotides (for example, 1, 2, 3, or 4 nucleotides) from SEQ ID NO: 1905, and the sense strand comprises a nucleotide sequence differing by no more than 4 nucleotides (for example, 1, 2, 3, or 4 nucleotides) from SEQ ID NO: 1299. In some embodiments, the antisense strand comprises the nucleotide sequence SEQ ID NO: 1905, and the sense strand comprises the nucleotide sequence SEQ ID NO: 1299. In some embodiments, the antisense strand consists of the nucleotide sequence SEQ ID NO: 1905, and the sense strand consists of the nucleotide sequence SEQ ID NO: 1299.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1919, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1313. In some embodiments, the antisense strand comprises a nucleotide sequence differing by no more than 4 nucleotides (for example, 1, 2, 3, or 4 nucleotides) from SEQ ID NO: 1919, and the sense strand comprises a nucleotide sequence differing by no more than 4 nucleotides (for example, 1, 2, 3, or 4 nucleotides) from SEQ ID NO: 1313. In some embodiments, the antisense strand comprises the nucleotide sequence SEQ ID NO: 1919, and the sense strand comprises the nucleotide sequence SEQ ID NO: 1313. In some embodiments, the antisense strand consists of the nucleotide sequence SEQ ID NO: 1919, and the sense strand consists of the nucleotide sequence SEQ ID NO: 1313.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1920, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1314. In some embodiments, the antisense strand comprises a nucleotide sequence differing by no more than 4 nucleotides (for example, 1, 2, 3, or 4 nucleotides) from SEQ ID NO: 1920, and the sense strand comprises a nucleotide sequence differing by no more than 4 nucleotides (for example, 1, 2, 3, or 4 nucleotides) from SEQ ID NO: 1314. In some embodiments, the antisense strand comprises the nucleotide sequence SEQ ID NO: 1920, and the sense strand comprises the nucleotide sequence SEQ ID NO: 1314. In some embodiments, the antisense strand consists of the nucleotide sequence SEQ ID NO: 1920, and the sense strand consists of the nucleotide sequence SEQ ID NO: 1314.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1933, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1327. In some embodiments, the antisense strand comprises a nucleotide sequence differing by no more than 4 nucleotides (for example, 1, 2, 3, or 4 nucleotides) from SEQ ID NO: 1933, and the sense strand comprises a nucleotide sequence differing by no more than 4 nucleotides (for example, 1, 2, 3, or 4 nucleotides) from SEQ ID NO: 1327. In some embodiments, the antisense strand comprises the nucleotide sequence SEQ ID NO: 1933, and the sense strand comprises the nucleotide sequence SEQ ID NO: 1327. In some embodiments, the antisense strand consists of the nucleotide sequence SEQ ID NO: 1933, and the sense strand consists of the nucleotide sequence SEQ ID NO: 1327.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1934, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1328. In some embodiments, the antisense strand comprises a nucleotide sequence differing by no more than 4 nucleotides (for example, 1, 2, 3, or 4 nucleotides) from SEQ ID NO: 1934, and the sense strand comprises a nucleotide sequence differing by no more than 4 nucleotides (for example, 1, 2, 3, or 4 nucleotides) from SEQ ID NO: 1328. In some embodiments, the antisense strand comprises the nucleotide sequence SEQ ID NO: 1934, and the sense strand comprises the nucleotide sequence SEQ ID NO: 1328. In some embodiments, the antisense strand consists of the nucleotide sequence SEQ ID NO: 1934, and the sense strand consists of the nucleotide sequence SEQ ID NO: 1328.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1968, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1362. In some embodiments, the antisense strand comprises a nucleotide sequence differing by no more than 4 nucleotides (for example, 1, 2, 3, or 4 nucleotides) from SEQ ID NO: 1968, and the sense strand comprises a nucleotide sequence differing by no more than 4 nucleotides (for example, 1, 2, 3, or 4 nucleotides) from SEQ ID NO: 1362. In some embodiments, the antisense strand comprises the nucleotide sequence SEQ ID NO: 1968, and the sense strand comprises the nucleotide sequence SEQ ID NO: 1362. In some embodiments, the antisense strand consists of the nucleotide sequence SEQ ID NO: 1968, and the sense strand consists of the nucleotide sequence SEQ ID NO: 1362.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1975, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1369. In some embodiments, the antisense strand comprises a nucleotide sequence differing by no more than 4 nucleotides (for example, 1, 2, 3, or 4 nucleotides) from SEQ ID NO: 1975, and the sense strand comprises a nucleotide sequence differing by no more than 4 nucleotides (for example, 1, 2, 3, or 4 nucleotides) from SEQ ID NO: 1369. In some embodiments, the antisense strand comprises the nucleotide sequence SEQ ID NO: 1975, and the sense strand comprises the nucleotide sequence SEQ ID NO: 1369. In some embodiments, the antisense strand consists of the nucleotide sequence SEQ ID NO: 1975, and the sense strand consists of the nucleotide sequence SEQ ID NO: 1369.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1982, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1376. In some embodiments, the antisense strand comprises a nucleotide sequence differing by no more than 4 nucleotides (for example, 1, 2, 3, or 4 nucleotides) from SEQ ID NO: 1982, and the sense strand comprises a nucleotide sequence differing by no more than 4 nucleotides (for example, 1, 2, 3, or 4 nucleotides) from SEQ ID NO: 1376. In some embodiments, the antisense strand comprises the nucleotide sequence SEQ ID NO: 1982, and the sense strand comprises the nucleotide sequence SEQ ID NO: 1376. In some embodiments, the antisense strand consists of the nucleotide sequence SEQ ID NO: 1982, and the sense strand consists of the nucleotide sequence SEQ ID NO: 1376.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1983, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1377. In some embodiments, the antisense strand comprises a nucleotide sequence differing by no more than 4 nucleotides (for example, 1, 2, 3, or 4 nucleotides) from SEQ ID NO: 1983, and the sense strand comprises a nucleotide sequence differing by no more than 4 nucleotides (for example, 1, 2, 3, or 4 nucleotides) from SEQ ID NO: 1377. In some embodiments, the antisense strand comprises the nucleotide sequence SEQ ID NO: 1983, and the sense strand comprises the nucleotide sequence SEQ ID NO: 1377. In some embodiments, the antisense strand consists of the nucleotide sequence SEQ ID NO: 1983, and the sense strand consists of the nucleotide sequence SEQ ID NO: 1377.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1984, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1378. In some embodiments, the antisense strand comprises a nucleotide sequence differing by no more than 4 nucleotides (for example, 1, 2, 3, or 4 nucleotides) from SEQ ID NO: 1984, and the sense strand comprises a nucleotide sequence differing by no more than 4 nucleotides (for example, 1, 2, 3, or 4 nucleotides) from SEQ ID NO: 1378. In some embodiments, the antisense strand comprises the nucleotide sequence SEQ ID NO: 1984, and the sense strand comprises the nucleotide sequence SEQ ID NO: 1378. In some embodiments, the antisense strand consists of the nucleotide sequence SEQ ID NO: 1984, and the sense strand consists of the nucleotide sequence SEQ ID NO: 1378.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1990, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1384. In some embodiments, the antisense strand comprises a nucleotide sequence differing by no more than 4 nucleotides (for example, 1, 2, 3, or 4 nucleotides) from SEQ ID NO: 1990, and the sense strand comprises a nucleotide sequence differing by no more than 4 nucleotides (for example, 1, 2, 3, or 4 nucleotides) from SEQ ID NO: 1384. In some embodiments, the antisense strand comprises the nucleotide sequence SEQ ID NO: 1990, and the sense strand comprises the nucleotide sequence SEQ ID NO: 1384. In some embodiments, the antisense strand consists of the nucleotide sequence SEQ ID NO: 1990, and the sense strand consists of the nucleotide sequence SEQ ID NO: 1384.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1998, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1392. In some embodiments, the antisense strand comprises a nucleotide sequence differing by no more than 4 nucleotides (for example, 1, 2, 3, or 4 nucleotides) from SEQ ID NO: 1998, and the sense strand comprises a nucleotide sequence differing by no more than 4 nucleotides (for example, 1, 2, 3, or 4 nucleotides) from SEQ ID NO: 1392. In some embodiments, the antisense strand comprises the nucleotide sequence SEQ ID NO: 1998, and the sense strand comprises the nucleotide sequence SEQ ID NO: 1392. In some embodiments, the antisense strand consists of the nucleotide sequence SEQ ID NO: 1998, and the sense strand consists of the nucleotide sequence SEQ ID NO: 1392.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1999, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1393. In some embodiments, the antisense strand comprises a nucleotide sequence differing by no more than 4 nucleotides (for example, 1, 2, 3, or 4 nucleotides) from SEQ ID NO: 1999, and the sense strand comprises a nucleotide sequence differing by no more than 4 nucleotides (for example, 1, 2, 3, or 4 nucleotides) from SEQ ID NO: 1393. In some embodiments, the antisense strand comprises the nucleotide sequence SEQ ID NO: 1999, and the sense strand comprises the nucleotide sequence SEQ ID NO: 1393. In some embodiments, the antisense strand consists of the nucleotide sequence SEQ ID NO: 1999, and the sense strand consists of the nucleotide sequence SEQ ID NO: 1393.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2005, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1399. In some embodiments, the antisense strand comprises a nucleotide sequence differing by no more than 4 nucleotides (for example, 1, 2, 3, or 4 nucleotides) from SEQ ID NO: 2005, and the sense strand comprises a nucleotide sequence differing by no more than 4 nucleotides (for example, 1, 2, 3, or 4 nucleotides) from SEQ ID NO: 1399. In some embodiments, the antisense strand comprises the nucleotide sequence SEQ ID NO: 2005, and the sense strand comprises the nucleotide sequence SEQ ID NO: 1399. In some embodiments, the antisense strand consists of the nucleotide sequence SEQ ID NO: 2005, and the sense strand consists of the nucleotide sequence SEQ ID NO: 1399.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2013, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1407. In some embodiments, the antisense strand comprises a nucleotide sequence differing by no more than 4 nucleotides (for example, 1, 2, 3, or 4 nucleotides) from SEQ ID NO: 2013, and the sense strand comprises a nucleotide sequence differing by no more than 4 nucleotides (for example, 1, 2, 3, or 4 nucleotides) from SEQ ID NO: 1407. In some embodiments, the antisense strand comprises the nucleotide sequence SEQ ID NO: 2013, and the sense strand comprises the nucleotide sequence SEQ ID NO: 1407. In some embodiments, the antisense strand consists of the nucleotide sequence SEQ ID NO: 2013, and the sense strand consists of the nucleotide sequence SEQ ID NO: 1407.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2014, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1408. In some embodiments, the antisense strand comprises a nucleotide sequence differing by no more than 4 nucleotides (for example, 1, 2, 3, or 4 nucleotides) from SEQ ID NO: 2014, and the sense strand comprises a nucleotide sequence differing by no more than 4 nucleotides (for example, 1, 2, 3, or 4 nucleotides) from SEQ ID NO: 1408. In some embodiments, the antisense strand comprises the nucleotide sequence SEQ ID NO: 2014, and the sense strand comprises the nucleotide sequence SEQ ID NO: 1408. In some embodiments, the antisense strand consists of the nucleotide sequence SEQ ID NO: 2014, and the sense strand consists of the nucleotide sequence SEQ ID NO: 1408.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2015, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1409. In some embodiments, the antisense strand comprises a nucleotide sequence differing by no more than 4 nucleotides (for example, 1, 2, 3, or 4 nucleotides) from SEQ ID NO: 2015, and the sense strand comprises a nucleotide sequence differing by no more than 4 nucleotides (for example, 1, 2, 3, or 4 nucleotides) from SEQ ID NO: 1409. In some embodiments, the antisense strand comprises the nucleotide sequence SEQ ID NO: 2015, and the sense strand comprises the nucleotide sequence SEQ ID NO: 1409. In some embodiments, the antisense strand consists of the nucleotide sequence SEQ ID NO: 2015, and the sense strand consists of the nucleotide sequence SEQ ID NO: 1409.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2044, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1438. In some embodiments, the antisense strand comprises a nucleotide sequence differing by no more than 4 nucleotides (for example, 1, 2, 3, or 4 nucleotides) from SEQ ID NO: 2044, and the sense strand comprises a nucleotide sequence differing by no more than 4 nucleotides (for example, 1, 2, 3, or 4 nucleotides) from SEQ ID NO: 1438. In some embodiments, the antisense strand comprises the nucleotide sequence SEQ ID NO: 2044, and the sense strand comprises the nucleotide sequence SEQ ID NO: 1438. In some embodiments, the antisense strand consists of the nucleotide sequence SEQ ID NO: 2044, and the sense strand consists of the nucleotide sequence SEQ ID NO: 1438.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2049, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1443. In some embodiments, the antisense strand comprises a nucleotide sequence differing by no more than 4 nucleotides (for example, 1, 2, 3, or 4 nucleotides) from SEQ ID NO: 2049, and the sense strand comprises a nucleotide sequence differing by no more than 4 nucleotides (for example, 1, 2, 3, or 4 nucleotides) from SEQ ID NO: 1443. In some embodiments, the antisense strand comprises the nucleotide sequence SEQ ID NO: 2049, and the sense strand comprises the nucleotide sequence SEQ ID NO: 1443. In some embodiments, the antisense strand consists of the nucleotide sequence SEQ ID NO: 2049, and the sense strand consists of the nucleotide sequence SEQ ID NO: 1443.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2050, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1444. In some embodiments, the antisense strand comprises a nucleotide sequence differing by no more than 4 nucleotides (for example, 1, 2, 3, or 4 nucleotides) from SEQ ID NO: 2050, and the sense strand comprises a nucleotide sequence differing by no more than 4 nucleotides (for example, 1, 2, 3, or 4 nucleotides) from SEQ ID NO: 1444. In some embodiments, the antisense strand comprises the nucleotide sequence SEQ ID NO: 2050, and the sense strand comprises the nucleotide sequence SEQ ID NO: 1444. In some embodiments, the antisense strand consists of the nucleotide sequence SEQ ID NO: 2050, and the sense strand consists of the nucleotide sequence SEQ ID NO: 1444.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2082, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1476. In some embodiments, the antisense strand comprises a nucleotide sequence differing by no more than 4 nucleotides (for example, 1, 2, 3, or 4 nucleotides) from SEQ ID NO: 2082, and the sense strand comprises a nucleotide sequence differing by no more than 4 nucleotides (for example, 1, 2, 3, or 4 nucleotides) from SEQ ID NO: 1476. In some embodiments, the antisense strand comprises the nucleotide sequence SEQ ID NO: 2082, and the sense strand comprises the nucleotide sequence SEQ ID NO: 1476. In some embodiments, the antisense strand consists of the nucleotide sequence SEQ ID NO: 2082, and the sense strand consists of the nucleotide sequence SEQ ID NO: 1476.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2083, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1477. In some embodiments, the antisense strand comprises a nucleotide sequence differing by no more than 4 nucleotides (for example, 1, 2, 3, or 4 nucleotides) from SEQ ID NO: 2083, and the sense strand comprises a nucleotide sequence differing by no more than 4 nucleotides (for example, 1, 2, 3, or 4 nucleotides) from SEQ ID NO: 1477. In some embodiments, the antisense strand comprises the nucleotide sequence SEQ ID NO: 2083, and the sense strand comprises the nucleotide sequence SEQ ID NO: 1477. In some embodiments, the antisense strand consists of the nucleotide sequence SEQ ID NO: 2083, and the sense strand consists of the nucleotide sequence SEQ ID NO: 1477.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2090, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1484. In some embodiments, the antisense strand comprises a nucleotide sequence differing by no more than 4 nucleotides (for example, 1, 2, 3, or 4 nucleotides) from SEQ ID NO: 2090, and the sense strand comprises a nucleotide sequence differing by no more than 4 nucleotides (for example, 1, 2, 3, or 4 nucleotides) from SEQ ID NO: 1484. In some embodiments, the antisense strand comprises the nucleotide sequence SEQ ID NO: 2090, and the sense strand comprises the nucleotide sequence SEQ ID NO: 1484. In some embodiments, the antisense strand consists of the nucleotide sequence SEQ ID NO: 2090, and the sense strand consists of the nucleotide sequence SEQ ID NO: 1484.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2091, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1485. In some embodiments, the antisense strand comprises a nucleotide sequence differing by no more than 4 nucleotides (for example, 1, 2, 3, or 4 nucleotides) from SEQ ID NO: 2091, and the sense strand comprises a nucleotide sequence differing by no more than 4 nucleotides (for example, 1, 2, 3, or 4 nucleotides) from SEQ ID NO: 1485. In some embodiments, the antisense strand comprises the nucleotide sequence SEQ ID NO: 2091, and the sense strand comprises the nucleotide sequence SEQ ID NO: 1485. In some embodiments, the antisense strand consists of the nucleotide sequence SEQ ID NO: 2091, and the sense strand consists of the nucleotide sequence SEQ ID NO: 1485.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2092, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1486. In some embodiments, the antisense strand comprises a nucleotide sequence differing by no more than 4 nucleotides (for example, 1, 2, 3, or 4 nucleotides) from SEQ ID NO: 2092, and the sense strand comprises a nucleotide sequence differing by no more than 4 nucleotides (for example, 1, 2, 3, or 4 nucleotides) from SEQ ID NO: 1486. In some embodiments, the antisense strand comprises the nucleotide sequence SEQ ID NO: 2092, and the sense strand comprises the nucleotide sequence SEQ ID NO: 1486. In some embodiments, the antisense strand consists of the nucleotide sequence SEQ ID NO: 2092, and the sense strand consists of the nucleotide sequence SEQ ID NO: 1486.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2105, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1499. In some embodiments, the antisense strand comprises a nucleotide sequence differing by no more than 4 nucleotides (for example, 1, 2, 3, or 4 nucleotides) from SEQ ID NO: 2105, and the sense strand comprises a nucleotide sequence differing by no more than 4 nucleotides (for example, 1, 2, 3, or 4 nucleotides) from SEQ ID NO: 1499. In some embodiments, the antisense strand comprises the nucleotide sequence SEQ ID NO: 2105, and the sense strand comprises the nucleotide sequence SEQ ID NO: 1499. In some embodiments, the antisense strand consists of the nucleotide sequence SEQ ID NO: 2105, and the sense strand consists of the nucleotide sequence SEQ ID NO: 1499.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2113, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1507. In some embodiments, the antisense strand comprises a nucleotide sequence differing by no more than 4 nucleotides (for example, 1, 2, 3, or 4 nucleotides) from SEQ ID NO: 2113, and the sense strand comprises a nucleotide sequence differing by no more than 4 nucleotides (for example, 1, 2, 3, or 4 nucleotides) from SEQ ID NO: 1507. In some embodiments, the antisense strand comprises the nucleotide sequence SEQ ID NO: 2113, and the sense strand comprises the nucleotide sequence SEQ ID NO: 1507. In some embodiments, the antisense strand consists of the nucleotide sequence SEQ ID NO: 2113, and the sense strand consists of the nucleotide sequence SEQ ID NO: 1507.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2114, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1508. In some embodiments, the antisense strand comprises a nucleotide sequence differing by no more than 4 nucleotides (for example, 1, 2, 3, or 4 nucleotides) from SEQ ID NO: 2114, and the sense strand comprises a nucleotide sequence differing by no more than 4 nucleotides (for example, 1, 2, 3, or 4 nucleotides) from SEQ ID NO: 1508. In some embodiments, the antisense strand comprises the nucleotide sequence SEQ ID NO: 2114, and the sense strand comprises the nucleotide sequence SEQ ID NO: 1508. In some embodiments, the antisense strand consists of the nucleotide sequence SEQ ID NO: 2114, and the sense strand consists of the nucleotide sequence SEQ ID NO: 1508.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2115, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1509. In some embodiments, the antisense strand comprises a nucleotide sequence differing by no more than 4 nucleotides (for example, 1, 2, 3, or 4 nucleotides) from SEQ ID NO: 2115, and the sense strand comprises a nucleotide sequence differing by no more than 4 nucleotides (for example, 1, 2, 3, or 4 nucleotides) from SEQ ID NO: 1509. In some embodiments, the antisense strand comprises the nucleotide sequence SEQ ID NO: 2115, and the sense strand comprises the nucleotide sequence SEQ ID NO: 1509. In some embodiments, the antisense strand consists of the nucleotide sequence SEQ ID NO: 2115, and the sense strand consists of the nucleotide sequence SEQ ID NO: 1509.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2132, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1526. In some embodiments, the antisense strand comprises a nucleotide sequence differing by no more than 4 nucleotides (for example, 1, 2, 3, or 4 nucleotides) from SEQ ID NO: 2132, and the sense strand comprises a nucleotide sequence differing by no more than 4 nucleotides (for example, 1, 2, 3, or 4 nucleotides) from SEQ ID NO: 1526. In some embodiments, the antisense strand comprises the nucleotide sequence SEQ ID NO: 2132, and the sense strand comprises the nucleotide sequence SEQ ID NO: 1526. In some embodiments, the antisense strand consists of the nucleotide sequence SEQ ID NO: 2132, and the sense strand consists of the nucleotide sequence SEQ ID NO: 1526.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2134, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1528. In some embodiments, the antisense strand comprises a nucleotide sequence differing by no more than 4 nucleotides (for example, 1, 2, 3, or 4 nucleotides) from SEQ ID NO: 2134, and the sense strand comprises a nucleotide sequence differing by no more than 4 nucleotides (for example, 1, 2, 3, or 4 nucleotides) from SEQ ID NO: 1528. In some embodiments, the antisense strand comprises the nucleotide sequence SEQ ID NO: 2134, and the sense strand comprises the nucleotide sequence SEQ ID NO: 1528. In some embodiments, the antisense strand consists of the nucleotide sequence SEQ ID NO: 2134, and the sense strand consists of the nucleotide sequence SEQ ID NO: 1528.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2143, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1537. In some embodiments, the antisense strand comprises a nucleotide sequence differing by no more than 4 nucleotides (for example, 1, 2, 3, or 4 nucleotides) from SEQ ID NO: 2143, and the sense strand comprises a nucleotide sequence differing by no more than 4 nucleotides (for example, 1, 2, 3, or 4 nucleotides) from SEQ ID NO: 1537. In some embodiments, the antisense strand comprises the nucleotide sequence SEQ ID NO: 2143, and the sense strand comprises the nucleotide sequence SEQ ID NO: 1537. In some embodiments, the antisense strand consists of the nucleotide sequence SEQ ID NO: 2143, and the sense strand consists of the nucleotide sequence SEQ ID NO: 1537.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2167, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1561. In some embodiments, the antisense strand comprises a nucleotide sequence differing by no more than 4 nucleotides (for example, 1, 2, 3, or 4 nucleotides) from SEQ ID NO: 2167, and the sense strand comprises a nucleotide sequence differing by no more than 4 nucleotides (for example, 1, 2, 3, or 4 nucleotides) from SEQ ID NO: 1561. In some embodiments, the antisense strand comprises the nucleotide sequence SEQ ID NO: 2167, and the sense strand comprises the nucleotide sequence SEQ ID NO: 1561. In some embodiments, the antisense strand consists of the nucleotide sequence SEQ ID NO: 2167, and the sense strand consists of the nucleotide sequence SEQ ID NO: 1561.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2186, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1580. In some embodiments, the antisense strand comprises a nucleotide sequence differing by no more than 4 nucleotides (for example, 1, 2, 3, or 4 nucleotides) from SEQ ID NO: 2186, and the sense strand comprises a nucleotide sequence differing by no more than 4 nucleotides (for example, 1, 2, 3, or 4 nucleotides) from SEQ ID NO: 1580. In some embodiments, the antisense strand comprises the nucleotide sequence SEQ ID NO: 2186, and the sense strand comprises the nucleotide sequence SEQ ID NO: 1580. In some embodiments, the antisense strand consists of the nucleotide sequence SEQ ID NO: 2186, and the sense strand consists of the nucleotide sequence SEQ ID NO: 1580.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2187, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1581. In some embodiments, the antisense strand comprises a nucleotide sequence differing by no more than 4 nucleotides (for example, 1, 2, 3, or 4 nucleotides) from SEQ ID NO: 2187, and the sense strand comprises a nucleotide sequence differing by no more than 4 nucleotides (for example, 1, 2, 3, or 4 nucleotides) from SEQ ID NO: 1581. In some embodiments, the antisense strand comprises the nucleotide sequence SEQ ID NO: 2187, and the sense strand comprises the nucleotide sequence SEQ ID NO: 1581. In some embodiments, the antisense strand consists of the nucleotide sequence SEQ ID NO: 2187, and the sense strand consists of the nucleotide sequence SEQ ID NO: 1581.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2190, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1584. In some embodiments, the antisense strand comprises a nucleotide sequence differing by no more than 4 nucleotides (for example, 1, 2, 3, or 4 nucleotides) from SEQ ID NO: 2190, and the sense strand comprises a nucleotide sequence differing by no more than 4 nucleotides (for example, 1, 2, 3, or 4 nucleotides) from SEQ ID NO: 1584. In some embodiments, the antisense strand comprises the nucleotide sequence SEQ ID NO: 2190, and the sense strand comprises the nucleotide sequence SEQ ID NO: 1584. In some embodiments, the antisense strand consists of the nucleotide sequence SEQ ID NO: 2190, and the sense strand consists of the nucleotide sequence SEQ ID NO: 1584.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2192, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1586. In some embodiments, the antisense strand comprises a nucleotide sequence differing by no more than 4 nucleotides (for example, 1, 2, 3, or 4 nucleotides) from SEQ ID NO: 2192, and the sense strand comprises a nucleotide sequence differing by no more than 4 nucleotides (for example, 1, 2, 3, or 4 nucleotides) from SEQ ID NO: 1586. In some embodiments, the antisense strand comprises the nucleotide sequence SEQ ID NO: 2192, and the sense strand comprises the nucleotide sequence SEQ ID NO: 1586. In some embodiments, the antisense strand consists of the nucleotide sequence SEQ ID NO: 2192, and the sense strand consists of the nucleotide sequence SEQ ID NO: 1586.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2198, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1592. In some embodiments, the antisense strand comprises a nucleotide sequence differing by no more than 4 nucleotides (for example, 1, 2, 3, or 4 nucleotides) from SEQ ID NO: 2198, and the sense strand comprises a nucleotide sequence differing by no more than 4 nucleotides (for example, 1, 2, 3, or 4 nucleotides) from SEQ ID NO: 1592. In some embodiments, the antisense strand comprises the nucleotide sequence SEQ ID NO: 2198, and the sense strand comprises the nucleotide sequence SEQ ID NO: 1592. In some embodiments, the antisense strand consists of the nucleotide sequence SEQ ID NO: 2198, and the sense strand consists of the nucleotide sequence SEQ ID NO: 1592.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2204, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1598. In some embodiments, the antisense strand comprises a nucleotide sequence differing by no more than 4 nucleotides (for example, 1, 2, 3, or 4 nucleotides) from SEQ ID NO: 2204, and the sense strand comprises a nucleotide sequence differing by no more than 4 nucleotides (for example, 1, 2, 3, or 4 nucleotides) from SEQ ID NO: 1598. In some embodiments, the antisense strand comprises the nucleotide sequence SEQ ID NO: 2204, and the sense strand comprises the nucleotide sequence SEQ ID NO: 1598. In some embodiments, the antisense strand consists of the nucleotide sequence SEQ ID NO: 2204, and the sense strand consists of the nucleotide sequence SEQ ID NO: 1598.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2205, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1599. In some embodiments, the antisense strand comprises a nucleotide sequence differing by no more than 4 nucleotides (for example, 1, 2, 3, or 4 nucleotides) from SEQ ID NO: 2205, and the sense strand comprises a nucleotide sequence differing by no more than 4 nucleotides (for example, 1, 2, 3, or 4 nucleotides) from SEQ ID NO: 1599. In some embodiments, the antisense strand comprises the nucleotide sequence SEQ ID NO: 2205, and the sense strand comprises the nucleotide sequence SEQ ID NO: 1599. In some embodiments, the antisense strand consists of the nucleotide sequence SEQ ID NO: 2205, and the sense strand consists of the nucleotide sequence SEQ ID NO: 1599.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2209, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1603. In some embodiments, the antisense strand comprises a nucleotide sequence differing by no more than 4 nucleotides (for example, 1, 2, 3, or 4 nucleotides) from SEQ ID NO: 2209, and the sense strand comprises a nucleotide sequence differing by no more than 4 nucleotides (for example, 1, 2, 3, or 4 nucleotides) from SEQ ID NO: 1603. In some embodiments, the antisense strand comprises the nucleotide sequence SEQ ID NO: 2209, and the sense strand comprises the nucleotide sequence SEQ ID NO: 1603. In some embodiments, the antisense strand consists of the nucleotide sequence SEQ ID NO: 2209, and the sense strand consists of the nucleotide sequence SEQ ID NO: 1603.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2210, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1604. In some embodiments, the antisense strand comprises a nucleotide sequence differing by no more than 4 nucleotides (for example, 1, 2, 3, or 4 nucleotides) from SEQ ID NO: 2210, and the sense strand comprises a nucleotide sequence differing by no more than 4 nucleotides (for example, 1, 2, 3, or 4 nucleotides) from SEQ ID NO: 1604. In some embodiments, the antisense strand comprises the nucleotide sequence SEQ ID NO: 2210, and the sense strand comprises the nucleotide sequence SEQ ID NO: 1604. In some embodiments, the antisense strand consists of the nucleotide sequence SEQ ID NO: 2210, and the sense strand consists of the nucleotide sequence SEQ ID NO: 1604.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2216, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1610. In some embodiments, the antisense strand comprises a nucleotide sequence differing by no more than 4 nucleotides (for example, 1, 2, 3, or 4 nucleotides) from SEQ ID NO: 2216, and the sense strand comprises a nucleotide sequence differing by no more than 4 nucleotides (for example, 1, 2, 3, or 4 nucleotides) from SEQ ID NO: 1610. In some embodiments, the antisense strand comprises the nucleotide sequence SEQ ID NO: 2216, and the sense strand comprises the nucleotide sequence SEQ ID NO: 1610. In some embodiments, the antisense strand consists of the nucleotide sequence SEQ ID NO: 2216, and the sense strand consists of the nucleotide sequence SEQ ID NO: 1610.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2217, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1611. In some embodiments, the antisense strand comprises a nucleotide sequence differing by no more than 4 nucleotides (for example, 1, 2, 3, or 4 nucleotides) from SEQ ID NO: 2217, and the sense strand comprises a nucleotide sequence differing by no more than 4 nucleotides (for example, 1, 2, 3, or 4 nucleotides) from SEQ ID NO: 1611. In some embodiments, the antisense strand comprises the nucleotide sequence SEQ ID NO: 2217, and the sense strand comprises the nucleotide sequence SEQ ID NO: 1611. In some embodiments, the antisense strand consists of the nucleotide sequence SEQ ID NO: 2217, and the sense strand consists of the nucleotide sequence SEQ ID NO: 1611.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2218, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1612. In some embodiments, the antisense strand comprises a nucleotide sequence differing by no more than 4 nucleotides (for example, 1, 2, 3, or 4 nucleotides) from SEQ ID NO: 2218, and the sense strand comprises a nucleotide sequence differing by no more than 4 nucleotides (for example, 1, 2, 3, or 4 nucleotides) from SEQ ID NO: 1612. In some embodiments, the antisense strand comprises the nucleotide sequence SEQ ID NO: 2218, and the sense strand comprises the nucleotide sequence SEQ ID NO: 1612. In some embodiments, the antisense strand consists of the nucleotide sequence SEQ ID NO: 2218, and the sense strand consists of the nucleotide sequence SEQ ID NO: 1612.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2232, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1626. In some embodiments, the antisense strand comprises a nucleotide sequence differing by no more than 4 nucleotides (for example, 1, 2, 3, or 4 nucleotides) from SEQ ID NO: 2232, and the sense strand comprises a nucleotide sequence differing by no more than 4 nucleotides (for example, 1, 2, 3, or 4 nucleotides) from SEQ ID NO: 1626. In some embodiments, the antisense strand comprises the nucleotide sequence SEQ ID NO: 2232, and the sense strand comprises the nucleotide sequence SEQ ID NO: 1626. In some embodiments, the antisense strand consists of the nucleotide sequence SEQ ID NO: 2232, and the sense strand consists of the nucleotide sequence SEQ ID NO: 1626.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2235, and the sense strand comprises a nucleotide sequence comprising at least 15 more than 4 nucleotides (for example, 1, 2, 3, or 4 nucleotides) from SEQ ID NO: 1629. In some embodiments, the antisense strand comprises a nucleotide sequence differing by no more than 4 nucleotides (for example, 1, 2, 3, or 4 nucleotides) from SEQ ID NO: 2235, and the sense strand comprises a nucleotide sequence differing by no more than 4 nucleotides (for example, 1, 2, 3, or 4 nucleotides) from SEQ ID NO: 1629. In some embodiments, the antisense strand comprises the nucleotide sequence SEQ ID NO: 2235, and the sense strand comprises the nucleotide sequence SEQ ID NO: 1629. In some embodiments, the antisense strand consists of the nucleotide sequence SEQ ID NO: 2235, and the sense strand consists of the nucleotide sequence SEQ ID NO: 1629.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2236, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1630. In some embodiments, the antisense strand comprises a nucleotide sequence differing by no more than 4 nucleotides (for example, 1, 2, 3, or 4 nucleotides) from SEQ ID NO: 2236, and the sense strand comprises a nucleotide sequence differing by no more than 4 nucleotides (for example, 1, 2, 3, or 4 nucleotides) from SEQ ID NO: 1630. In some embodiments, the antisense strand comprises the nucleotide sequence SEQ ID NO: 2236, and the sense strand comprises the nucleotide sequence SEQ ID NO: 1630. In some embodiments, the antisense strand consists of the nucleotide sequence SEQ ID NO: 2236, and the sense strand consists of the nucleotide sequence SEQ ID NO: 1630.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2251, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1645. In some embodiments, the antisense strand comprises a nucleotide sequence differing by no more than 4 nucleotides (for example, 1, 2, 3, or 4 nucleotides) from SEQ ID NO: 2251, and the sense strand comprises a nucleotide sequence differing by no more than 4 nucleotides (for example, 1, 2, 3, or 4 nucleotides) from SEQ ID NO: 1645. In some embodiments, the antisense strand comprises the nucleotide sequence SEQ ID NO: 2251, and the sense strand comprises the nucleotide sequence SEQ ID NO: 1645. In some embodiments, the antisense strand consists of the nucleotide sequence SEQ ID NO: 2251, and the sense strand consists of the nucleotide sequence SEQ ID NO: 1645.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2260, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1654. In some embodiments, the antisense strand comprises a nucleotide sequence differing by no more than 4 nucleotides (for example, 1, 2, 3, or 4 nucleotides) from SEQ ID NO: 2260, and the sense strand comprises a nucleotide sequence differing by no more than 4 nucleotides (for example, 1, 2, 3, or 4 nucleotides) from SEQ ID NO: 1654. In some embodiments, the antisense strand comprises the nucleotide sequence SEQ ID NO: 2260, and the sense strand comprises the nucleotide sequence SEQ ID NO: 1654. In some embodiments, the antisense strand consists of the nucleotide sequence SEQ ID NO: 2260, and the sense strand consists of the nucleotide sequence SEQ ID NO: 1654.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2261, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1655. In some embodiments, the antisense strand comprises a nucleotide sequence differing by no more than 4 nucleotides (for example, 1, 2, 3, or 4 nucleotides) from SEQ ID NO: 2261, and the sense strand comprises a nucleotide sequence differing by no more than 4 nucleotides (for example, 1, 2, 3, or 4 nucleotides) from SEQ ID NO: 1655. In some embodiments, the antisense strand comprises the nucleotide sequence SEQ ID NO: 2261, and the sense strand comprises the nucleotide sequence SEQ ID NO: 1655. In some embodiments, the antisense strand consists of the nucleotide sequence SEQ ID NO: 2261, and the sense strand consists of the nucleotide sequence SEQ ID NO: 1655.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2267, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1661. In some embodiments, the antisense strand comprises a nucleotide sequence differing by no more than 4 nucleotides (for example, 1, 2, 3, or 4 nucleotides) from SEQ ID NO: 2267, and the sense strand comprises a nucleotide sequence differing by no more than 4 nucleotides (for example, 1, 2, 3, or 4 nucleotides) from SEQ ID NO: 1661. In some embodiments, the antisense strand comprises the nucleotide sequence SEQ ID NO: 2267, and the sense strand comprises the nucleotide sequence SEQ ID NO: 1661. In some embodiments, the antisense strand consists of the nucleotide sequence SEQ ID NO: 2267, and the sense strand consists of the nucleotide sequence SEQ ID NO: 1661.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2268, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1662. In some embodiments, the antisense strand comprises a nucleotide sequence differing by no more than 4 nucleotides (for example, 1, 2, 3, or 4 nucleotides) from SEQ ID NO: 2268, and the sense strand comprises a nucleotide sequence differing by no more than 4 nucleotides (for example, 1, 2, 3, or 4 nucleotides) from SEQ ID NO: 1662. In some embodiments, the antisense strand comprises the nucleotide sequence SEQ ID NO: 2268, and the sense strand comprises the nucleotide sequence SEQ ID NO: 1662. In some embodiments, the antisense strand consists of the nucleotide sequence SEQ ID NO: 2268, and the sense strand consists of the nucleotide sequence SEQ ID NO: 1662.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2269, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1663. In some embodiments, the antisense strand comprises a nucleotide sequence differing by no more than 4 nucleotides (for example, 1, 2, 3, or 4 nucleotides) from SEQ ID NO: 2269, and the sense strand comprises a nucleotide sequence differing by no more than 4 nucleotides (for example, 1, 2, 3, or 4 nucleotides) from SEQ ID NO: 1663. In some embodiments, the antisense strand comprises the nucleotide sequence SEQ ID NO: 2269, and the sense strand comprises the nucleotide sequence SEQ ID NO: 1663. In some embodiments, the antisense strand consists of the nucleotide sequence SEQ ID NO: 2269, and the sense strand consists of the nucleotide sequence SEQ ID NO: 1663.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2270, and the sense strand comprises a nucleotide sequence comprising at least 15 more than 4 nucleotides (for example, 1, 2, 3, or 4 nucleotides) from SEQ ID NO: 1664. In some embodiments, the antisense strand comprises a nucleotide sequence differing by no more than 4 nucleotides (for example, 1, 2, 3, or 4 nucleotides) from SEQ ID NO: 2270, and the sense strand comprises a nucleotide sequence differing by no more than 4 nucleotides (for example, 1, 2, 3, or 4 nucleotides) from SEQ ID NO: 1664. In some embodiments, the antisense strand comprises the nucleotide sequence SEQ ID NO: 2270, and the sense strand comprises the nucleotide sequence SEQ ID NO: 1664. In some embodiments, the antisense strand consists of the nucleotide sequence SEQ ID NO: 2270, and the sense strand consists of the nucleotide sequence SEQ ID NO: 1664.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2271, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1665. In some embodiments, the antisense strand comprises a nucleotide sequence differing by no more than 4 nucleotides (for example, 1, 2, 3, or 4 nucleotides) from SEQ ID NO: 2271, and the sense strand comprises a nucleotide sequence differing by no more than 4 nucleotides (for example, 1, 2, 3, or 4 nucleotides) from SEQ ID NO: 1665. In some embodiments, the antisense strand comprises the nucleotide sequence SEQ ID NO: 2271, and the sense strand comprises the nucleotide sequence SEQ ID NO: 1665. In some embodiments, the antisense strand consists of the nucleotide sequence SEQ ID NO: 2271, and the sense strand consists of the nucleotide sequence SEQ ID NO: 1665.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2276, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1670. In some embodiments, the antisense strand comprises a nucleotide sequence differing by no more than 4 nucleotides (for example, 1, 2, 3, or 4 nucleotides) from SEQ ID NO: 2276, and the sense strand comprises a nucleotide sequence differing by no more than 4 nucleotides (for example, 1, 2, 3, or 4 nucleotides) from SEQ ID NO: 1670. In some embodiments, the antisense strand comprises the nucleotide sequence SEQ ID NO: 2276, and the sense strand comprises the nucleotide sequence SEQ ID NO: 1670. In some embodiments, the antisense strand consists of the nucleotide sequence SEQ ID NO: 2276, and the sense strand consists of the nucleotide sequence SEQ ID NO: 1670.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2277, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1671. In some embodiments, the antisense strand comprises a nucleotide sequence differing by no more than 4 nucleotides (for example, 1, 2, 3, or 4 nucleotides) from SEQ ID NO: 2277, and the sense strand comprises a nucleotide sequence differing by no more than 4 nucleotides (for example, 1, 2, 3, or 4 nucleotides) from SEQ ID NO: 1671. In some embodiments, the antisense strand comprises the nucleotide sequence SEQ ID NO: 2277, and the sense strand comprises the nucleotide sequence SEQ ID NO: 1671. In some embodiments, the antisense strand consists of the nucleotide sequence SEQ ID NO: 2277, and the sense strand consists of the nucleotide sequence SEQ ID NO: 1671.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2278, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1672. In some embodiments, the antisense strand comprises a nucleotide sequence differing by no more than 4 nucleotides (for example, 1, 2, 3, or 4 nucleotides) from SEQ ID NO: 2278, and the sense strand comprises a nucleotide sequence differing by no more than 4 nucleotides (for example, 1, 2, 3, or 4 nucleotides) from SEQ ID NO: 1672. In some embodiments, the antisense strand comprises the nucleotide sequence SEQ ID NO: 2278, and the sense strand comprises the nucleotide sequence SEQ ID NO: 1672. In some embodiments, the antisense strand consists of the nucleotide sequence SEQ ID NO: 2278, and the sense strand consists of the nucleotide sequence SEQ ID NO: 1672.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2279, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1673. In some embodiments, the antisense strand comprises a nucleotide sequence differing by no more than 4 nucleotides (for example, 1, 2, 3, or 4 nucleotides) from SEQ ID NO: 2279, and the sense strand comprises a nucleotide sequence differing by no more than 4 nucleotides (for example, 1, 2, 3, or 4 nucleotides) from SEQ ID NO: 1673. In some embodiments, the antisense strand comprises the nucleotide sequence SEQ ID NO: 2279, and the sense strand comprises the nucleotide sequence SEQ ID NO: 1673. In some embodiments, the antisense strand consists of the nucleotide sequence SEQ ID NO: 2279, and the sense strand consists of the nucleotide sequence SEQ ID NO: 1673.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2280, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1674. In some embodiments, the antisense strand comprises a nucleotide sequence differing by no more than 4 nucleotides (for example, 1, 2, 3, or 4 nucleotides) from SEQ ID NO: 2280, and the sense strand comprises a nucleotide sequence differing by no more than 4 nucleotides (for example, 1, 2, 3, or 4 nucleotides) from SEQ ID NO: 1674. In some embodiments, the antisense strand comprises the nucleotide sequence SEQ ID NO: 2280, and the sense strand comprises the nucleotide sequence SEQ ID NO: 1674. In some embodiments, the antisense strand consists of the nucleotide sequence SEQ ID NO: 2280, and the sense strand consists of the nucleotide sequence SEQ ID NO: 1674.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2281, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1675. In some embodiments, the antisense strand comprises a nucleotide sequence differing by no more than 4 nucleotides (for example, 1, 2, 3, or 4 nucleotides) from SEQ ID NO: 2281, and the sense strand comprises a nucleotide sequence differing by no more than 4 nucleotides (for example, 1, 2, 3, or 4 nucleotides) from SEQ ID NO: 1675. In some embodiments, the antisense strand comprises the nucleotide sequence SEQ ID NO: 2281, and the sense strand comprises the nucleotide sequence SEQ ID NO: 1675. In some embodiments, the antisense strand consists of the nucleotide sequence SEQ ID NO: 2281, and the sense strand consists of the nucleotide sequence SEQ ID NO: 1675.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2283, and the sense strand comprises a nucleotide sequence comprising at least 15 more than 4 nucleotides (for example, 1, 2, 3, or 4 nucleotides) from SEQ ID NO: 1677. In some embodiments, the antisense strand comprises a nucleotide sequence differing by no more than 4 nucleotides (for example, 1, 2, 3, or 4 nucleotides) from SEQ ID NO: 2283, and the sense strand comprises a nucleotide sequence differing by no more than 4 nucleotides (for example, 1, 2, 3, or 4 nucleotides) from SEQ ID NO: 1677. In some embodiments, the antisense strand comprises the nucleotide sequence SEQ ID NO: 2283, and the sense strand comprises the nucleotide sequence SEQ ID NO: 1677. In some embodiments, the antisense strand consists of the nucleotide sequence SEQ ID NO: 2283, and the sense strand consists of the nucleotide sequence SEQ ID NO: 1677.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2284, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1678. In some embodiments, the antisense strand comprises a nucleotide sequence differing by no more than 4 nucleotides (for example, 1, 2, 3, or 4 nucleotides) from SEQ ID NO: 2284, and the sense strand comprises a nucleotide sequence differing by no more than 4 nucleotides (for example, 1, 2, 3, or 4 nucleotides) from SEQ ID NO: 1678. In some embodiments, the antisense strand comprises the nucleotide sequence SEQ ID NO: 2284, and the sense strand comprises the nucleotide sequence SEQ ID NO: 1678. In some embodiments, the antisense strand consists of the nucleotide sequence SEQ ID NO: 2284, and the sense strand consists of the nucleotide sequence SEQ ID NO: 1678.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2292, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1686. In some embodiments, the antisense strand comprises a nucleotide sequence differing by no more than 4 nucleotides (for example, 1, 2, 3, or 4 nucleotides) from SEQ ID NO: 2292, and the sense strand comprises a nucleotide sequence differing by no more than 4 nucleotides (for example, 1, 2, 3, or 4 nucleotides) from SEQ ID NO: 1686. In some embodiments, the antisense strand comprises the nucleotide sequence SEQ ID NO: 2292, and the sense strand comprises the nucleotide sequence SEQ ID NO: 1686. In some embodiments, the antisense strand consists of the nucleotide sequence SEQ ID NO: 2292, and the sense strand consists of the nucleotide sequence SEQ ID NO: 1686.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2293, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1687. In some embodiments, the antisense strand comprises a nucleotide sequence differing by no more than 4 nucleotides (for example, 1, 2, 3, or 4 nucleotides) from SEQ ID NO: 2293, and the sense strand comprises a nucleotide sequence differing by no more than 4 nucleotides (for example, 1, 2, 3, or 4 nucleotides) from SEQ ID NO: 1687. In some embodiments, the antisense strand comprises the nucleotide sequence SEQ ID NO: 2293, and the sense strand comprises the nucleotide sequence SEQ ID NO: 1687. In some embodiments, the antisense strand consists of the nucleotide sequence SEQ ID NO: 2293, and the sense strand consists of the nucleotide sequence SEQ ID NO: 1687.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2299, and the sense strand comprises a nucleotide sequence comprising at least 15 contiguous nucleotides (for example, 15, 16, 17, 18, or 19 contiguous nucleotides)

differing by no more than 4 nucleotides (for example, 1, 2, 3, or 4 nucleotides) from SEQ ID NO: 1693. In some embodiments, the antisense strand comprises a nucleotide sequence differing by no more than 4 nucleotides (for example, 1, 2, 3, or 4 nucleotides) from SEQ ID NO: 2299, and the sense strand comprises a nucleotide sequence differing by no more than 4 nucleotides (for example, 1, 2, 3, or 4 nucleotides) from SEQ ID NO: 1693. In some embodiments, the antisense strand comprises the nucleotide sequence SEQ ID NO: 2299, and the sense strand comprises the nucleotide sequence SEQ ID NO: 1693. In some embodiments, the antisense strand consists of the nucleotide sequence SEQ ID NO: 2299, and the sense strand consists of the nucleotide sequence SEQ ID NO: 1693.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2300, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1694. In some embodiments, the antisense strand comprises a nucleotide sequence differing by no more than 4 nucleotides (for example, 1, 2, 3, or 4 nucleotides) from SEQ ID NO: 2300, and the sense strand comprises a nucleotide sequence differing by no more than 4 nucleotides (for example, 1, 2, 3, or 4 nucleotides) from SEQ ID NO: 1694. In some embodiments, the antisense strand comprises the nucleotide sequence SEQ ID NO: 2300, and the sense strand comprises the nucleotide sequence SEQ ID NO: 1694. In some embodiments, the antisense strand consists of the nucleotide sequence SEQ ID NO: 2300, and the sense strand consists of the nucleotide sequence SEQ ID NO: 1694.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2305, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1699. In some embodiments, the antisense strand comprises a nucleotide sequence differing by no more than 4 nucleotides (for example, 1, 2, 3, or 4 nucleotides) from SEQ ID NO: 2305, and the sense strand comprises a nucleotide sequence differing by no more than 4 nucleotides (for example, 1, 2, 3, or 4 nucleotides) from SEQ ID NO: 1699. In some embodiments, the antisense strand comprises the nucleotide sequence SEQ ID NO: 2305, and the sense strand comprises the nucleotide sequence SEQ ID NO: 1699. In some embodiments, the antisense strand consists of the nucleotide sequence SEQ ID NO: 2305, and the sense strand consists of the nucleotide sequence SEQ ID NO: 1699.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2306, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1700. In some embodiments, the antisense strand comprises a nucleotide sequence differing by no more than 4 nucleotides (for example, 1, 2, 3, or 4 nucleotides) from SEQ ID NO: 2306, and the sense strand comprises a nucleotide sequence differing by no more than 4 nucleotides (for example, 1, 2, 3, or 4 nucleotides) from SEQ ID NO: 1700. In some embodiments, the antisense strand comprises the nucleotide sequence SEQ ID NO: 2306, and the sense strand comprises the nucleotide sequence SEQ ID NO: 1700. In some embodiments, the antisense strand consists of the nucleotide sequence SEQ ID NO: 2306, and the sense strand consists of the nucleotide sequence SEQ ID NO: 1700.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2307, and the sense strand comprises a nucleotide sequence comprising at least 15 more than 4 nucleotides (for example, 1, 2, 3, or 4 nucleotides) from SEQ ID NO: 1701. In some embodiments, the antisense strand comprises a nucleotide sequence differing by no more than 4 nucleotides (for example, 1, 2, 3, or 4 nucleotides) from SEQ ID NO: 2307, and the sense strand comprises a nucleotide sequence differing by no more than 4 nucleotides (for example, 1, 2, 3, or 4 nucleotides) from SEQ ID NO: 1701. In some embodiments, the antisense strand comprises the nucleotide sequence SEQ ID NO: 2307, and the sense strand comprises the nucleotide sequence SEQ ID NO: 1701. In some embodiments, the antisense strand consists of the nucleotide sequence SEQ ID NO: 2307, and the sense strand consists of the nucleotide sequence SEQ ID NO: 1701.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2308, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1702. In some embodiments, the antisense strand comprises a nucleotide sequence differing by no more than 4 nucleotides (for example, 1, 2, 3, or 4 nucleotides) from SEQ ID NO: 2308, and the sense strand comprises a nucleotide sequence differing by no more than 4 nucleotides (for example, 1, 2, 3, or 4 nucleotides) from SEQ ID NO: 1702. In some embodiments, the antisense strand comprises the nucleotide sequence SEQ ID NO: 2308, and the sense strand comprises the nucleotide sequence SEQ ID NO: 1702. In some embodiments, the antisense strand consists of the nucleotide sequence SEQ ID NO: 2308, and the sense strand consists of the nucleotide sequence SEQ ID NO: 1702.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2317, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1711. In some embodiments, the antisense strand comprises a nucleotide sequence differing by no more than 4 nucleotides (for example, 1, 2, 3, or 4 nucleotides) from SEQ ID NO: 2317, and the sense strand comprises a nucleotide sequence differing by no more than 4 nucleotides (for example, 1, 2, 3, or 4 nucleotides) from SEQ ID NO: 1711. In some embodiments, the antisense strand comprises the nucleotide sequence SEQ ID NO: 2317, and the sense strand comprises the nucleotide sequence SEQ ID NO: 1711. In some embodiments, the antisense strand consists of the nucleotide sequence SEQ ID NO: 2317, and the sense strand consists of the nucleotide sequence SEQ ID NO: 1711.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2318, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1712. In some embodiments, the antisense strand comprises a nucleotide sequence differing by no more than 4 nucleotides (for example, 1, 2, 3, or 4 nucleotides) from SEQ ID NO: 2318, and the sense strand comprises a nucleotide sequence differing by no more than 4 nucleotides (for example, 1, 2, 3, or 4 nucleotides) from SEQ ID NO: 1712. In some embodiments, the antisense strand comprises the nucleotide sequence SEQ ID NO: 2318, and the sense strand comprises the nucleotide sequence SEQ ID NO: 1712. In some embodiments, the antisense strand consists of the nucleotide sequence SEQ ID NO: 2318, and the sense strand consists of the nucleotide sequence SEQ ID NO: 1712.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2319, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1713. In some embodiments, the antisense strand comprises a nucleotide sequence differing by no more than 4 nucleotides (for example, 1, 2, 3, or 4 nucleotides) from SEQ ID NO: 2319, and the sense strand comprises a nucleotide sequence differing by no more than 4 nucleotides (for example, 1, 2, 3, or 4 nucleotides) from SEQ ID NO: 1713. In some embodiments, the antisense strand comprises the nucleotide sequence SEQ ID NO: 2319, and the sense strand comprises the nucleotide sequence SEQ ID NO: 1713. In some embodiments, the antisense strand consists of the nucleotide sequence SEQ ID NO: 2319, and the sense strand consists of the nucleotide sequence SEQ ID NO: 1713.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2321, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1715. In some embodiments, the antisense strand comprises a nucleotide sequence differing by no more than 4 nucleotides (for example, 1, 2, 3, or 4 nucleotides) from SEQ ID NO: 2321, and the sense strand comprises a nucleotide sequence differing by no more than 4 nucleotides (for example, 1, 2, 3, or 4 nucleotides) from SEQ ID NO: 1715. In some embodiments, the antisense strand comprises the nucleotide sequence SEQ ID NO: 2321, and the sense strand comprises the nucleotide sequence SEQ ID NO: 1715. In some embodiments, the antisense strand consists of the nucleotide sequence SEQ ID NO: 2321, and the sense strand consists of the nucleotide sequence SEQ ID NO: 1715.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2324, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1718. In some embodiments, the antisense strand comprises a nucleotide sequence differing by no more than 4 nucleotides (for example, 1, 2, 3, or 4 nucleotides) from SEQ ID NO: 2324, and the sense strand comprises a nucleotide sequence differing by no more than 4 nucleotides (for example, 1, 2, 3, or 4 nucleotides) from SEQ ID NO: 1718. In some embodiments, the antisense strand comprises the nucleotide sequence SEQ ID NO: 2324, and the sense strand comprises the nucleotide sequence SEQ ID NO: 1718. In some embodiments, the antisense strand consists of the nucleotide sequence SEQ ID NO: 2324, and the sense strand consists of the nucleotide sequence SEQ ID NO: 1718.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2325, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1719. In some embodiments, the antisense strand comprises a nucleotide sequence differing by no more than 4 nucleotides (for example, 1, 2, 3, or 4 nucleotides) from SEQ ID NO: 2325, and the sense strand comprises a nucleotide sequence differing by no more than 4 nucleotides (for example, 1, 2, 3, or 4 nucleotides) from SEQ ID NO: 1719. In some embodiments, the antisense strand comprises the nucleotide sequence SEQ ID NO: 2325, and the sense strand comprises the nucleotide sequence SEQ ID NO: 1719. In some embodiments, the antisense strand consists of the nucleotide sequence SEQ ID NO: 2325, and the sense strand consists of the nucleotide sequence SEQ ID NO: 1719.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2326, and the sense strand comprises a nucleotide sequence comprising at least 15 more than 4 nucleotides (for example, 1, 2, 3, or 4 nucleotides) from SEQ ID NO: 1720. In some embodiments, the antisense strand comprises a nucleotide sequence differing by no more than 4 nucleotides (for example, 1, 2, 3, or 4 nucleotides) from SEQ ID NO: 2326, and the sense strand comprises a nucleotide sequence differing by no more than 4 nucleotides (for example, 1, 2, 3, or 4 nucleotides) from SEQ ID NO: 1720. In some embodiments, the antisense strand comprises the nucleotide sequence SEQ ID NO: 2326, and the sense strand comprises the nucleotide sequence SEQ ID NO: 1720. In some embodiments, the antisense strand consists of the nucleotide sequence SEQ ID NO: 2326, and the sense strand consists of the nucleotide sequence SEQ ID NO: 1720.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2330, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1724. In some embodiments, the antisense strand comprises a nucleotide sequence differing by no more than 4 nucleotides (for example, 1, 2, 3, or 4 nucleotides) from SEQ ID NO: 2330, and the sense strand comprises a nucleotide sequence differing by no more than 4 nucleotides (for example, 1, 2, 3, or 4 nucleotides) from SEQ ID NO: 1724. In some embodiments, the antisense strand comprises the nucleotide sequence SEQ ID NO: 2330, and the sense strand comprises the nucleotide sequence SEQ ID NO: 1724. In some embodiments, the antisense strand consists of the nucleotide sequence SEQ ID NO: 2330, and the sense strand consists of the nucleotide sequence SEQ ID NO: 1724.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2331, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1725. In some embodiments, the antisense strand comprises a nucleotide sequence differing by no more than 4 nucleotides (for example, 1, 2, 3, or 4 nucleotides) from SEQ ID NO: 2331, and the sense strand comprises a nucleotide sequence differing by no more than 4 nucleotides (for example, 1, 2, 3, or 4 nucleotides) from SEQ ID NO: 1725. In some embodiments, the antisense strand comprises the nucleotide sequence SEQ ID NO: 2331, and the sense strand comprises the nucleotide sequence SEQ ID NO: 1725. In some embodiments, the antisense strand consists of the nucleotide sequence SEQ ID NO: 2331, and the sense strand consists of the nucleotide sequence SEQ ID NO: 1725.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2333, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1727. In some embodiments, the antisense strand comprises a nucleotide sequence differing by no more than 4 nucleotides (for example, 1, 2, 3, or 4 nucleotides) from SEQ ID NO: 2333, and the sense strand comprises a nucleotide sequence differing by no more than 4 nucleotides (for example, 1, 2, 3, or 4 nucleotides) from SEQ ID NO: 1727. In some embodiments, the antisense strand comprises the nucleotide sequence SEQ ID NO: 2333, and the sense strand comprises the nucleotide sequence SEQ ID NO: 1727. In some embodiments, the antisense strand consists of the nucleotide sequence SEQ ID NO: 2333, and the sense strand consists of the nucleotide sequence SEQ ID NO: 1727.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2334, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1728. In some embodiments, the antisense strand comprises a nucleotide sequence differing by no more than 4 nucleotides (for example, 1, 2, 3, or 4 nucleotides) from SEQ ID NO: 2334, and the sense strand comprises a nucleotide sequence differing by no more than 4 nucleotides (for example, 1, 2, 3, or 4 nucleotides) from SEQ ID NO: 1728. In some embodiments, the antisense strand comprises the nucleotide sequence SEQ ID NO: 2334, and the sense strand comprises the nucleotide sequence SEQ ID NO: 1728. In some embodiments, the antisense strand consists of the nucleotide sequence SEQ ID NO: 2334, and the sense strand consists of the nucleotide sequence SEQ ID NO: 1728.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2336, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1730. In some embodiments, the antisense strand comprises a nucleotide sequence differing by no more than 4 nucleotides (for example, 1, 2, 3, or 4 nucleotides) from SEQ ID NO: 2336, and the sense strand comprises a nucleotide sequence differing by no more than 4 nucleotides (for example, 1, 2, 3, or 4 nucleotides) from SEQ ID NO: 1730. In some embodiments, the antisense strand comprises the nucleotide sequence SEQ ID NO: 2336, and the sense strand comprises the nucleotide sequence SEQ ID NO: 1730. In some embodiments, the antisense strand consists of the nucleotide sequence SEQ ID NO: 2336, and the sense strand consists of the nucleotide sequence SEQ ID NO: 1730.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2338, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1732. In some embodiments, the antisense strand comprises a nucleotide sequence differing by no more than 4 nucleotides (for example, 1, 2, 3, or 4 nucleotides) from SEQ ID NO: 2338, and the sense strand comprises a nucleotide sequence differing by no more than 4 nucleotides (for example, 1, 2, 3, or 4 nucleotides) from SEQ ID NO: 1732. In some embodiments, the antisense strand comprises the nucleotide sequence SEQ ID NO: 2338, and the sense strand comprises the nucleotide sequence SEQ ID NO: 1732. In some embodiments, the antisense strand consists of the nucleotide sequence SEQ ID NO: 2338, and the sense strand consists of the nucleotide sequence SEQ ID NO: 1732.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2339, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1733. In some embodiments, the antisense strand comprises a nucleotide sequence differing by no more than 4 nucleotides (for example, 1, 2, 3, or 4 nucleotides) from SEQ ID NO: 2339, and the sense strand comprises a nucleotide sequence differing by no more than 4 nucleotides (for example, 1, 2, 3, or 4 nucleotides) from SEQ ID NO: 1733. In some embodiments, the antisense strand comprises the nucleotide sequence SEQ ID NO: 2339, and the sense strand comprises the nucleotide sequence SEQ ID NO: 1733. In some embodiments, the antisense strand consists of the nucleotide sequence SEQ ID NO: 2339, and the sense strand consists of the nucleotide sequence SEQ ID NO: 1733.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2340, and the sense strand comprises a nucleotide sequence comprising at least 15 more than 4 nucleotides (for example, 1, 2, 3, or 4 nucleotides) from SEQ ID NO: 1734. In some embodiments, the antisense strand comprises a nucleotide sequence differing by no more than 4 nucleotides (for example, 1, 2, 3, or 4 nucleotides) from SEQ ID NO: 2340, and the sense strand comprises a nucleotide sequence differing by no more than 4 nucleotides (for example, 1, 2, 3, or 4 nucleotides) from SEQ ID NO: 1734. In some embodiments, the antisense strand comprises the nucleotide sequence SEQ ID NO: 2340, and the sense strand comprises the nucleotide sequence SEQ ID NO: 1734. In some embodiments, the antisense strand consists of the nucleotide sequence SEQ ID NO: 2340, and the sense strand consists of the nucleotide sequence SEQ ID NO: 1734.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2341, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1735. In some embodiments, the antisense strand comprises a nucleotide sequence differing by no more than 4 nucleotides (for example, 1, 2, 3, or 4 nucleotides) from SEQ ID NO: 2341, and the sense strand comprises a nucleotide sequence differing by no more than 4 nucleotides (for example, 1, 2, 3, or 4 nucleotides) from SEQ ID NO: 1735. In some embodiments, the antisense strand comprises the nucleotide sequence SEQ ID NO: 2341, and the sense strand comprises the nucleotide sequence SEQ ID NO: 1735. In some embodiments, the antisense strand consists of the nucleotide sequence SEQ ID NO: 2341, and the sense strand consists of the nucleotide sequence SEQ ID NO: 1735.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2345, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1739. In some embodiments, the antisense strand comprises a nucleotide sequence differing by no more than 4 nucleotides (for example, 1, 2, 3, or 4 nucleotides) from SEQ ID NO: 2345, and the sense strand comprises a nucleotide sequence differing by no more than 4 nucleotides (for example, 1, 2, 3, or 4 nucleotides) from SEQ ID NO: 1739. In some embodiments, the antisense strand comprises the nucleotide sequence SEQ ID NO: 2345, and the sense strand comprises the nucleotide sequence SEQ ID NO: 1739. In some embodiments, the antisense strand consists of the nucleotide sequence SEQ ID NO: 2345, and the sense strand consists of the nucleotide sequence SEQ ID NO: 1739.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2346, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1740. In some embodiments, the antisense strand comprises a nucleotide sequence differing by no more than 4 nucleotides (for example, 1, 2, 3, or 4 nucleotides) from SEQ ID NO: 2346, and the sense strand comprises a nucleotide sequence differing by no more than 4 nucleotides (for example, 1, 2, 3, or 4 nucleotides) from SEQ ID NO: 1740. In some embodiments, the antisense strand comprises the nucleotide sequence SEQ ID NO: 2346, and the sense strand comprises the nucleotide sequence SEQ ID NO: 1740. In some embodiments, the antisense strand consists of the nucleotide sequence SEQ ID NO: 2346, and the sense strand consists of the nucleotide sequence SEQ ID NO: 1740.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2349, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1743. In some embodiments, the antisense strand comprises a nucleotide sequence differing by no more than 4 nucleotides (for example, 1, 2, 3, or 4 nucleotides) from SEQ ID NO: 2349, and the sense strand comprises a nucleotide sequence differing by no more than 4 nucleotides (for example, 1, 2, 3, or 4 nucleotides) from SEQ ID NO: 1743. In some embodiments, the antisense strand comprises the nucleotide sequence SEQ ID NO: 2349, and the sense strand comprises the nucleotide sequence SEQ ID NO: 1743. In some embodiments, the antisense strand consists of the nucleotide sequence SEQ ID NO: 2349, and the sense strand consists of the nucleotide sequence SEQ ID NO: 1743.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2350, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1744. In some embodiments, the antisense strand comprises a nucleotide sequence differing by no more than 4 nucleotides (for example, 1, 2, 3, or 4 nucleotides) from SEQ ID NO: 2350, and the sense strand comprises a nucleotide sequence differing by no more than 4 nucleotides (for example, 1, 2, 3, or 4 nucleotides) from SEQ ID NO: 1744. In some embodiments, the antisense strand comprises the nucleotide sequence SEQ ID NO: 2350, and the sense strand comprises the nucleotide sequence SEQ ID NO: 1744. In some embodiments, the antisense strand consists of the nucleotide sequence SEQ ID NO: 2350, and the sense strand consists of the nucleotide sequence SEQ ID NO: 1744.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2353, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1747. In some embodiments, the antisense strand comprises a nucleotide sequence differing by no more than 4 nucleotides (for example, 1, 2, 3, or 4 nucleotides) from SEQ ID NO: 2353, and the sense strand comprises a nucleotide sequence differing by no more than 4 nucleotides (for example, 1, 2, 3, or 4 nucleotides) from SEQ ID NO: 1747. In some embodiments, the antisense strand comprises the nucleotide sequence SEQ ID NO: 2353, and the sense strand comprises the nucleotide sequence SEQ ID NO: 1747. In some embodiments, the antisense strand consists of the nucleotide sequence SEQ ID NO: 2353, and the sense strand consists of the nucleotide sequence SEQ ID NO: 1747.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2354, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1748. In some embodiments, the antisense strand comprises a nucleotide sequence differing by no more than 4 nucleotides (for example, 1, 2, 3, or 4 nucleotides) from SEQ ID NO: 2354, and the sense strand comprises a nucleotide sequence differing by no more than 4 nucleotides (for example, 1, 2, 3, or 4 nucleotides) from SEQ ID NO: 1748. In some embodiments, the antisense strand comprises the nucleotide sequence SEQ ID NO: 2354, and the sense strand comprises the nucleotide sequence SEQ ID NO: 1748. In some embodiments, the antisense strand consists of the nucleotide sequence SEQ ID NO: 2354, and the sense strand consists of the nucleotide sequence SEQ ID NO: 1748.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2355, and the sense strand comprises a nucleotide sequence comprising at least 15 more than 4 nucleotides (for example, 1, 2, 3, or 4 nucleotides) from SEQ ID NO: 1749. In some embodiments, the antisense strand comprises a nucleotide sequence differing by no more than 4 nucleotides (for example, 1, 2, 3, or 4 nucleotides) from SEQ ID NO: 2355, and the sense strand comprises a nucleotide sequence differing by no more than 4 nucleotides (for example, 1, 2, 3, or 4 nucleotides) from SEQ ID NO: 1749. In some embodiments, the antisense strand comprises the nucleotide sequence SEQ ID NO: 2355, and the sense strand comprises the nucleotide sequence SEQ ID NO: 1749. In some embodiments, the antisense strand consists of the nucleotide sequence SEQ ID NO: 2355, and the sense strand consists of the nucleotide sequence SEQ ID NO: 1749.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2361, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1755. In some embodiments, the antisense strand comprises a nucleotide sequence differing by no more than 4 nucleotides (for example, 1, 2, 3, or 4 nucleotides) from SEQ ID NO: 2361, and the sense strand comprises a nucleotide sequence differing by no more than 4 nucleotides (for example, 1, 2, 3, or 4 nucleotides) from SEQ ID NO: 1755. In some embodiments, the antisense strand comprises the nucleotide sequence SEQ ID NO: 2361, and the sense strand comprises the nucleotide sequence SEQ ID NO: 1755. In some embodiments, the antisense strand consists of the nucleotide sequence SEQ ID NO: 2361, and the sense strand consists of the nucleotide sequence SEQ ID NO: 1755.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2362, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1756. In some embodiments, the antisense strand comprises a nucleotide sequence differing by no more than 4 nucleotides (for example, 1, 2, 3, or 4 nucleotides) from SEQ ID NO: 2362, and the sense strand comprises a nucleotide sequence differing by no more than 4 nucleotides (for example, 1, 2, 3, or 4 nucleotides) from SEQ ID NO: 1756. In some embodiments, the antisense strand comprises the nucleotide sequence SEQ ID NO: 2362, and the sense strand comprises the nucleotide sequence SEQ ID NO: 1756. In some embodiments, the antisense strand consists of the nucleotide sequence SEQ ID NO: 2362, and the sense strand consists of the nucleotide sequence SEQ ID NO: 1756.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2363, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1757. In some embodiments, the antisense strand comprises a nucleotide sequence differing by no more than 4 nucleotides (for example, 1, 2, 3, or 4 nucleotides) from SEQ ID NO: 2363, and the sense strand comprises a nucleotide sequence differing by no more than 4 nucleotides (for example, 1, 2, 3, or 4 nucleotides) from SEQ ID NO: 1757. In some embodiments, the antisense strand comprises the nucleotide sequence SEQ ID NO: 2363, and the sense strand comprises the nucleotide sequence SEQ ID NO: 1757. In some embodiments, the antisense strand consists of the nucleotide sequence SEQ ID NO: 2363, and the sense strand consists of the nucleotide sequence SEQ ID NO: 1757.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2367, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1761. In some embodiments, the antisense strand comprises a nucleotide sequence differing by no more than 4 nucleotides (for example, 1, 2, 3, or 4 nucleotides) from SEQ ID NO: 2367, and the sense strand comprises a nucleotide sequence differing by no more than 4 nucleotides (for example, 1, 2, 3, or 4 nucleotides) from SEQ ID NO: 1761. In some embodiments, the antisense strand comprises the nucleotide sequence SEQ ID NO: 2367, and the sense strand comprises the nucleotide sequence SEQ ID NO: 1761. In some embodiments, the antisense strand consists of the nucleotide sequence SEQ ID NO: 2367, and the sense strand consists of the nucleotide sequence SEQ ID NO: 1761.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2369, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1763. In some embodiments, the antisense strand comprises a nucleotide sequence differing by no more than 4 nucleotides (for example, 1, 2, 3, or 4 nucleotides) from SEQ ID NO: 2369, and the sense strand comprises a nucleotide sequence differing by no more than 4 nucleotides (for example, 1, 2, 3, or 4 nucleotides) from SEQ ID NO: 1763. In some embodiments, the antisense strand comprises the nucleotide sequence SEQ ID NO: 2369, and the sense strand comprises the nucleotide sequence SEQ ID NO: 1763. In some embodiments, the antisense strand consists of the nucleotide sequence SEQ ID NO: 2369, and the sense strand consists of the nucleotide sequence SEQ ID NO: 1763.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2371, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1765. In some embodiments, the antisense strand comprises a nucleotide sequence differing by no more than 4 nucleotides (for example, 1, 2, 3, or 4 nucleotides) from SEQ ID NO: 2371, and the sense strand comprises a nucleotide sequence differing by no more than 4 nucleotides (for example, 1, 2, 3, or 4 nucleotides) from SEQ ID NO: 1765. In some embodiments, the antisense strand comprises the nucleotide sequence SEQ ID NO: 2371, and the sense strand comprises the nucleotide sequence SEQ ID NO: 1765. In some embodiments, the antisense strand consists of the nucleotide sequence SEQ ID NO: 2371, and the sense strand consists of the nucleotide sequence SEQ ID NO: 1765.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2372, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1766. In some embodiments, the antisense strand comprises a nucleotide sequence differing by no more than 4 nucleotides (for example, 1, 2, 3, or 4 nucleotides) from SEQ ID NO: 2372, and the sense strand comprises a nucleotide sequence differing by no more than 4 nucleotides (for example, 1, 2, 3, or 4 nucleotides) from SEQ ID NO: 1766. In some embodiments, the antisense strand comprises the nucleotide sequence SEQ ID NO: 2372, and the sense strand comprises the nucleotide sequence SEQ ID NO: 1766. In some embodiments, the antisense strand consists of the nucleotide sequence SEQ ID NO: 2372, and the sense strand consists of the nucleotide sequence SEQ ID NO: 1766.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2373, and the sense strand comprises a nucleotide sequence comprising at least 15 more than 4 nucleotides (for example, 1, 2, 3, or 4 nucleotides) from SEQ ID NO: 1767. In some embodiments, the antisense strand comprises a nucleotide sequence differing by no more than 4 nucleotides (for example, 1, 2, 3, or 4 nucleotides) from SEQ ID NO: 2373, and the sense strand comprises a nucleotide sequence differing by no more than 4 nucleotides (for example, 1, 2, 3, or 4 nucleotides) from SEQ ID NO: 1767. In some embodiments, the antisense strand comprises the nucleotide sequence SEQ ID NO: 2373, and the sense strand comprises the nucleotide sequence SEQ ID NO: 1767. In some embodiments, the antisense strand consists of the nucleotide sequence SEQ ID NO: 2373, and the sense strand consists of the nucleotide sequence SEQ ID NO: 1767.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2380, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1774. In some embodiments, the antisense strand comprises a nucleotide sequence differing by no more than 4 nucleotides (for example, 1, 2, 3, or 4 nucleotides) from SEQ ID NO: 2380, and the sense strand comprises a nucleotide sequence differing by no more than 4 nucleotides (for example, 1, 2, 3, or 4 nucleotides) from SEQ ID NO: 1774. In some embodiments, the antisense strand comprises the nucleotide sequence SEQ ID NO: 2380, and the sense strand comprises the nucleotide sequence SEQ ID NO: 1774. In some embodiments, the antisense strand consists of the nucleotide sequence SEQ ID NO: 2380, and the sense strand consists of the nucleotide sequence SEQ ID NO: 1774.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2381, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1775. In some embodiments, the antisense strand comprises a nucleotide sequence differing by no more than 4 nucleotides (for example, 1, 2, 3, or 4 nucleotides) from SEQ ID NO: 2381, and the sense strand comprises a nucleotide sequence differing by no more than 4 nucleotides (for example, 1, 2, 3, or 4 nucleotides) from SEQ ID NO: 1775. In some embodiments, the antisense strand comprises the nucleotide sequence SEQ ID NO: 2381, and the sense strand comprises the nucleotide sequence SEQ ID NO: 1775. In some embodiments, the antisense strand consists of the nucleotide sequence SEQ ID NO: 2381, and the sense strand consists of the nucleotide sequence SEQ ID NO: 1775.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2387, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1781. In some embodiments, the antisense strand comprises a nucleotide sequence differing by no more than 4 nucleotides (for example, 1, 2, 3, or 4 nucleotides) from SEQ ID NO: 2387, and the sense strand comprises a nucleotide sequence differing by no more than 4 nucleotides (for example, 1, 2, 3, or 4 nucleotides) from SEQ ID NO: 1781. In some embodiments, the antisense strand comprises the nucleotide sequence SEQ ID NO: 2387, and the sense strand comprises the nucleotide sequence SEQ ID NO: 1781. In some embodiments, the antisense strand consists of the nucleotide sequence SEQ ID NO: 2387, and the sense strand consists of the nucleotide sequence SEQ ID NO: 1781.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2389, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1783. In some embodiments, the antisense strand comprises a nucleotide sequence differing by no more than 4 nucleotides (for example, 1, 2, 3, or 4 nucleotides) from SEQ ID NO: 2389, and the sense strand comprises a nucleotide sequence differing by no more than 4 nucleotides (for example, 1, 2, 3, or 4 nucleotides) from SEQ ID NO: 1783. In some embodiments, the antisense strand comprises the nucleotide sequence SEQ ID NO: 2389, and the sense strand comprises the nucleotide sequence SEQ ID NO: 1783. In some embodiments, the antisense strand consists of the nucleotide sequence SEQ ID NO: 2389, and the sense strand consists of the nucleotide sequence SEQ ID NO: 1783.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2392, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1786. In some embodiments, the antisense strand comprises a nucleotide sequence differing by no more than 4 nucleotides (for example, 1, 2, 3, or 4 nucleotides) from SEQ ID NO: 2392, and the sense strand comprises a nucleotide sequence differing by no more than 4 nucleotides (for example, 1, 2, 3, or 4 nucleotides) from SEQ ID NO: 1786. In some embodiments, the antisense strand comprises the nucleotide sequence SEQ ID NO: 2392, and the sense strand comprises the nucleotide sequence SEQ ID NO: 1786. In some embodiments, the antisense strand consists of the nucleotide sequence SEQ ID NO: 2392, and the sense strand consists of the nucleotide sequence SEQ ID NO: 1786.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2393, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1787. In some embodiments, the antisense strand comprises a nucleotide sequence differing by no more than 4 nucleotides (for example, 1, 2, 3, or 4 nucleotides) from SEQ ID NO: 2393, and the sense strand comprises a nucleotide sequence differing by no more than 4 nucleotides (for example, 1, 2, 3, or 4 nucleotides) from SEQ ID NO: 1787. In some embodiments, the antisense strand comprises the nucleotide sequence SEQ ID NO: 2393, and the sense strand comprises the nucleotide sequence SEQ ID NO: 1787. In some embodiments, the antisense strand consists of the nucleotide sequence SEQ ID NO: 2393, and the sense strand consists of the nucleotide sequence SEQ ID NO: 1787.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2396, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1790. In some embodiments, the antisense strand comprises a nucleotide sequence differing by no more than 4 nucleotides (for example, 1, 2, 3, or 4 nucleotides) from SEQ ID NO: 2396, and the sense strand comprises a nucleotide sequence differing by no more than 4 nucleotides (for example, 1, 2, 3, or 4 nucleotides) from SEQ ID NO: 1790. In some embodiments, the antisense strand comprises the nucleotide sequence SEQ ID NO: 2396, and the sense strand comprises the nucleotide sequence SEQ ID NO: 1790. In some embodiments, the antisense strand consists of the nucleotide sequence SEQ ID NO: 2396, and the sense strand consists of the nucleotide sequence SEQ ID NO: 1790.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2397, and the sense strand comprises a nucleotide sequence comprising at least 15 more than 4 nucleotides (for example, 1, 2, 3, or 4 nucleotides) from SEQ ID NO: 1791. In some embodiments, the antisense strand comprises a nucleotide sequence differing by no more than 4 nucleotides (for example, 1, 2, 3, or 4 nucleotides) from SEQ ID NO: 2397, and the sense strand comprises a nucleotide sequence differing by no more than 4 nucleotides (for example, 1, 2, 3, or 4 nucleotides) from SEQ ID NO: 1791. In some embodiments, the antisense strand comprises the nucleotide sequence SEQ ID NO: 2397, and the sense strand comprises the nucleotide sequence SEQ ID NO: 1791. In some embodiments, the antisense strand consists of the nucleotide sequence SEQ ID NO: 2397, and the sense strand consists of the nucleotide sequence SEQ ID NO: 1791.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2398, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1792. In some embodiments, the antisense strand comprises a nucleotide sequence differing by no more than 4 nucleotides (for example, 1, 2, 3, or 4 nucleotides) from SEQ ID NO: 2398, and the sense strand comprises a nucleotide sequence differing by no more than 4 nucleotides (for example, 1, 2, 3, or 4 nucleotides) from SEQ ID NO: 1792. In some embodiments, the antisense strand comprises the nucleotide sequence SEQ ID NO: 2398, and the sense strand comprises the nucleotide sequence SEQ ID NO: 1792. In some embodiments, the antisense strand consists of the nucleotide sequence SEQ ID NO: 2398, and the sense strand consists of the nucleotide sequence SEQ ID NO: 1792.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2402, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1796. In some embodiments, the antisense strand comprises a nucleotide sequence differing by no more than 4 nucleotides (for example, 1, 2, 3, or 4 nucleotides) from SEQ ID NO: 2402, and the sense strand comprises a nucleotide sequence differing by no more than 4 nucleotides (for example, 1, 2, 3, or 4 nucleotides) from SEQ ID NO: 1796. In some embodiments, the antisense strand comprises the nucleotide sequence SEQ ID NO: 2402, and the sense strand comprises the nucleotide sequence SEQ ID NO: 1796. In some embodiments, the antisense strand consists of the nucleotide sequence SEQ ID NO: 2402, and the sense strand consists of the nucleotide sequence SEQ ID NO: 1796.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2403, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1797. In some embodiments, the antisense strand comprises a nucleotide sequence differing by no more than 4 nucleotides (for example, 1, 2, 3, or 4 nucleotides) from SEQ ID NO: 2403, and the sense strand comprises a nucleotide sequence differing by no more than 4 nucleotides (for example, 1, 2, 3, or 4 nucleotides) from SEQ ID NO: 1797. In some embodiments, the antisense strand comprises the nucleotide sequence SEQ ID NO: 2403, and the sense strand comprises the nucleotide sequence SEQ ID NO: 1797. In some embodiments, the antisense strand consists of the nucleotide sequence SEQ ID NO: 2403, and the sense strand consists of the nucleotide sequence SEQ ID NO: 1797.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2404, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1798. In some embodiments, the antisense strand comprises a nucleotide sequence differing by no more than 4 nucleotides (for example, 1, 2, 3, or 4 nucleotides) from SEQ ID NO: 2404, and the sense strand comprises a nucleotide sequence differing by no more than 4 nucleotides (for example, 1, 2, 3, or 4 nucleotides) from SEQ ID NO: 1798. In some embodiments, the antisense strand comprises the nucleotide sequence SEQ ID NO: 2404, and the sense strand comprises the nucleotide sequence SEQ ID NO: 1798. In some embodiments, the antisense strand consists of the nucleotide sequence SEQ ID NO: 2404, and the sense strand consists of the nucleotide sequence SEQ ID NO: 1798.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2405, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1799. In some embodiments, the antisense strand comprises a nucleotide sequence differing by no more than 4 nucleotides (for example, 1, 2, 3, or 4 nucleotides) from SEQ ID NO: 2405, and the sense strand comprises a nucleotide sequence differing by no more than 4 nucleotides (for example, 1, 2, 3, or 4 nucleotides) from SEQ ID NO: 1799. In some embodiments, the antisense strand comprises the nucleotide sequence SEQ ID NO: 2405, and the sense strand comprises the nucleotide sequence SEQ ID NO: 1799. In some embodiments, the antisense strand consists of the nucleotide sequence SEQ ID NO: 2405, and the sense strand consists of the nucleotide sequence SEQ ID NO: 1799.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2406, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1800. In some embodiments, the antisense strand comprises a nucleotide sequence differing by no more than 4 nucleotides (for example, 1, 2, 3, or 4 nucleotides) from SEQ ID NO: 2406, and the sense strand comprises a nucleotide sequence differing by no more than 4 nucleotides (for example, 1, 2, 3, or 4 nucleotides) from SEQ ID NO: 1800. In some embodiments, the antisense strand comprises the nucleotide sequence SEQ ID NO: 2406, and the sense strand comprises the nucleotide sequence SEQ ID NO: 1800. In some embodiments, the antisense strand consists of the nucleotide sequence SEQ ID NO: 2406, and the sense strand consists of the nucleotide sequence SEQ ID NO: 1800.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2407, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1801. In some embodiments, the antisense strand comprises a nucleotide sequence differing by no more than 4 nucleotides (for example, 1, 2, 3, or 4 nucleotides) from SEQ ID NO: 2407, and the sense strand comprises a nucleotide sequence differing by no more than 4 nucleotides (for example, 1, 2, 3, or 4 nucleotides) from SEQ ID NO: 1801. In some embodiments, the antisense strand comprises the nucleotide sequence SEQ ID NO: 2407, and the sense strand comprises the nucleotide sequence SEQ ID NO: 1801. In some embodiments, the antisense strand consists of the nucleotide sequence SEQ ID NO: 2407, and the sense strand consists of the nucleotide sequence SEQ ID NO: 1801.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2412, and the sense strand comprises a nucleotide sequence comprising at least 15 more than 4 nucleotides (for example, 1, 2, 3, or 4 nucleotides) from SEQ ID NO: 1806. In some embodiments, the antisense strand comprises a nucleotide sequence differing by no more than 4 nucleotides (for example, 1, 2, 3, or 4 nucleotides) from SEQ ID NO: 2412, and the sense strand comprises a nucleotide sequence differing by no more than 4 nucleotides (for example, 1, 2, 3, or 4 nucleotides) from SEQ ID NO: 1806. In some embodiments, the antisense strand comprises the nucleotide sequence SEQ ID NO: 2412, and the sense strand comprises the nucleotide sequence SEQ ID NO: 1806. In some embodiments, the antisense strand consists of the nucleotide sequence SEQ ID NO: 2412, and the sense strand consists of the nucleotide sequence SEQ ID NO: 1806.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2416, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1810. In some embodiments, the antisense strand comprises a nucleotide sequence differing by no more than 4 nucleotides (for example, 1, 2, 3, or 4 nucleotides) from SEQ ID NO: 2416, and the sense strand comprises a nucleotide sequence differing by no more than 4 nucleotides (for example, 1, 2, 3, or 4 nucleotides) from SEQ ID NO: 1810. In some embodiments, the antisense strand comprises the nucleotide sequence SEQ ID NO: 2416, and the sense strand comprises the nucleotide sequence SEQ ID NO: 1810. In some embodiments, the antisense strand consists of the nucleotide sequence SEQ ID NO: 2416, and the sense strand consists of the nucleotide sequence SEQ ID NO: 1810.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2419, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1813. In some embodiments, the antisense strand comprises a nucleotide sequence differing by no more than 4 nucleotides (for example, 1, 2, 3, or 4 nucleotides) from SEQ ID NO: 2419, and the sense strand comprises a nucleotide sequence differing by no more than 4 nucleotides (for example, 1, 2, 3, or 4 nucleotides) from SEQ ID NO: 1813. In some embodiments, the antisense strand comprises the nucleotide sequence SEQ ID NO: 2419, and the sense strand comprises the nucleotide sequence SEQ ID NO: 1813. In some embodiments, the antisense strand consists of the nucleotide sequence SEQ ID NO: 2419, and the sense strand consists of the nucleotide sequence SEQ ID NO: 1813.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2420, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 1814. In some embodiments, the antisense strand comprises a nucleotide sequence differing by no more than 4 nucleotides (for example, 1, 2, 3, or 4 nucleotides) from SEQ ID NO: 2420, and the sense strand comprises a nucleotide sequence differing by no more than 4 nucleotides (for example, 1, 2, 3, or 4 nucleotides) from SEQ ID NO: 1814. In some embodiments, the antisense strand comprises the nucleotide sequence SEQ ID NO: 2420, and the sense strand comprises the nucleotide sequence SEQ ID NO: 1814. In some embodiments, the antisense strand consists of the nucleotide sequence SEQ ID NO: 2420, and the sense strand consists of the nucleotide sequence SEQ ID NO: 1814.

In some embodiments, the oligonucleotide of the present disclosure targets a sequence of nucleotides corresponding to any one of positions 61-79, 404-422, 412-430, 420-438, 668-686, 1163-1181, 1619-1637, 1628-1646, 1629-1647, 1635-1653, 1636-1654, 1651-1669, 1652-1670, 1653-1671, 1654-1672, 1655-1673, 1656-1674, 1213-1231, and 1267-1285 of SEQ ID NO: 2425 (NM_001306068.3).

In some embodiments, the oligonucleotide of the present disclosure targets a sequence of nucleotides corresponding to any one of positions 668-686, 1628-1646, 1635-1653, 1652-1670, 1654-1672, 1655-1673, and 1656-1674 of SEQ ID NO: 2425 (NM_001306068.3).

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from the nucleotide sequence of any one of SEQ ID NOs: 634, 832, 837, 838, 1020, 1039, 1048, 1049, 1055, 1056, 1064, 1065, 1066, 1067, 1068, 1069, 1122, 1169, 1184, 1846, 2044, 2049, 2232, 2251, 2260, 2261, 2267, 2268, 2276, 2277, 2278, 2279, 2280, 2281, 2381, 2396, 2050, 2437, 2438, 2439, 2440, 2441, 2442, 2443, 2334, 2444, 2445, 2446, and 2447, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from the nucleotide sequence of any one of SEQ ID NOs: 28, 226, 231, 232, 414, 433, 442, 443, 449, 450, 458, 459, 460, 461, 462, 463, 516, 563, 578, 1240, 1438, 1443, 1626, 1645, 1654, 1655, 1661, 1662, 1670, 1671, 1672, 1673, 1674, 1675, 1775, 1790, 1444, 2426, 2427, 2428, 2429, 2430, 2431, 2432, 1728, 2433, 2434, 2435, and 2436. In some embodiments, the antisense strand comprises a nucleotide sequence differing by no more than 4 nucleotides (for example, 1, 2, 3, or 4 nucleotides) from the nucleotide sequence of any one of SEQ ID NOs: 634, 832, 837, 838, 1020, 1039, 1048, 1049, 1055, 1056, 1064, 1065, 1066, 1067, 1068, 1069, 1122, 1169, 1184, 1846, 2044, 2049, 2232, 2251, 2260, 2261, 2267, 2268, 2276, 2277, 2278, 2279, 2280, 2281, 2381, 2396, 2050, 2437, 2438, 2439, 2440, 2441, 2442, 2443, 2334, 2444, 2445, 2446, and 2447, and the sense strand comprises a nucleotide sequence differing by no more than 4 nucleotides (for example, 1, 2, 3, or 4 nucleotides) from the nucleotide sequence of any one of SEQ ID NOs: 28, 226, 231, 232, 414, 433, 442, 443, 449, 450, 458, 459, 460, 461, 462, 463, 516, 563, 578, 1240, 1438, 1443, 1626, 1645, 1654, 1655, 1661, 1662, 1670, 1671, 1672, 1673, 1674, 1675, 1775, 1790, 1444, 2426, 2427, 2428, 2429, 2430, 2431, 2432, 1728, 2433, 2434, 2435, and 2436. In some embodiments, the antisense strand comprises the nucleotide sequence of any one of SEQ ID NOs: 634, 832, 837, 838, 1020, 1039, 1048, 1049, 1055, 1056, 1064, 1065, 1066, 1067, 1068, 1069, 1122, 1169, 1184, 1846, 2044, 2049, 2232, 2251, 2260, 2261, 2267, 2268, 2276, 2277, 2278, 2279, 2280, 2281, 2381, 2396, 2050, 2437, 2438, 2439, 2440, 2441, 2442, 2443, 2334, 2444, 2445, 2446, and 2447, and the sense strand comprises the nucleotide sequence of any one of SEQ ID NOs: 28, 226, 231, 232, 414, 433, 442, 443, 449, 450, 458, 459, 460, 461, 462, 463, 516, 563, 578, 1240, 1438, 1443, 1626, 1645, 1654, 1655, 1661, 1662, 1670, 1671, 1672, 1673, 1674, 1675, 1775, 1790, 1444, 2426, 2427, 2428, 2429, 2430, 2431, 2432, 1728, 2433, 2434, 2435, and 2436. In some embodiments, the antisense strand consists of the nucleotide sequence of any one of SEQ ID NOs: 634, 832, 837, 838, 1020, 1039, 1048, 1049, 1055, 1056, 1064, 1065, 1066, 1067, 1068, 1069, 1122, 1169, 1184, 1846, 2044, 2049, 2232, 2251, 2260, 2261, 2267, 2268, 2276, 2277, 2278, 2279, 2280, 2281, 2381, 2396, 2050, 2437, 2438, 2439, 2440, 2441, 2442, 2443, 2334, 2444, 2445, 2446, and 2447, and the sense strand consists of the nucleotide sequence of any one of SEQ ID NOs: 28, 226, 231, 232, 414, 433, 442, 443, 449, 450, 458, 459, 460, 461, 462, 463, 516, 563, 578, 1240, 1438, 1443, 1626, 1645, 1654, 1655, 1661, 1662, 1670, 1671, 1672, 1673, 1674, 1675, 1775, 1790, 1444, 2426, 2427, 2428, 2429, 2430, 2431, 2432, 1728, 2433, 2434, 2435, and 2436.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from an antisense strand selected from Table 1D, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from a sense strand selected from Table 1D. In some embodiments, the antisense strand comprises a nucleotide sequence differing by no more than 4 nucleotides (for example, 1, 2, 3, or 4 nucleotides) from an antisense strand selected from Table 1D, and the sense strand comprises a nucleotide sequence differing by no more than 4 nucleotides (for example, 1, 2, 3, or 4 nucleotides) from a sense strand selected from Table 1D. In some embodiments, the antisense strand comprises an antisense strand selected from Table 1D, and the sense strand comprises a sense strand selected from Table 1D. In some embodiments, the antisense strand consists of an antisense strand selected from Table 1D, and the sense strand consists of a sense strand selected from Table 1D.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from an antisense strand selected from Table 1E, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from a sense strand selected from Table 1E. In some embodiments, the antisense strand comprises a nucleotide sequence differing by no more than 4 nucleotides (for example, 1, 2, 3, or 4 nucleotides) from an antisense strand selected from Table 1E, and the sense strand comprises a nucleotide sequence differing by no more than 4 nucleotides (for example, 1, 2, 3, or 4 nucleotides) from a sense strand selected from Table 1E. In some embodiments, the antisense strand comprises an antisense strand selected from Table 1E, and the sense strand comprises a sense strand selected from Table 1E. In some embodiments, the antisense strand consists of an antisense strand selected from Table 1E, and the sense strand consists of a sense strand selected from Table 1E.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NOs: 634, 832, 837, 838, 1020, 1039, 1048, 1049, 1055, 1056, 1064, 1065, 1066, 1067, 1068, 1069, 1122, 1169, and 1184, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NOs: 28, 226, 231, 232, 414, 433, 442, 443, 449, 450, 458, 459, 460, 461, 462, 463, 516, 563, and 578. In some embodiments, the antisense strand comprises a nucleotide sequence differing by no more than 4 nucleotides (for example, 1, 2, 3, or 4 nucleotides) from SEQ ID NOs: 634, 832, 837, 838, 1020, 1039, 1048, 1049, 1055, 1056, 1064, 1065, 1066, 1067, 1068, 1069, 1122, 1169, and 1184, and the sense strand comprises a nucleotide sequence differing by no more than 4 nucleotides (for example, 1, 2, 3, or 4 nucleotides) from SEQ ID NOs: 28, 226, 231, 232, 414, 433, 442, 443, 449, 450, 458, 459, 460, 461, 462, 463, 516, 563, and 578. In some embodiments, the antisense strand comprises the nucleotide sequence SEQ ID NOs: 634, 832, 837, 838, 1020, 1039, 1048, 1049, 1055, 1056, 1064, 1065, 1066, 1067, 1068, 1069, 1122, 1169, and 1184, and the sense strand comprises the nucleotide sequence SEQ ID NOs: 28, 226, 231, 232, 414, 433, 442, 443, 449, 450, 458, 459, 460, 461, 462, 463, 516, 563, and 578. In some embodiments, the antisense strand consists of the nucleotide sequence SEQ ID NOs: 634, 832, 837, 838, 1020, 1039, 1048, 1049, 1055, 1056, 1064, 1065, 1066, 1067, 1068, 1069, 1122, 1169, and 1184, and the sense strand consists of the nucleotide sequence SEQ ID NOs: 28, 226, 231, 232, 414, 433, 442, 443, 449, 450, 458, 459, 460, 461, 462, 463, 516, 563, and 578.

In some embodiments, the antisense strand comprises a nucleotide sequence comprising at least 15 contiguous nucleotides (for example, 15, 16, 17, 18, 19, 20, or 21 contiguous nucleotides) differing by no more than 1, 2, 3, or 4 nucleotides from a sequence selected from SEQ ID NOs: 1048, 1055, 1065, 1067, 1068, 1069, and 1122. In some embodiments, the sense strand comprises a nucleotide sequence comprising at least 15 contiguous nucleotides (for example, 15, 16, 17, 18, or 19 contiguous nucleotides) differing by no more than 1, 2, 3, or 4 nucleotides from a nucleotide sequence selected from SEQ ID NOs: 442, 449, 459, 461, 462, 463, and 516.

In some embodiments, the antisense strand comprises a nucleotide sequence comprising at least 15 contiguous nucleotides (for example, 15, 16, 17, 18, 19, 20, or 21 contiguous nucleotides) differing by no more than 1, 2, 3, or 4 nucleotides from a sequence selected from SEQ ID NOs: 3441, 3448, 3458, 3460, 3461, 3462, and 3514. In some embodiments, the sense strand comprises a nucleotide sequence comprising at least 15 contiguous nucleotides (for example, 15, 16, 17, 18, or 19 contiguous nucleotides) differing by no more than 1, 2, 3, or 4 nucleotides from a nucleotide sequence selected from SEQ ID NOs: 2861, 2868, 2878, 2880, 2881, 2882, and 2923.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1048, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 442. In some embodiments, the antisense strand comprises a nucleotide sequence differing by no more than 4 nucleotides (for example, 1, 2, 3, or 4 nucleotides) from SEQ ID NO: 1048, and the sense strand comprises a nucleotide sequence differing by no more than 4 nucleotides (for example, 1, 2, 3, or 4 nucleotides) from SEQ ID NO: 442. In some embodiments, the antisense strand comprises the nucleotide sequence SEQ ID NO: 1048, and the sense strand comprises the nucleotide sequence SEQ ID NO: 442. In some embodiments, the antisense strand consists of the nucleotide sequence SEQ ID NO: 1048, and the sense strand consists of the nucleotide sequence SEQ ID NO: 442.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1055, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 449. In some embodiments, the antisense strand comprises a nucleotide sequence differing by no more than 4 nucleotides (for example, 1, 2, 3, or 4 nucleotides) from SEQ ID NO: 1055, and the sense strand comprises a nucleotide sequence differing by no more than 4 nucleotides (for example, 1, 2, 3, or 4 nucleotides) from SEQ ID NO: 449. In some embodiments, the antisense strand comprises the nucleotide sequence SEQ ID NO: 1055, and the sense strand comprises the nucleotide sequence SEQ ID NO: 449. In some embodiments, the antisense strand consists of the nucleotide sequence SEQ ID NO: 1055, and the sense strand consists of the nucleotide sequence SEQ ID NO: 449.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1065, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 459. In some embodiments, the antisense strand comprises a nucleotide sequence differing by no more than 4 nucleotides (for example, 1, 2, 3, or 4 nucleotides) from SEQ ID NO: 1065, and the sense strand comprises a nucleotide sequence differing by no more than 4 nucleotides (for example, 1, 2, 3, or 4 nucleotides) from SEQ ID NO: 459. In some embodiments, the antisense strand comprises the nucleotide sequence SEQ ID NO: 1065, and the sense strand comprises the nucleotide sequence SEQ ID NO: 459. In some embodiments, the antisense strand consists of the nucleotide sequence SEQ ID NO: 1065, and the sense strand consists of the nucleotide sequence SEQ ID NO: 459.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1067, and the sense strand comprises a nucleotide sequence comprising at least 15 contiguous nucleotides (for example, 15, 16, 17, 18, or 19 contiguous nucleotides)

differing by no more than 4 nucleotides (for example, 1, 2, 3, or 4 nucleotides) from SEQ ID NO: 461. In some embodiments, the antisense strand comprises a nucleotide sequence differing by no more than 4 nucleotides (for example, 1, 2, 3, or 4 nucleotides) from SEQ ID NO: 1067, and the sense strand comprises a nucleotide sequence differing by no more than 4 nucleotides (for example, 1, 2, 3, or 4 nucleotides) from SEQ ID NO: 461. In some embodiments, the antisense strand comprises the nucleotide sequence SEQ ID NO: 1067, and the sense strand comprises the nucleotide sequence SEQ ID NO: 461. In some embodiments, the antisense strand consists of the nucleotide sequence SEQ ID NO: 1067, and the sense strand consists of the nucleotide sequence SEQ ID NO: 461.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1068, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 462. In some embodiments, the antisense strand comprises a nucleotide sequence differing by no more than 4 nucleotides (for example, 1, 2, 3, or 4 nucleotides) from SEQ ID NO: 1068, and the sense strand comprises a nucleotide sequence differing by no more than 4 nucleotides (for example, 1, 2, 3, or 4 nucleotides) from SEQ ID NO: 462. In some embodiments, the antisense strand comprises the nucleotide sequence SEQ ID NO: 1068, and the sense strand comprises the nucleotide sequence SEQ ID NO: 462. In some embodiments, the antisense strand consists of the nucleotide sequence SEQ ID NO: 1068, and the sense strand consists of the nucleotide sequence SEQ ID NO: 462.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1069, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 463. In some embodiments, the antisense strand comprises a nucleotide sequence differing by no more than 4 nucleotides (for example, 1, 2, 3, or 4 nucleotides) from SEQ ID NO: 1069, and the sense strand comprises a nucleotide sequence differing by no more than 4 nucleotides (for example, 1, 2, 3, or 4 nucleotides) from SEQ ID NO: 463. In some embodiments, the antisense strand comprises the nucleotide sequence SEQ ID NO: 1069, and the sense strand comprises the nucleotide sequence SEQ ID NO: 463. In some embodiments, the antisense strand consists of the nucleotide sequence SEQ ID NO: 1069, and the sense strand consists of the nucleotide sequence SEQ ID NO: 463.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 1122, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 516. In some embodiments, the antisense strand comprises a nucleotide sequence differing by no more than 4 nucleotides (for example, 1, 2, 3, or 4 nucleotides) from SEQ ID NO: 1122, and the sense strand comprises a nucleotide sequence differing by no more than 4 nucleotides (for example, 1, 2, 3, or 4 nucleotides) from SEQ ID NO: 516. In some embodiments, the antisense strand comprises the nucleotide sequence SEQ ID NO: 1122, and the sense strand comprises the nucleotide sequence SEQ ID NO: 516. In some embodiments, the antisense strand consists of the nucleotide sequence SEQ ID NO: 1122, and the sense strand consists of the nucleotide sequence SEQ ID NO: 516.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2437, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2426. In some embodiments, the antisense strand comprises a nucleotide sequence differing by no more than 4 nucleotides (for example, 1, 2, 3, or 4 nucleotides) from SEQ ID NO: 2437, and the sense strand comprises a nucleotide sequence differing by no more than 4 nucleotides (for example, 1, 2, 3, or 4 nucleotides) from SEQ ID NO: 2426. In some embodiments, the antisense strand comprises the nucleotide sequence SEQ ID NO: 2437, and the sense strand comprises the nucleotide sequence SEQ ID NO: 2426. In some embodiments, the antisense strand consists of the nucleotide sequence SEQ ID NO: 2437, and the sense strand consists of the nucleotide sequence SEQ ID NO: 2426.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2438, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2427. In some embodiments, the antisense strand comprises a nucleotide sequence differing by no more than 4 nucleotides (for example, 1, 2, 3, or 4 nucleotides) from SEQ ID NO: 2438, and the sense strand comprises a nucleotide sequence differing by no more than 4 nucleotides (for example, 1, 2, 3, or 4 nucleotides) from SEQ ID NO: 2427. In some embodiments, the antisense strand comprises the nucleotide sequence SEQ ID NO: 2438, and the sense strand comprises the nucleotide sequence SEQ ID NO: 2427. In some embodiments, the antisense strand consists of the nucleotide sequence SEQ ID NO: 2438, and the sense strand consists of the nucleotide sequence SEQ ID NO: 2427.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2439, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2428. In some embodiments, the antisense strand comprises a nucleotide sequence differing by no more than 4 nucleotides (for example, 1, 2, 3, or 4 nucleotides) from SEQ ID NO: 2439, and the sense strand comprises a nucleotide sequence differing by no more than 4 nucleotides (for example, 1, 2, 3, or 4 nucleotides) from SEQ ID NO: 2428. In some embodiments, the antisense strand comprises the nucleotide sequence SEQ ID NO: 2439, and the sense strand comprises the nucleotide sequence SEQ ID NO: 2428. In some embodiments, the antisense strand consists of the nucleotide sequence SEQ ID NO: 2439, and the sense strand consists of the nucleotide sequence SEQ ID NO: 2428.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2440, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2429. In some embodiments, the antisense strand comprises a nucleotide sequence differing by no more than 4 nucleotides (for example, 1, 2, 3, or 4 nucleotides) from SEQ ID NO: 2440, and the sense strand comprises a nucleotide sequence differing by no more than 4 nucleotides (for example, 1, 2, 3, or 4 nucleotides) from SEQ ID NO: 2429. In some embodiments, the antisense strand comprises the nucleotide sequence SEQ ID NO: 2440, and the sense strand comprises the nucleotide sequence SEQ ID NO: 2429. In some embodiments, the antisense strand consists of the nucleotide sequence SEQ ID NO: 2440, and the sense strand consists of the nucleotide sequence SEQ ID NO: 2429.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2441, and the sense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2430. In some embodiments, the antisense strand comprises a nucleotide sequence differing by no more than 4 nucleotides (for example, 1, 2, 3, or 4 nucleotides) from SEQ ID NO: 2441, and the sense strand comprises a nucleotide sequence differing by no more than 4 nucleotides (for example, 1, 2, 3, or 4 nucleotides) from SEQ ID NO: 2430. In some embodiments, the antisense strand comprises the nucleotide sequence SEQ ID NO: 2441, and the sense strand comprises the nucleotide sequence SEQ ID NO: 2430. In some embodiments, the antisense strand consists of the nucleotide sequence SEQ ID NO: 2441, and the sense strand consists of the nucleotide sequence SEQ ID NO: 2430.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2442, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2431. In some embodiments, the antisense strand comprises a nucleotide sequence differing by no more than 4 nucleotides (for example, 1, 2, 3, or 4 nucleotides) from SEQ ID NO: 2442, and the sense strand comprises a nucleotide sequence differing by no more than 4 nucleotides (for example, 1, 2, 3, or 4 nucleotides) from SEQ ID NO: 2431. In some embodiments, the antisense strand comprises the nucleotide sequence SEQ ID NO: 2442, and the sense strand comprises the nucleotide sequence SEQ ID NO: 2431. In some embodiments, the antisense strand consists of the nucleotide sequence SEQ ID NO: 2442, and the sense strand consists of the nucleotide sequence SEQ ID NO: 2431.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2443, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2432. In some embodiments, the antisense strand comprises a nucleotide sequence differing by no more than 4 nucleotides (for example, 1, 2, 3, or 4 nucleotides) from SEQ ID NO: 2443, and the sense strand comprises a nucleotide sequence differing by no more than 4 nucleotides (for example, 1, 2, 3, or 4 nucleotides) from SEQ ID NO: 2432. In some embodiments, the antisense strand comprises the nucleotide sequence SEQ ID NO: 2443, and the sense strand comprises the nucleotide sequence SEQ ID NO: 2432. In some embodiments, the antisense strand consists of the nucleotide sequence SEQ ID NO: 2443, and the sense strand consists of the nucleotide sequence SEQ ID NO: 2432.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2444, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2433. In some embodiments, the antisense strand comprises a nucleotide sequence differing by no more than 4 nucleotides (for example, 1, 2, 3, or 4 nucleotides) from SEQ ID NO: 2444, and the sense strand comprises a nucleotide sequence differing by no more than 4 nucleotides (for example, 1, 2, 3, or 4 nucleotides) from SEQ ID NO: 2433. In some embodiments, the antisense strand comprises the nucleotide sequence SEQ ID NO: 2444, and the sense strand comprises the nucleotide sequence SEQ ID NO: 2433. In some embodiments, the antisense strand consists of the nucleotide sequence SEQ ID NO: 2444, and the sense strand consists of the nucleotide sequence SEQ ID NO: 2433.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2445, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2434. In some embodiments, the antisense strand comprises a nucleotide sequence differing by no more than 4 nucleotides (for example, 1, 2, 3, or 4 nucleotides) from SEQ ID NO: 2445, and the sense strand comprises a nucleotide sequence differing by no more than 4 nucleotides (for example, 1, 2, 3, or 4 nucleotides) from SEQ ID NO: 2434. In some embodiments, the antisense strand comprises the nucleotide sequence SEQ ID NO: 2445, and the sense strand comprises the nucleotide sequence SEQ ID NO: 2434. In some embodiments, the antisense strand consists of the nucleotide sequence SEQ ID NO: 2445, and the sense strand consists of the nucleotide sequence SEQ ID NO: 2434.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2446, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2435. In some embodiments, the antisense strand comprises a nucleotide sequence differing by no more than 4 nucleotides (for example, 1, 2, 3, or 4 nucleotides) from SEQ ID NO: 2446, and the sense strand comprises a nucleotide sequence differing by no more than 4 nucleotides (for example, 1, 2, 3, or 4 nucleotides) from SEQ ID NO: 2435. In some embodiments, the antisense strand comprises the nucleotide sequence SEQ ID NO: 2446, and the sense strand comprises the nucleotide sequence SEQ ID NO: 2435. In some embodiments, the antisense strand consists of the nucleotide sequence SEQ ID NO: 2446, and the sense strand consists of the nucleotide sequence SEQ ID NO: 2435.

In some embodiments, the antisense strand comprises a nucleotide sequence comprising at least 15 contiguous nucleotides (for example, 15, 16, 17, 18, 19, 20, or 21 contiguous nucleotides) differing by no more than 4 nucleotides (for example, 1, 2, 3, or 4 nucleotides) from SEQ ID NO: 2447, and the sense strand comprises a nucleotide sequence comprising at least 15 contiguous nucleotides (for example, 15, 16, 17, 18, or 19 contiguous nucleotides) differing by no more than 4 nucleotides (for example, 1, 2, 3, or 4 nucleotides) from SEQ ID NO: 2436. In some embodiments, the antisense strand comprises a nucleotide sequence differing by no more than 4 nucleotides (for example, 1, 2, 3, or 4 nucleotides) from SEQ ID NO: 2447, and the sense strand comprises a nucleotide sequence differing by no more than 4 nucleotides (for example, 1, 2, 3, or 4 nucleotides) from SEQ ID NO: 2436. In some embodiments, the antisense strand comprises the nucleotide sequence SEQ ID NO: 2447, and the sense strand comprises the nucleotide sequence SEQ ID NO: 2436. In some embodiments, the antisense strand consists of the nucleotide sequence SEQ ID NO: 2447, and the sense strand consists of the nucleotide sequence SEQ ID NO: 2436.

A DUX4 RNAi agent described herein can contain one or more mismatches to the target sequence. In some embodiments, a DUX4 RNAi agent as described herein contains no more than 4 mismatches (e.g., no more than 4, 3, 2, 1, or 0 mismatches to the target sequence). If the antisense strand of the RNAi agent contains mismatches to a target sequence, it may be preferable that the area of mismatch is not located in the center of the region of complementarity. If the antisense strand of the RNAi agent contains mismatches to the target sequence, it may be preferable that the mismatch be restricted to be within the last 5 nucleotides from either the 5'- or 3'-end of the region of complementarity. For example, for a 21 nucleotide RNAi agent, the strand which is complementary to a region of, e.g., DUX4, generally does not contain any mismatch within the central 11 nucleotides. The methods described herein or methods known in the art can be used to determine whether an RNAi agent containing a mismatch to a target sequence is effective in inhibiting the expression of DUX4. Consideration of the efficacy of RNAi agents with mismatches in inhibiting expression of a target gene is important, especially if the particular region of complementarity in a target gene is known to have polymorphic sequence variation within the population.

In some embodiments, any one of the RNAi agents described herein can reduce expression levels of DUX4. In some embodiments, reduction in expression levels is assayed using a DUX4 reporter construct, e.g., see Examples 1 and 2. In some embodiments, DUX4 RNA expression is measured using a reporter or tag (e.g., luciferase, or fluorescent tag). The skilled artisan will appreciate that various approaches to generating a reporter construct for assessing RNAi agent activity may be used in the art, including commercially available kits, e.g., the psiCHECK-2 vector (Promega). In some embodiments, any one of the RNAi agents described herein can reduce expression levels of a DUX4 reporter when assayed in cultured cells. Any suitable cells known in the art may be used to assess the RNAi agents. In some embodiments, the cultured cells are Hepal-6. In some embodiments, administration of any one of the RNAi agents disclosed herein to a cultured cell results in a reduction in expression level of a DUX4. In some embodiments, administration of the RNAi agent results in at least a 55% reduction in expression levels of the DUX4 reporter. In some embodiments, administration of the RNAi agent results in at least a 60% reduction in expression levels of the DUX4 reporter. In some embodiments, administration of the RNAi agent results in at least a 65% reduction in expression levels of the DUX4 reporter. In some embodiments, administration of the RNAi agent results in at least a 70% reduction in expression levels of the DUX4 reporter. In some embodiments, administration of the RNAi agent results in at least a 75% reduction in expression levels of the DUX4 reporter. In some embodiments, administration of the RNAi agent results in at least an 80% reduction in expression levels of the DUX4 reporter. In some embodiments, administration of the RNAi agent results in at least a 85% reduction in expression levels of the DUX4 reporter. In some embodiments, administration of the RNAi agent results in at least a 90% reduction in expression levels of the DUX4 reporter. In some embodiments, administration of the RNAi agent results in at least a 95% reduction in expression levels of the DUX4 reporter.

In some embodiments, reduction in expression levels is assayed using an RT-qPCR assay, e.g., see Example 3, to perform relative quantification of mRNA expression of a DUX4 panel, e.g., a panel of DUX4's targets, in cardiomyocytes (e.g., FSHD MB200 cells, which is human myoblast cell line used to study facioscapulohumeral muscular dystrophy (FSHD)). In some embodiments, reduction in DUX4 expression is assessed by determining the mRNA expression level of a panel of DUX4 targets, e.g., a DUX4 panel comprising one or more gene of CCNA1, SLC34A2, ZSCAN4, PRAMEF2, PRAMEF17, PRAMEF12, LEUTX, HNRNPCL1, RFPL4B, PRAMEF1, PRAMEF19, TRIM43B, TRIM43, PRAMEF14, PRAMEF11, KDM4E, RFPL2, PRAMEF15, PRAMEF6, ZNF280A, PRAMEF9, TRIM49, KHDC1P1, PRAMEF4, TPRX1, TRIM49B, TRIM51CP, KLF17, TRIM51BP, TRIM53CP, C1DP2, TRIM53AP, TRIM51, PRAMEF8, MBD3L2B, KHDC1L, ALPG, TRIM49C, MBD3L2, ZNF705G, MBD3L3, PRAMEF7, TRIM43CP, PRAMEF10, HNRNPCL4, TRIM53BP, TRIM51EP, or MBD3L5. In some embodiments, the reduction in DUX4 expression is assessed by determining the mRNA expression level of a panel of DUX4 targets, e.g., a DUX4 panel comprising one or more of LEUTX, TRIM43, KHDC1L, MBD3L2, CCNA1, ZSCAN4, SLC34A2, or PRAMEF6. In some embodiments, the reduction in DUX4 expression is assessed by determining the mRNA expression level of a panel of DUX4 targets, e.g., a DUX4 panel comprising one or more of KHDC1L, LEUTX, MBD3L2, and ZSCAN4. The skilled artisan will appreciate that various approaches to quantify knockdown of DUX4 expression (e.g., via quantify of expression of the DUX4 panel) for assessing RNAi agent activity may be used in the art, including commercially available kits, e.g., from Thermo. In some embodiments, any one of the RNAi agents described herein can reduce mRNA expression level of the DUX4 panel when assayed in cultured cells. Any suitable cells known in the art may be used to assess the RNAi agents. In some embodiments, the cultured cells are FSHD MB200 cells. In some embodiments, administration of any one of the RNAi agents disclosed herein to a cultured cell results in a reduction in mRNA expression level of the DUX4 panel. In some embodiments, administration of the RNAi agent results in at least a 30% reduction in mRNA expression level of the DUX4 panel. In some embodiments, administration of the RNAi agent results in at least a 35% reduction in mRNA expression level of the DUX4 panel. In some embodiments, administration of the RNAi agent results in at least a 40% reduction in mRNA expression level of the DUX4 panel. In some embodiments, administration of the RNAi agent results in at least a 45% reduction in mRNA expression level of the DUX4 panel. In some embodiments, administration of the RNAi agent results in at least a 50% reduction in mRNA expression level of the DUX4 panel. In some embodiments, administration of the RNAi agent results in at least a 55% reduction in mRNA expression level of the DUX4 panel. In some embodiments, administration of the RNAi agent results in at least a 60% reduction in mRNA expression level of the DUX4 panel. In some embodiments, administration of the RNAi agent results in at least a 65% reduction in mRNA expression level of the DUX4 panel. In some embodiments, administration of the RNAi agent results in at least a 70% reduction in mRNA expression level of the DUX4 panel. In some embodiments, administration of the RNAi agent results in at least a 75% reduction in mRNA expression level of the DUX4 panel. In some embodiments, administration of the RNAi agent results in at least an 80% reduction in mRNA expression level of the DUX4 panel. In some embodiments, administration of the RNAi agent results in at least an 85% reduction in mRNA expression level of the DUX4 panel. In some embodiments, administration of the RNAi agent results in at least a 90% reduction in mRNA expression level of the DUX4 panel. In some embodiments, administration of the RNAi agent results in at least a 95% reduction in mRNA expression level of the DUX4 panel.

Single-Stranded Antisense Oligonucleotides

In some embodiments, the oligonucleotide is a single-stranded antisense oligonucleotide, or "ASO." ASOs comprise an antisense strand with at least partial complementary to a target sequence in an RNA. Upon binding to a target sequence, downregulation of the RNA may be achieved through various mechanisms, including, but not limited to, sterically blocking translation or recruitment of RNase H.

In some embodiments, the ASO comprises a nucleic acid sequence of at least 14 contiguous nucleotides (for example, 14, 15, 16, 17, 18, 19, 20, or 21 contiguous nucleotides) that differ by no more than 1, 2, 3, or 4 nucleotides from any one of SEQ ID NOs: 607-1212 or 1819-2424. In some embodiments, the ASO comprises a nucleotide sequence of any one of SEQ ID NOs: 607-1212 or 1819-2424. In some embodiments, the ASO comprises a nucleic acid sequence of at least 14 contiguous nucleotides (for example, 14, 15, 16, 17, 18, 19, 20, or 21 contiguous nucleotides) that differ by no more than 1, 2, 3, or 4 nucleotides from any one of SEQ ID NOs: 2437-2447. In some embodiments, the ASO comprises a nucleotide sequence of any one of SEQ ID NOs: 2437-2447.

In some embodiments, the single-stranded ASO comprises a nucleic acid sequence comprising at least 14, 15, 16, 17, 18, 19, 20, or 21 contiguous nucleotides that differ by no more than 1, 2, 3, or 4 nucleotides from any one of SEQ ID NOs: 634, 832, 837, 838, 1020, 1039, 1048, 1049, 1055, 1056, 1064, 1065, 1066, 1067, 1068, 1069, 1122, 1169, 1184, 1846, 2044, 2049, 2232, 2251, 2260, 2261, 2267, 2268, 2276, 2277, 2278, 2279, 2280, 2281, 2381, 2396, 2050, 2437, 2438, 2439, 2440, 2441, 2442, 2443, 2334, 2444, 2445, 2446, and 2447.

In some embodiments, the ASO comprises 2'-deoxy ribonucleotides and phosphorothioate internucleoside linkages.

In some embodiments, the ASO is a "gapmer" ASO comprising a 2'-deoxy "gap" region flanked by "wings" having nucleotides with 2'-modified ribonucleotides. In some embodiments, the ASO is an "MOE gapmer" in which the 2'-modified ribonucleotide is a 2'-O-methoxyethyl (2'-MOE or simply MOE) modification, and each of the internucleoside linkages is a phosphorothioate.

Modified Nucleotides

The oligonucleotides disclosed herein may be modified or unmodified. In some embodiments, any one of the oligonucleotides contain one or more modifications. As used herein, a modification to a nucleotide or "modified nucleotide" refers to any nucleotide other than the canonical ribonucleotides adenine, guanine, cytosine, and uracil.

In some embodiments, the oligonucleotide comprises one or more modified nucleotides. In some embodiments, no more than 1, 2, 3, 4, or 5 of the nucleotides of the oligonucleotide are unmodified nucleotides. In some embodiments, all nucleotides of the oligonucleotide are modified nucleotides.

In some embodiments, wherein the oligonucleotide is an RNAi agent, the antisense strand comprises one or more modified nucleotides. In some embodiments, no more than 1, 2, 3, 4, or 5 of the nucleotides of the antisense strand are unmodified nucleotides. In some embodiments, all nucleotides of the antisense strand are modified nucleotides.

In some embodiments, wherein the oligonucleotide is an RNAi agent, the sense strand comprises one or more modified nucleotides. In some embodiments, no more than 1, 2, 3, 4, or 5 of the nucleotides of the sense strand are unmodified nucleotides. In some embodiments, all nucleotides of the sense strand are modified nucleotides.

Modified nucleotides include, but are not limited to 2'-modified nucleotides, 3' to 3' linkages (inverted) nucleotides, bridged nucleotides, 2',3'-seco nucleotide mimics (e.g., unlocked nucleobase analogues (UNAs), locked nucleotides (LNAs), 5'-(S)-methyl-2'-deoxy-2'-fluoronucleotide (5'Me-Nf), vinyl phosphonate deoxyribonucleotides, vinyl phosphonate nucleotides, a nucleotide comprising a 5'-phosphorothioate group, a nucleotide comprising a 5'-methylphosphonate group, a nucleotide comprising a 5' phosphate or 5' phosphate mimic and N-(methane sulfonyl) phosphoramidate group. In some embodiments, 2'-modified nucleotides (e.g., a nucleotide with a group other than a hydroxyl group at the 2' position of the five-membered sugar ring) include, but are not limited to, 2'-O-methyl nucleotides (represented herein as a lower case letter n in a nucleotide sequence), 2'-deoxy-2'-fluoro nucleotides (represented herein as Nf, also represented herein as 2'-fluoro nucleotide). In some embodiments, a modified nucleotide is a nucleotide comprising a 5'-methylphosphate group. In some embodiments, a modified nucleotide is a nucleotide comprising a 5'-C-methylphosphate group.

In some embodiments, modified nucleotides include, but are not limited to, deoxyribonucleotides, nucleotide mimics, abasic nucleotides, 5' to 5' linkages (inverted) nucleotides, non-natural base-comprising nucleotides, peptide nucleic acids (PNAs), 3'-O-methoxy (2' internucleoside linked) nucleotides, 2'-deoxy-2'-fluoro-arabino nucleotides, cyclopropyl phosphonate nucleotides (cPrpN), vinyl phosphonate 2'-(methoxyethyl) unlocked nucleotides, a nucleotide comprising 2-hydroxymethyl-tetrahydrofurane-5-phosphate, 2'-deoxy nucleotides (represented herein as dN), 2'-methoxy ethyloxy (2'-O-(2-methoxylethyl)) nucleotides, 2'-amino nucleotides, and 2'-alkyl nucleotides. It is not necessary for all positions in a given compound to be uniformly modified. Conversely, more than one modification may be incorporated in a single oligonucleotide. Modification at one nucleotide is independent of modification at another nucleotide.

In some embodiments, the nucleotide modification comprises a deoxyribonucleotide, a 3'-terminal deoxythymidine (dT) nucleotide, an abasic nucleotide, a 2'-modified nucleotide, a 3' to 3' linkages (inverted) nucleotide, a 5' to 5' linkages (inverted) nucleotide, a non-natural base-comprising nucleotide, a nucleotide comprising a 5'-phosphorothioate group, a nucleotide comprising a 5'-methylphosphonate group, a nucleotide comprising a 5' phosphate or 5' phosphate mimic, a nucleotide comprising 2-hydroxymethyl-tetrahydrofurane-5-phosphate, or a nucleotide comprising a N-(methane sulfonyl) phosphoramidate group. In some embodiments, the nucleotide modification comprises a nucleotide comprising a 5'-methylphosphate group. In some embodiments, a modified nucleotide is a nucleotide comprising a 5'-C-methylphosphate group. In some embodiments, the oligonucleotide comprises a modified nucleotide selected from the group consisting of a deoxy nucleotide, a 3'-terminal deoxythymidine (dT) nucleotide, a 3'-3' inverted nucleotide linkage, a 5'-5' inverted nucleotide linkage, a 5'-(E)-vinylphosphonate-2'-O-methyl-uridine-3'-phosphate, a 5'-(E)-vinylphosphonate-2'-O-methyl-uridine-3'-phosphorothioate, and a combination thereof.

In some embodiments, the one or more modifications is selected from a ribose modification, a backbone modification, a nucleobase modification, or a combination thereof. In some embodiments, the one or more modifications is a combination of a ribose modification, a backbone modification, and/or a nucleobase modification.

In some embodiments, the ribose modification comprises a locked nucleic acid (LNA), a tricyclo-DNA (tcDNA), 2'-deoxy-2'-fluoro, 2'-O-methyl, 2'-methoxyethyl (2'-MOE), 2'-deoxy-2'-arabino-fluoro, 2'-O-benzyl, 2'-O-methyl-4-pyridine, 2' cyclic ethyl (cET), phosphorodiamidate morpholino (PMO), glycol nucleic acid (GNA), unlocked nucleic acid (UNA), a threose nucleic acid (TNA), or a combination thereof. In some embodiments, the ribose modification comprises a 2'-deoxy-2'-fluoro, 2'-O-methyl, 2'-methoxyethyl (2'-MOE), glycol nucleic acid (GNA), unlocked nucleic acid (UNA), a threose nucleic acid (TNA), or a combination thereof. In some embodiments, the ribose modification comprises a 2'-deoxy-2'-fluoro, 2'-O-methyl, glycol nucleic acid (GNA), unlocked nucleic acid (UNA), a threose nucleic acid (TNA), or a combination thereof. In some embodiments, the ribose modification is 2'-deoxy-2'-fluoro modification, a 2'-O-methyl modification, or a combination thereof.

In some embodiments, the oligonucleotide comprises one or more nucleobase modifications. Nucleobase modifications include, for example, synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine, or combinations thereof.

In some embodiments, the oligonucleotide comprises one or more backbone modification or non-standard linkages (e.g., modified internucleoside linkages). In some embodiments, a backbone modification is a non-phosphate-containing covalent internucleoside linkage. Modified internucleoside linkages or backbones include, but are not limited to, 5'-phosphorothioate groups (represented herein as a lower case “s”), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified backbone or modified internucleoside linkage lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioform acetyl backbones, alkene-containing backbones, sulfamate backbones, methyieneimino and methylenehydrazino backbones, sulfonate and sulfonamide backbones, amide backbones, and other backbones having mixed N, O, S, and $CH_2$ components.

In some embodiments, the backbone modification comprises phosphorothioate.

In some embodiments, any one of the oligonucleotides disclosed herein further comprise a sequence of 3'-terminal deoxythymidine (dT) nucleotides. In some embodiments, any one of the antisense strands described herein further comprises at least one terminal dT nucleotide. In some embodiments, any one of the antisense strands described herein further comprises 2 or more terminal dT nucleotides, e.g., 2, 3, 4, or more terminal dT nucleotides. In some embodiments, wherein the oligonucleotide is an RNAi agent, any one of the sense strands described herein further comprises at least one terminal dT nucleotide. In some embodiments, any one of the sense strands described herein further comprises 2 or more terminal dT nucleotides, e.g., 2, 3, 4, or more terminal dT nucleotides. In some embodiments, the antisense and sense strand of an RNAi agent herein each contain one or more terminal dT nucleotides.

In some embodiments, any one of the oligonucleotides disclosed herein further comprises at least one phosphorothioate internucleoside or phosphorodithioate internucleoside linkage. In some embodiments, any one of the oligonucleotides disclosed herein further comprises at least one phosphorothioate internucleoside linkage. In some embodiments, at least one phosphorothioate internucleoside linkage is at the 5' end of the antisense strand. In some embodiments, the oligonucleotide comprises at least 2 phosphorothioate internucleoside linkages at the 5' end of the antisense strand. In some embodiments, at least one phosphorothioate internucleoside linkage is at the 3' end of the antisense strand. In some embodiments, the oligonucleotide comprises at least 2 phosphorothioate internucleoside linkages at the 3' end of the antisense strand. In some embodiments, wherein the oligonucleotide is an RNAi agent, the at least one phosphorothioate internucleoside linkage is at the 5' end of the sense strand. In some embodiments, the oligonucleotide comprises at least 2 phosphorothioate internucleoside linkages at the 5' end of the sense strand. In some embodiments, the at least one phosphorothioate internucleoside linkage is at the 3' end of the sense strand. In some embodiments, the oligonucleotide comprises at least 2 phosphorothioate internucleoside linkages at the 3' end of the sense strand.

In some embodiments, any one of the oligonucleotides disclosed herein further comprises a terminal, chiral modification. In some embodiments, the terminal chiral modification is at the first internucleoside linkage at the 3' end of the sense and/or antisense strand. In some embodiments, the terminal chiral modification is at the first and second internucleoside linkage at the 3' end of the sense and/or antisense strand. In some embodiments, the chiral modification comprises a phosphorus atom of the internucleoside linkage being in either Rp or Sp configuration. In some embodiments, the siRNA agent further comprises a terminal, chiral modification occurring at the first internucleoside linkage at the 3' end of the antisense strand, having the linkage phosphorus atom in Sp configuration, a terminal, chiral modification occurring at the first internucleoside linkage at the 5' end of the antisense strand, having the linkage phosphorus atom in Rp configuration, and a terminal, chiral modification occurring at the first internucleoside linkage at the 5' end of the sense strand, having the linkage phosphorus atom in either Rp configuration or Sp configuration. In some embodiments, the siRNA agent further comprises a terminal, chiral modification occurring at the first and second internucleoside linkages at the 3' end of the antisense strand, having the linkage phosphorus atom in Sp configuration, a terminal, chiral modification occurring at the first internucleoside linkage at the 5' end of the antisense strand, having the linkage phosphorus atom in Rp configuration, and a terminal, chiral modification occurring at the first internucleoside linkage at the 5' end of the sense strand, having the linkage phosphorus atom in either Rp or Sp configuration. In some embodiments, the siRNA agent further comprises a terminal, chiral modification occurring at the first, second, and third internucleoside linkages at the 3' end of the antisense strand, having the linkage phosphorus atom in Sp configuration, a terminal, chiral modification occurring at the first internucleoside linkage at the 5' end of the antisense strand, having the linkage phosphorus atom in Rp configuration, and a terminal, chiral modification occurring at the first internucleoside linkage at the 5' end of the sense strand, having the linkage phosphorus atom in either Rp or Sp configuration. In some embodiments, the siRNA agent further comprises a terminal, chiral modification occurring at the first and second internucleoside linkages at the 3' end of the antisense strand, having the linkage phosphorus atom in Sp configuration, a terminal, chiral modification occurring at the third internucleoside linkages at the 3' end of the antisense strand, having the linkage phosphorus atom in Rp configuration, a terminal, chiral modification occurring at the first internucleoside linkage at the 5' end of the antisense strand, having the linkage phosphorus atom in Rp configuration, and a terminal, chiral modification occurring at the first internucleoside linkage at the 5' end of the sense strand, having the linkage phosphorus atom in either Rp or Sp configuration. In some embodiments, the siRNA agent further comprises a terminal, chiral modification occurring at the first and second internucleoside linkages at the 3' end of the antisense strand, having the linkage phosphorus atom in Sp configuration, a terminal, chiral modification occurring at the first and second internucleoside linkages at the 5' end of the antisense strand, having the linkage phosphorus atom in Rp configuration, and a terminal, chiral modification occurring at the first internucleoside linkage at the 5' end of the sense strand, having the linkage phosphorus atom in either Rp or Sp configuration.

In some embodiments, any one of the oligonucleotides disclosed herein further comprises a phosphate or phosphate mimic at the 5'-end of the antisense strand. In some embodiments, a phosphate or phosphate mimic at the 5'-end of the antisense strand is a 5'-vinyl phosphonate (VP). In some embodiments, a phosphate or phosphate mimic at the 5'-end of the antisense strand is a 5'-(E)-vinyl phosphonate (VP).

RNAi Agent Modification Motifs

In some embodiments, any one of the antisense or sense strands disclosed herein are modified according to a modification motif or pattern.

In some embodiments, an antisense strand disclosed herein comprises a modification pattern nsNfsnnnNfnNfNfnnnnNfnNfnnnsnsn, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, an antisense strand disclosed herein comprises a modification pattern vpUs-NfsnnnNfnNfNfnnnnNfnNfnnnsnsn, wherein vpUs is a 5'-vinylphosphonate-2'-O-methyl-uridine-3'-phosphorothioate; ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, a sense strand disclosed herein comprises a modification pattern nsnsnnNfnNfNfNfnnnnnnnnnn, wherein ns is a 2'-O-methyl-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, a sense strand disclosed herein comprises a modification pattern NfsnsNfnNfnNfnNfnNfnNfnNfnNfnNf, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, an RNAi agent disclosed herein comprises a sense strand and an antisense strand, wherein the sense strand comprises a modification pattern nsnsnnNfnNfNfNfnnnnnnnnnn, and the antisense strand comprises a modification pattern nsNfsnnnNfnNf NfnnnnNfnNfnnnsnsn, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, an RNAi agent disclosed herein comprises a sense strand and an antisense strand, wherein the sense strand comprises a modification pattern nsnsnnNfnNfNfNfnnnnnnnnnn, and the antisense strand comprises a modification pattern vpUsNfsnnn NfnNfNfnnnnNfnNfnnnsnsn, wherein vpUs is a 5'-vinylphosphonate-2'-O-methyl-uridine-3'-phosphorothioate; ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

In some embodiments, a strand of an RNAi agent comprises a modification pattern according to $Nfs_a(nNf)_bns_cn$, wherein n is a 2'-O-methyl-nucleoside-3'-phosphate; Nfs is a 2'-deoxy-2'-fluoro-nucleoside-3'-phosphorothioate; Nf is a 2'-deoxy-2'-fluoro-nucleoside-3'-phosphate; and ns is a 2'-O-methyl-nucleoside-3'-phosphorothioate; and wherein a is at least 1, b is 5-10, and c is at least 1. In some embodiments, a is at least 2, b is at least 8, and c is at least 2. In some embodiments, a is 2, b is 8, and c is 2. In some embodiments, the strand of the RNAi agent comprises the modification pattern NfsNfsnNfnNfnNfnNfnNfnNfnNfnNfnsnsn. In some embodiments, the strand is the antisense strand. In some embodiments, the antisense strand comprises the sequence of any one of SEQ ID Nos: 607-1212 or 1819-2424. In some embodiments, the antisense strand comprises the sequence of any one of SEQ ID NOs: 2437-2447. In some embodiments, the strand is the sense strand. In some embodiments, the sense strand comprises the sequence of any one of SEQ ID NOs: 1-606 or 1213-1818. In some embodiments, the sense strand comprises the sequence of any one of SEQ ID NOs: 2426-2436.

In some embodiments, a strand of an RNAi agent comprises a modification pattern according $ns_d(Nfn)_eNf$, wherein n is a 2'-O-methyl-nucleoside-3'-phosphate; Nf is a 2'-deoxy-2'-fluoro-nucleoside-3'-phosphate; and ns is a 2'-O-methyl-nucleoside-3'-phosphorothioate; and wherein d is at least 1, and e is 5-10. In some embodiments, d is at least 2 and e is at least 8. In some embodiments, the RNAi agent comprises the modification pattern nsnsNfnNfn NfnNfnNfnNfnNfnNfnNf. In some embodiments, the strand is the sense strand. In some embodiments, the sense strand comprises the sequence of any one of SEQ ID NOs: 1-606 or 1213-1818. In some embodiments, the sense strand comprises the sequence of any one of SEQ ID NOs: 2426-2436. In some embodiments, the RNAi agent comprises the modification pattern nsnsNfnNfnNfnNfnNfnNfn NfnNfnNfnsn. In some embodiments, the strand is the antisense strand. In some embodiments, the antisense strand comprises the sequence of any one of SEQ ID NOs: 607-1212 or 1819-2424. In some embodiments, the antisense strand comprises the sequence of any one of SEQ ID NOs: 2437-2447.

In some embodiments, the antisense strand comprises a modification pattern according to $Nfs_a(nNf)_bns_cn$, wherein n is a 2'-O-methyl-nucleoside-3'-phosphate; Nfs is a 2'-deoxy-2'-fluoro-nucleoside-3'-phosphorothioate; Nf is a 2'-deoxy-2'-fluoro-nucleoside-3'-phosphate; and ns is a 2'-O-methyl-nucleoside-3'-phosphorothioate; and wherein a is at least 1, b is 5-10, and c is at least 1, and the sense strand comprises a modification pattern according to $ns_d(Nfn)_eNf$, wherein n is a 2'-O-methyl-nucleoside-3'-phosphate; Nf is a 2'-deoxy-2'-fluoro-nucleoside-3'-phosphate; and ns is a 2'-O-methyl-nucleoside-3'-phosphorothioate; and wherein d is at least 1, and e is 5-10. In some embodiments, the antisense strand comprises a nucleotide sequence according to any one of SEQ ID NOs: 607-1212 or 1819-2424. In some embodiments, the sense strand comprises a nucleotide sequence according to any one of SEQ ID NOs: 1-606 or 1213-1818. In some embodiments, the antisense strand comprises a nucleotide sequence according to any one of SEQ ID NOs: 2437-2447. In some embodiments, the sense strand comprises a nucleotide sequence according to any one of SEQ ID NOs: 2426-2436.

In some embodiments, any one of the RNAi agents disclosed herein comprises a modification pattern wherein the antisense strand comprises the motif F(SF)nSnn, wherein n is from 2 to about 20, nn is 0 or 1, one of F and S is a 2'-deoxy-2'-fluoro modified nucleoside and the other of F and S is a 2'-O-methyl modified nucleoside. In some embodiments, each of the antisense and the sense strand is 17-23 nucleotides in length. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand sequence in Table 1F. In some embodiments, the sense strand corresponds to the unmodified sense strand sequence in Table 1F.

In some embodiments, any one of the RNAi agents disclosed herein comprises a modification pattern wherein the antisense strand comprises the chemical modification pattern of nNfnnnNfnNfNfnnnnNfnNfnnnnn and the sense strand comprises the chemical modification nnnnnnNfnNfNfNfnnnnnnnn, wherein n is a 2'-O-methyl-nucleoside and Nf is a 2'-deoxy-2'-fluoro-nucleoside. In some embodiments, the antisense strand corresponds to the unmodified nucleobase sequence according to any one of SEQ ID NOs: 607-1212. In some embodiments, the sense strand corresponds to the unmodified nucleobase sequence of any one according to SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand comprises a region having the formula X1-Y—X2, wherein Y is a subregion of from about 5 to about 12 linked nucleosides and each of X1 subregion and X2 subregion is, independently, a plurality of linked nucleosides having the formula FSFS, where one of F and S is a 2'-deoxy-2'-fluoro modified nucleoside and the other of F and S is a 2'-O-methyl modified nucleoside; and each internucleoside linkage of said X1 subregion and X2 subregion is, independently, a phosphodiester or a phosphorothioate internucleoside linkage. In some embodiments, each of the antisense and the sense strand is 20-23 nucleotides in length. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand comprises a contiguous sequence of linked nucleosides that define an alternating motif of the formula: 5'-Q(-L-Z-L-Q)n(-L-Z)nn-3', wherein: each L is an internucleoside linking group; either each Q is a 2'-deoxy-2'-fluoro nucleoside and each Z is a 2'-O-methyl nucleoside; or each Q is a 2'-O-methyl nucleoside and each Z is a 2'-deoxy-2'-fluoro nucleoside; and n is from 8 to 14 and nn is 0 or 1. In some embodiments, the antisense strand corresponds to the unmodified nucleobase sequence according to any one of SEQ ID NOs: 607-1212.

In some embodiments, any one of the RNAi agents disclosed herein comprises a modification pattern wherein the antisense strand is represented by the formula:

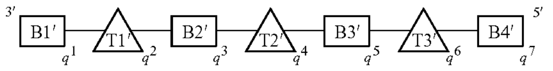

wherein, B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA; T1', T2', and T3' each independently represent a nucleotide comprising a chemical modification selected from the group consisting of DNA, RNA, LNA, 2'-deoxy-2'-fluoronucleotide, and 5'-(S)-methyl2'-deoxy-2'-fluoronucleotide; q1 is 4 to 15 nucleotides in length; q3 or q7 is independently 1-6 nucleotide(s) in length; q2 or q6 is independently 1-3 nucleotide(s) in length; q4 is 0-3 nucleotide(s) in length; and q5 is 0-10 nucleotide(s) in length; and wherein: the antisense strand has 2'-deoxy-2'-fluoro modifications, and wherein the 2'-deoxy-2'-fluoro modifications on the antisense strand consist of four, and only four, 2'-deoxy-2'-fluoro modifications or six, and only six, 2'-deoxy-2'-fluoro modifications. In some embodiments, the antisense strand is 19-25 nucleotides in length. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand and the sense strand are represented by the formula:

(I

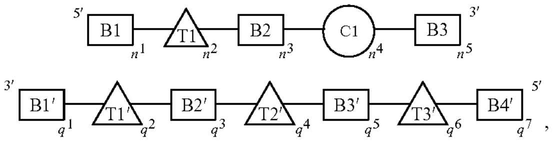

, wherein B1, B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA; C1 is a thermally destabilizing nucleotide, selected from the group consisting of i) a nucleotide that forms a mismatch pair with the opposing nucleotide in the antisense strand, ii) a nucleotide having an abasic modification, and iii) a nucleotide having a sugar modification, and placed at a site opposite to the seed region (positions 2-8) of the antisense strand; T1', T2', and T3' each independently represent a nucleotide comprising a modification providing the nucleotide a steric bulk that is less than or equal to the steric bulk of a 2'-OMe modification, wherein the modification is at the 2'-position of a ribose sugar of the nucleotide or at a position of a non-ribose nucleotide similar to the 2'-position of a ribose sugar; each n1, and q1 is independently 4 to 15 nucleotides in length; each q3, and q7 is independently 1-6 nucleotide (s) in length; each q2 and q6 is independently 1-3 nucleotide(s) in length; q5 is 0-10 nucleotide(s) in length; each n4, and q4 is independently 0-3 nucleotide (s) in length; n2 is 3 nucleotides in length, and T1 each are 2'-deoxy-2'-fluoronucleotides; n3 is 7 nucleotides in length, and B2 each are 2'-OMe nucleotides; and n5 is 3 nucleotides in length, and B3 each are 2'-OMe nucleotides. In some embodiments, wherein the antisense strand and sense strand are each 14 to 40 nucleotides. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand is represented by the formula:

(Is)

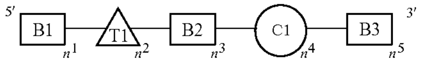

wherein: B1, B2, and B3 each independently represent a nucleotide containing a modification selected from the group consisting of 2'-O-alkyl, 2'-substituted alkoxy, 2'-substituted alkyl, 2'-halo, ENA, and BNA/LNA; C1 is a thermally destabilizing nucleotide, selected from the group consisting of i) a nucleotide that forms a mismatch pair with the opposing nucleotide in the antisense strand, ii) a nucleotide having an abasic modification, and iii) a nucleotide having a sugar modification, and placed at a site opposite to the seed region (positions 2-8) of the antisense strand; T1 represents a nucleotide comprising a 2'-deoxy-2'-fluoro modification; n1 or n3 is independently 4 to 15 nucleotides in length; n5 is 1-6 nucleotide(s) in length; n2 is 3; n4 is 0-3 nucleotide(s) in length; and wherein the sense strand has 2'-deoxy-2'-fluoro modifications, and wherein the 2'-deoxy-2'-fluoro modifications on the sense strand consist of four, and only four, 2'-deoxy-2'-fluoro modifications, wherein the four 2'-deoxy-2'-fluoro modifications are at positions 7 and 9-11 from the 5'-end of the sense strand. In some embodiments, wherein the antisense strand and sense strand are each 19-25 nucleotides. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand is complementary to at least one portion of a mRNA of the target gene (e.g., DUX4), wherein the oligonucleotide is represented by the formula:

(I)

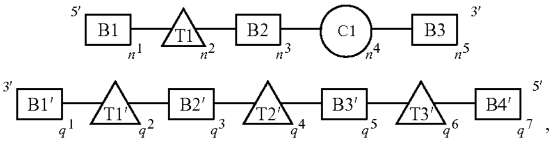

wherein: B1', B2', B3', and B4' each independently represent a nucleotide containing a modification selected from the group consisting of 2'-O-methyl and 2'-deoxy-2'-fluoro; each B1, B2, and B3 is 2'-OMe; C1 is glycerol nucleic acid (GNA) placed at a site opposite to the seed region (positions 2-8) of the antisense strand; T1', T2', and T3' are each 2'-deoxy-2'-fluoronucleotides, wherein: T1' is at position 14 from the 5' end of the antisense strand, and q2 is 1; and T3' is at position 2 from the 5' end of the antisense strand, and q6 and q7 are 1; each n1, n3, and q1 is independently 4 to 15 nucleotides in length; each n5 and q3 is independently 1-6 nucleotide(s) in length; q5 is 0-10 nucleotide(s) in length; each n4 and q4 is independently 0-3 nucleotide (s) in length; n2 is 3 nucleotides in length, and T1 each are 2'-deoxy-2'-fluoro nucleotides, and wherein (a) the oligonucleotide is covalently conjugated to at least one ligand; and (b) one of the T1 nucleotides is at position 11 from the 5' end of the sense strand. In some embodiments, the sense strand comprises 19-22 nucleotides and the antisense strand comprises 19-25 nucleotides. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the oligonucleotide is represented by the formula:

(I)

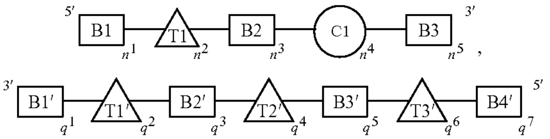

wherein B1', B2', B3', and B4' each independently represent a nucleotide containing a modification selected from the group consisting of 2'-O-methyl and 2'-deoxy-2'-fluoro; each B1, B2, and B3 is 2'-Ome nucleotides; C1 is glycerol nucleic acid (GNA) placed at a site opposite to the seed region (positions 2-8) of the antisense strand; T1', T2', and T3' are each 2'-deoxy-2'-fluoro nucleotides, wherein: T1' is at position 14 from the 5' end of the antisense strand, and q2 is 1; and T3' is at position 2 from the 5' end of the antisense strand, and q6 and q7 are 1; each n1, n3, and q1 is independently 4 to 15 nucleotides in length; each n5 and q3 is independently 1-6 nucleotide(s) in length; q5 is 0-10 nucleotide(s) in length; each n4 and q4 is independently 0-3 nucleotide(s) in length; n2 is 3 nucleotides in length, and T1 each are 2'-deoxy-2'-fluoro nucleotides, and wherein (a) the oligonucleotide is covalently conjugated to at least one ligand; and (b) one of the T1 nucleotides is at a position in the sense strand that is opposite to position 11 from the 5' end of the antisense strand; and (c) the oligonucleotide comprises at least one phosphorothioate internucleoside linkage. In some embodiments, the sense strand comprises 19-22 nucleotides and the antisense strand comprises 19-25 nucleotides. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

In some embodiments, any one of the RNAi agents disclosed herein comprises a modification pattern wherein the antisense strand has sufficient complementarity to a target sequence to mediate RNA interference, wherein said sense strand comprises at least one thermally destabilizing modification of the duplex within the first 9 nucleotide positions of the 5' region of the antisense strand or a precursor thereof, wherein the antisense strand further comprises one or both of the following characteristics: (i) 2, 3, 4, 5 or 6 2'-deoxy-2'-fluoro modifications; and (ii) 1, 2, 3, 4 or 5 phosphorothioate internucleoside linkages; and said sense strand comprises one or both of the following characteristics: (iii) 2, 3, 4, or 5 2'-deoxy-2'-fluoro modifications; and (iv) 1, 2, 3, 4 or 5 phosphorothioate internucleoside linkages. In some embodiments, the antisense strand and sense strand are each 14 to 40 nucleotides. In some embodiments, the antisense strand corresponds to the unmodified nucleobase sequence according to any one of SEQ ID NOs: 607-1212. In some embodiments, the sense strand corresponds to the unmodified nucleobase sequence according to any one of SEQ ID NOs: 1-606. In some embodiments, the antisense strand corresponds to the unmodified antisense strand in Table 1F. In some embodiments, the sense strand corresponds to the unmodified sense strand in Table 1F.

Synthesis, Purification, and Analysis of the Oligonucleotides Described Herein

Oligomer synthesis of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713). The oligonucleotides provided herein can be conveniently and routinely made through the well-known technique of solid phase synthesis. Equipment for such synthesis is sold by several vendors including, for example, LGC (Alexandria, MN). Any other means for such synthesis known in the art may additionally or alternatively be employed. It is well known to use similar techniques to prepare oligonucleotides such as the phosphorothioates and alkylated derivatives. Methods of purification and analysis of oligomeric compounds are known to those skilled in the art. Analysis methods include capillary electrophoresis (CE), reverse-phase high performance liquid chromatography (RP-HPLC), and electrospray-mass spectroscopy (ESI-MS). Such synthesis and analysis methods can be performed in multi-well plates. The oligonucleotides of the invention can be prepared using solution-phase or solid-phase organic synthesis, or enzymatically by methods known in the art. Organic synthesis offers the advantage that the oligomeric strands comprising non-natural or modified nucleotides can be easily prepared. Any other means for such synthesis known in the art can additionally or alternatively be employed. It is also known to use similar techniques to prepare other oligonucleotides, such as those comprising phosphorothioates, phosphorodithioates and alkylated derivatives of internucleoside linkages. The double-stranded oligonucleotides of the invention can be prepared using a two-step procedure. First, the individual strands of the double-stranded oligonucleotides are prepared separately. Then, the component strands are annealed. Regardless of the method of synthesis, the oligonucleotides can be prepared in a solution (e.g., an aqueous and/or organic solution) that is appropriate for formulation. For example, the oligonucleotides preparation can be precipitated and redissolved in pure double-distilled water, and lyophilized. The dried oligonucleotides can then be resuspended in a solution appropriate for the intended formulation process. Teachings regarding the synthesis of particular modified oligonucleotides can be found in the following U.S. patents or pending patent applications. U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof, U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having beta-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262,241, and 5,459,255, drawn to, inter alia, methods of synthesizing 2'-deoxy-2'-fluoro-oligonucleotides. In some embodiments, the oligonucleotides described herein are chemically synthesized using a phosphoramidite approach, e.g., the method by Roy et al. Molecules. 2013; 18(11): 14268-14284; Hayakawa et al. Journal of the American Chemical Society. 1998; 120(48):12395-401; Beaucage, S. L. (1993). Oligodeoxyribonucleotides synthesis: Phosphoramidite approach. In Protocols for Oligonucleotides and Analogs: Synthesis and Properties (pp. 33-61). Humana Press, each of which is hereby incorporated by reference.

Pharmaceutical Compositions

The present disclosure also includes pharmaceutical compositions and formulations comprising the oligonucleotides (e.g., an RNAi agent or ASO) described herein, or a pharmaceutically acceptable salt thereof. In one embodiment, provided herein are pharmaceutical compositions comprising an oligonucleotide (e.g., an RNAi agent or ASO), as described herein, or a pharmaceutically acceptable salt thereof, and a pharmaceutically acceptable carrier or excipient. The pharmaceutical compositions comprising the oligonucleotides described herein are useful for treating or preventing a condition or symptoms associated with DUX4 expression. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. In some embodiments, an oligonucleotide is formulated in buffer solutions such as phosphate-buffered saline solutions, liposomes, micellar structures, and capsids. In some embodiments, naked oligonucleotides or conjugates thereof are formulated in water or in an aqueous solution (e.g., water with pH adjustments). In some embodiments, naked oligonucleotides or conjugates thereof are formulated in basic buffered aqueous solutions (e.g., PBS). The pharmaceutical compositions of the invention may be administered in dosages sufficient to inhibit expression of the target gene.

A "pharmaceutically acceptable carrier or excipient" is a pharmaceutically acceptable solvent, suspending agent, or any other pharmacologically inert vehicle for delivering one or more oligonucleotides to a subject. The excipient can be liquid or solid and is selected, with the planned manner of administration in mind, so as to provide for the desired bulk, consistency, etc., when combined with the oligonucleotide and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

In some embodiments, the present disclosure also includes a pharmaceutical composition suitable for injectable use, which comprises sterile aqueous solutions (where water soluble) or dispersions and sterile powders for the extemporaneous preparation of sterile injectable solutions or dispersions. For intravenous or subcutaneous administration, suitable carriers include physiological saline, bacteriostatic water, Cremophor EL® (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. In many cases, it will be preferable to include isotonic agents, for example, sugars, polyalcohols such as mannitol, sorbitol, and sodium chloride in the composition. Sterile injectable solutions can be prepared by incorporating the oligonucleotides in a required amount in a selected solvent with one or a combination of ingredients enumerated above, as required, followed by filtered sterilization.

Formulations for topical administration of oligonucleotides can include sterile and non-sterile aqueous solutions, non-aqueous solutions in common solvents such as alcohols, or solutions of the oligonucleotides in liquid or solid oil bases. The solutions can also contain buffers, diluents and other suitable additives. Pharmaceutically acceptable organic or inorganic excipients suitable for non-parenteral administration which do not deleteriously react with nucleic acids can also be used to formulate the compositions of the present disclosure. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

In some embodiments, the oligonucleotides herein are conjugated to one or more non-nucleotide groups including, but not limited to, a targeting group/targeting moiety, linking group, delivery polymer, or a delivery vehicle. The non-nucleotide group can enhance targeting, delivery, or attachment of the oligonucleotide.

In some embodiments, at least one nucleotide of the oligonucleotide herein is conjugated to one or more targeting ligands, such as a carbohydrate, amino sugar, cholesterol, polypeptide, or lipid. Exemplary targeting ligands include, but are not limited to, thyrotropin, melanotropin, lectin, a glycoprotein, surfactant protein A, mucin carbohydrate, a multivalent lactose moiety, a multivalent galactose moiety, a N-acetylgalactosamine (GalNAc) moiety, a N-acetyl-glucosamine moiety, a multivalent mannose moiety, a multivalent fucose moiety, a glycosylated polypeptide, transferrin or an antibody, antibody fragment, protein, peptide, or aptamer capable of binding the transferrin receptor, bisphosphonate, polyglutamate, polyaspartate, cholesterol, bile acid, folate, vitamin B12, biotin, an RGD peptide, or an RGD peptide mimetic. In some embodiments, the targeting ligand comprises a N-acetylgalactosamine (GalNAc) moiety. In some embodiments, the GalNAc moiety comprises a monovalent GalNAc moiety, a bivalent GalNAc moiety, a trivalent GalNAc moiety, or a tetravalent GalNAc moiety.

The non-nucleotide group can be covalently linked to the 3' and/or 5' end of either the antisense strand and/or the sense strand, when present. In some embodiments, when the oligonucleotide is an RNAi agent, the RNAi agent contains a non-nucleotide group linked to the 3' and/or 5' end of the sense strand. In some embodiments, a non-nucleotide group is linked to the 5' end of a DUX4 RNAi agent sense strand. A non-nucleotide group may be linked directly or indirectly to the oligonucleotide via a linker/linking group. In some embodiments, a non-nucleotide group is linked to the oligonucleotide via a labile, cleavable, or reversible bond or linker.

In some embodiments, the targeting moiety is a targeting ligand. In some embodiments, the targeting ligand is small molecule-based, sugar-based (e.g., saccharide-based), fatty acid-based, protein-based, or nucleic acid-based targeting ligand. In some embodiments, the targeting moiety is a protein-based targeting ligand. In some embodiments, the protein-based targeting ligand is an antibody, nanobody, affibody, a peptibody, or a peptide. In some embodiments, the protein-based targeting ligand is an antibody, a functional fragment thereof, or an antigen-binding fragment thereof.

Various formulations have been developed to facilitate oligonucleotide use. For example, oligonucleotides can be delivered to a subject or a cellular environment using a formulation that minimizes degradation, facilitates delivery and/or uptake, or provides another beneficial property to the oligonucleotides in the formulation. In some embodiments, an oligonucleotide herein is formulated in buffer solutions such as phosphate buffered saline solutions, liposomes, micellar structures and capsids. Formulations of oligonucleotides with cationic lipids can be used to facilitate transfection of the oligonucleotides into cells. For example, cationic lipids, such as lipofectin, cationic glycerol derivatives, and polycationic molecules (e.g., polylysine), can be used. Suitable lipids include Oligofectamine, Lipofectamine (Life Technologies), NC388 (Ribozyme Pharmaceuticals, Inc., Boulder, Colo.), or FuGene 6 (Roche), all of which can be used according to the manufacturer's instructions. Accordingly, in some embodiments, a formulation herein comprises a lipid nanoparticle. In some embodiments, an excipient comprises a liposome, a lipid, a lipid complex, a microsphere, a microparticle, a nanosphere or a nanoparticle, or may be otherwise formulated for administration to the cells, tissues, organs, or body of a subject in need thereof (see, e.g., Remington: THE SCIENCE AND PRACTICE OF PHARMACY, 22nd edition, Pharmaceutical Press, 2013). In some embodiments, the formulations herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethylsulfoxide or mineral oil). In some embodiments, an oligonucleotide is lyophilized for extending its shelf-life and then made into a solution before use (e.g., administration to a subject). Accordingly, an excipient in a composition comprising any one of the oligonucleotides described herein may be a lyoprotectant (e.g., mannitol, lactose, polyethylene glycol or polyvinylpyrrolidone) or a collapse temperature modifier (e.g., dextran, Ficoll® or gelatin).

Methods of Treatment

The present disclosure also provides methods of using any one of the oligonucleotides disclosed herein, or a pharmaceutically acceptable salt thereof, or any one of the pharmaceutical compositions as described herein, to reduce or inhibit DUX4 expression in a subject. The methods include contacting one or more cells in a subject with an oligonucleotide of the disclosure, or a pharmaceutically acceptable salt thereof, or any one of the pharmaceutical compositions as described herein, thereby inhibiting expression of DUX4 in the cells. The present disclosure also provides use of any one of the oligonucleotides disclosed herein, or a pharmaceutically acceptable salt thereof, or any one of the pharmaceutical compositions as described herein, in the manufacture of a medicament for reducing or inhibiting DUX4 expression in a subject, or for preventing or treating a DUX4 related disorder in a subject. In some embodiments, the terms "inhibiting DUX4 expression" and "reducing DUX4 expression" are interchangeable.

Reduction in DUX4 expression can be assessed by any methods known in the art. For example, a reduction in the expression of DUX4 may be determined by determining the mRNA expression level of DUX4 or a panel of its targets using methods routine to one of ordinary skill in the art, e.g., northern blotting, qRT-PCR; by determining the protein level of DUX4 using methods routine to one of ordinary skill in the art, such as western blotting, immunological techniques.

In some embodiments, the reduction of DUX4 expression is determined by measuring DUX4 expression or a panel of its targets in a population of muscle cells derived from the subject. In some embodiments, reduction in DUX4 expression is assessed by determining the mRNA expression level of a panel of DUX4's targets, e.g., a panel comprising one or more of LEUTX, TRIM43, KHDC1L, MBD3L2, CCNA1, ZSCAN4, SLC34A2, or PRAMEF6. In some embodiments, reduction in DUX4 expression is assessed by determining the mRNA expression level of a panel of DUX4's targets, e.g., a panel comprising one or more of CCNA1, SLC34A2, ZSCAN4, PRAMEF2, PRAMEF17, PRAMEF12, LEUTX, HNRNPCL1, RFPL4B, PRAMEF1, PRAMEF19, TRIM43B, TRIM43, PRAMEF14, PRAMEF11, KDM4E, RFPL2, PRAMEF15, PRAMEF6, ZNF280A, PRAMEF9, TRIM49, KHDC1P1, PRAMEF4, TPRX1, TRIM49B, TRIM51CP, KLF17, TRIM51BP, TRIM53CP, C1DP2, TRIM53AP, TRIM51, PRAMEF8, MBD3L2B, KHDC1L, ALPG, TRIM49C, MBD3L2, ZNF705G, MBD3L3, PRAMEF7, TRIM43CP, PRAMEF1O, HNRNPCL4, TRIM53BP, TRIM51EP, or MBD3L5. In some embodiments, the reduction in DUX4 expression is assessed by determining the mRNA expression level of a panel of DUX4's targets, e.g., a DUX4 panel comprising one or more of KHDC1L, LEUTX, MBD3L2, and ZSCAN4. In some embodiments, the reduction of DUX4 expression is assessed by determining the mRNA or protein expression of one or more circulating DUX4 targets (e.g., KHDC1L).

In some embodiments, the reduction of DUX4 expression is determined by measuring mRNA expression of DUX4 or its targets in a population of cancer cells derived from the subject. In some embodiments, the cancer cells are primary cancer cells or metastatic cancer cells. In some embodiments, the cancer cells are selected from malignant B cells, melanoma cancer cells, breast cancer cells, kidney cancer cells, bladder cancer cells, and prostate cancer cells. In some embodiments, the subject has one or more DUX4 related conditions selected from Capicua transcriptional repressor (CIC)-rearranged sarcoma, undifferentiated round cell sarcoma, embryonal rhabdomyosarcoma (ERMS), acute myeloid leukemia (AML; e.g., erythromegakaryoblastic leukemia), B-cell acute lymphoblastic leukemia (B-ALL), cutaneous melanoma, breast invasive carcinoma, renal clear cell carcinoma, urothelial carcinoma, prostate adenocarcinoma, adrenocortical carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pancreatic ductal adenocarcinoma, pheochromocytoma, paraganglioma, rectum adenocarcinoma, sarcoma, stomach adenocarcinoma, testicular germ cell tumors, thyroid carcinoma, thymoma, uterine corpus endometrial carcinoma, uterine carcinosarcoma, and uveal melanoma.

In some embodiments, the reduction of DUX4 expression is determined by measuring mRNA expression of DUX4 or its targets in a population of cells derived from a subject. In some embodiments, the subject is affected by viral infections caused by viruses such as herpesviruses (e.g., HSV-1, HSV-2, cytomegalovirus (HCMV)).

In some embodiments, the reduction of DUX4 mRNA or protein expression levels is measured in tissues derived from the subject. In some embodiments, the reduction of DUX4 mRNA or protein expression levels is determined by measuring the mRNA or protein expression levels of DUX4 biomarkers (e.g., one or more of the DUX4's targets described herein) in serum derived from the subject.

The present disclosure further provides methods of treatment of a subject in need thereof. The methods of treatment include administering an oligonucleotide of the disclosure to a subject, e.g., a subject that would benefit from inhibition of DUX4 expression, in a therapeutically effective amount of an oligonucleotide targeting a DUX4 gene or a pharmaceutical composition comprising an oligonucleotide targeting a DUX4 gene.

The in vivo methods of the disclosure may include administering to a subject a composition containing an oligonucleotide disclosed herein, or a pharmaceutically acceptable salt, wherein the oligonucleotide includes a nucleotide sequence that is complementary to at least a part of a sequence of nucleotides encoding DUX4 of the subject to be treated.

The oligonucleotide can be administered by any means known in the art including, but not limited to, oral, intraperitoneal, or parenteral routes, including intracranial (e.g., intraventricular, intraparenchymal, and intrathecal), intravenous, intramuscular, intravitreal, subcutaneous, transdermal, airway (aerosol), nasal, rectal, and topical (including buccal and sublingual) administration. In certain embodiments, the compositions are administered by intravenous infusion or injection. In certain embodiments, the compositions are administered by subcutaneous injection. In certain embodiments, the compositions are administered by intrathecal injection. The administration of the oligonucleotide may be repeated over a period of time. The administration may be repeated on a regular basis. In some embodiments, after an initial treatment regimen, the treatments can be administered on a less frequent basis. A repeat-dose regimen may include administration of a therapeutic amount of an oligonucleotide on a regular basis.

The present disclosure also provides methods of using any one of the oligonucleotides disclosed herein, or a pharmaceutically acceptable salt thereof, to treat or prevent a DUX4-related disorder in a subject. The present disclosure also provides a method for inhibiting DUX4 expression or treating a DUX4 related disorder in a subject, the method comprising administering to the subject an effective amount of an oligonucleotide for inhibiting expression of DUX4, or a pharmaceutically acceptable salt thereof, or a pharmaceutical composition comprising the oligonucleotide for inhibiting expression of DUX4. Non-limiting examples of DUX4 related disorders include facioscapulohumeral muscular dystrophy (FSHD; e.g., FSHD1 and FSHD2), DUX4-related cancers such as Capicua transcriptional repressor (CIC)-rearranged sarcoma, undifferentiated round cell sarcoma, embryonal rhabdomyosarcoma (ERMS), acute myeloid leukemia (AML; e.g., erythromegakaryoblastic leukemia), B-cell acute lymphoblastic leukemia (B-ALL), cutaneous melanoma, breast invasive carcinoma, renal clear cell carcinoma, urothelial carcinoma, prostate adenocarcinoma, adrenocortical carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pancreatic ductal adenocarcinoma, pheochromocytoma, paraganglioma, rectum adenocarcinoma, sarcoma, stomach adenocarcinoma, testicular germ cell tumors, thyroid carcinoma, thymoma, uterine corpus endometrial carcinoma, uterine carcinosarcoma, and uveal melanoma; and DUX4-mediated viral diseases caused by viruses such as herpesviruses (e.g., HSV-1, HSV-2, cytomegalovirus (HCMV)). In some embodiments, the DUX4-related disorder is facioscapulohumeral muscular dystrophy (FSHD), a DUX4-related cancer, or a DUX4-medicated viral disease. In some embodiments, the DUX4-related disorder is facioscapulohumeral muscular dystrophy (FSHD). In some embodiments, the DUX4-related disorder is a DUX4-related cancer such as Capicua transcriptional repressor (CIC)-rearranged sarcoma. In some embodiments, the DUX4-related disorder is a DUX4-mediated viral disease, such as herpes viral infection caused by HSV-1, HSV-2, or cytomegalovirus (HCMV).

In some embodiments, the present disclosure provides a method of treating facioscapulohumeral muscular dystrophy (FSHD), comprising administering an oligonucleotide disclosed herein, or a pharmaceutically acceptable salt thereof, to a subject in need thereof.

In some embodiments, the present disclosure provides a method of treating Capicua transcriptional repressor (CIC)-rearranged sarcoma, comprising administering an oligonucleotide disclosed herein, or a pharmaceutically acceptable salt thereof, to a subject in need thereof.

In some embodiments, the present disclosure provides a method of treating herpes viral infection, comprising administering an oligonucleotide disclosed herein, or a pharmaceutically acceptable salt thereof, to a subject in need thereof.

An oligonucleotide of the disclosure may be administered as a "free oligonucleotide." A free oligonucleotide is administered in the absence of a transfection agent. The naked oligonucleotide may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the oligonucleotide can be adjusted such that it is suitable for administering to a subject. Alternatively, an RNAi agent of the disclosure may be administered as a pharmaceutical composition, such as a dsRNA liposomal formulation.

In some embodiments, the methods herein may further comprise administering to the subject an additional agent or therapy suitable for treatment or prevention of a DUX4 related disorder. Non-limiting examples of such additional agents or therapies include anti-ACVR2B antibodies, beta2-agonists, creatine, myostatin inhibitors, and anti-inflammatories or antioxidants such glucocorticoids and nutraceuticals.

EXEMPLARY EMBODIMENTS

Embodiment 1: An oligonucleotide for inhibiting expression of DUX4, wherein the oligonucleotide comprises an antisense strand comprising at least 14 contiguous nucleotides substantially complementary to a sequence of nucleotides encoding DUX4, with no more than 4 mismatched nucleotides.

Embodiment 2: The oligonucleotide of Embodiment 1, wherein the sequence of nucleotides encoding DUX4 comprises a nucleotide sequence having at least 90% nucleotide sequence identity to SEQ ID NO: 2425.

Embodiment 3: The oligonucleotide of Embodiment 1 or 2, wherein the oligonucleotide targets a sequence of nucleotides corresponding to positions of SEQ ID NO: 2425 selected from Table 4.

Embodiment 4: The oligonucleotide of any one of Embodiments 1-3, wherein the antisense strand is substantially or completely complementary to a sequence of nucleotides corresponding to an untranslated region of the DUX4 transcript.

Embodiment 5: The oligonucleotide of any one of Embodiments 1-4, wherein the oligonucleotide is an RNAi agent.

Embodiment 6: The oligonucleotide of Embodiment 5, wherein the oligonucleotide is a double stranded small interfering RNA, a short hairpin RNA, or a Dicer-substrate siRNA (DsiRNA).

Embodiment 7: The oligonucleotide of Embodiment 6, wherein the RNAi agent is a double-stranded small interfering RNA (siRNA) further comprising a sense strand, wherein the sense strand and antisense strand form a double stranded region.

Embodiment 8: The oligonucleotide of any one of Embodiments 1-7, wherein the antisense strand comprises a nucleotide sequence comprising at least 15 contiguous nucleotides (for example, 15, 16, 17, 18, 19, 20, or 21 contiguous nucleotides) differing by no more than 4, 3, 2, or 1 nucleotides from the nucleotide sequence of any one of SEQ ID NOs: 607-1212, 1819-2424, 2437-2447, or 3012-3602, or a nucleotide sequence having at least 90% nucleotide sequence identity to a portion of the nucleotide sequence of any one of SEQ ID NOs: 607-1212, 1819-2424, 2437-2447, or 3012-3602.

Embodiment 9: The oligonucleotide of any one of Embodiments 1-8, wherein the antisense strand comprises the nucleotide sequence of any one of SEQ ID NOs: 607-1212, 1819-2424, 2437-2447, or 3012-3602.

Embodiment 10: The oligonucleotide of any one of Embodiments 7-9, wherein the sense strand comprises a nucleotide sequence differing by no more than 4, 3, 2, or 1 nucleotides from the nucleotide sequence of any one of SEQ ID Nos: 1-606, 1213-1818, 2426-2436, or 2448-3011, or a nucleotide sequence having at least 90% nucleotide sequence identity to a portion of the nucleotide sequence of any one of SEQ ID NOs: 1-606, 1213-1818, 2426-2436, or 2448-3011.

Embodiment 11: The oligonucleotide of any one of Embodiments 7-10, wherein the sense strand comprises the nucleotide sequence of any one of SEQ ID NOs: 1-606, 1213-1818, 2426-2436, or 2448-3011.

Embodiment 12: The oligonucleotide of any one of Embodiments 7-11, wherein the antisense strand comprises a nucleotide sequence of any one of SEQ ID NOs: 607-1212, 1819-2424, 2437-2447, or 3012-3602, and the sense strand comprises a nucleotide sequence of any one of SEQ ID NOs: 1-606, 1213-1818, 2426-2436, or 2448-3011.

Embodiment 13: The oligonucleotide of any one of Embodiments 7-12, wherein each strand is no more than 30 nucleotides in length, or 19-30 nucleotides in length, or 19-23 nucleotides in length, or 19-21 nucleotides in length.

Embodiment 14: The oligonucleotide of any one of Embodiments 7-13, wherein at least one strand comprises a 3' overhang of at least 1 nucleotide or at least 2 nucleotides.

Embodiment 15: The oligonucleotide of any one of Embodiments 7-14, wherein at least one strand comprises a 5' overhang of at least 1 nucleotide or at least 2 nucleotides.

Embodiment 16: The oligonucleotide of any one of Embodiments 7-15, wherein the double stranded region is 15-30 nucleotide pairs in length, or 15-23 nucleotide pairs in length, or 17-25 nucleotide pairs in length, or 19-23 nucleotide pairs in length, or 19-21 nucleotide pairs in length.

Embodiment 17: The oligonucleotide of any one of Embodiments 7-16, wherein the antisense strand is 21 nucleotides in length and the sense strand is 19 nucleotides in length, or the antisense strand is 19 nucleotides in length and the sense strand is 19 nucleotides in length.

Embodiment 18: The oligonucleotide of any one of Embodiments 1-4, wherein the oligonucleotide is a single-stranded antisense oligonucleotide (ASO).

Embodiment 19: The oligonucleotide of Embodiment 18, wherein the ASO comprises a nucleic acid sequence comprising at least 14 contiguous nucleotides (for example, 14, 15, 16, 17, 18, 19, 20, or 21 contiguous nucleotides) that differ by no more than 1, 2, 3, or 4 nucleotides from any one of SEQ ID NOs: 607-1212 or 3012-3602.

Embodiment 20: The oligonucleotide of Embodiment 18 or 19, wherein the ASO comprises a nucleic acid sequence comprising at least 14 contiguous nucleotides (for example, 14, 15, 16, 17, 18, 19, 20, or 21 contiguous nucleotides) that differ by no more than 1, 2, 3 or 4 nucleotides from any one of SEQ ID NOs: 1819-2424 or 2437-2447.

Embodiment 21: The oligonucleotide of any one of Embodiments 1-20, wherein the oligonucleotide comprises one or more modifications.

Embodiment 22: The oligonucleotide of Embodiment 21, wherein the one or more modifications is selected from a ribose modification, a backbone modification, a nucleobase modification, or a combination thereof.

Embodiment 23: The oligonucleotide of Embodiment 22, wherein the ribose modification comprises a locked nucleic acid (LNA), a tricyclo-DNA (tcDNA), 2'-deoxy-2'-fluoro, 2'-O-methyl, 2'-methoxyethyl (2'-MOE), 2'-deoxy-2'-arabino-fluoro, 2'-O-benzyl, 2'-O-methyl-4-pyridine, 2' cyclic ethyl (cET), phosphorodiamidate morpholino (PMO), glycol nucleic acid (GNA), unlocked nucleic acid (UNA), a threose nucleic acid (TNA), or a combination thereof.

Embodiment 24: The oligonucleotide of Embodiment 23, wherein the ribose modification comprises a 2'-deoxy-2'-fluoro, 2'-O-methyl, glycol nucleic acid (GNA), unlocked nucleic acid (UNA), a threose nucleic acid (TNA), or a combination thereof.

Embodiment 25: The oligonucleotide of Embodiment 23 or 24, wherein the ribose modification is a 2'-deoxy-2'-fluoro modification, a 2'-O-methyl modification, or a combination thereof.

Embodiment 26: The oligonucleotide of any one of Embodiments 22-25, wherein the backbone modification comprises phosphorothioate, phosphorodithioate, methylphosphonate, methyoxypropyl-phosphonate, 5'-(E)-vinylphosphonate, 5'-methyl phosphonate, 5'-methyl phosphate, 5'-phosphorothioate, peptide nucleic acid (PNA), or a combination thereof.

Embodiment 27: The oligonucleotide of Embodiment 26, wherein the backbone modification comprises a phosphorothioate.

Embodiment 28: The oligonucleotide of any one of Embodiments 22-27, wherein the backbone modification comprises a phosphorothioate modification.

Embodiment 29: The oligonucleotide of any one of Embodiments 22-28, wherein the nucleobase modification comprises 5-substituted pyrimidines, 6-azapyrimidines and N-2, N-6 and 0-6 substituted purines, 5-methylcytosine (5-Me-C), 5-hydroxymethyl cytosine, xanthine, hypoxanthine, 2-aminoadenine, N6-alkyl derivatives, N2-alkyl, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxy, 5-halo, 5-trifluoromethyl, N7-methylguanine, N7-methyladenine, 8-azaguanine, 8-azaadenine, 7-deazaguanine, 7-deazaadenine, 3-deazaguanine, 3-deazaadenine, or any combination thereof.

Embodiment 30: The oligonucleotide of Embodiment 29, wherein the oligonucleotide comprises at least one modified nucleotide selected from the group consisting of a deoxy nucleotide, a 3'-terminal deoxythymidine (dT) nucleotide, a 2'-O-methyl modified nucleotide, a 2'-deoxy-2'-fluoro modified nucleotide, a 2'-deoxy-modified nucleotide, a 2'-5'-linked ribonucleotide (3'-RNA), a locked nucleotide, an unlocked nucleotide, a conformationally restricted nucleotide, a constrained ethyl nucleotide, an abasic nucleotide, a 2'-amino-modified nucleotide, a 2'-O-allyl-modified nucleotide, 2'-C-alkyl-modified nucleotide, 2'-hydroxyl-modified nucleotide, a 2'-O-(methoxy ethyl) modified nucleotide, a 2'-O-alkyl-modified nucleotide, a morpholino nucleotide, a phosphoramidate morpholino, a non-natural base comprising nucleotide, a tetrahydropyran modified nucleotide, a 1,5-anhydrohexitol modified nucleotide, a cyclohexenyl modified nucleotide, a nucleotide comprising a 5'-phosphorothioate group, a nucleotide comprising a 5'-methylphosphonate group, a nucleotide comprising a 5'-methylphosphate group, a nucleotide comprising a 5' phosphate or 5' phosphate mimic, a nucleotide comprising vinyl phosphonate, a glycol nucleic acid (GNA), a glycol nucleic acid S-Isomer (S-GNA), a nucleotide comprising 2-hydroxymethyl-tetrahydrofurane-5-phosphate, a nucleotide comprising 2'-deoxythymidine-3'phosphate, a nucleotide comprising 2'-deoxyguanosine-3'-phosphate; a cytidine-2'-phosphate, a guanosine-2'-phosphate, a uridine-2'-phosphate, an adenosine-2'-phosphate, a 2'-O-hexadecyl-adenosine-3'-phosphate, a 2'-O-hexadecyl-cytidine-3'-phosphate, a 2'-O-hexadecyl-guanosine-3'-phosphate, and a 2'-O-hexadecyl-uridine-3'-phosphate, a 3'-3' inverted nucleotide linkage, a 5'-5' inverted nucleotide linkage, TNA, and combinations thereof.

Embodiment 31: The oligonucleotide of Embodiment 30, wherein the oligonucleotide comprises a modified nucleotide selected from the group consisting of a deoxy nucleotide, a 3'-terminal deoxythymidine (dT) nucleotide, a 3'-3' inverted nucleotide linkage, a 5'-5' inverted nucleotide linkage, a 5'-(E)-vinylphosphonate-2'-O-methyl-uridine-3'-phosphate, and a combination thereof.

Embodiment 32: The oligonucleotide of Embodiment 30 or 31, wherein the oligonucleotide comprises 5'-(E)-vinylphosphonate-2'-O-methyl-uridine-3'-phosphate.

Embodiment 33: The oligonucleotide of Embodiment 21, wherein at least one of the modifications is a thermally destabilizing nucleotide modification.

Embodiment 34: The oligonucleotide of Embodiment 33, wherein the thermally destabilizing nucleotide modification is selected from the group consisting of an abasic modification; a mismatch with the opposing nucleotide in the duplex; destabilizing sugar modification; a 2'-deoxy modification, an acyclic nucleotide, an unlocked nucleic acids (UNA); a glycerol nucleic acid (GNA), and a combination thereof.

Embodiment 35: The oligonucleotide of Embodiment 31, wherein the modification comprises a short sequence of 3'-terminal deoxythymidine nucleotide (dT).

Embodiment 36: The oligonucleotide of any one of Embodiments 21-35, wherein the modifications on the nucleotides are 2'-O-methyl and 2'deoxy-2'-fluoro modifications.

Embodiment 37: The oligonucleotide of any one of Embodiments 21-36, wherein the oligonucleotide comprises at least one phosphorothioate internucleoside or phosphorodithioate internucleoside linkage.

Embodiment 38: The oligonucleotide of Embodiment 37, wherein the oligonucleotide comprises 6-8 phosphorothioate internucleoside linkages.

Embodiment 39: The oligonucleotide of Embodiments 37 or 38, wherein the oligonucleotide comprises at least 1, or at least 2, phosphorothioate internucleoside linkage at a 5' end of the sense strand.

Embodiment 40: The oligonucleotide of any one of Embodiments 37-39, wherein the oligonucleotide comprises at least 1 phosphorothioate internucleoside linkage at a 3' end of the sense strand.

Embodiment 41: The oligonucleotide of any one of Embodiments 37-40, wherein the oligonucleotide comprises at least 1, or at least 2, phosphorothioate internucleoside linkage at a 5' end of the antisense strand.

Embodiment 42: The oligonucleotide of any one of Embodiments 37-41, wherein the oligonucleotide comprises at least 1 phosphorothioate internucleoside linkage at a 3' end of the antisense strand.

Embodiment 43: The oligonucleotide of any one of Embodiments 37-42, wherein no more than five of the nucleotides of the antisense strand are unmodified nucleotides.

Embodiment 44: The oligonucleotide of any one of Embodiments 37-43, wherein all the nucleotides of the antisense strand are modified oligonucleotides.

Embodiment 45: The oligonucleotide of any one of Embodiments 37-44, wherein no more than five of the nucleotides of the sense strand are unmodified nucleotides.

Embodiment 46: The oligonucleotide of any one of Embodiments 37-45, wherein all the nucleotides of the sense strand are modified nucleotides.

Embodiment 47: The oligonucleotide of any one of Embodiments 7-46 wherein the antisense strand comprises a chemical modification pattern according to $(Nfs)_a(nNf)_b(ns)_cn$, wherein:

n is a 2'-O-methyl-nucleoside-3'-phosphate;

Nfs is a 2'-deoxy-2'-fluoro-nucleoside-3'-phosphorothioate;

Nf is a 2'-deoxy-2'-fluoro-nucleoside-3'-phosphate;

ns is a 2'-O-methyl-nucleoside-3'-phosphorothioate, a is at least 1;

b is 5-10; and c is at least 1.

Embodiment 48: The oligonucleotide of Embodiment 47, wherein the antisense strand comprises the chemical modification pattern NfsNfsnNfnNfnNfnNfnNfnNfnNfnNfnsnsn.

Embodiment 49: The oligonucleotide of any one of Embodiments 7-48 wherein the sense strand comprises a chemical modification pattern according to $(ns)_a(Nfn)_eNf$, wherein:

n is a 2'-O-methyl-nucleoside-3'-phosphate;

Nf is a 2'-deoxy-2'-fluoro-nucleoside-3'-phosphate;

ns is a 2'-O-methyl-nucleoside-3'-phosphorothioate;

d is at least 1; and e is 5-10.

Embodiment 50: The oligonucleotide of Embodiment 49, wherein the sense strand comprises the chemical modification pattern nsnsNfnNfnNfnNfnNfnNfnNfnNfnNf.

Embodiment 51: The oligonucleotide of any one of Embodiments 7-50 wherein each of the antisense and the sense strand is independently 17-23 nucleotides in length, wherein the antisense strand comprises the motif F(SF)nSnn, wherein n is from 2 to about 20, nn is 0 or 1, one of F and S is a 2'-deoxy-2'-fluoro modified nucleoside and the other of F and S is a 2'-O-methyl modified nucleoside.

Embodiment 52: The oligonucleotide of any one of Embodiments 7-51 wherein the antisense strand comprises the chemical modification pattern of nNfnnnNfnNfNfnnnnNfnNfnnnnn and the sense strand comprises the chemical modification nnnnnnNfnNfNfNfnnnnnnnn, wherein n is a 2'-O-methyl-nucleoside and Nf is a 2'-deoxy-2'-fluoro-nucleoside.

Embodiment 53: The oligonucleotide of any one of Embodiments 7-52, wherein each of the antisense and the sense strand is independently 20-23 nucleotides in length, wherein the antisense strand comprises a region having the formula X1-Y—X2, wherein Y is a subregion of from about 5 to about 12 linked nucleosides and each of X1 subregion and X2 subregion is, independently, a plurality of linked nucleosides having the formula FSFS, where one of F and S is a 2'-deoxy-2'-fluoro modified nucleoside and the other of F and S is a 2'-O-methyl modified nucleoside; and each internucleoside linkage of said X1 subregion and X2 subregion is, independently, a phosphodiester or a phosphorothioate internucleoside linkage.

Embodiment 54: The oligonucleotide of any one of Embodiments 7-53 wherein each of the antisense and the sense strand is independently 17-23 nucleotides in length, wherein the antisense strand comprises a contiguous sequence of linked nucleosides that define an alternating motif of the formula:

5'-Q(—L—Z—L—Q)n(—L—Z)nn-3' wherein:

each L is an internucleoside linking group;

either each Q is a 2'-deoxy-2'-fluoro-nucleoside and each Z is a 2'-O-methyl nucleoside; or each Q is a 2'-O-methyl nucleoside and each Z is a 2'-deoxy-2'-fluoro nucleoside; and n is from 8 to 14 and nn is 0 or 1.

Embodiment 55: The oligonucleotide of any one of Embodiments 7-54 wherein the antisense strand is 19-25 nucleotides in length and is represented by the formula:

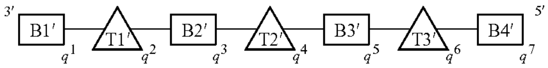

wherein:

B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA;

T1', T2', and T3' each independently represent a nucleotide comprising a chemical modification selected from the group consisting of DNA, RNA, LNA, 2'-deoxy-2'-fluoro, and 5'-methyl-2'-deoxy-2'-fluoro nucleotides;

q1 is 4 to 15 nucleotides in length;

q3 or q7 is independently 1-6 nucleotide(s) in length;

q2 or q6 is independently 1-3 nucleotide(s) in length;

q4 is 0-3 nucleotide(s) in length; and q5 is 0-10 nucleotide(s) in length; and wherein:

the antisense strand has 2'-deoxy-2'-fluoro modifications, and wherein the 2'-deoxy-2'-fluoro modifications on the antisense strand consist of four, and only four, 2'-deoxy-2'-fluoro modifications or six, and only six, 2'-deoxy-2'-fluoro modifications.

Embodiment 56: The oligonucleotide of any one of Embodiments 7-55 wherein the antisense strand and sense strand are each 14 to 40 nucleotides, and is represented by the formula:

(I

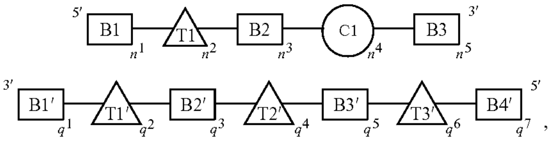

, wherein:

B1, B1', B2', B3', and B4' each independently represent a nucleotide containing a modification selected from the group consisting of 2'-O-alkyl, 2'-substituted alkoxy, 2'-substituted alkyl, 2'-halo, ENA, and BNA/LNA;

C1 is a thermally destabilizing nucleotide, selected from the group consisting of i) a nucleotide that forms a mismatch pair with the opposing nucleotide in the antisense strand, ii) a nucleotide having an abasic modification, and iii) a nucleotide having a sugar modification, and placed at a site opposite to the seed region (positions 2-8) of the antisense strand;

T1', T2', and T3' each independently represent a nucleotide comprising a modification providing the nucleotide a steric bulk that is less than or equal to the steric bulk of a 2'-OMe modification, wherein the modification is at the 2'-position of a ribose sugar of the nucleotide or at a position of a non-ribose nucleotide similar to the 2'-position of a ribose sugar;

each n1, and q1 is independently 4 to 15 nucleotides in length;

each q3, and q7 is independently 1-6 nucleotide(s) in length;

each q2 and q6 is independently 1-3 nucleotide(s) in length;

q5 is 0-10 nucleotide(s) in length;

each n4, and q4 is independently 0-3 nucleotide(s) in length;

n2 is 3 nucleotides in length, and T1 each are 2'-deoxy-2'-fluoro nucleotides;

n3 is 7 nucleotides in length, and B2 each are 2'-OMe nucleotides; and n5 is 3 nucleotides in length, and B3 each are 2'-OMe nucleotides.

Embodiment 57: The oligonucleotide of any one of Embodiments 7-56 wherein the antisense strand and sense strand are each 19-25 nucleotides in length, wherein the sense strand is represented by the formula:

(Is)

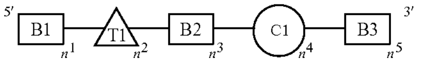

wherein:

B1, B2, and B3 each independently represent a nucleotide containing a modification selected from the group consisting of 2'-O-alkyl, 2'-substituted alkoxy, 2'-substituted alkyl, 2'-halo, ENA, and BNA/LNA;

C1 is a thermally destabilizing nucleotide, selected from the group consisting of i) a nucleotide that forms a mismatch pair with the opposing nucleotide in the antisense strand, ii) a nucleotide having an abasic modification, and iii) a nucleotide having a sugar modification, and placed at a site opposite to the seed region (positions 2-8) of the antisense strand;

T1 represents a nucleotide comprising a 2'-deoxy-2'-fluoro modification;

n1 or n3 is independently 4 to 15 nucleotides in length;

n5 is 1-6 nucleotide(s) in length;

n2 is 3;

n4 is 0-3 nucleotide(s) in length; and wherein the sense strand has 2'-deoxy-2'-fluoro modifications, and wherein the 2'-deoxy-2'-fluoro modifications on the sense strand consist of four, and only four, 2'-deoxy-2'-fluoro modifications, wherein the four 2'-deoxy-2'-fluoro modifications are at positions 7 and 9-11 from the 5'-end of the sense strand.

Embodiment 58: The oligonucleotide of any one of Embodiments 7-57, wherein the antisense strand is complementary to at least one portion of a mRNA of the target gene (e.g., DUX4), wherein:

the sense strand comprises 19-22 nucleotides, the antisense strand comprises 19-25 nucleotides; and the oligonucleotide is represented by the formula:

(I)

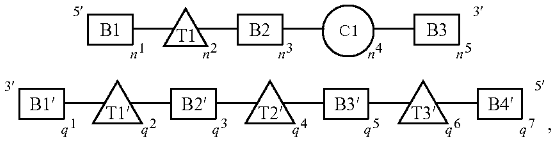

, wherein:

B1', B2', B3', and B4' each independently represent a nucleotide containing a modification selected from the group consisting of 2'-O-methyl and 2'-deoxy-2'-fluoro;

each B1, B2, and B3 is 2'-O-methyl nucleotide;

C1 is glycerol nucleic acid (GNA) placed at a site opposite to the seed region (positions 2-8) of the antisense strand;

T1', T2', and T3' are each 2'-F, wherein:

T1' is at position 14 from the 5' end of the antisense strand, and q2 is 1; and

T3' is at position 2 from the 5' end of the antisense strand, and q6 and q7 are 1;

each n1, n3, and q1 is independently 4 to 15 nucleotides in length;

each n5 and q3 is independently 1-6 nucleotide(s) in length;

q5 is 0-10 nucleotide(s) in length;

each n4 and q4 is independently 0-3 nucleotide(s) in length;

n2 is 3 nucleotides in length, and T1 each are 2'-deoxy-2'-fluoro nucleotides, and wherein (a) the oligonucleotide is covalently conjugated to at least one ligand; and (b) one of the T1 nucleotides is at position 11 from the 5' end of the sense strand.

Embodiment 59: The oligonucleotide of any one of Embodiments 7-58, wherein the sense strand comprises 19-22 nucleotides, the antisense strand comprises 19-25 nucleotides; and the oligonucleotide is represented by the formula:

(I)

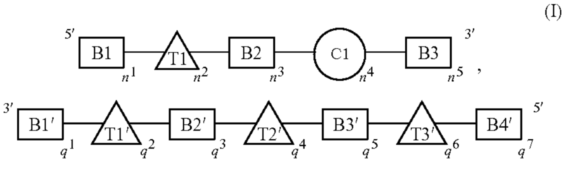

wherein:

B1', B2', B3', and B4' each independently represent a nucleotide containing a modification selected from the group consisting of 2'-O-methyl and 2'-deoxy-2'-fluoro;

each B1, B2, and B3 is 2'-OMe;

C1 is glycerol nucleic acid (GNA) placed at a site opposite to the seed region (positions 2-8) of the antisense strand;

T1', T2', and T3' are each 2'-deoxy-2'-fluoro, wherein:

T1' is at position 14 from the 5' end of the antisense strand, and q2 is 1; and

T3' is at position 2 from the 5' end of the antisense strand, and q6 and q7 are 1;

each n1, n3, and q1 is independently 4 to 15 nucleotides in length;

each n5 and q3 is independently 1-6 nucleotide(s) in length;

q5 is 0-10 nucleotide(s) in length;

each n4 and q4 is independently 0-3 nucleotide(s) in length;

n2 is 3 nucleotides in length, and T1 each are 2'-deoxy-2'-fluoro, and wherein (a) the oligonucleotide is covalently conjugated to at least one ligand; and (b) one of the T1 nucleotides is at a position in the sense strand that is opposite to position 11 from the 5' end of the antisense strand; and (c) the oligonucleotide comprises at least one phosphorothioate internucleoside linkage.

Embodiment 60: The oligonucleotide of any one of Embodiments 7-59, wherein the antisense strand and sense strand are each 14 to 40 nucleotides, wherein the antisense strand has sufficient complementarity to a target sequence to mediate RNA interference, wherein said sense strand comprises at least one thermally destabilizing modification of the duplex within the first 9 nucleotide positions of the 5' region of the antisense strand or a precursor thereof, wherein the antisense strand further comprises one or both of the following characteristics:

(i) 2, 3, 4, 5 or 6 2'-deoxy-2'-fluoro modifications; and (ii) 1, 2, 3, 4 or 5 phosphorothioate internucleoside linkages; and said sense strand comprises one or both of the following characteristics:

(iii) 2, 3, 4, or 5 2'-deoxy-2'-fluoro modifications; and (iv) 1, 2, 3, 4 or 5 phosphorothioate internucleoside linkages.

Embodiment 61: The oligonucleotide of any one of Embodiments 7-46, wherein the antisense strand comprises a modification pattern nsNfsnnnNfnNfNfnnnnNfnNfnnnsnsn, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

Embodiment 62: The oligonucleotide of any one of Embodiments 7-46, wherein the antisense strand disclosed herein comprises a modification pattern vpUs-NfsnnnNfnNfNfnnnnNfnNfnnnsnsn, wherein vpUs is a 5'-vinylphosphonate-2'-O-methyl-uridine-3'-phosphorothioate; ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

Embodiment 63: The oligonucleotide of any one of Embodiments 7-46, wherein the sense strand disclosed herein comprises a modification pattern nsnsnnNfnNfNfNfnnnnnnnnnn, wherein ns is a 2'-O-methyl-nucleoside-3'-phosphorothioate; n is a 2'-O-methyl-nucleoside-3'-phosphate; and Nf is a 2'-deoxy-2'-fluoro-nucleoside-3'-phosphate.

Embodiment 64: The oligonucleotide of any one of Embodiments 7-46, wherein the sense strand disclosed herein comprises a modification pattern NfsnsNfnNfnNfnNfnNfnNfnNfnNfnNf, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

Embodiment 65: The oligonucleotide of any one of Embodiments 7-46, wherein the sense strand comprises a modification pattern nsnsnnNfnNfNfNfnnnnnnnnnn, and the antisense strand comprises a modification pattern nsNfsnnnNfnNfNfnnnnNfnNfnnnsnsn, wherein ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

Embodiment 66: The oligonucleotide of any one of Embodiments 7-46, wherein the sense strand comprises a modification pattern nsnsnnNfnNfNfNfnnnnnnnnnn, and the antisense strand comprises a modification pattern vpUs-NfsnnnNfnNfNfnnnnNfnNfnnnsnsn, wherein vpUs is a 5'-vinylphosphonate-2'-O-methyl-uridine-3'-phosphorothioate; ns is a 2'-O-methyl-nucleoside-3'-phosphorothioate; Nfs is a 2'-deoxy-2'-fluoro-nucleoside-3'-phosphorothioate; n is a 2'-O-methyl-nucleoside-3'-phosphate; and Nf is a 2'-deoxy-2'-fluoro-nucleoside-3'-phosphate.

Embodiment 67: The oligonucleotide of any one of Embodiments 7-66, wherein the antisense strand comprises a nucleotide sequence according to any one of SEQ ID NOs: 1819-2424 or 2437-2447.

Embodiment 68: The oligonucleotide of Embodiment 67, wherein the sense strand comprises a nucleotide sequence according to any one of SEQ ID NOs: 1213-1818 or 2426-2436.

Embodiment 69: The oligonucleotide of any one of Embodiments 7-68, further comprising a terminal, chiral modification occurring at the first internucleoside linkage at the 3'-end of the antisense strand, having the linkage phosphorus atom in Sp configuration, a terminal, chiral modification occurring at the first internucleoside linkage at the 5'-end of the antisense strand, having the linkage phosphorus atom in Rp configuration, and a terminal, chiral modification occurring at the first internucleoside linkage at the 5'-end of the sense strand, having the linkage phosphorus atom in either Rp configuration or Sp configuration.

Embodiment 70: The oligonucleotide of any one of Embodiments 7-69, further comprising a terminal, chiral modification occurring at the first and second internucleoside linkages at the 3'-end of the antisense strand, having the linkage phosphorus atom in Sp configuration, a terminal, chiral modification occurring at the first internucleoside linkage at the 5'-end of the antisense strand, having the linkage phosphorus atom in Rp configuration, and a terminal, chiral modification occurring at the first internucleoside linkage at the 5'-end of the sense strand, having the linkage phosphorus atom in either Rp or Sp configuration.

Embodiment 71: The oligonucleotide of any one of Embodiments 7-70, further comprising a terminal, chiral modification occurring at the first, second and third internucleoside linkages at the 3' end of the antisense strand, having the linkage phosphorus atom in Sp configuration, a terminal, chiral modification occurring at the first internucleoside linkage at the 5'-end of the antisense strand, having the linkage phosphorus atom in Rp configuration, and a terminal, chiral modification occurring at the first internucleoside linkage at the 5'-end of the sense strand, having the linkage phosphorus atom in either Rp or Sp configuration.

Embodiment 72: The oligonucleotide of any one of Embodiments 7-71, further comprising a terminal, chiral modification occurring at the first, and second internucleoside linkages at the 3' end of the antisense strand, having the linkage phosphorus atom in Sp configuration, a terminal, chiral modification occurring at the third internucleoside linkages at the 3'-end of the antisense strand, having the linkage phosphorus atom in Rp configuration, a terminal, chiral modification occurring at the first internucleoside linkage at the 5'-end of the antisense strand, having the linkage phosphorus atom in Rp configuration, and a terminal, chiral modification occurring at the first internucleoside linkage at the 5'-end of the sense strand, having the linkage phosphorus atom in either Rp or Sp configuration.

Embodiment 73: The oligonucleotide of any one of Embodiments 7-72, further comprising a terminal, chiral modification occurring at the first, and second internucleoside linkages at the 3'-end of the antisense strand, having the linkage phosphorus atom in Sp configuration, a terminal, chiral modification occurring at the first, and second internucleoside linkages at the 5'-end of the antisense strand, having the linkage phosphorus atom in Rp configuration, and a terminal, chiral modification occurring at the first internucleoside linkage at the 5'-end of the sense strand, having the linkage phosphorus atom in either Rp or Sp configuration.

Embodiment 74: The oligonucleotide of any one of Embodiments 1-73, further comprising a phosphate or phosphate mimic at the 5'-end of the antisense strand.

Embodiment 75: The oligonucleotide of Embodiment 74, wherein the phosphate mimic is a 5'-vinyl phosphonate (VP).

Embodiment 76: The oligonucleotide of any one of Embodiments 1-75, further comprising a targeting ligand.

Embodiment 77: The oligonucleotide of Embodiment 76, wherein the targeting ligand is a small molecule-based, sugar-based (e.g., saccharide-based), fatty acid-based, protein-based, or nucleic acid-based targeting ligand.

Embodiment 78: The oligonucleotide of Embodiment 77, wherein the protein-based targeting ligand is an antibody, nanobody, affibody, peptibody, or a peptide.

Embodiment 79: An oligonucleotide selected from the sense strands, antisense strands, and RNAi agents as listed in Tables 1A, 1B, or 1F, or a pharmaceutically acceptable salt thereof.

Embodiment 80: A pharmaceutical composition comprising the oligonucleotide of any one of Embodiments 1-79, or a pharmaceutically acceptable salt thereof, and a pharmaceutically acceptable carrier or excipient.

Embodiment 81: A method for inhibiting DUX4 expression or treating a DUX4 related disorder in a subject, the method comprising administering an effective amount of the oligonucleotide of any one of Embodiments 1-79, or a pharmaceutically acceptable salt thereof, or the pharmaceutical composition of Embodiment 80 to the subject.

Embodiment 82: The method of Embodiment 81, wherein the subject is a human.

Embodiment 83: The method of Embodiment 81 or 82, wherein the reduction of DUX4 mRNA or protein expression levels is measured in a population of myocytes or cardiomyocytes derived from the subject.

Embodiment 84: The method of any one of Embodiments 81-83, wherein the reduction of DUX4 mRNA or protein expression levels is measured in tissues derived from the subject.

Embodiment 85: The method of any one of Embodiments 81-84, wherein the DUX4-related disorder is facioscapulohumeral muscular dystrophy, a DUX4-related cancer, or a DUX4-medicated viral disease.

Embodiment 86: The method of any one of Embodiments 81-85, further comprising administering to the subject an additional agent or a therapy suitable for treatment or prevention of a DUX4 related disorder.

Embodiment 87: An RNAi oligonucleotide comprising a sense strand and an antisense strand, wherein the sense strand and the antisense strand form a duplex, wherein the sense strand and antisense strands are selected from the group consisting of:

| SEQ ID NO: | Sense strand | SEQ ID NO: | Antisense strand |
|---|---|---|---|
| 1240 | csgsacGfgAfGfAfcucguuugga | 1846 | usCfscaaAfcGfAfgucuCfcGfucgsusu |
| 1438 | asgsucCfaGfGfAfuucagaucua | 2044 | usAfsgauCfuGfAfauccUfgGfacususu |
| 1443 | asusucAfgAfUfCfugguuucaga | 2049 | usCfsugaAfaCfCfagauCfuGfaausus u |
| 1626 | asasccUfcUfCfCfuagaaacgga | 2232 | usCfscguUfuCfUfaggaGfaGfguususu |
| 1645 | ascsgcUfgUfCfUfaggcaaacca | 2251 | usGfsguuUfgCfCfuagaCfaGfcgususu |
| 1654 | asgsgcAfaAfCfCfuggauuagaa | 2260 | usUfscuaAfuCfCfagguUfuGfccususu |
| 1655 | gsgscaAfaCfCfUfggauuagaga | 2261 | usCfsucuAfaUfCfcaggUfuUfgccsusu |
| 1661 | cscsugGfaUfUfAfgaguuacaua | 2267 | usAfsuguAfaCfUfcuaaUfcCfaggsusu |
| 1662 | csusggAfuUfAfGfaguuacauca | 2268 | usGfsaugUfaAfCfucuaAfuCfcagsusu |
| 1670 | asuscuCfcUfGfGfaugauuagua | 2276 | usAfscuaAfuCfAfuccaGfgAfgausus u |
| 1671 | uscsucCfuGfGfAfugauuaguua | 2277 | usAfsacuAfaUfCfauccAfgGfagasusu |
| 1672 | csusccUfgGfAfUfgauuaguuca | 2278 | usGfsaacUfaAfUfcaucCfaGfgagsusu |
| 1673 | uscscuGfgAfUfGfauuaguucaa | 2279 | usUfsgaaCfuAfAfucauCfcAfggasusu |
| 1674 | cscsugGfaUfGfAfuuaguucaga | 2280 | usCfsugaAfcUfAfaucaUfcCfaggsusu |
| 1675 | csusggAfuGfAfUfuaguucagaa | 2281 | usUfscugAfaCfUfaaucAfuCfcagsusu |
| 1775 | gscscgCfcUfCfGfcuggaagcaa | 2381 | usUfsgcuUfcCfAfgcgaGfgCfggcsusu |
| 1790 | gsasgcUfuUfAfGfgacgcgggga | 2396 | usCfscccGfcGfUfccuaAfaGfcucsusu |
| 1444 | csusggUfuUfCfAfgaaucgaaga | 2050 | usCfsuucGfaUfUfcugaAfaCfcagsusu |
| 2426 | csusGfguuUfCfAfgaAfucgaAfsgsa | 2437 | vpUsCfsuucgauucugaAfaccagsusu |
| 2427 | asgsGfcaaAfCfCfugGfauuaGfsasa | 2438 | vpUsUfscuaauccagguUfugccususu |
| 2428 | gsgsCfaaaCfCfUfggAfuuagAfsgsa | 2439 | vpUsCfsucuaauccaggUfuugccsusu |
| 2429 | cscsUfggaUfUfAfgaGfuuacAfsusa | 2440 | vpUsAfsuguaacucuaaUfccaggsusu |
| 2430 | csusGfgauUfAfGfagUfuacaUfscsa | 2441 | vpUsGfsauguaacucuaAfuccagsusu |
| 2431 | uscsUfccuGfGfAfugAfuuagUfsusa | 2442 | vpUsAfsacuaaucauccAfggagasusu |
| 2432 | csusCfcugGfAfUfgaUfuaguUfscsa | 2443 | vpUsGfsaacuaaucaucCfaggagsusu |
| 1728 | cscsgcGfcCfGfGfcagaggggaa | 2334 | usUfsccccfuCfUfgccgGfcGfcggsusu |
| 2433 | cscsGfcgcCfGfGfcaGfagggGfsasa | 2444 | vpUsUfsccccucugccgGfcgcggsusu |
| 2434 | uscsCfuggAfUfGfauUfaguuCfaa | 2445 | vpUsUfsgaacuaaucauCfcaggasusu |
| 2435 | cscsUfggaUfGfAfuuAfguucAfga | 2446 | vpUsCfsugaacuaaucaUfccaggsusu |
| 2436 | csusGfgauGfAfUfuaGfuucaGfaa | 2447 | vpUsUfscugaacuaaucAfuccagsusu |

Af represents 2'-deoxy-2'-fluoro-adenosine-3'-phosphate;

Afs represents 2'-deoxy-2'-fluoro-adenosine-3'-phosphorothioate;

Cf represents 2'-deoxy-2'-fluoro-cytidine-3'-phosphate;

Cfs represents 2'-deoxy-2'-fluoro-cytidine-3'-phosphorothioate;

Gf represents 2'-deoxy-2'-fluoro-guanosine-3'-phosphate;

Gfs represents 2'-deoxy-2'-fluoro-guanosine-3'-phosphorothioate;

Uf represents 2'-deoxy-2'-fluoro-uridine-3'-phosphate;

Ufs represents 2'-deoxy-2'-fluoro-uridine-3'-phosphorothioate;

a represents 2'-O-methyl-adenosine-3'-phosphate;

as represents 2'-O-methyl-adenosine-3'-phosphorothioate;

c represents 2'-O-methyl-cytidine-3'-phosphate;

cs represents 2'-O-methyl-cytidine-3'-phosphorothioate;

g represents 2'-O-methyl-guanosine-3'-phosphate;

gs represents 2'-O-methyl-guanosine-3'-phosphorothioate;

u represents 2'-O-methyl-uri dine-3'-phosphate;

us represents 2'-O-methyl-uridine-3'-phosphorothioate; and vpUs represents 5'-vinylphosphonate-2'-O-methyl-uridine-3'-phosphorothioate.

Embodiment 88: The RNAi oligonucleotide of Embodiment 87, wherein (i) the sense strand is csgsacGfgAfGfAfcucguuugga (SEQ ID NO: 1240), and the antisense strand is usCfscaaAfcGfAfgucuCfcGfucgsusu (SEQ ID NO: 1846); or (ii) the sense strand is asasccUfcUfCfCfuagaaacgga (SEQ ID NO: 1626), and the antisense strand is usCfscguUfuCfUfaggaGfaGfguususu (SEQ ID NO: 2232); or (iii) the sense strand is gscscgCfcUfCfGfcuggaagcaa (SEQ ID NO: 1775), and the antisense strand is usUfsgcuUfcCfAfgcgaGfgCfggcsusu (SEQ ID NO: 2381).

Embodiment 89: The RNAi oligonucleotide of Embodiment 87, wherein the sense strand is asgsucCfaGfGfAfuucagaucua (SEQ ID NO: 1438), and the antisense strand is usAfsgauCfuGfAfauccUfgGfacususu (SEQ ID NO: 2044).

Embodiment 90: The RNAi oligonucleotide of Embodiment 87, wherein the sense strand is asusucAfgAfUfCfugguuucaga (SEQ ID NO: 1443), and the antisense strand is usCfsugaAfaCfCfagauCfuGfaaususu (SEQ ID NO: 2049).

Embodiment 91: The RNAi oligonucleotide of Embodiment 87, wherein the sense strand is ascsgcUfgUfCfUfaggcaaacca (SEQ ID NO: 1645), and the antisense strand is usGfsguuUfgCfCfuagaCfaGfcgususu (SEQ ID NO: 2251).

Embodiment 92: The RNAi oligonucleotide of Embodiment 87, wherein the sense strand is asgsgcAfaAfCfCfuggauuagaa (SEQ ID NO: 1654), and the antisense strand is usUfscuaAfuCfCfagguUfuGfccususu (SEQ ID NO: 2260).

Embodiment 93: The RNAi oligonucleotide of Embodiment 87, wherein the sense strand is gsgscaAfaCfCfUfggauuagaga (SEQ ID NO: 1655), and the antisense strand is usCfsucuAfaUfCfcaggUfuUfgccsusu (SEQ ID NO: 2261).

Embodiment 94: The RNAi oligonucleotide of Embodiment 87, wherein the sense strand is cscsugGfaUfUfAfgaguuacaua (SEQ ID NO: 1661), and the antisense strand is usAfsuguAfaCfUfcuaaUfcCfaggsusu (SEQ ID NO: 2267).

Embodiment 95: The RNAi oligonucleotide of Embodiment 87, wherein the sense strand is csusggAfuUfAfGfaguuacauca (SEQ ID NO: 1662), and the antisense strand is usGfsaugUfaAfCfucuaAfuCfcagsusu (SEQ ID NO: 2268).

Embodiment 96: The RNAi oligonucleotide of Embodiment 87, wherein the sense strand is asuscuCfcUfGfGfaugauuagua (SEQ ID NO: 1670), and the antisense strand is usAfscuaAfuCfAfuccaGfgAfgaususu (SEQ ID NO: 2276).

Embodiment 97: The RNAi oligonucleotide of Embodiment 87, wherein the sense strand is uscsucCfuGfGfAfugauuaguua (SEQ ID NO: 1671), and the antisense strand is usAfsacuAfaUfCfauccAfgGfagasusu (SEQ ID NO: 2277).

Embodiment 98: The RNAi oligonucleotide of Embodiment 87, wherein the sense strand is csusccUfgGfAfUfgauuaguuca (SEQ ID NO: 1672), and the antisense strand is usGfsaacUfaAfUfcaucCfaGfgagsusu (SEQ ID NO: 2278).

Embodiment 99: The RNAi oligonucleotide of Embodiment 87, wherein the sense strand is uscscuGfgAfUfGfauuaguucaa (SEQ ID NO: 1673), and the antisense strand is usUfsgaaCfuAfAfucauCfcAfggasusu (SEQ ID NO: 2279).

Embodiment 100: The RNAi oligonucleotide of Embodiment 87, wherein the sense strand is cscsugGfaUfGfAfuuaguucaga (SEQ ID NO: 1674), and the antisense strand is usCfsugaAfcUfAfaucaUfcCfaggsusu (SEQ ID NO: 2280).

Embodiment 101: The RNAi oligonucleotide of Embodiment 87, wherein the sense strand is csusggAfuGfAfUfuaguucagaa (SEQ ID NO: 1675), and the antisense strand is usUfscugAfaCfUfaaucAfuCfcagsusu (SEQ ID NO: 2281).

Embodiment 102: The RNAi oligonucleotide of Embodiment 87, wherein the sense strand is gsasgcUfuUfAfGfgacgcgggga (SEQ ID NO: 1790), and the antisense strand is usCfscccGfcGfUfccuaAfaGfcucsusu (SEQ ID NO: 2396).

Embodiment 103: The RNAi oligonucleotide of Embodiment 87, wherein the sense strand is csusggUfuUfCfAfgaaucgaaga (SEQ ID NO: 1444), and the antisense strand is usCfsuucGfaUfUfcugaAfaCfcagsusu (SEQ ID NO: 2050).

Embodiment 104: The RNAi oligonucleotide of Embodiment 87, wherein the sense strand is csusGfguuUfCfAfgaAfucgaAfsgsa (SEQ ID NO: 2426), and the antisense strand is vpUsCfsuucgauucugaAfaccagsusu (SEQ ID NO: 2437).

Embodiment 105: The RNAi oligonucleotide of Embodiment 87, wherein the sense strand is asgsGfcaaAfCfCfugGfauuaGfsasa (SEQ ID NO: 2427), and the antisense strand is vpUsUfscuaauccagguUfugccususu (SEQ ID NO: 2438).

Embodiment 106: The RNAi oligonucleotide of Embodiment 87, wherein the sense strand is gsgsCfaaaCfCfUfggAfuuagAfsgsa (SEQ ID NO: 2428), and the antisense strand is vpUsCfsucuaauccaggUfuugccsusu (SEQ ID NO: 2439).

Embodiment 107: The RNAi oligonucleotide of Embodiment 87, wherein the sense strand is cscsUfggaUfUfAfgaGfuuacAfsusa (SEQ ID NO: 2429), and the antisense strand is vpUsAfsuguaacucuaaUfccaggsusu (SEQ ID NO: 2440).

Embodiment 108: The RNAi oligonucleotide of Embodiment 87, wherein the sense strand is csusGfgauUfAfGfagUfuacaUfscsa (SEQ ID NO: 2430), and the antisense strand is vpUsGfsauguaacucuaAfuccagsusu (SEQ ID NO: 2441).

Embodiment 109: The RNAi oligonucleotide of Embodiment 87, wherein the sense strand is uscsUfccuGfGfAfugAfuuagUfsusa (SEQ ID NO: 2431), and the antisense strand is vpUsAfsacuaaucauccAfggagasusu (SEQ ID NO: 2442).

Embodiment 110: The RNAi oligonucleotide of Embodiment 87, wherein the sense strand is csusCfcugGfAfUfgaUfuaguUfscsa (SEQ ID NO: 2432), and the antisense strand is vpUsGfsaacuaaucaucCfaggagsusu (SEQ ID NO: 2443).

Embodiment 111: The RNAi oligonucleotide of Embodiment 87, wherein the sense strand is cscsgcGfcCfGfGfcagaggggaa (SEQ ID NO: 1728), and the antisense strand is usUfscccCfuCfUfgccgGfcGfcggsusu (SEQ ID NO: 2334).

Embodiment 112: The RNAi oligonucleotide of Embodiment 87, wherein the sense strand is cscsGfcgcCfGfGfcaGfagggGfsasa (SEQ ID NO: 2433), and the antisense strand is vpUsUfsccccucugccgGfcgcggsusu (SEQ ID NO: 2444).

Embodiment 113: The RNAi oligonucleotide of Embodiment 87, wherein the sense strand is uscsCfuggAfUfGfauUfaguuCfaa (SEQ ID NO: 2434), and the antisense strand is vpUsUfsgaacuaaucauCfcaggasusu (SEQ ID NO: 2445).

Embodiment 114: The RNAi oligonucleotide of Embodiment 87, wherein the sense strand is cscsUfggaUfGfAfuuAfguucAfga (SEQ ID NO: 2435), and the antisense strand is vpUsCfsugaacuaaucaUfccaggsusu (SEQ ID NO: 2446).

Embodiment 115: The RNAi oligonucleotide of Embodiment 87, wherein the sense strand is csusGfgauGfAfUfuaGfuucaGfaa (SEQ ID NO: 2436), and the antisense strand is vpUsUfscugaacuaaucAfuccagsusu (SEQ ID NO: 2447).

Embodiment 116: A method for inhibiting DUX4 expression or treating a DUX4 related disorder in a subject, the method comprising administering to the subject an effective amount of the RNAi oligonucleotide of Embodiment 87, or a pharmaceutically acceptable salt thereof.

The term "about" as used herein refers to the usual error range for the respective value readily known to the skilled person in this technical field. Reference to "about" a value or parameter herein includes (and describes) embodiments that are directed to that value or parameter per se.

As used herein, the singular forms "a," "an," and "the" include plural referents unless the context clearly dictates otherwise. For example, "a" or "an" means "at least one" or "one or more."

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: DUX4 siRNA Design and Evaluation

A set of siRNAs were designed to target DUX4 (shown here as SEQ ID NO: 2425. A detailed list of the unmodified siRNA sense and antisense strand sequences is shown in Tables 1A and 1F below. A detailed list of modified siRNAs is shown in Table 1B below. Table 2 provides names for the nucleotide abbreviations used in the nucleic acid sequences herein. Oligonucleotides are chemically synthesized using phosphoramidite approach and after quality control using UV- and mass-spectroscopy sense and antisense strands were annealed to perform screening HEK293T cells were plated at a density of about 20,000 cells/well. siRNA and psiCHECK2-DUX4 plasmid transfection were carried out by adding siRNA duplexes, psiCHECK2-DUX4 plasmid, and Lipofectamine®2000 to each well. Opti-MEM® media was used to adjust the transfection mix to a final siRNA concentration of 10 nM, 5 nM, 2.5 nM, 1.25 nM, 0.625 nM, 0.3125 nM, 0.1563 nM, 0.0781 nM, 0.0391 nM, or 0.0195 nM. The cells were then incubated at room temperature for 15 minutes. The transfected cells were incubated at 37 °C in an atmosphere of 5% $CO_2$.

24 hours after transfection, Firefly (transfection control) and *Renilla* (fused to full-length DUX4 luciferase are measured. First, media is removed from cells. Then Firefly luciferase activity is measured by adding a volume of DUAL-GLO® Luciferase Reagent equal to the culture medium volume to each well. The mixture is incubated at room temperature for 30 minutes before luminescence (500 nm) was measured to detect the Firefly luciferase signal. *Renilla* luciferase activity is measured by adding DUAL-GLO® STOP & GLO® Reagent to each well and the plates are incubated for 10-15 minutes before luminescence is again measured to determine the *Renilla* luciferase signal. The DUAL-GLO® STOP & GLO® Reagent, quenches the firefly luciferase signal and sustains luminescence for the *Renilla* luciferase reaction. siRNA activity is determined by normalizing the *Renilla* (DUX4) signal to the Firefly (control) signal within each well. The magnitude of siRNA activity is then assessed relative to cells that were transfected with the same vector but were not treated with siRNA or were treated with a non-targeting siRNA.

Example 2: DUX4 siRNA Synthesis and Evaluation Using Reporter Plasmids

A set of siRNAs were designed to target DUX4 (shown here as SEQ ID NO: 2425. A detailed list of the unmodified siRNA sense and antisense strand sequences is shown in Tables 1A and 1F below. A detailed list of modified siRNAs is shown in Table 1B below. Evaluation results of knockdown efficiency are shown in Tables 1C and 1E below. Table 2 provides names for the nucleotide abbreviations used in the nucleic acid sequences herein. Oligonucleotides were chemically synthesized using phosphoramidite approach, and after quality control using UV- and mass-spectroscopy, sense and antisense strands were annealed to form duplexes suitable for screening.

Hepa1-6 cells (ATCC, CRL-1830) were maintained by biweekly passing in DMEM GlutaMAX (ThermoFisher, 10569) supplemented with 10% heat-inactivated FBS (Sigma, F4135) (D10). Hepa1-6 cells were purchased and cultured as per the manufacturer's handling guidelines to generate frozen stocks in heat-inactivated FBS supplemented with 10% DMSO. Each aliquot of cells was thawed using a 37 °C water bath for 5 minutes, and cells were transferred and quenched using D10 in 50 mL conical. Cells were then pelleted by centrifuging at 300×g for 5 minutes, spent media was aspirated, and cell pellet was resuspended to appropriate density and seeded for continuous culture.

One day prior to transfection, Hepa1-6 cells were dissociated using 1×TrypLE™ Express Enzyme (ThermoFisher, 12605010) and seeded into solid white 96-well TC plates (ThermoFisher, 136102) at 30,000 cells/well in 100 μL of D10. 96-well plates were stored overnight in a 37 °C, 5% $CO_2$ incubator.

On the day of transfection, dual transfection of siRNA and plasmid DNA were performed using two master mixes for siRNA and the reporter plasmid DNA. Previously, a designed construct of the DUX4 cDNA was inserted into a psiCheck-2 vector (Promega, C8021) and assessed for stability and luminescence intensity.

Before the transfection, individual siRNA at 5 uM were diluted into OptiMEM to make a high dose. 1:10 Serial dilutions were prepared in 96-well plates for the following doses 40, 4.0, and 0.4 nM. A negative control containing 1×phosphate buffered saline (PBS), OptiMEM, and RNAiMax were also prepared following the top dose calculations. Plasmid DNA transfection master mixes were prepared as per manufacturer's protocol, where a Lipofectamine 3000 mix (L3) was prepared by adding 0.2 μL/well of Lipofectamine 3000 (ThermoFisher, L3000075) to 5 μL/well of OptiMEM media (ThermoFisher, 31985062). The P3000 enhancer reagent master mix (P3) was prepared by adding 100 ng/well of plasmid DNA and P3000 enhancer reagent at 0.2 μL/well to 5 μL/well of OptiMEM media. Subsequently, L3 and P3 master mixes were combined 1:1 to make the L3P3 master mix and incubated at room temperature for 25 minutes. During the incubation for L3 and P3, a master mix of Lipofectamine RNAiMax (ThermoFisher, 13778150) at 0.05 μL/well and OptiMEM 30 μL/well was created. 30 μL of RNAiMax master mix was added to each diluted siRNA well for a total of 60 μL per preparation well and allowed to incubate at room temperature for 15 minutes.

Post-25-minute incubation of L3P3, previously plated cells were removed from the incubator. The spent media was aspirated and replaced with 40 μL of fresh warm OptiMEM. 10 μL of L3P3 master mix was then added to each well by multichannel pipetting. Immediately following L3P3 addition and post-15-minute incubation, 50 μL of siRNA+RNAiMax mixes were added to the appropriate replicate wells following the plate map. Following additions of both L3P3 and siRNA+RNAiMax master mixes, the cell plates were placed into a 37 °C, 5% $CO_2$ incubator.

24 hours after transfection, activities of Firefly (transfection control) and *Renilla* (fused to full-length DUX4) luciferase were measured. First, an appropriate amount of Dual-Glo Luciferase (Promega, E1960) kits containing Luciferase Assay Reagent II (LARII) and Stop-&-Glo (S&G) reagents were thawed and prepared as per manufacturer's instructions and a 1× passive lysis buffer (PLB) (Promega, E1941) was prepared from a 5× stock for 20 μL per well. The plates containing cells were removed from the 37 °C, 5% $CO_2$ incubator, and the spent media was aspirated, and 20 μL of 1×PLB was added to each well. Plates were then placed on a digital microplate shaker (Corning, CLS67804) at 800 rpm for 15 minutes at room temperature.

Post-shaking, the lysed cell plates were transferred to +4 °C storage while readouts were captured. Then, Firefly luciferase activity was measured by adding DUAL-GLO® Luciferase Reagent kit (Promega, E1960) containing Luciferase Assay Reagent II (LARII) and STOP & GLO® (S&G) reagents to each well. A Synergy H1 multimode plate reader (Agilent, 8041000N) equipped with dual injectors was used to dispense LARII and S&G, capture and read luminescence. 100 μL of LARII reagent was dispensed per well and the luminescence was captured. Following LARII reagent dispense, 100 μL of S&G was dispensed per well and the second luminescent readout was captured. The DUAL-GLO® STOP & GLO® Reagent works by quenching the firefly luciferase signal and sustaining luminescence for the *Renilla* luciferase reaction. siRNA efficacy was determined by normalizing the *Renilla*-DUX4 signal to the Firefly (control) signal within each well. The magnitude of siRNA activity was then assessed relative to cells that were transfected with the same vector but were not treated with siRNA or were treated with a non-targeting siRNA (see Tables 1C and 1E).

Example 3: DUX4 siRNA Evaluation Using Patient-Derived Cell Line

A detailed list of the unmodified siRNA sense and antisense strand sequences is shown in Tables 1A and 1F below. A detailed list of modified siRNAs is shown in Table 1B below. Evaluation results of exemplary modified siRNAs include IC50 values shown in Table 1D. Table 2 provides names for the nucleotide abbreviations used in the nucleic acid sequences disclosed herein.

FSHD MB200 cells (immortalized human myoblast cell line developed by Campbell et al., Skelet Muscle. 2017; 7(1):16) were thawed following previously established cell thawing and seeding protocol. Complete FSHD media consisting of Ham's F-10 (Gibco, 1150-043) base media and the following additives at the final concentrations: 15% FBS (CytivaHyClone, SH3007.03), 1 μM dexamethasone (Sigma, D4902), 10 ng/mL rhFGF (Peprotech, 100-18b) was used for maintenance of the MB200 cells. Cells were maintained at a density of 12,000 cells/$cm^2$ with media changes every 2 days at 37 °C, 5% $CO_2$ until cell seeding for transfection.

Cell Seeding (Day 1): On the day of cell seeding, cells were harvested from culture vessels using a 1×PBS wash followed by a 5-minute incubation with 0.25% trypsin-EDTA solution ThermoFisher, 25200056). Trypsinized cell solution was then quenched using 15 mL of fresh FSHD media, cells were then pelleted by centrifugation 300×g for 5 mins and resuspended in 10 mL of fresh FSHD media. The cell viability was assessed using a Countess 3 Cell Counter, cell solutions ≥92% viability were then set to a density of 90,000 cells per mL in warm complete FSHD media. Following 90,000 cells per mL dilution, a double confirmatory cell suspension count was carried out and a range of ±10% of target density was acceptable. 1 mL of cell solution was then plated per well of a 12-well TC plate (Falcon, 353043). Cells were then placed in a 37 °C 5% $CO_2$ incubator overnight.

Transfection for Single Dose (Day 2): 24 hours later, cells were transfected using the following protocol. siRNAs (5 μM stock) were thawed to room temperature. A 4× working stock of siRNA was prepared in 250 μL of OptiMEM (ThermoFisher, 11058021) for complexing with lipid master mix by creating a 4 nM stock from previously mentioned 5 μM stocks. A master mix of Lipofectamine RNAiMax (ThermoFisher, 13778150) at 3.0 μL/well and OptiMEM at 250 μL/well was created. 250 μL of RNAiMax master mix was then added to 250 μL of 4× siRNA in OptiMEM, and complexed for 15 minutes to generate a 500 μL/well 2× target concentration of siRNA. Cells were removed from the 37 °C 5% $CO_2$ incubator, spent FHSD media was removed and 500 μL of fresh, warm, complete FSHD media was then added to each well. Post-siRNA complexing, 500 μL of siRNA-OptiMEM-RNAiMax mix was added to each well containing cells for a dosed concentration of 1 nM. For the transfection control wells, 1×PBS was used in place of siRNA. Cells were then maintained at 37 °C 5% $CO_2$.

Transfection for IC50 Determination (Day 2): Individual siRNA at 5 μM were diluted into OptiMEM to make a top 4× dose at 40 nM for serial dilution 1:3 Serial dilutions of RNA in OptiMEM were prepared in 96-well deep plates to generate the final concentrations 10, 3, 1, $3.33\times10^{-1}$, $1.11\times10^{-1}$, $3.70\times10^{-2}$, $1.23\times10^{-2}$, $4.12\times10^{-3}$, $1.37\times10^{-3}$, $4.57\times10^{-4}$, $1.52\times10^{-4}$, $5.08\times10^{-5}$ nM. A negative control containing 1× phosphate buffered saline (PBS), OptiMEM, and RNAiMax was also prepared following the top dose calculations. Similarly to previous single dose screening, a master mix of Lipofectamine RNAiMax (ThermoFisher, 13778150) at 3.0 µL/well and OptiMEM at 250 µL/well was created. 250 µL of master mix was added to each well containing 250 µL of siRNA in OptiMEM and allowed to complex for 15-minutes. Cells were removed from the 37 °C 5% $CO_2$ incubator, spent FHSD media was removed and 500 µL of fresh, warm, complete, FSHD media was then added to each well. Post-siRNA complexing, 500 µL of siRNA-OptiMEM-RNAiMax mix was added to each well containing cells for a dosed concentration curve outlined above. Cells were maintained at 37 °C 5% $CO_2$.

Myotube Differentiation (Day 3): 24 hours post-transfection, differentiation media was prepared using DMEM Glutamax (ThermoFisher, 10569) supplemented with 10 µg/mL insulin (Sigma, 11882) and 10 µg/mL transferrin (Sigma, T0665). Cells were then removed from 37 °C 5% $CO_2$ incubator and inspected. Wells containing cells for differentiation were aspirated and 1 mL of complete differentiation media was added. For the other wells, media was removed and replaced with warm, fresh, complete FSHD media. Cells were then returned to 37 °C 5% $CO_2$ incubator for 72 hours to undergo differentiation.

Harvest (Day 6): After 72 hours, FSHD cells were harvested by completely removing media from wells and adding 500 µL Trizol for cell lysis, mixing by pipette action and transferring lysates to 96 deep well round bottom plates. Plates were labelled, sealed using aluminum foil plate seals, and then stored at −80 °C for downstream RNA isolation and RT-qPCR gene expression analysis.

RNA Isolation: RNA was isolated using the DirectZol-96 RNA kit (Zymo Research, Catalog #R2056) as per manufacturers protocol. RNA was eluted in 30 ul of RNAase/DNAse free Water and concentration was determined using a Nanodrop.

RT-qPCR: cDNA was prepared using Maxima First Strand Synthesis kit (ThermoFisher, K1641) and Taqman qPCR assays were performed using the TaqMan™ Universal PCR Master Mix (ThermoFisher, 4326708) according to the manufacturers protocol. qPCR reactions were performed for a panel of four DUX4's targets: KHDC1L (FAM, ThermoFisher, Hs1024323_g1), LEUTX (FAM, ThermoFisher, Hs01028718_m1), MBD3L2 (FAM, IDT, Hs.PT.58.24718123) and ZSCAN4 (FAM, ThermoFisher, Hs00537549_m1) multiplexed with human TBP (VIC, ThermoFisher, 4326322E) as the housekeeping gene control. Primer efficiency was determined prior to use. Thermocycling and data acquisition was performed using CFX Opus 384 Real-Time PCR System.

The mRNA levels of the target genes and the efficiency of siRNA-mediated knockdown were assessed using relative quantification. Cq values for both the target and reference (housekeeping) genes were obtained via quantitative PCR (qPCR) for each sample. Combined gene panel for KHDC1L, LEUTX, MBD3L2 and ZSCAN4 was calculated by taking the average Cq of each target and housekeeping gene. The relative expression of the target gene and gene panel was then calculated using the $2^{(-\Delta\Delta Cq)}$ method, where ΔCq represents the difference between the Cq values of the target and reference genes and ΔΔCq refers to the difference between the ΔCq values for treatment samples and only lipofectamine treated control samples.

IC50 Determination: IC50 for siRNA (as shown in Table 1D) was determined by plotting the average of the percentage of target gene expression (KHDC1L, LEUTX, MBD3L2 and ZSCAN4) against the logarithm of siRNA concentrations. A sigmoidal dose-response (variable slope) curve was fitted to the data using the Curve Fitting function in GraphPad Prism (version 7.0). The IC50 value was defined as the siRNA concentration resulting in 50% gene knockdown (see Table 1D).

TABLE 1A provides exemplary siRNAs with the sequences of the sense strand and the antisense strand.

| Position in transcript | SEQ ID NO: | Sense strand | SEQ ID NO: | Antisense strand |
|---|---|---|---|---|
| 1 | 1 | ATGGCCCTCCCGACACCCT | 607 | AGGGTGTCGGGAGGGCCAT |
| 2 | 2 | TGGCCCTCCCGACACCCTC | 608 | GAGGGTGTCGGGAGGGCCA |
| 11 | 3 | CGACACCCTCGGACAGCAC | 609 | GTGCTGTCCGAGGGTGTCG |
| 12 | 4 | GACACCCTCGGACAGCACC | 610 | GGTGCTGTCCGAGGGTGTC |
| 13 | 5 | ACACCCTCGGACAGCACCC | 611 | GGGTGCTGTCCGAGGGTGT |
| 14 | 6 | CACCCTCGGACAGCACCCT | 612 | AGGGTGCTGTCCGAGGGTG |
| 15 | 7 | ACCCTCGGACAGCACCCTC | 613 | GAGGGTGCTGTCCGAGGGT |
| 16 | 8 | CCCTCGGACAGCACCCTCC | 614 | GGAGGGTGCTGTCCGAGGG |
| 17 | 9 | CCTCGGACAGCACCCTCCC | 615 | GGGAGGGTGCTGTCCGAGG |
| 18 | 10 | CTCGGACAGCACCCTCCCC | 616 | GGGGAGGGTGCTGTCCGAG |
| 19 | 11 | TCGGACAGCACCCTCCCCG | 617 | CGGGGAGGGTGCTGTCCGA |
| 23 | 12 | ACAGCACCCTCCCCGCGGA | 618 | TCCGCGGGGAGGGTGCTGT |
| 24 | 13 | CAGCACCCTCCCCGCGGAA | 619 | TTCCGCGGGGAGGGTGCTG |
| 25 | 14 | AGCACCCTCCCCGCGGAAG | 620 | CTTCCGCGGGGAGGGTGCT |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 39 | 15 | GGAAGCCCGGGGACGAGGA | 621 | TCCTCGTCCCCGGGCTTCC |
| 40 | 16 | GAAGCCCGGGGACGAGGAC | 622 | GTCCTCGTCCCCGGGCTTC |
| 41 | 17 | AAGCCCGGGGACGAGGACG | 623 | CGTCCTCGTCCCCGGGCTT |
| 49 | 18 | GGACGAGGACGGCGACGGA | 624 | TCCGTCGCCGTCCTCGTCC |
| 50 | 19 | GACGAGGACGGCGACGGAG | 625 | CTCCGTCGCCGTCCTCGTC |
| 51 | 20 | ACGAGGACGGCGACGGAGA | 626 | TCTCCGTCGCCGTCCTCGT |
| 52 | 21 | CGAGGACGGCGACGGAGAC | 627 | GTCTCCGTCGCCGTCCTCG |
| 53 | 22 | GAGGACGGCGACGGAGACT | 628 | AGTCTCCGTCGCCGTCCTC |
| 54 | 23 | AGGACGGCGACGGAGACTC | 629 | GAGTCTCCGTCGCCGTCCT |
| 55 | 24 | GGACGGCGACGGAGACTCG | 630 | CGAGTCTCCGTCGCCGTCC |
| 56 | 25 | GACGGCGACGGAGACTCGT | 631 | ACGAGTCTCCGTCGCCGTC |
| 57 | 26 | ACGGCGACGGAGACTCGTT | 632 | AACGAGTCTCCGTCGCCGT |
| 60 | 27 | GCGACGGAGACTCGTTTGG | 633 | CCAAACGAGTCTCCGTCGC |
| 61 | 28 | CGACGGAGACTCGTTTGGA | 634 | TCCAAACGAGTCTCCGTCG |
| 62 | 29 | GACGGAGACTCGTTTGGAC | 635 | GTCCAAACGAGTCTCCGTC |
| 63 | 30 | ACGGAGACTCGTTTGGACC | 636 | GGTCCAAACGAGTCTCCGT |
| 64 | 31 | CGGAGACTCGTTTGGACCC | 637 | GGGTCCAAACGAGTCTCCG |
| 65 | 32 | GGAGACTCGTTTGGACCCC | 638 | GGGGTCCAAACGAGTCTCC |
| 66 | 33 | GAGACTCGTTTGGACCCCG | 639 | CGGGGTCCAAACGAGTCTC |
| 67 | 34 | AGACTCGTTTGGACCCCGA | 640 | TCGGGGTCCAAACGAGTCT |
| 71 | 35 | TCGTTTGGACCCCGAGCCA | 641 | TGGCTCGGGGTCCAAACGA |
| 76 | 36 | TGGACCCCGAGCCAAAGCG | 642 | CGCTTTGGCTCGGGGTCCA |
| 77 | 37 | GGACCCCGAGCCAAAGCGA | 643 | TCGCTTTGGCTCGGGGTCC |
| 78 | 38 | GACCCCGAGCCAAAGCGAG | 644 | CTCGCTTTGGCTCGGGGTC |
| 79 | 39 | ACCCCGAGCCAAAGCGAGG | 645 | CCTCGCTTTGGCTCGGGGT |
| 80 | 40 | CCCCGAGCCAAAGCGAGGC | 646 | GCCTCGCTTTGGCTCGGGG |
| 81 | 41 | CCCGAGCCAAAGCGAGGCC | 647 | GGCCTCGCTTTGGCTCGGG |
| 82 | 42 | CCGAGCCAAAGCGAGGCCC | 648 | GGGCCTCGCTTTGGCTCGG |
| 83 | 43 | CGAGCCAAAGCGAGGCCCT | 649 | AGGGCCTCGCTTTGGCTCG |
| 84 | 44 | GAGCCAAAGCGAGGCCCTG | 650 | CAGGGCCTCGCTTTGGCTC |
| 85 | 45 | AGCCAAAGCGAGGCCCTGC | 651 | GCAGGGCCTCGCTTTGGCT |
| 86 | 46 | GCCAAAGCGAGGCCCTGCG | 652 | CGCAGGGCCTCGCTTTGGC |
| 87 | 47 | CCAAAGCGAGGCCCTGCGA | 653 | TCGCAGGGCCTCGCTTTGG |
| 88 | 48 | CAAAGCGAGGCCCTGCGAG | 654 | CTCGCAGGGCCTCGCTTTG |
| 89 | 49 | AAAGCGAGGCCCTGCGAGC | 655 | GCTCGCAGGGCCTCGCTTT |
| 90 | 50 | AAGCGAGGCCCTGCGAGCC | 656 | GGCTCGCAGGGCCTCGCTT |
| 108 | 51 | CTGCTTTGAGCGGAACCCG | 657 | CGGGTTCCGCTCAAAGCAG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 109 | 52 | TGCTTTGAGCGGAACCCGT | 658 | ACGGGTTCCGCTCAAAGCA |
| 110 | 53 | GCTTTGAGCGGAACCCGTA | 659 | TACGGGTTCCGCTCAAAGC |
| 111 | 54 | CTTTGAGCGGAACCCGTAC | 660 | GTACGGGTTCCGCTCAAAG |
| 112 | 55 | TTTGAGCGGAACCCGTACC | 661 | GGTACGGGTTCCGCTCAAA |
| 113 | 56 | TTGAGCGGAACCCGTACCC | 662 | GGGTACGGGTTCCGCTCAA |
| 114 | 57 | TGAGCGGAACCCGTACCCG | 663 | CGGGTACGGGTTCCGCTCA |
| 115 | 58 | GAGCGGAACCCGTACCCGG | 664 | CCGGGTACGGGTTCCGCTC |
| 116 | 59 | AGCGGAACCCGTACCCGGG | 665 | CCCGGGTACGGGTTCCGCT |
| 124 | 60 | CCGTACCCGGGCATCGCCA | 666 | TGGCGATGCCCGGGTACGG |
| 125 | 61 | CGTACCCGGGCATCGCCAC | 667 | GTGGCGATGCCCGGGTACG |
| 126 | 62 | GTACCCGGGCATCGCCACC | 668 | GGTGGCGATGCCCGGGTAC |
| 127 | 63 | TACCCGGGCATCGCCACCA | 669 | TGGTGGCGATGCCCGGGTA |
| 129 | 64 | CCCGGGCATCGCCACCAGA | 670 | TCTGGTGGCGATGCCCGGG |
| 130 | 65 | CCGGGCATCGCCACCAGAG | 671 | CTCTGGTGGCGATGCCCGG |
| 131 | 66 | CGGGCATCGCCACCAGAGA | 672 | TCTCTGGTGGCGATGCCCG |
| 132 | 67 | GGGCATCGCCACCAGAGAA | 673 | TTCTCTGGTGGCGATGCCC |
| 133 | 68 | GGCATCGCCACCAGAGAAC | 674 | GTTCTCTGGTGGCGATGCC |
| 134 | 69 | GCATCGCCACCAGAGAACG | 675 | CGTTCTCTGGTGGCGATGC |
| 135 | 70 | CATCGCCACCAGAGAACGG | 676 | CCGTTCTCTGGTGGCGATG |
| 136 | 71 | ATCGCCACCAGAGAACGGC | 677 | GCCGTTCTCTGGTGGCGAT |
| 137 | 72 | TCGCCACCAGAGAACGGCT | 678 | AGCCGTTCTCTGGTGGCGA |
| 138 | 73 | CGCCACCAGAGAACGGCTG | 679 | CAGCCGTTCTCTGGTGGCG |
| 144 | 74 | CAGAGAACGGCTGGCCCAG | 680 | CTGGGCCAGCCGTTCTCTG |
| 145 | 75 | AGAGAACGGCTGGCCCAGG | 681 | CCTGGGCCAGCCGTTCTCT |
| 146 | 76 | GAGAACGGCTGGCCCAGGC | 682 | GCCTGGGCCAGCCGTTCTC |
| 147 | 77 | AGAACGGCTGGCCCAGGCC | 683 | GGCCTGGGCCAGCCGTTCT |
| 148 | 78 | GAACGGCTGGCCCAGGCCA | 684 | TGGCCTGGGCCAGCCGTTC |
| 157 | 79 | GCCCAGGCCATCGGCATTC | 685 | GAATGCCGATGGCCTGGGC |
| 158 | 80 | CCCAGGCCATCGGCATTCC | 686 | GGAATGCCGATGGCCTGGG |
| 159 | 81 | CCAGGCCATCGGCATTCCG | 687 | CGGAATGCCGATGGCCTGG |
| 160 | 82 | CAGGCCATCGGCATTCCGG | 688 | CCGGAATGCCGATGGCCTG |
| 161 | 83 | AGGCCATCGGCATTCCGGA | 689 | TCCGGAATGCCGATGGCCT |
| 162 | 84 | GGCCATCGGCATTCCGGAG | 690 | CTCCGGAATGCCGATGGCC |
| 163 | 85 | GCCATCGGCATTCCGGAGC | 691 | GCTCCGGAATGCCGATGGC |
| 164 | 86 | CCATCGGCATTCCGGAGCC | 692 | GGCTCCGGAATGCCGATGG |
| 165 | 87 | CATCGGCATTCCGGAGCCC | 693 | GGGCTCCGGAATGCCGATG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 166 | 88 | ATCGGCATTCCGGAGCCCA | 694 | TGGGCTCCGGAATGCCGAT |
| 167 | 89 | TCGGCATTCCGGAGCCCAG | 695 | CTGGGCTCCGGAATGCCGA |
| 168 | 90 | CGGCATTCCGGAGCCCAGG | 696 | CCTGGGCTCCGGAATGCCG |
| 169 | 91 | GGCATTCCGGAGCCCAGGG | 697 | CCCTGGGCTCCGGAATGCC |
| 170 | 92 | GCATTCCGGAGCCCAGGGT | 698 | ACCCTGGGCTCCGGAATGC |
| 171 | 93 | CATTCCGGAGCCCAGGGTC | 699 | GACCCTGGGCTCCGGAATG |
| 172 | 94 | ATTCCGGAGCCCAGGGTCC | 700 | GGACCCTGGGCTCCGGAAT |
| 173 | 95 | TTCCGGAGCCCAGGGTCCA | 701 | TGGACCCTGGGCTCCGGAA |
| 174 | 96 | TCCGGAGCCCAGGGTCCAG | 702 | CTGGACCCTGGGCTCCGGA |
| 175 | 97 | CCGGAGCCCAGGGTCCAGA | 703 | TCTGGACCCTGGGCTCCGG |
| 176 | 98 | CGGAGCCCAGGGTCCAGAT | 704 | ATCTGGACCCTGGGCTCCG |
| 177 | 99 | GGAGCCCAGGGTCCAGATT | 705 | AATCTGGACCCTGGGCTCC |
| 186 | 100 | GGTCCAGATTTGGTTTCAG | 706 | CTGAAACCAAATCTGGACC |
| 187 | 101 | GTCCAGATTTGGTTTCAGA | 707 | TCTGAAACCAAATCTGGAC |
| 188 | 102 | TCCAGATTTGGTTTCAGAA | 708 | TTCTGAAACCAAATCTGGA |
| 189 | 103 | CCAGATTTGGTTTCAGAAT | 709 | ATTCTGAAACCAAATCTGG |
| 190 | 104 | CAGATTTGGTTTCAGAATG | 710 | CATTCTGAAACCAAATCTG |
| 192 | 105 | GATTTGGTTTCAGAATGAG | 711 | CTCATTCTGAAACCAAATC |
| 194 | 106 | TTTGGTTTCAGAATGAGAG | 712 | CTCTCATTCTGAAACCAAA |
| 195 | 107 | TTGGTTTCAGAATGAGAGG | 713 | CCTCTCATTCTGAAACCAA |
| 196 | 108 | TGGTTTCAGAATGAGAGGT | 714 | ACCTCTCATTCTGAAACCA |
| 197 | 109 | GGTTTCAGAATGAGAGGTC | 715 | GACCTCTCATTCTGAAACC |
| 198 | 110 | GTTTCAGAATGAGAGGTCA | 716 | TGACCTCTCATTCTGAAAC |
| 199 | 111 | TTTCAGAATGAGAGGTCAC | 717 | GTGACCTCTCATTCTGAAA |
| 200 | 112 | TTCAGAATGAGAGGTCACG | 718 | CGTGACCTCTCATTCTGAA |
| 201 | 113 | TCAGAATGAGAGGTCACGC | 719 | GCGTGACCTCTCATTCTGA |
| 202 | 114 | CAGAATGAGAGGTCACGCC | 720 | GGCGTGACCTCTCATTCTG |
| 203 | 115 | AGAATGAGAGGTCACGCCA | 721 | TGGCGTGACCTCTCATTCT |
| 204 | 116 | GAATGAGAGGTCACGCCAG | 722 | CTGGCGTGACCTCTCATTC |
| 205 | 117 | AATGAGAGGTCACGCCAGC | 723 | GCTGGCGTGACCTCTCATT |
| 206 | 118 | ATGAGAGGTCACGCCAGCT | 724 | AGCTGGCGTGACCTCTCAT |
| 207 | 119 | TGAGAGGTCACGCCAGCTG | 725 | CAGCTGGCGTGACCTCTCA |
| 208 | 120 | GAGAGGTCACGCCAGCTGA | 726 | TCAGCTGGCGTGACCTCTC |
| 209 | 121 | AGAGGTCACGCCAGCTGAG | 727 | CTCAGCTGGCGTGACCTCT |
| 210 | 122 | GAGGTCACGCCAGCTGAGG | 728 | CCTCAGCTGGCGTGACCTC |
| 211 | 123 | AGGTCACGCCAGCTGAGGC | 729 | GCCTCAGCTGGCGTGACCT |
| 212 | 124 | GGTCACGCCAGCTGAGGCA | 730 | TGCCTCAGCTGGCGTGACC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 213 | 125 | GTCACGCCAGCTGAGGCAG | 731 | CTGCCTCAGCTGGCGTGAC |
| 214 | 126 | TCACGCCAGCTGAGGCAGC | 732 | GCTGCCTCAGCTGGCGTGA |
| 215 | 127 | CACGCCAGCTGAGGCAGCA | 733 | TGCTGCCTCAGCTGGCGTG |
| 224 | 128 | TGAGGCAGCACCGGGGGGA | 734 | TCCCGCCGGTGCTGCCTCA |
| 225 | 129 | GAGGCAGCACCGGGGGGAA | 735 | TTCCCGCCGGTGCTGCCTC |
| 226 | 130 | AGGCAGCACCGGCGGGAAT | 736 | ATTCCCGCCGGTGCTGCCT |
| 227 | 131 | GGCAGCACCGGCGGGAATC | 737 | GATTCCCGCCGGTGCTGCC |
| 228 | 132 | GCAGCACCGGCGGGAATCT | 738 | AGATTCCCGCCGGTGCTGC |
| 229 | 133 | CAGCACCGGCGGGAATCTC | 739 | GAGATTCCCGCCGGTGCTG |
| 230 | 134 | AGCACCGGCGGGAATCTCG | 740 | CGAGATTCCCGCCGGTGCT |
| 231 | 135 | GCACCGGCGGGAATCTCGG | 741 | CCGAGATTCCCGCCGGTGC |
| 232 | 136 | CACCGGCGGGAATCTCGGC | 742 | GCCGAGATTCCCGCCGGTG |
| 235 | 137 | CGGCGGGAATCTCGGCCCT | 743 | AGGGCCGAGATTCCCGCCG |
| 236 | 138 | GGCGGGAATCTCGGCCCTG | 744 | CAGGGCCGAGATTCCCGCC |
| 237 | 139 | GCGGGAATCTCGGCCCTGG | 745 | CCAGGGCCGAGATTCCCGC |
| 238 | 140 | CGGGAATCTCGGCCCTGGC | 746 | GCCAGGGCCGAGATTCCCG |
| 239 | 141 | GGGAATCTCGGCCCTGGCC | 747 | GGCCAGGGCCGAGATTCCC |
| 240 | 142 | GGAATCTCGGCCCTGGCCC | 748 | GGGCCAGGGCCGAGATTCC |
| 241 | 143 | GAATCTCGGCCCTGGCCCG | 749 | CGGGCCAGGGCCGAGATTC |
| 261 | 144 | GAGACGCGGCCCGCCAGAA | 750 | TTCTGGCGGGCCGCGTCTC |
| 262 | 145 | AGACGCGGCCCGCCAGAAG | 751 | CTTCTGGCGGGCCGCGTCT |
| 273 | 146 | GCCAGAAGGCCGGCGAAAG | 752 | CTTTCGCCGGCCTTCTGGC |
| 274 | 147 | CCAGAAGGCCGGCGAAAGC | 753 | GCTTTCGCCGGCCTTCTGG |
| 275 | 148 | CAGAAGGCCGGCGAAAGCG | 754 | CGCTTTCGCCGGCCTTCTG |
| 276 | 149 | AGAAGGCCGGCGAAAGCGG | 755 | CCGCTTTCGCCGGCCTTCT |
| 277 | 150 | GAAGGCCGGCGAAAGCGGA | 756 | TCCGCTTTCGCCGGCCTTC |
| 278 | 151 | AAGGCCGGCGAAAGCGGAC | 757 | GTCCGCTTTCGCCGGCCTT |
| 285 | 152 | GCGAAAGCGGACCGCCGTC | 758 | GACGGCGGTCCGCTTTCGC |
| 286 | 153 | CGAAAGCGGACCGCCGTCA | 759 | TGACGGCGGTCCGCTTTCG |
| 287 | 154 | GAAAGCGGACCGCCGTCAC | 760 | GTGACGGCGGTCCGCTTTC |
| 288 | 155 | AAAGCGGACCGCCGTCACC | 761 | GGTGACGGCGGTCCGCTTT |
| 289 | 156 | AAGCGGACCGCCGTCACCG | 762 | CGGTGACGGCGGTCCGCTT |
| 292 | 157 | CGGACCGCCGTCACCGGAT | 763 | ATCCGGTGACGGCGGTCCG |
| 293 | 158 | GGACCGCCGTCACCGGATC | 764 | GATCCGGTGACGGCGGTCC |
| 294 | 159 | GACCGCCGTCACCGGATCC | 765 | GGATCCGGTGACGGCGGTC |
| 295 | 160 | ACCGCCGTCACCGGATCCC | 766 | GGGATCCGGTGACGGCGGT |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 296 | 161 | CCGCCGTCACCGGATCCCA | 767 | TGGGATCCGGTGACGGCGG |
| 297 | 162 | CGCCGTCACCGGATCCCAG | 768 | CTGGGATCCGGTGACGGCG |
| 298 | 163 | GCCGTCACCGGATCCCAGA | 769 | TCTGGGATCCGGTGACGGC |
| 299 | 164 | CCGTCACCGGATCCCAGAC | 770 | GTCTGGGATCCGGTGACGG |
| 300 | 165 | CGTCACCGGATCCCAGACC | 771 | GGTCTGGGATCCGGTGACG |
| 301 | 166 | GTCACCGGATCCCAGACCG | 772 | CGGTCTGGGATCCGGTGAC |
| 302 | 167 | TCACCGGATCCCAGACCGC | 773 | GCGGTCTGGGATCCGGTGA |
| 303 | 168 | CACCGGATCCCAGACCGCC | 774 | GGCGGTCTGGGATCCGGTG |
| 304 | 169 | ACCGGATCCCAGACCGCCC | 775 | GGGCGGTCTGGGATCCGGT |
| 305 | 170 | CCGGATCCCAGACCGCCCT | 776 | AGGGCGGTCTGGGATCCGG |
| 306 | 171 | CGGATCCCAGACCGCCCTG | 777 | CAGGGCGGTCTGGGATCCG |
| 307 | 172 | GGATCCCAGACCGCCCTGC | 778 | GCAGGGCGGTCTGGGATCC |
| 308 | 173 | GATCCCAGACCGCCCTGCT | 779 | AGCAGGGCGGTCTGGGATC |
| 309 | 174 | ATCCCAGACCGCCCTGCTC | 780 | GAGCAGGGCGGTCTGGGAT |
| 310 | 175 | TCCCAGACCGCCCTGCTCC | 781 | GGAGCAGGGCGGTCTGGGA |
| 311 | 176 | CCCAGACCGCCCTGCTCCT | 782 | AGGAGCAGGGCGGTCTGGG |
| 312 | 177 | CCAGACCGCCCTGCTCCTC | 783 | GAGGAGCAGGGCGGTCTGG |
| 313 | 178 | CAGACCGCCCTGCTCCTCC | 784 | GGAGGAGCAGGGCGGTCTG |
| 314 | 179 | AGACCGCCCTGCTCCTCCG | 785 | CGGAGGAGCAGGGGGGTCT |
| 315 | 180 | GACCGCCCTGCTCCTCCGA | 786 | TCGGAGGAGCAGGGCGGTC |
| 316 | 181 | ACCGCCCTGCTCCTCCGAG | 787 | CTCGGAGGAGCAGGGCGGT |
| 325 | 182 | CTCCTCCGAGCCTTTGAGA | 788 | TCTCAAAGGCTCGGAGGAG |
| 328 | 183 | CTCCGAGCCTTTGAGAAGG | 789 | CCTTCTCAAAGGCTCGGAG |
| 336 | 184 | CTTTGAGAAGGATCGCTTT | 790 | AAAGCGATCCTTCTCAAAG |
| 337 | 185 | TTTGAGAAGGATCGCTTTC | 791 | GAAAGCGATCCTTCTCAAA |
| 338 | 186 | TTGAGAAGGATCGCTTTCC | 792 | GGAAAGCGATCCTTCTCAA |
| 339 | 187 | TGAGAAGGATCGCTTTCCA | 793 | TGGAAAGCGATCCTTCTCA |
| 340 | 188 | GAGAAGGATCGCTTTCCAG | 794 | CTGGAAAGCGATCCTTCTC |
| 341 | 189 | AGAAGGATCGCTTTCCAGG | 795 | CCTGGAAAGCGATCCTTCT |
| 342 | 190 | GAAGGATCGCTTTCCAGGC | 796 | GCCTGGAAAGCGATCCTTC |
| 343 | 191 | AAGGATCGCTTTCCAGGCA | 797 | TGCCTGGAAAGCGATCCTT |
| 344 | 192 | AGGATCGCTTTCCAGGCAT | 798 | ATGCCTGGAAAGCGATCCT |
| 345 | 193 | GGATCGCTTTCCAGGCATC | 799 | GATGCCTGGAAAGCGATCC |
| 346 | 194 | GATCGCTTTCCAGGCATCG | 800 | CGATGCCTGGAAAGCGATC |
| 347 | 195 | ATCGCTTTCCAGGCATCGC | 801 | GCGATGCCTGGAAAGCGAT |
| 348 | 196 | TCGCTTTCCAGGCATCGCC | 802 | GGCGATGCCTGGAAAGCGA |
| 349 | 197 | CGCTTTCCAGGCATCGCCG | 803 | CGGCGATGCCTGGAAAGCG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 350 | 198 | GCTTTCCAGGCATCGCCGC | 804 | GCGGCGATGCCTGGAAAGC |
| 351 | 199 | CTTTCCAGGCATCGCCGCC | 805 | GGCGGCGATGCCTGGAAAG |
| 352 | 200 | TTTCCAGGCATCGCCGCCC | 806 | GGGCGGCGATGCCTGGAAA |
| 353 | 201 | TTCCAGGCATCGCCGCCCG | 807 | CGGGGGGCGATGCCTGGAA |
| 369 | 202 | CCGGGAGGAGCTGGCCAGA | 808 | TCTGGCCAGCTCCTCCCGG |
| 370 | 203 | CGGGAGGAGCTGGCCAGAG | 809 | CTCTGGCCAGCTCCTCCCG |
| 371 | 204 | GGGAGGAGCTGGCCAGAGA | 810 | TCTCTGGCCAGCTCCTCCC |
| 372 | 205 | GGAGGAGCTGGCCAGAGAG | 811 | CTCTCTGGCCAGCTCCTCC |
| 373 | 206 | GAGGAGCTGGCCAGAGAGA | 812 | TCTCTCTGGCCAGCTCCTC |
| 374 | 207 | AGGAGCTGGCCAGAGAGAC | 813 | GTCTCTCTGGCCAGCTCCT |
| 375 | 208 | GGAGCTGGCCAGAGAGACG | 814 | CGTCTCTCTGGCCAGCTCC |
| 376 | 209 | GAGCTGGCCAGAGAGACGG | 815 | CCGTCTCTCTGGCCAGCTC |
| 377 | 210 | AGCTGGCCAGAGAGACGGG | 816 | CCCGTCTCTCTGGCCAGCT |
| 378 | 211 | GCTGGCCAGAGAGACGGGC | 817 | GCCCGTCTCTCTGGCCAGC |
| 382 | 212 | GCCAGAGAGACGGGCCTCC | 818 | GGAGGCCCGTCTCTCTGGC |
| 383 | 213 | CCAGAGAGACGGGCCTCCC | 819 | GGGAGGCCCGTCTCTCTGG |
| 384 | 214 | CAGAGAGACGGGCCTCCCG | 820 | CGGGAGGCCCGTCTCTCTG |
| 385 | 215 | AGAGAGACGGGCCTCCCGG | 821 | CCGGGAGGCCCGTCTCTCT |
| 394 | 216 | GGCCTCCCGGAGTCCAGGA | 822 | TCCTGGACTCCGGGAGGCC |
| 395 | 217 | GCCTCCCGGAGTCCAGGAT | 823 | ATCCTGGACTCCGGGAGGC |
| 396 | 218 | CCTCCCGGAGTCCAGGATT | 824 | AATCCTGGACTCCGGGAGG |
| 397 | 219 | CTCCCGGAGTCCAGGATTC | 825 | GAATCCTGGACTCCGGGAG |
| 398 | 220 | TCCCGGAGTCCAGGATTCA | 826 | TGAATCCTGGACTCCGGGA |
| 399 | 221 | CCCGGAGTCCAGGATTCAG | 827 | CTGAATCCTGGACTCCGGG |
| 400 | 222 | CCGGAGTCCAGGATTCAGA | 828 | TCTGAATCCTGGACTCCGG |
| 401 | 223 | CGGAGTCCAGGATTCAGAT | 829 | ATCTGAATCCTGGACTCCG |
| 402 | 224 | GGAGTCCAGGATTCAGATC | 830 | GATCTGAATCCTGGACTCC |
| 403 | 225 | GAGTCCAGGATTCAGATCT | 831 | AGATCTGAATCCTGGACTC |
| 404 | 226 | AGTCCAGGATTCAGATCTG | 832 | CAGATCTGAATCCTGGACT |
| 408 | 227 | CAGGATTCAGATCTGGTTT | 833 | AAACCAGATCTGAATCCTG |
| 409 | 228 | AGGATTCAGATCTGGTTTC | 834 | GAAACCAGATCTGAATCCT |
| 410 | 229 | GGATTCAGATCTGGTTTCA | 835 | TGAAACCAGATCTGAATCC |
| 411 | 230 | GATTCAGATCTGGTTTCAG | 836 | CTGAAACCAGATCTGAATC |
| 412 | 231 | ATTCAGATCTGGTTTCAGA | 837 | TCTGAAACCAGATCTGAAT |
| 420 | 232 | CTGGTTTCAGAATCGAAGG | 838 | CCTTCGATTCTGAAACCAG |
| 421 | 233 | TGGTTTCAGAATCGAAGGG | 839 | CCCTTCGATTCTGAAACCA |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 422 | 234 | GGTTTCAGAATCGAAGGGC | 840 | GCCCTTCGATTCTGAAACC |
| 423 | 235 | GTTTCAGAATCGAAGGGCC | 841 | GGCCCTTCGATTCTGAAAC |
| 424 | 236 | TTTCAGAATCGAAGGGCCA | 842 | TGGCCCTTCGATTCTGAAA |
| 425 | 237 | TTCAGAATCGAAGGGCCAG | 843 | CTGGCCCTTCGATTCTGAA |
| 426 | 238 | TCAGAATCGAAGGGCCAGG | 844 | CCTGGCCCTTCGATTCTGA |
| 427 | 239 | CAGAATCGAAGGGCCAGGC | 845 | GCCTGGCCCTTCGATTCTG |
| 428 | 240 | AGAATCGAAGGGCCAGGCA | 846 | TGCCTGGCCCTTCGATTCT |
| 429 | 241 | GAATCGAAGGGCCAGGCAC | 847 | GTGCCTGGCCCTTCGATTO |
| 430 | 242 | AATCGAAGGGCCAGGCACC | 848 | GGTGCCTGGCCCTTCGATT |
| 431 | 243 | ATCGAAGGGCCAGGCACCC | 849 | GGGTGCCTGGCCCTTCGAT |
| 432 | 244 | TCGAAGGGCCAGGCACCCG | 850 | CGGGTGCCTGGCCCTTCGA |
| 509 | 245 | GGGGTCACCCTGCTCCCTC | 851 | GAGGGAGCAGGGTGACCCC |
| 510 | 246 | GGGTCACCCTGCTCCCTCG | 852 | CGAGGGAGCAGGGTGACCC |
| 511 | 247 | GGTCACCCTGCTCCCTCGT | 853 | ACGAGGGAGCAGGGTGACC |
| 512 | 248 | GTCACCCTGCTCCCTCGTG | 854 | CACGAGGGAGCAGGGTGAC |
| 513 | 249 | TCACCCTGCTCCCTCGTGG | 855 | CCACGAGGGAGCAGGGTGA |
| 514 | 250 | CACCCTGCTCCCTCGTGGG | 856 | CCCACGAGGGAGCAGGGTG |
| 516 | 251 | CCCTGCTCCCTCGTGGGTC | 857 | GACCCACGAGGGAGCAGGG |
| 517 | 252 | CCTGCTCCCTCGTGGGTCG | 858 | CGACCCACGAGGGAGCAGG |
| 518 | 253 | CTGCTCCCTCGTGGGTCGC | 859 | GCGACCCACGAGGGAGCAG |
| 519 | 254 | TGCTCCCTCGTGGGTCGCC | 860 | GGCGACCCACGAGGGAGCA |
| 520 | 255 | GCTCCCTCGTGGGTCGCCT | 861 | AGGCGACCCACGAGGGAGC |
| 521 | 256 | CTCCCTCGTGGGTCGCCTT | 862 | AAGGCGACCCACGAGGGAG |
| 522 | 257 | TCCCTCGTGGGTCGCCTTC | 863 | GAAGGCGACCCACGAGGGA |
| 523 | 258 | CCCTCGTGGGTCGCCTTCG | 864 | CGAAGGCGACCCACGAGGG |
| 524 | 259 | CCTCGTGGGTCGCCTTCGC | 865 | GCGAAGGCGACCCACGAGG |
| 525 | 260 | CTCGTGGGTCGCCTTCGCC | 866 | GGCGAAGGCGACCCACGAG |
| 526 | 261 | TCGTGGGTCGCCTTCGCCC | 867 | GGGCGAAGGCGACCCACGA |
| 530 | 262 | GGGTCGCCTTCGCCCACAC | 868 | GTGTGGGCGAAGGCGACCC |
| 531 | 263 | GGTCGCCTTCGCCCACACC | 869 | GGTGTGGGCGAAGGCGACC |
| 532 | 264 | GTCGCCTTCGCCCACACCG | 870 | CGGTGTGGGCGAAGGCGAC |
| 533 | 265 | TCGCCTTCGCCCACACCGG | 871 | CCGGTGTGGGCGAAGGCGA |
| 544 | 266 | CACACCGGCGCGTGGGGAA | 872 | TTCCCCACGCGCCGGTGTG |
| 545 | 267 | ACACCGGCGCGTGGGGAAC | 873 | GTTCCCCACGCGCCGGTGT |
| 552 | 268 | CGCGTGGGGAACGGGGCTT | 874 | AAGCCCCGTTCCCCACGCG |
| 553 | 269 | GCGTGGGGAACGGGGCTTC | 875 | GAAGCCCCGTTCCCCACGC |
| 566 | 270 | GGCTTCCCGCACCCCACGT | 876 | ACGTGGGGTGCGGGAAGCC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 567 | 271 | GCTTCCCGCACCCCACGTG | 877 | CACGTGGGGTGCGGGAAGC |
| 619 | 272 | TTCGTGAGCCAGGCAGCGA | 878 | TCGCTGCCTGGCTCACGAA |
| 620 | 273 | TCGTGAGCCAGGCAGCGAG | 879 | CTCGCTGCCTGGCTCACGA |
| 621 | 274 | CGTGAGCCAGGCAGCGAGG | 880 | CCTCGCTGCCTGGCTCACG |
| 622 | 275 | GTGAGCCAGGCAGCGAGGG | 881 | CCCTCGCTGCCTGGCTCAC |
| 671 | 276 | CGCCGGCAGAGGGGATCTC | 882 | GAGATCCCCTCTGCCGGCG |
| 672 | 277 | GCCGGCAGAGGGGATCTCC | 883 | GGAGATCCCCTCTGCCGGC |
| 673 | 278 | CCGGCAGAGGGGATCTCCC | 884 | GGGAGATCCCCTCTGCCGG |
| 674 | 279 | CGGCAGAGGGGATCTCCCA | 885 | TGGGAGATCCCCTCTGCCG |
| 675 | 280 | GGCAGAGGGGATCTCCCAA | 886 | TTGGGAGATCCCCTCTGCC |
| 683 | 281 | GGATCTCCCAACCTGCCCC | 887 | GGGGCAGGTTGGGAGATCC |
| 684 | 282 | GATCTCCCAACCTGCCCCG | 888 | CGGGGCAGGTTGGGAGATC |
| 685 | 283 | ATCTCCCAACCTGCCCCGG | 889 | CCGGGGCAGGTTGGGAGAT |
| 686 | 284 | TCTCCCAACCTGCCCCGGC | 890 | GCCGGGGCAGGTTGGGAGA |
| 706 | 285 | CGCGGGGATTTCGCCTACG | 891 | CGTAGGCGAAATCCCCGCG |
| 707 | 286 | GCGGGGATTTCGCCTACGC | 892 | GCGTAGGCGAAATCCCCGC |
| 708 | 287 | CGGGGATTTCGCCTACGCC | 893 | GGCGTAGGCGAAATCCCCG |
| 709 | 288 | GGGGATTTCGCCTACGCCG | 894 | CGGCGTAGGCGAAATCCCC |
| 710 | 289 | GGGATTTCGCCTACGCCGC | 895 | GCGGCGTAGGCGAAATCCC |
| 711 | 290 | GGATTTCGCCTACGCCGCC | 896 | GGCGGCGTAGGCGAAATCC |
| 712 | 291 | GATTTCGCCTACGCCGCCC | 897 | GGGCGGCGTAGGCGAAATC |
| 713 | 292 | ATTTCGCCTACGCCGCCCC | 898 | GGGGCGGCGTAGGCGAAAT |
| 714 | 293 | TTTCGCCTACGCCGCCCCG | 899 | CGGGGCGGCGTAGGCGAAA |
| 746 | 294 | GGGCGCTCTCCCACCCTCA | 900 | TGAGGGTGGGAGAGCGCCC |
| 747 | 295 | GGCGCTCTCCCACCCTCAG | 901 | CTGAGGGTGGGAGAGCGCC |
| 748 | 296 | GCGCTCTCCCACCCTCAGG | 902 | CCTGAGGGTGGGAGAGCGC |
| 749 | 297 | CGCTCTCCCACCCTCAGGC | 903 | GCCTGAGGGTGGGAGAGCG |
| 750 | 298 | GCTCTCCCACCCTCAGGCT | 904 | AGCCTGAGGGTGGGAGAGC |
| 751 | 299 | CTCTCCCACCCTCAGGCTC | 905 | GAGCCTGAGGGTGGGAGAG |
| 752 | 300 | TCTCCCACCCTCAGGCTCC | 906 | GGAGCCTGAGGGTGGGAGA |
| 753 | 301 | CTCCCACCCTCAGGCTCCT | 907 | AGGAGCCTGAGGGTGGGAG |
| 754 | 302 | TCCCACCCTCAGGCTCCTC | 908 | GAGGAGCCTGAGGGTGGGA |
| 755 | 303 | CCCACCCTCAGGCTCCTCG | 909 | CGAGGAGCCTGAGGGTGGG |
| 756 | 304 | CCACCCTCAGGCTCCTCGG | 910 | CCGAGGAGCCTGAGGGTGG |
| 757 | 305 | CACCCTCAGGCTCCTCGGT | 911 | ACCGAGGAGCCTGAGGGTG |
| 758 | 306 | ACCCTCAGGCTCCTCGGTG | 912 | CACCGAGGAGCCTGAGGGT |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 759 | 307 | CCCTCAGGCTCCTCGGTGG | 913 | CCACCGAGGAGCCTGAGGG |
| 760 | 308 | CCTCAGGCTCCTCGGTGGC | 914 | GCCACCGAGGAGCCTGAGG |
| 761 | 309 | CTCAGGCTCCTCGGTGGCC | 915 | GGCCACCGAGGAGCCTGAG |
| 767 | 310 | CTCCTCGGTGGCCTCCGCA | 916 | TGCGGAGGCCACCGAGGAG |
| 768 | 311 | TCCTCGGTGGCCTCCGCAC | 917 | GTGCGGAGGCCACCGAGGA |
| 777 | 312 | GCCTCCGCACCCGGGCAAA | 918 | TTTGCCCGGGTGCGGAGGC |
| 778 | 313 | CCTCCGCACCCGGGCAAAA | 919 | TTTTGCCCGGGTGCGGAGG |
| 779 | 314 | CTCCGCACCCGGGCAAAAG | 920 | CTTTTGCCCGGGTGCGGAG |
| 780 | 315 | TCCGCACCCGGGCAAAAGC | 921 | GCTTTTGCCCGGGTGCGGA |
| 781 | 316 | CCGCACCCGGGCAAAAGCC | 922 | GGCTTTTGCCCGGGTGCGG |
| 782 | 317 | CGCACCCGGGCAAAAGCCG | 923 | CGGCTTTTGCCCGGGTGCG |
| 788 | 318 | CGGGCAAAAGCCGGGAGGA | 924 | TCCTCCCGGCTTTTGCCCG |
| 789 | 319 | GGGCAAAAGCCGGGAGGAC | 925 | GTCCTCCCGGCTTTTGCCC |
| 790 | 320 | GGCAAAAGCCGGGAGGACC | 926 | GGTCCTCCCGGCTTTTGCC |
| 791 | 321 | GCAAAAGCCGGGAGGACCG | 927 | CGGTCCTCCCGGCTTTTGC |
| 840 | 322 | CTGCGCGGTGGCACAGCCT | 928 | AGGCTGTGCCACCGCGCAG |
| 841 | 323 | TGCGCGGTGGCACAGCCTG | 929 | CAGGCTGTGCCACCGCGCA |
| 851 | 324 | CACAGCCTGGGCCCGCTCA | 930 | TGAGCGGGCCCAGGCTGTG |
| 852 | 325 | ACAGCCTGGGCCCGCTCAA | 931 | TTGAGCGGGCCCAGGCTGT |
| 853 | 326 | CAGCCTGGGCCCGCTCAAG | 932 | CTTGAGCGGGCCCAGGCTG |
| 854 | 327 | AGCCTGGGCCCGCTCAAGC | 933 | GCTTGAGCGGGCCCAGGCT |
| 878 | 328 | CGCAGGGCCAAGGGGTGCT | 934 | AGCACCCCTTGGCCCTGCG |
| 879 | 329 | GCAGGGCCAAGGGGTGCTT | 935 | AAGCACCCCTTGGCCCTGC |
| 901 | 330 | CCACCCACGTCCCAGGGGA | 936 | TCCCCTGGGACGTGGGTGG |
| 902 | 331 | CACCCACGTCCCAGGGGAG | 937 | CTCCCCTGGGACGTGGGTG |
| 903 | 332 | ACCCACGTCCCAGGGGAGT | 938 | ACTCCCCTGGGACGTGGGT |
| 911 | 333 | CCCAGGGGAGTCCGTGGTG | 939 | CACCACGGACTCCCCTGGG |
| 912 | 334 | CCAGGGGAGTCCGTGGTGG | 940 | CCACCACGGACTCCCCTGG |
| 913 | 335 | CAGGGGAGTCCGTGGTGGG | 941 | CCCACCACGGACTCCCCTG |
| 914 | 336 | AGGGGAGTCCGTGGTGGGG | 942 | CCCCACCACGGACTCCCCT |
| 960 | 337 | GGCGGCGTGGGAACCCCAA | 943 | TTGGGGTTCCCACGCCGCC |
| 975 | 338 | CCAAGCCGGGGCAGCTCCA | 944 | TGGAGCTGCCCCGGCTTGG |
| 976 | 339 | CAAGCCGGGGCAGCTCCAC | 945 | GTGGAGCTGCCCCGGCTTG |
| 977 | 340 | AAGCCGGGGCAGCTCCACC | 946 | GGTGGAGCTGCCCCGGCTT |
| 983 | 341 | GGGCAGCTCCACCTCCCCA | 947 | TGGGGAGGTGGAGCTGCCC |
| 984 | 342 | GGCAGCTCCACCTCCCCAG | 948 | CTGGGGAGGTGGAGCTGCC |
| 985 | 343 | GCAGCTCCACCTCCCCAGC | 949 | GCTGGGGAGGTGGAGCTGC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 986 | 344 | CAGCTCCACCTCCCCAGCC | 950 | GGCTGGGGAGGTGGAGCTG |
| 1031 | 345 | CGCGGCAGGGGCAGATGCA | 951 | TGCATCTGCCCCTGCCGCG |
| 1033 | 346 | CGGCAGGGGCAGATGCAAG | 952 | CTTGCATCTGCCCCTGCCG |
| 1034 | 347 | GGCAGGGGCAGATGCAAGG | 953 | CCTTGCATCTGCCCCTGCC |
| 1035 | 348 | GCAGGGGCAGATGCAAGGC | 954 | GCCTTGCATCTGCCCCTGC |
| 1036 | 349 | CAGGGGCAGATGCAAGGCA | 955 | TGCCTTGCATCTGCCCCTG |
| 1037 | 350 | AGGGGCAGATGCAAGGCAT | 956 | ATGCCTTGCATCTGCCCCT |
| 1046 | 351 | TGCAAGGCATCCCGGCGCC | 957 | GGCGCCGGGATGCCTTGCA |
| 1048 | 352 | CAAGGCATCCCGGCGCCCT | 958 | AGGGCGCCGGGATGCCTTG |
| 1049 | 353 | AAGGCATCCCGGCGCCCTC | 959 | GAGGGCGCCGGGATGCCTT |
| 1064 | 354 | CCTCCCAGGCGCTCCAGGA | 960 | TCCTGGAGCGCCTGGGAGG |
| 1086 | 355 | GGCGCCCTGGTCTGCACTC | 961 | GAGTGCAGACCAGGGCGCC |
| 1087 | 356 | GCGCCCTGGTCTGCACTCC | 962 | GGAGTGCAGACCAGGGCGC |
| 1088 | 357 | CGCCCTGGTCTGCACTCCC | 963 | GGGAGTGCAGACCAGGGCG |
| 1089 | 358 | GCCCTGGTCTGCACTCCCC | 964 | GGGGAGTGCAGACCAGGGC |
| 1090 | 359 | CCCTGGTCTGCACTCCCCT | 965 | AGGGGAGTGCAGACCAGGG |
| 1091 | 360 | CCTGGTCTGCACTCCCCTG | 966 | CAGGGGAGTGCAGACCAGG |
| 1092 | 361 | CTGGTCTGCACTCCCCTGC | 967 | GCAGGGGAGTGCAGACCAG |
| 1093 | 362 | TGGTCTGCACTCCCCTGCG | 968 | CGCAGGGGAGTGCAGACCA |
| 1094 | 363 | GGTCTGCACTCCCCTGCGG | 969 | CCGCAGGGGAGTGCAGACC |
| 1095 | 364 | GTCTGCACTCCCCTGCGGC | 970 | GCCGCAGGGGAGTGCAGAC |
| 1096 | 365 | TCTGCACTCCCCTGCGGCC | 971 | GGCCGCAGGGGAGTGCAGA |
| 1097 | 366 | CTGCACTCCCCTGCGGCCT | 972 | AGGCCGCAGGGGAGTGCAG |
| 1098 | 367 | TGCACTCCCCTGCGGCCTG | 973 | CAGGCCGCAGGGGAGTGCA |
| 1100 | 368 | CACTCCCCTGCGGCCTGCT | 974 | AGCAGGCCGCAGGGGAGTG |
| 1101 | 369 | ACTCCCCTGCGGCCTGCTG | 975 | CAGCAGGCCGCAGGGGAGT |
| 1103 | 370 | TCCCCTGCGGCCTGCTGCT | 976 | AGCAGCAGGCCGCAGGGGA |
| 1106 | 371 | CCTGCGGCCTGCTGCTGGA | 977 | TCCAGCAGCAGGCCGCAGG |
| 1107 | 372 | CTGCGGCCTGCTGCTGGAT | 978 | ATCCAGCAGCAGGCCGCAG |
| 1108 | 373 | TGCGGCCTGCTGCTGGATG | 979 | CATCCAGCAGCAGGCCGCA |
| 1109 | 374 | GCGGCCTGCTGCTGGATGA | 980 | TCATCCAGCAGCAGGCCGC |
| 1110 | 375 | CGGCCTGCTGCTGGATGAG | 981 | CTCATCCAGCAGCAGGCCG |
| 1111 | 376 | GGCCTGCTGCTGGATGAGC | 982 | GCTCATCCAGCAGCAGGCC |
| 1112 | 377 | GCCTGCTGCTGGATGAGCT | 983 | AGCTCATCCAGCAGCAGGC |
| 1113 | 378 | CCTGCTGCTGGATGAGCTC | 984 | GAGCTCATCCAGCAGCAGG |
| 1114 | 379 | CTGCTGCTGGATGAGCTCC | 985 | GGAGCTCATCCAGCAGCAG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 1115 | 380 | TGCTGCTGGATGAGCTCCT | 986 | AGGAGCTCATCCAGCAGCA |
| 1116 | 381 | GCTGCTGGATGAGCTCCTG | 987 | CAGGAGCTCATCCAGCAGC |
| 1117 | 382 | CTGCTGGATGAGCTCCTGG | 988 | CCAGGAGCTCATCCAGCAG |
| 1118 | 383 | TGCTGGATGAGCTCCTGGC | 989 | GCCAGGAGCTCATCCAGCA |
| 1119 | 384 | GCTGGATGAGCTCCTGGCG | 990 | CGCCAGGAGCTCATCCAGC |
| 1130 | 385 | TCCTGGCGAGCCCGGAGTT | 991 | AACTCCGGGCTCGCCAGGA |
| 1131 | 386 | CCTGGCGAGCCCGGAGTTT | 992 | AAACTCCGGGCTCGCCAGG |
| 1132 | 387 | CTGGCGAGCCCGGAGTTTC | 993 | GAAACTCCGGGCTCGCCAG |
| 1137 | 388 | GAGCCCGGAGTTTCTGCAG | 994 | CTGCAGAAACTCCGGGCTC |
| 1138 | 389 | AGCCCGGAGTTTCTGCAGC | 995 | GCTGCAGAAACTCCGGGCT |
| 1139 | 390 | GCCCGGAGTTTCTGCAGCA | 996 | TGCTGCAGAAACTCCGGGC |
| 1140 | 391 | CCCGGAGTTTCTGCAGCAG | 997 | CTGCTGCAGAAACTCCGGG |
| 1141 | 392 | CCGGAGTTTCTGCAGCAGG | 998 | CCTGCTGCAGAAACTCCGG |
| 1142 | 393 | CGGAGTTTCTGCAGCAGGC | 999 | GCCTGCTGCAGAAACTCCG |
| 1143 | 394 | GGAGTTTCTGCAGCAGGCG | 1000 | CGCCTGCTGCAGAAACTCC |
| 1144 | 395 | GAGTTTCTGCAGCAGGCGC | 1001 | GCGCCTGCTGCAGAAACTC |
| 1145 | 396 | AGTTTCTGCAGCAGGCGCA | 1002 | TGCGCCTGCTGCAGAAACT |
| 1146 | 397 | GTTTCTGCAGCAGGCGCAA | 1003 | TTGCGCCTGCTGCAGAAAC |
| 1147 | 398 | TTTCTGCAGCAGGCGCAAC | 1004 | GTTGCGCCTGCTGCAGAAA |
| 1148 | 399 | TTCTGCAGCAGGCGCAACC | 1005 | GGTTGCGCCTGCTGCAGAA |
| 1149 | 400 | TCTGCAGCAGGCGCAACCT | 1006 | AGGTTGCGCCTGCTGCAGA |
| 1150 | 401 | CTGCAGCAGGCGCAACCTC | 1007 | GAGGTTGCGCCTGCTGCAG |
| 1151 | 402 | TGCAGCAGGCGCAACCTCT | 1008 | AGAGGTTGCGCCTGCTGCA |
| 1152 | 403 | GCAGCAGGCGCAACCTCTC | 1009 | GAGAGGTTGCGCCTGCTGC |
| 1153 | 404 | CAGCAGGCGCAACCTCTCC | 1010 | GGAGAGGTTGCGCCTGCTG |
| 1154 | 405 | AGCAGGCGCAACCTCTCCT | 1011 | AGGAGAGGTTGCGCCTGCT |
| 1155 | 406 | GCAGGCGCAACCTCTCCTA | 1012 | TAGGAGAGGTTGCGCCTGC |
| 1156 | 407 | CAGGCGCAACCTCTCCTAG | 1013 | CTAGGAGAGGTTGCGCCTG |
| 1157 | 408 | AGGCGCAACCTCTCCTAGA | 1014 | TCTAGGAGAGGTTGCGCCT |
| 1158 | 409 | GGCGCAACCTCTCCTAGAA | 1015 | TTCTAGGAGAGGTTGCGCC |
| 1159 | 410 | GCGCAACCTCTCCTAGAAA | 1016 | TTTCTAGGAGAGGTTGCGC |
| 1160 | 411 | CGCAACCTCTCCTAGAAAC | 1017 | GTTTCTAGGAGAGGTTGCG |
| 1161 | 412 | GCAACCTCTCCTAGAAACG | 1018 | CGTTTCTAGGAGAGGTTGC |
| 1162 | 413 | CAACCTCTCCTAGAAACGG | 1019 | CCGTTTCTAGGAGAGGTTG |
| 1163 | 414 | AACCTCTCCTAGAAACGGA | 1020 | TCCGTTTCTAGGAGAGGTT |
| 1169 | 415 | TCCTAGAAACGGAGGCCCC | 1021 | GGGGCCTCCGTTTCTAGGA |
| 1170 | 416 | CCTAGAAACGGAGGCCCCG | 1022 | CGGGGCCTCCGTTTCTAGG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 1171 | 417 | CTAGAAACGGAGGCCCCGG | 1023 | CCGGGGCCTCCGTTTCTAG |
| 1428 | 418 | CCGGTGAGAGACTCCACTC | 1024 | GAGTGGAGTCTCTCACCGG |
| 1429 | 419 | CGGTGAGAGACTCCACTCC | 1025 | GGAGTGGAGTCTCTCACCG |
| 1430 | 420 | GGTGAGAGACTCCACTCCG | 1026 | CGGAGTGGAGTCTCTCACC |
| 1570 | 421 | CCCTTGTTCTTCCGTGAAA | 1027 | TTTCACGGAAGAACAAGGG |
| 1571 | 422 | CCTTGTTCTTCCGTGAAAT | 1028 | ATTTCACGGAAGAACAAGG |
| 1572 | 423 | CTTGTTCTTCCGTGAAATT | 1029 | AATTTCACGGAAGAACAAG |
| 1573 | 424 | TTGTTCTTCCGTGAAATTC | 1030 | GAATTTCACGGAAGAACAA |
| 1574 | 425 | TGTTCTTCCGTGAAATTCT | 1031 | AGAATTTCACGGAAGAACA |
| 1575 | 426 | GTTCTTCCGTGAAATTCTG | 1032 | CAGAATTTCACGGAAGAAC |
| 1576 | 427 | TTCTTCCGTGAAATTCTGG | 1033 | CCAGAATTTCACGGAAGAA |
| 1577 | 428 | TCTTCCGTGAAATTCTGGC | 1034 | GCCAGAATTTCACGGAAGA |
| 1578 | 429 | CTTCCGTGAAATTCTGGCT | 1035 | AGCCAGAATTTCACGGAAG |
| 1589 | 430 | TTCTGGCTGAATGTCTCCC | 1036 | GGGAGACATTCAGCCAGAA |
| 1590 | 431 | TCTGGCTGAATGTCTCCCC | 1037 | GGGGAGACATTCAGCCAGA |
| 1618 | 432 | GACGCTGTCTAGGCAAACC | 1038 | GGTTTGCCTAGACAGCGTC |
| 1619 | 433 | ACGCTGTCTAGGCAAACCT | 1039 | AGGTTTGCCTAGACAGCGT |
| 1620 | 434 | CGCTGTCTAGGCAAACCTG | 1040 | CAGGTTTGCCTAGACAGCG |
| 1621 | 435 | GCTGTCTAGGCAAACCTGG | 1041 | CCAGGTTTGCCTAGACAGC |
| 1622 | 436 | CTGTCTAGGCAAACCTGGA | 1042 | TCCAGGTTTGCCTAGACAG |
| 1623 | 437 | TGTCTAGGCAAACCTGGAT | 1043 | ATCCAGGTTTGCCTAGACA |
| 1624 | 438 | GTCTAGGCAAACCTGGATT | 1044 | AATCCAGGTTTGCCTAGAC |
| 1625 | 439 | TCTAGGCAAACCTGGATTA | 1045 | TAATCCAGGTTTGCCTAGA |
| 1626 | 440 | CTAGGCAAACCTGGATTAG | 1046 | CTAATCCAGGTTTGCCTAG |
| 1627 | 441 | TAGGCAAACCTGGATTAGA | 1047 | TCTAATCCAGGTTTGCCTA |
| 1628 | 442 | AGGCAAACCTGGATTAGAG | 1048 | CTCTAATCCAGGTTTGCCT |
| 1629 | 443 | GGCAAACCTGGATTAGAGT | 1049 | ACTCTAATCCAGGTTTGCC |
| 1630 | 444 | GCAAACCTGGATTAGAGTT | 1050 | AACTCTAATCCAGGTTTGC |
| 1631 | 445 | CAAACCTGGATTAGAGTTA | 1051 | TAACTCTAATCCAGGTTTG |
| 1632 | 446 | AAACCTGGATTAGAGTTAC | 1052 | GTAACTCTAATCCAGGTTT |
| 1633 | 447 | AACCTGGATTAGAGTTACA | 1053 | TGTAACTCTAATCCAGGTT |
| 1634 | 448 | ACCTGGATTAGAGTTACAT | 1054 | ATGTAACTCTAATCCAGGT |
| 1635 | 449 | CCTGGATTAGAGTTACATC | 1055 | GATGTAACTCTAATCCAGG |
| 1636 | 450 | CTGGATTAGAGTTACATCT | 1056 | AGATGTAACTCTAATCCAG |
| 1637 | 451 | TGGATTAGAGTTACATCTC | 1057 | GAGATGTAACTCTAATCCA |
| 1638 | 452 | GGATTAGAGTTACATCTCC | 1058 | GGAGATGTAACTCTAATCC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 1639 | 453 | GATTAGAGTTACATCTCCT | 1059 | AGGAGATGTAACTCTAATC |
| 1640 | 454 | ATTAGAGTTACATCTCCTG | 1060 | CAGGAGATGTAACTCTAAT |
| 1641 | 455 | TTAGAGTTACATCTCCTGG | 1061 | CCAGGAGATGTAACTCTAA |
| 1642 | 456 | TAGAGTTACATCTCCTGGA | 1062 | TCCAGGAGATGTAACTCTA |
| 1643 | 457 | AGAGTTACATCTCCTGGAT | 1063 | ATCCAGGAGATGTAACTCT |
| 1651 | 458 | ATCTCCTGGATGATTAGTT | 1064 | AACTAATCATCCAGGAGAT |
| 1652 | 459 | TCTCCTGGATGATTAGTTC | 1065 | GAACTAATCATCCAGGAGA |
| 1653 | 460 | CTCCTGGATGATTAGTTCA | 1066 | TGAACTAATCATCCAGGAG |
| 1654 | 461 | TCCTGGATGATTAGTTCAG | 1067 | CTGAACTAATCATCCAGGA |
| 1655 | 462 | CCTGGATGATTAGTTCAGA | 1068 | TCTGAACTAATCATCCAGG |
| 1656 | 463 | CTGGATGATTAGTTCAGAG | 1069 | CTCTGAACTAATCATCCAG |
| 26 | 464 | GCACCCTCCCCGCGGAAGC | 1070 | GCTTCCGCGGGGAGGGTGC |
| 27 | 465 | CACCCTCCCCGCGGAAGCC | 1071 | GGCTTCCGCGGGGAGGGTG |
| 28 | 466 | ACCCTCCCCGOGGAAGCCC | 1072 | GGGCTTCCGCGGGGAGGGT |
| 30 | 467 | CCTCCCCGCGGAAGCCCGG | 1073 | CCGGGCTTCCGCGGGGAGG |
| 35 | 468 | CCGCGGAAGCCCGGGGACG | 1074 | CGTCCCCGGGCTTCCGCGG |
| 37 | 469 | GCGGAAGCCCGGGGACGAG | 1075 | CTCGTCCCCGGGCTTCCGC |
| 38 | 470 | CGGAAGCCCGGGGACGAGG | 1076 | CCTCGTCCCCGGGCTTCCG |
| 193 | 471 | ATTTGGTTTCAGAATGAGA | 1077 | TCTCATTCTGAAACCAAAT |
| 233 | 472 | ACCGGCGGGAATCTCGGCC | 1078 | GGCCGAGATTCCCGCCGGT |
| 250 | 473 | CCCTGGCCCGGGAGACGCG | 1079 | CGCGTCTCCCGGGCCAGGG |
| 251 | 474 | CCTGGCCCGGGAGACGCGG | 1080 | CCGCGTCTCCCGGGCCAGG |
| 252 | 475 | CTGGCCCGGGAGACGCGGC | 1081 | GCCGCGTCTCCCGGGCCAG |
| 263 | 476 | GACGCGGCCCGCCAGAAGG | 1082 | CCTTCTGGGGGGCCGCGTC |
| 264 | 477 | ACGCGGCCCGCCAGAAGGC | 1083 | GCCTTCTGGCGGGCCGCGT |
| 279 | 478 | AGGCCGGCGAAAGCGGACC | 1084 | GGTCCGCTTTCGCCGGCCT |
| 280 | 479 | GGCCGGCGAAAGCGGACCG | 1085 | CGGTCCGCTTTCGCCGGCC |
| 281 | 480 | GCCGGCGAAAGCGGACCGC | 1086 | GCGGTCCGCTTTCGCCGGC |
| 317 | 481 | CCGCCCTGCTCCTCCGAGC | 1087 | GCTCGGAGGAGCAGGGCGG |
| 355 | 482 | CCAGGCATCGCCGCCCGGG | 1088 | CCCGGGGGGCGATGCCTGG |
| 359 | 483 | GCATCGCCGCCCGGGAGGA | 1089 | TCCTCCCGGGGGGCGATGC |
| 360 | 484 | CATCGCCGCCCGGGAGGAG | 1090 | CTCCTCCCGGGCGGCGATG |
| 361 | 485 | ATCGCCGCCCGGGAGGAGC | 1091 | GCTCCTCCCGGGGGGCGAT |
| 362 | 486 | TCGCCGCCCGGGAGGAGCT | 1092 | AGCTCCTCCCGGGCGGCGA |
| 363 | 487 | CGCCGCCCGGGAGGAGCTG | 1093 | CAGCTCCTCCCGGGGGGCG |
| 437 | 488 | GGGCCAGGCACCCGGGACA | 1094 | TGTCCCGGGTGCCTGGCCC |
| 452 | 489 | GACAGGGTGGCAGGGCGCC | 1095 | GGCGCCCTGCCACCCTGTC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 453 | 490 | ACAGGGTGGCAGGGCGCCC | 1096 | GGGCGCCCTGCCACCCTGT |
| 455 | 491 | AGGGTGGCAGGGCGCCCGC | 1097 | GCGGGCGCCCTGCCACCCT |
| 456 | 492 | GGGTGGCAGGGCGCCCGCG | 1098 | CGCGGGCGCCCTGCCACCC |
| 458 | 493 | GTGGCAGGGCGCCCGCGCA | 1099 | TGCGCGGGCGCCCTGCCAC |
| 480 | 494 | AGGCGGCCTGTGCAGCGCG | 1100 | CGCGCTGCACAGGCCGCCT |
| 481 | 495 | GGCGGCCTGTGCAGCGCGG | 1101 | CCGCGCTGCACAGGCCGCC |
| 482 | 496 | GCGGCCTGTGCAGCGCGGC | 1102 | GCCGCGCTGCACAGGCCGC |
| 534 | 497 | CGCCTTCGCCCACACCGGC | 1103 | GCCGGTGTGGGCGAAGGCG |
| 546 | 498 | CACCGGCGCGTGGGGAACG | 1104 | CGTTCCCCACGCGCCGGTG |
| 547 | 499 | ACCGGCGCGTGGGGAACGG | 1105 | CCGTTCCCCACGCGCCGGT |
| 548 | 500 | CCGGCGCGTGGGGAACGGG | 1106 | CCCGTTCCCCACGCGCCGG |
| 549 | 501 | CGGCGCGTGGGGAACGGGG | 1107 | CCCCGTTCCCCACGCGCCG |
| 551 | 502 | GCGCGTGGGGAACGGGGCT | 1108 | AGCCCCGTTCCCCACGCGC |
| 565 | 503 | GGGCTTCCCGCACCCCACG | 1109 | CGTGGGGTGCGGGAAGCCC |
| 575 | 504 | CACCCCACGTGCCCTGCGC | 1110 | GCGCAGGGCACGTGGGGTG |
| 577 | 505 | CCCCACGTGCCCTGCGCGC | 1111 | GCGCGCAGGGCACGTGGGG |
| 579 | 506 | CCACGTGCCCTGCGCGCCT | 1112 | AGGCGCGCAGGGCACGTGG |
| 581 | 507 | ACGTGCCCTGCGCGCCTGG | 1113 | CCAGGCGCGCAGGGCACGT |
| 588 | 508 | CTGCGCGCCTGGGGCTCTC | 1114 | GAGAGCCCCAGGCGCGCAG |
| 616 | 509 | GCTTTCGTGAGCCAGGCAG | 1115 | CTGCCTGGCTCACGAAAGC |
| 617 | 510 | CTTTCGTGAGCCAGGCAGC | 1116 | GCTGCCTGGCTCACGAAAG |
| 618 | 511 | TTTCGTGAGCCAGGCAGCG | 1117 | CGCTGCCTGGCTCACGAAA |
| 627 | 512 | CCAGGCAGCGAGGGCCGCC | 1118 | GGCGGCCCTCGCTGCCTGG |
| 652 | 513 | CTGCAGCCCAGCCAGGCCG | 1119 | CGGCCTGGCTGGGCTGCAG |
| 654 | 514 | GCAGCCCAGCCAGGCCGCG | 1120 | CGCGGCCTGGCTGGGCTGC |
| 659 | 515 | CCAGCCAGGCCGCGCCGGC | 112 | GCCGGCGCGGCCTGGCTGG |
| 668 | 516 | CCGCGCCGGCAGAGGGGAT | 1122 | ATCCCCTCTGCCGGCGCGG |
| 690 | 517 | CCAACCTGCCCCGGCGCGC | 1123 | GCGCGCCGGGGCAGGTTGG |
| 692 | 518 | AACCTGCCCCGGCGCGCGG | 1124 | CCGCGCGCCGGGGCAGGTT |
| 705 | 519 | GCGCGGGGATTTCGCCTAC | 1125 | GTAGGCGAAATCCCCGCGC |
| 715 | 520 | TTCGCCTACGCCGCCCCGG | 1126 | CCGGGGCGGCGTAGGCGAA |
| 717 | 521 | CGCCTACGCCGCCCCGGCT | 1127 | AGCCGGGGCGGCGTAGGCG |
| 732 | 522 | GGCTCCTCCGGACGGGGCG | 1128 | CGCCCCGTCCGGAGGAGCC |
| 733 | 523 | GCTCCTCCGGACGGGGCGC | 1129 | GCGCCCCGTCCGGAGGAGC |
| 745 | 524 | GGGGCGCTCTCCCACCCTC | 1130 | GAGGGTGGGAGAGCGCCCC |
| 802 | 525 | GAGGACCGGGACCCGCAGC | 1131 | GCTGCGGGTCCCGGTCCTC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 809 | 526 | GGGACCCGCAGCGCGACGG | 1132 | CCGTCGCGCTGCGGGTCCC |
| 813 | 527 | CCCGCAGCGCGACGGCCTG | 1133 | CAGGCCGTCGCGCTGCGGG |
| 827 | 528 | GCCTGCCGGGCCCCTGCGC | 1134 | GCGCAGGGGCCCGGCAGGC |
| 839 | 529 | CCTGCGCGGTGGCACAGCC | 1135 | GGCTGTGCCACCGCGCAGG |
| 842 | 530 | GCGCGGTGGCACAGCCTGG | 1136 | CCAGGCTGTGCCACCGCGC |
| 843 | 531 | CGCGGTGGCACAGCCTGGG | 1137 | CCCAGGCTGTGCCACCGCG |
| 845 | 532 | CGGTGGCACAGCCTGGGCC | 1138 | GGCCCAGGCTGTGCCACCG |
| 850 | 533 | GCACAGCCTGGGCCCGCTC | 1139 | GAGCGGGCCCAGGCTGTGC |
| 856 | 534 | CCTGGGCCCGCTCAAGCGG | 1140 | CCGCTTGAGCGGGCCCAGG |
| 877 | 535 | CCGCAGGGCCAAGGGGTGC | 1141 | GCACCCCTTGGCCCTGCGG |
| 892 | 536 | GTGCTTGCGCCACCCACGT | 1142 | ACGTGGGTGGCGCAAGCAC |
| 893 | 537 | TGCTTGCGCCACCCACGTC | 1143 | GACGTGGGTGGCGCAAGCA |
| 894 | 538 | GCTTGCGCCACCCACGTCC | 1144 | GGACGTGGGTGGCGCAAGC |
| 895 | 539 | CTTGCGCCACCCACGTCCC | 1145 | GGGACGTGGGTGGCGCAAG |
| 897 | 540 | TGCGCCACCCACGTCCCAG | 1146 | CTGGGACGTGGGTGGCGCA |
| 919 | 541 | AGTCCGTGGTGGGGCTGGG | 1147 | CCCAGCCCCACCACGGACT |
| 936 | 542 | GGGCCGGGGTCCCCAGGTC | 1148 | GACCTGGGGACCCCGGCCC |
| 939 | 543 | CCGGGGTCCCCAGGTCGCC | 1149 | GGCGACCTGGGGACCCCGG |
| 956 | 544 | CCGGGGCGGCGTGGGAACC | 1150 | GGTTCCCACGCCGCCCCGG |
| 989 | 545 | CTCCACCTCCCCAGCCCGC | 1151 | GCGGGCTGGGGAGGTGGAG |
| 992 | 546 | CACCTCCCCAGCCCGCGCC | 1152 | GGCGCGGGCTGGGGAGGTG |
| 994 | 547 | CCTCCCCAGCCCGCGCCCC | 1153 | GGGGCGCGGGCTGGGGAG G |
| 1023 | 548 | CGCCTCCGCGCGGCAGGGG | 1154 | CCCCTGCCGCGCGGAGGCG |
| 1028 | 549 | CCGCGCGGCAGGGGCAGAT | 1155 | ATCTGCCCCTGCCGCGCGG |
| 1030 | 550 | GCGCGGCAGGGGCAGATGC | 1156 | GCATCTGCCCCTGCCGCGC |
| 1067 | 551 | CCCAGGCGCTCCAGGAGCC | 1157 | GGCTCCTGGAGCGCCTGGG |
| 1081 | 552 | GAGCCGGCGCCCTGGTCTG | 1158 | CAGACCAGGGCGCCGGCTC |
| 1083 | 553 | GCCGGCGCCCTGGTCTGCA | 1159 | TGCAGACCAGGGCGCCGGC |
| 1084 | 554 | CCGGCGCCCTGGTCTGCAC | 1160 | GTGCAGACCAGGGCGCCGG |
| 1085 | 555 | CGGCGCCCTGGTCTGCACT | 1161 | AGTGCAGACCAGGGCGCCG |
| 1102 | 556 | CTCCCCTGCGGCCTGCTGC | 1162 | GCAGCAGGCCGCAGGGGAG |
| 1120 | 557 | CTGGATGAGCTCCTGGCGA | 1163 | TCGCCAGGAGCTCATCCAG |
| 1189 | 558 | GGGGAGCTGGAGGCCTCGG | 1164 | CCGAGGCCTCCAGCTCCCC |
| 1192 | 559 | GAGCTGGAGGCCTCGGAAG | 1165 | CTTCCGAGGCCTCCAGCTC |
| 1193 | 560 | AGCTGGAGGCCTCGGAAGA | 1166 | TCTTCCGAGGCCTCCAGCT |
| 1194 | 561 | GCTGGAGGCCTCGGAAGAG | 1167 | CTCTTCCGAGGCCTCCAGC |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 1212 | 562 | GGCCGCCTCGCTGGAAGCA | 1168 | TGCTTCCAGCGAGGCGGCC |
| 1213 | 563 | GCCGCCTCGCTGGAAGCAC | 1169 | GTGCTTCCAGCGAGGCGGC |
| 1214 | 564 | CCGCCTCGCTGGAAGCACC | 1170 | GGTGCTTCCAGCGAGGCGG |
| 1215 | 565 | CGCCTCGCTGGAAGCACCC | 1171 | GGGTGCTTCCAGCGAGGCG |
| 1216 | 566 | GCCTCGCTGGAAGCACCCC | 1172 | GGGGTGCTTCCAGCGAGGC |
| 1218 | 567 | CTCGCTGGAAGCACCCCTC | 1173 | GAGGGGTGCTTCCAGCGAG |
| 1234 | 568 | CTCAGCGAGGAAGAATACC | 1174 | GGTATTCTTCCTCGCTGAG |
| 1235 | 569 | TCAGCGAGGAAGAATACCG | 1175 | CGGTATTCTTCCTCGCTGA |
| 1242 | 570 | GGAAGAATACCGGGCTCTG | 1176 | CAGAGCCCGGTATTCTTCC |
| 1251 | 571 | CCGGGCTCTGCTGGAGGAG | 1177 | CTCCTCCAGCAGAGCCCGG |
| 1257 | 572 | TCTGCTGGAGGAGCTTTAG | 1178 | CTAAAGCTCCTCCAGCAGA |
| 1258 | 573 | CTGCTGGAGGAGCTTTAGG | 1179 | CCTAAAGCTCCTCCAGCAG |
| 1260 | 574 | GCTGGAGGAGCTTTAGGAC | 1180 | GTCCTAAAGCTCCTCCAGC |
| 1261 | 575 | CTGGAGGAGCTTTAGGACG | 1181 | CGTCCTAAAGCTCCTCCAG |
| 1265 | 576 | AGGAGCTTTAGGACGCGGG | 1182 | CCCGCGTCCTAAAGCTCCT |
| 1266 | 577 | GGAGCTTTAGGACGCGGGG | 1183 | CCCCGCGTCCTAAAGCTCC |
| 1267 | 578 | GAGCTTTAGGACGCGGGGT | 1184 | ACCCCGCGTCCTAAAGCTC |
| 1268 | 579 | AGCTTTAGGACGCGGGGTT | 1185 | AACCCCGCGTCCTAAAGCT |
| 1269 | 580 | GCTTTAGGACGCGGGGTTG | 1186 | CAACCCCGCGTCCTAAAGC |
| 1270 | 581 | CTTTAGGACGCGGGGTTGG | 1187 | CCAACCCCGCGTCCTAAAG |
| 1271 | 582 | TTTAGGACGCGGGGTTGGG | 1188 | CCCAACCCCGCGTCCTAAA |
| 1272 | 583 | TTAGGACGCGGGGTTGGGA | 1189 | TCCCAACCCCGCGTCCTAA |
| 1274 | 584 | AGGACGCGGGGTTGGGACG | 1190 | CGTCCCAACCCCGCGTCCT |
| 1279 | 585 | GCGGGGTTGGGACGGGGTC | 1191 | GACCCCGTCCCAACCCCGC |
| 1284 | 586 | GTTGGGACGGGGTCGGGTG | 1192 | CACCCGACCCCGTCCCAAC |
| 1288 | 587 | GGACGGGGTCGGGTGGTTC | 1193 | GAACCACCCGACCCCGTCC |
| 1389 | 588 | GGCTGACCGGCCTGGGATT | 1194 | AATCCCAGGCCGGTCAGCC |
| 1390 | 589 | GCTGACCGGCCTGGGATTC | 1195 | GAATCCCAGGCCGGTCAGC |
| 1400 | 590 | CTGGGATTCCTGCCTTCTA | 1196 | TAGAAGGCAGGAATCCCAG |
| 1401 | 591 | TGGGATTCCTGCCTTCTAG | 1197 | CTAGAAGGCAGGAATCCCA |
| 1419 | 592 | GGTCTAGGCCCGGTGAGAG | 1198 | CTCTCACCGGGCCTAGACC |
| 1420 | 593 | GTCTAGGCCCGGTGAGAGA | 1199 | TCTCTCACCGGGCCTAGAC |
| 1421 | 594 | TCTAGGCCCGGTGAGAGAC | 1200 | GTCTCTCACCGGGCCTAGA |
| 1422 | 595 | CTAGGCCCGGTGAGAGACT | 1201 | AGTCTCTCACCGGGCCTAG |
| 1425 | 596 | GGCCCGGTGAGAGACTCCA | 1202 | TGGAGTCTCTCACCGGGCC |
| 1426 | 597 | GCCCGGTGAGAGACTCCAC | 1203 | GTGGAGTCTCTCACCGGGC |
| 1427 | 598 | CCCGGTGAGAGACTCCACT | 1204 | AGTGGAGTCTCTCACCGGG |

TABLE 1A-continued provides exemplary siRNAs with the sequences of the sense strand and the antisense strand.

| Position in transcript | SEQ ID NO: | Sense strand | SEQ ID NO: | Antisense strand |
|---|---|---|---|---|
| 1607 | 599 | CCCCACCTTCCGACGCTGT | 1205 | ACAGCGTCGGAAGGTGGGG |
| 1608 | 600 | CCCACCTTCCGACGCTGTC | 1206 | GACAGCGTCGGAAGGTGGG |
| 1612 | 601 | CCTTCCGACGCTGTCTAGG | 1207 | CCTAGACAGCGTCGGAAGG |
| 1613 | 602 | CTTCCGACGCTGTCTAGGC | 1208 | GCCTAGACAGCGTCGGAAG |
| 1614 | 603 | TTCCGACGCTGTCTAGGCA | 1209 | TGCCTAGACAGCGTCGGAA |
| 1615 | 604 | TCCGACGCTGTCTAGGCAA | 1210 | TTGCCTAGACAGCGTCGGA |
| 1616 | 605 | CCGACGCTGTCTAGGCAAA | 1211 | TTTGCCTAGACAGCGTCGG |
| 1617 | 606 | CGACGCTGTCTAGGCAAAC | 1212 | GTTTGCCTAGACAGCGTCG |

Column 1 shows the beginning position of the target sequence in DUX4_human_#NM_001306068.3 (SEQ ID NO: 2425).
The target sequence is 19 nucleotide long starting from the beginning position.
For example, row 1 shows that the beginning position of the target sequence is 1, which means that the target sequence is the sequence corresponding to positions 1-19 of DUX4_human_#NM_001306068.3 (SEQ ID NO: 2425).
The sequences of the sense strands and antisense strands are shown from the 5' end to the 3' end.

TABLE 1B provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1 | 1213 | asusggCfcCfUfCfccgacaccca | 1819 | usGfsgguGfuCfGfggagGfgCfca ususu |
| 2 | 1214 | usgsgcCfcUfCfCfcgacacccua | 1820 | usAfsgggUfgUfCfgggaGfgGfcc asusu |
| 11 | 1215 | csgsacAfcCfCfUfcggacagcaa | 1821 | usUfsgcuGfuCfCfgaggGfuGfuc gsusu |
| 12 | 1216 | gsascaCfcCfUfCfggacagcaca | 1822 | usGfsugcUfgUfCfcgagGfgUfgu csusu |
| 13 | 1217 | ascsacCfcUfCfGfgacagcacca | 1823 | usGfsgugCfuGfUfccgaGfgGfug ususu |
| 14 | 1218 | csasccCfuCfGfGfacagcaccca | 1824 | usGfsgguGfcUfGfuccgAfgGfgu gsusu |
| 15 | 1219 | ascsccUfcGfGfAfcagcacccua | 1825 | usAfsgggUfgCfUfguccGfaGfgg ususu |
| 16 | 1220 | cscscuCfgGfAfCfagcacccuca | 1826 | usGfsaggGfuGfCfugucCfgAfgg gsusu |
| 17 | 1221 | cscsucGfgAfCfAfgcacccucca | 1827 | usGfsgagGfgUfGfcuguCfcGfag gsusu |
| 18 | 1222 | csuscgGfaCfAfGfcacccuccca | 1828 | usGfsggaGfgGfUfgcugUfcCfga gsusu |
| 19 | 1223 | uscsggAfcAfGfCfacccuccccca | 1829 | usGfsgggAfgGfGfugcuGfuCfcg asusu |
| 23 | 1224 | ascsagCfaCfCfCfuccccgcgga | 1830 | usCfscgcGfgGfGfagggUfgCfug ususu |
| 24 | 1225 | csasgcAfcCfCfUfccccgcggaa | 1831 | usUfsccgCfgGfGfgaggGfuGfcu gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 25 | 1226 | asgscaCfcCfUfCfcccgcggaaa | 1832 | usUfsuccGfcGfGfggagGfgUfgcususu |
| 39 | 1227 | gsgsaaGfcCfCfGfgggacgagga | 1833 | usCfscucGfuCfCfccggGfcUfuccsusu |
| 40 | 1228 | gsasagCfcCfGfGfggacgaggaa | 1834 | usUfsccuCfgUfCfcccgGfgCfuucsusu |
| 41 | 1229 | asasgcCfcGfGfGfgacgaggaca | 1835 | usGfsuccUfcGfUfccccGfgGfcuususu |
| 49 | 1230 | gsgsacGfaGfGfAfcggcgacgga | 1836 | usCfscguCfgCfCfguccUfcGfuccsusu |
| 50 | 1231 | gsascgAfgGfAfCfggcgacggaa | 1837 | usUfsccgUfcGfCfcgucCfuCfgucsusu |
| 51 | 1232 | ascsgaGfgAfCfGfgcgacggaga | 1838 | usCfsuccGfuCfGfccguCfcUfcgususu |
| 52 | 1233 | csgsagGfaCfGfGfcgacggagaa | 1839 | usUfscucCfgUfCfgccgUfcCfucgsusu |
| 53 | 1234 | gsasggAfcGfGfCfgacggagaca | 1840 | usGfsucuCfcGfUfcgccGfuCfcucsusu |
| 54 | 1235 | asgsgaCfgGfCfGfacggagacua | 1841 | usAfsgucUfcCfGfucgcCfgUfccususu |
| 55 | 1236 | gsgsacGfgCfGfAfcggagacuca | 1842 | usGfsaguCfuCfCfgucgCfcGfuccsusu |
| 56 | 1237 | gsascgGfcGfAfCfggagacucga | 1843 | usCfsgagUfcUfCfcgucGfcCfgucsusu |
| 57 | 1238 | ascsggCfgAfCfGfgagacucgua | 1844 | usAfscgaGfuCfUfccguCfgCfcgususu |
| 60 | 1239 | gscsgaCfgGfAfGfacucguuuga | 1845 | usCfsaaaCfgAfGfucucCfgUfcgcsusu |
| 61 | 1240 | csgsacGfgAfGfAfcucguuugga | 1846 | usCfscaaAfcGfAfgucuCfcGfucgsusu |
| 62 | 1241 | gsascgGfaGfAfCfucguuuggaa | 1847 | usUfsccaAfaCfGfagucUfcCfgucsusu |
| 63 | 1242 | ascsggAfgAfCfUfcguuuggaca | 1848 | usGfsuccAfaAfCfgaguCfuCfcgususu |
| 64 | 1243 | csgsgaGfaCfUfCfguuuggacca | 1849 | usGfsgucCfaAfAfcgagUfcUfccgsusu |
| 65 | 1244 | gsgsagAfcUfCfGfuuuggaccca | 1850 | usGfsgguCfcAfAfacgaGfuCfuccsusu |
| 66 | 1245 | gsasgaCfuCfGfUfuuggacccca | 1851 | usGfsgggUfcCfAfaacgAfgUfcucsusu |
| 67 | 1246 | asgsacUfcGfUfUfuggaccccga | 1852 | usCfsgggGfuCfCfaaacGfaGfucususu |
| 71 | 1247 | uscsguUfuGfGfAfccccgagcca | 1853 | usGfsgcuCfgGfGfguccAfaAfcgasusu |
| 76 | 1248 | usgsgaCfcCfCfGfagccaaagca | 1854 | usGfscuuUfgGfCfucggGfgUfccasusu |
| 77 | 1249 | gsgsacCfcCfGfAfgccaaagcga | 1855 | usCfsgcuUfuGfGfcucgGfgGfuccsusu |
| 78 | 1250 | gsasccCfcGfAfGfccaaagcgaa | 1856 | usUfscgcUfuUfGfgcucGfgGfgu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| | | | | csusu |
| 79 | 1251 | ascsccCfgAfGfCfcaaagcgaga | 1857 | usCfsucgCfuUfUfggcuCfgGfgg ususu |
| 80 | 1252 | cscsccGfaGfCfCfaaagcgagga | 1858 | usCfscucGfcUfUfuggcUfcGfgg gsusu |
| 81 | 1253 | cscscgAfgCfCfAfaagcgaggca | 1859 | usGfsccuCfgCfUfuuggCfuCfgg gsusu |
| 82 | 1254 | cscsgaGfcCfAfAfagcgaggcca | 1860 | usGfsgccUfcGfCfuuugGfcUfcg gsusu |
| 83 | 1255 | csgsagCfcAfAfAfgcgaggccca | 1861 | usGfsggcCfuCfGfcuuuGfgCfuc gsusu |
| 84 | 1256 | gsasgcCfaAfAfGfcgaggcccua | 1862 | usAfsgggCfcUfCfgcuuUfgGfcu csusu |
| 85 | 1257 | asgsccAfaAfGfCfgaggcccuga | 1863 | usCfsaggGfcCfUfcgcuUfuGfgc ususu |
| 86 | 1258 | gscscaAfaGfCfGfaggcccugca | 1864 | usGfscagGfgCfCfucgcUfuUfgg csusu |
| 87 | 1259 | cscsaaAfgCfGfAfggcccugcga | 1865 | usCfsgcaGfgGfCfcucgCfuUfug gsusu |
| 88 | 1260 | csasaaGfcGfAfGfgcccugcgaa | 1866 | usUfscgcAfgGfGfccucGfcUfuu gsusu |
| 89 | 1261 | asasagCfgAfGfGfcccugcgaga | 1867 | usCfsucgCfaGfGfgccuCfgCfuu ususu |
| 90 | 1262 | asasgcGfaGfGfCfccugcgagca | 1868 | usGfscucGfcAfGfggccUfcGfcu ususu |
| 108 | 1263 | csusgcUfuUfGfAfgcggaaccca | 1869 | usGfsgguUfcCfGfcucaAfaGfca gsusu |
| 109 | 1264 | usgscuUfuGfAfGfcggaacccga | 1870 | usCfsgggUfuCfCfgcucAfaAfgc asusu |
| 110 | 1265 | gscsuuUfgAfGfCfggaacccgua | 1871 | usAfscggGfuUfCfcgcuCfaAfag csusu |
| 111 | 1266 | csusuuGfaGfCfGfgaacccguaa | 1872 | usUfsacgGfgUfUfccgcUfcAfaa gsusu |
| 112 | 1267 | ususugAfgCfGfGfaacccguaca | 1873 | usGfsuacGfgGfUfuccgCfuCfaa asusu |
| 113 | 1268 | ususgaGfcGfGfAfacccguacca | 1874 | usGfsguaCfgGfGfuuccGfcUfca asusu |
| 114 | 1269 | usgsagCfgGfAfAfcccguaccca | 1875 | usGfsgguAfcGfGfguucCfgCfuc asusu |
| 115 | 1270 | gsasgcGfgAfAfCfccguacccga | 1876 | usCfsgggUfaCfGfgguuCfcGfcu csusu |
| 116 | 1271 | asgscgGfaAfCfCfcguacccgga | 1877 | usCfscggGfuAfCfggguUfcCfgc ususu |
| 124 | 1272 | cscsguAfcCfCfGfggcaucgcca | 1878 | usGfsgcgAfuGfCfccggGfuAfcg gsusu |
| 125 | 1273 | csgsuaCfcCfGfGfgcaucgccaa | 1879 | usUfsggcGfaUfGfcccgGfgUfac gsusu |
| 126 | 1274 | gsusacCfcGfGfGfcaucgccaca | 1880 | usGfsuggCfgAfUfgcccGfgGfua csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 127 | 1275 | usasccCfgGfGfCfaucgccacca | 1881 | usGfsgugGfcGfAfugccCfgGfgu asusu |
| 129 | 1276 | cscscgGfgCfAfUfcgccaccaga | 1882 | usCfsuggUfgGfCfgaugCfcCfgg gsusu |
| 130 | 1277 | cscsggGfcAfUfCfgccaccagaa | 1883 | usUfscugGfuGfGfcgauGfcCfcg gsusu |
| 131 | 1278 | csgsggCfaUfCfGfccaccagaga | 1884 | usCfsucuGfgUfGfgcgaUfgCfcc gsusu |
| 132 | 1279 | gsgsgcAfuCfGfCfcaccagagaa | 1885 | usUfscucUfgGfUfggcgAfuGfcc csusu |
| 133 | 1280 | gsgscaUfcGfCfCfaccagagaaa | 1886 | usUfsucuCfuGfGfuggcGfaUfgc csusu |
| 134 | 1281 | gscsauCfgCfCfAfccagagaaca | 1887 | usGfsuucUfcUfGfguggCfgAfug csusu |
| 135 | 1282 | csasucGfcCfAfCfcagagaacga | 1888 | usCfsguuCfuCfUfggugGfcGfau gsusu |
| 136 | 1283 | asuscgCfcAfCfCfagagaacgga | 1889 | usCfscguUfcUfCfugguGfgCfga ususu |
| 137 | 1284 | uscsgcCfaCfCfAfgagaacggca | 1890 | usGfsccgUfuCfUfcuggUfgGfcg asusu |
| 138 | 1285 | csgsccAfcCfAfGfagaacggcua | 1891 | usAfsgccGfuUfCfucugGfuGfgc gsusu |
| 144 | 1286 | csasgaGfaAfCfGfgcuggcccaa | 1892 | usUfsgggCfcAfGfccguUfcUfcu gsusu |
| 145 | 1287 | asgsagAfaCfGfGfcuggcccaga | 1893 | usCfsuggGfcCfAfgccgUfuCfuc ususu |
| 146 | 1288 | gsasgaAfcGfGfCfuggcccagga | 1894 | usCfscugGfgCfCfagccGfuUfcu csusu |
| 147 | 1289 | asgsaaCfgGfCfUfggcccaggca | 1895 | usGfsccuGfgGfCfcagcCfgUfuc ususu |
| 148 | 1290 | gsasacGfgCfUfGfgcccaggcca | 1896 | usGfsgccUfgGfGfccagCfcGfuu csusu |
| 157 | 1291 | gscsccAfgGfCfCfaucggcauua | 1897 | usAfsaugCfcGfAfuggcCfuGfgg csusu |
| 158 | 1292 | cscscaGfgCfCfAfucggcauuca | 1898 | usGfsaauGfcCfGfauggCfcUfgg gsusu |
| 159 | 1293 | cscsagGfcCfAfUfcggcauucca | 1899 | usGfsgaaUfgCfCfgaugGfcCfug gsusu |
| 160 | 1294 | csasggCfcAfUfCfggcauuccga | 1900 | usCfsggaAfuGfCfcgauGfgCfcu gsusu |
| 161 | 1295 | asgsgcCfaUfCfGfgcauuccgga | 1901 | usCfscggAfaUfGfccgaUfgGfcc ususu |
| 162 | 1296 | gsgsccAfuCfGfGfcauuccggaa | 1902 | usUfsccgGfaAfUfgccgAfuGfgc csusu |
| 163 | 1297 | gscscaUfcGfGfCfauuccggaga | 1903 | usCfsuccGfgAfAfugccGfaUfgg csusu |
| 164 | 1298 | cscsauCfgGfCfAfuuccggagca | 1904 | usGfscucCfgGfAfaugcCfgAfug gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 165 | 1299 | csasucGfgCfAfUfuccggagcca | 1905 | usGfsgcuCfcGfGfaaugCfcGfau gsusu |
| 166 | 1300 | asuscgGfcAfUfUfccggagccca | 1906 | usGfsggcUfcCfGfgaauGfcCfga ususu |
| 167 | 1301 | uscsggCfaUfUfCfcggagcccaa | 1907 | usUfsgggCfuCfCfggaaUfgCfcg asusu |
| 168 | 1302 | csgsgcAfuUfCfCfggagcccaga | 1908 | usCfsuggGfcUfCfcggaAfuGfcc gsusu |
| 169 | 1303 | gsgscaUfuCfCfGfgagcccagga | 1909 | usCfscugGfgCfUfccggAfaUfgc csusu |
| 170 | 1304 | gscsauUfcCfGfGfagcccaggga | 1910 | usCfsccuGfgGfCfuccgGfaAfug csusu |
| 171 | 1305 | csasuuCfcGfGfAfgcccagggua | 1911 | usAfscccUfgGfGfcuccGfgAfau gsusu |
| 172 | 1306 | asusucCfgGfAfGfcccaggguca | 1912 | usGfsaccCfuGfGfgcucCfgGfaa ususu |
| 173 | 1307 | ususccGfgAfGfCfccaggggucca | 1913 | usGfsgacCfcUfGfggcuCfcGfga asusu |
| 174 | 1308 | uscscgGfaGfCfCfcaggguccaa | 1914 | usUfsggaCfcCfUfgggcUfcCfgg asusu |
| 175 | 1309 | cscsggAfgCfCfCfaggguccaga | 1915 | usCfsuggAfcCfCfugggCfuCfcg gsusu |
| 176 | 1310 | csgsgaGfcCfCfAfggguccagaa | 1916 | usUfscugGfaCfCfcuggGfcUfcc gsusu |
| 177 | 1311 | gsgsagCfcCfAfGfgguccagaua | 1917 | usAfsucuGfgAfCfccugGfgCfuc csusu |
| 186 | 1312 | gsgsucCfaGfAfUfuugguuucaa | 1918 | usUfsgaaAfcCfAfaaucUfgGfac csusu |
| 187 | 1313 | gsusccAfgAfUfUfugguuucaga | 1919 | usCfsugaAfaCfCfaaauCfuGfga csusu |
| 188 | 1314 | uscscaGfaUfUfUfgguuucagaa | 1920 | usUfscugAfaAfCfcaaaUfcUfgg asusu |
| 189 | 1315 | cscsagAfuUfUfGfguuucagaaa | 1921 | usUfsucuGfaAfAfccaaAfuCfug gsusu |
| 190 | 1316 | csasgaUfuUfGfGfuuucagaaua | 1922 | usAfsuucUfgAfAfaccaAfaUfcu gsusu |
| 192 | 1317 | gsasuuUfgGfUfUfucagaaugaa | 1923 | usUfscauUfcUfGfaaacCfaAfau csusu |
| 194 | 1318 | ususugGfuUfUfCfagaaugagaa | 1924 | usUfscucAfuUfCfugaaAfcCfaa asusu |
| 195 | 1319 | ususggUfuUfCfAfgaaugagaga | 1925 | usCfsucuCfaUfUfcugaAfaCfca asusu |
| 196 | 1320 | usgsguUfuCfAfGfaaugagagga | 1926 | usCfscucUfcAfUfucugAfaAfcc asusu |
| 197 | 1321 | gsgsuuUfcAfGfAfaugagaggua | 1927 | usAfsccuCfuCfAfuucuGfaAfac csusu |
| 198 | 1322 | gsusuuCfaGfAfAfugagagguca | 1928 | usGfsaccUfcUfCfauucUfgAfaa csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 199 | 1323 | ususucAfgAfAfUfgagaggucaa | 1929 | usUfsgacCfuCfUfcauuCfuGfaa asusu |
| 200 | 1324 | ususcaGfaAfUfGfagaggucaca | 1930 | usGfsugaCfcUfCfucauUfcUfga asusu |
| 201 | 1325 | uscsagAfaUfGfAfgaggucacga | 1931 | usCfsgugAfcCfUfcucaUfuCfug asusu |
| 202 | 1326 | csasgaAfuGfAfGfaggucacgca | 1932 | usGfscguGfaCfCfucucAfuUfcu gsusu |
| 203 | 1327 | asgsaaUfgAfGfAfggucacgcca | 1933 | usGfsgcgUfgAfCfcucuCfaUfuc ususu |
| 204 | 1328 | gsasauGfaGfAfGfgucacgccaa | 1934 | usUfsggcGfuGfAfccucUfcAfuu csusu |
| 205 | 1329 | asasugAfgAfGfGfucacgccaga | 1935 | usCfsuggCfgUfGfaccuCfuCfau ususu |
| 206 | 1330 | asusgaGfaGfGfUfcacgccagca | 1936 | usGfscugGfcGfUfgaccUfcUfca ususu |
| 207 | 1331 | usgsagAfgGfUfCfacgccagcua | 1937 | usAfsgcuGfgCfGfugacCfuCfuc asusu |
| 208 | 1332 | gsasgaGfgUfCfAfcgccagcuga | 1938 | usCfsagcUfgGfCfgugaCfcUfcu csusu |
| 209 | 1333 | asgsagGfuCfAfCfgccagcugaa | 1939 | usUfscagCfuGfGfcgugAfcCfuc ususu |
| 210 | 1334 | gsasggUfcAfCfGfccagcugaga | 1940 | usCfsucaGfcUfGfgcguGfaCfcu csusu |
| 211 | 1335 | asgsguCfaCfGfCfcagcugagga | 1941 | usCfscucAfgCfUfggcgUfgAfcc ususu |
| 212 | 1336 | gsgsucAfcGfCfCfagcugaggca | 1942 | usGfsccuCfaGfCfuggcGfuGfac csusu |
| 213 | 1337 | gsuscaCfgCfCfAfgcugaggcaa | 1943 | usUfsgccUfcAfGfcuggCfgUfga csusu |
| 214 | 1338 | uscsacGfcCfAfGfcugaggcaga | 1944 | usCfsugcCfuCfAfgcugGfcGfug asusu |
| 215 | 1339 | csascgCfcAfGfCfugaggcagca | 1945 | usGfscugCfcUfCfagcuGfgCfgu gsusu |
| 224 | 1340 | usgsagGfcAfGfCfaccggcggga | 1946 | usCfsccgCfcGfGfugcuGfcCfuc asusu |
| 225 | 1341 | gsasggCfaGfCfAfccggcgggaa | 1947 | usUfscccGfcCfGfgugcUfgCfcu csusu |
| 226 | 1342 | asgsgcAfgCfAfCfcggcgggaaa | 1948 | usUfsuccCfgCfCfggugCfuGfcc ususu |
| 227 | 1343 | gsgscaGfcAfCfCfggcgggaaua | 1949 | usAfsuucCfcGfCfcgguGfcUfgc csusu |
| 228 | 1344 | gscsagCfaCfCfGfgcgggaauca | 1950 | usGfsauuCfcCfGfccggUfgCfug csusu |
| 229 | 1345 | csasgcAfcCfGfGfcgggaaucua | 1951 | usAfsgauUfcCfCfgccgGfuGfcu gsusu |
| 230 | 1346 | asgscaCfcGfGfCfgggaaucuca | 1952 | usGfsagaUfuCfCfcgccGfgUfgc ususu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 231 | 1347 | gscsacCfgGfCfGfggaaucucga | 1953 | usCfsgagAfuUfCfccgcCfgGfug csusu |
| 232 | 1348 | csasccGfgCfGfGfgaaucucgga | 1954 | usCfscgaGfaUfUfcccgCfcGfgu gsusu |
| 235 | 1349 | csgsgcGfgGfAfAfucucggccca | 1955 | usGfsggcCfgAfGfauucCfcGfcc gsusu |
| 236 | 1350 | gsgscgGfgAfAfUfcucggcccua | 1956 | usAfsgggCfcGfAfgauuCfcCfgc csusu |
| 237 | 1351 | gscsggGfaAfUfCfucggcccuga | 1957 | usCfsaggGfcCfGfagauUfcCfcg csusu |
| 238 | 1352 | csgsggAfaUfCfUfcggcccugga | 1958 | usCfscagGfgCfCfgagaUfuCfcc gsusu |
| 239 | 1353 | gsgsgaAfuCfUfCfggcccuggca | 1959 | usGfsccaGfgGfCfcgagAfuUfcc csusu |
| 240 | 1354 | gsgsaaUfcUfCfGfgcccuggcca | 1960 | usGfsgccAfgGfGfccgaGfaUfuc csusu |
| 241 | 1355 | gsasauCfuCfGfGfcccuggccca | 1961 | usGfsggcCfaGfGfgccgAfgAfuu csusu |
| 261 | 1356 | gsasgaCfgCfGfGfcccgccagaa | 1962 | usUfscugGfcGfGfgccgCfgUfcu csusu |
| 262 | 1357 | asgsacGfcGfGfCfccgccagaaa | 1963 | usUfsucuGfgCfGfggccGfcGfuc ususu |
| 273 | 1358 | gscscaGfaAfGfGfccggcgaaaa | 1964 | usUfsuucGfcCfGfgccuUfcUfgg csusu |
| 274 | 1359 | cscsagAfaGfGfCfcggcgaaaga | 1965 | usCfsuuuCfgCfCfggccUfuCfug gsusu |
| 275 | 1360 | csasgaAfgGfCfCfggcgaaagca | 1966 | usGfscuuUfcGfCfcggcCfuUfcu gsusu |
| 276 | 1361 | asgsaaGfgCfCfGfgcgaaagcga | 1967 | usCfsgcuUfuCfGfccggCfcUfuc ususu |
| 277 | 1362 | gsasagGfcCfGfGfcgaaagcgga | 1968 | usCfscgcUfuUfCfgccgGfcCfuu csusu |
| 278 | 1363 | asasggCfcGfGfCfgaaagcggaa | 1969 | usUfsccgCfuUfUfcgccGfgCfcu ususu |
| 285 | 1364 | gscsgaAfaGfCfGfgaccgccgua | 1970 | usAfscggCfgGfUfccgcUfuUfcg csusu |
| 286 | 1365 | csgsaaAfgCfGfGfaccgccguca | 1971 | usGfsacgGfcGfGfuccgCfuUfuc gsusu |
| 287 | 1366 | gsasaaGfcGfGfAfccgccgucaa | 1972 | usUfsgacGfgCfGfguccGfcUfuu csusu |
| 288 | 1367 | asasagCfgGfAfCfcgccgucaca | 1973 | usGfsugaCfgGfCfggucCfgCfuu ususu |
| 289 | 1368 | asasgcGfgAfCfCfgccgucacca | 1974 | usGfsgugAfcGfGfcgguCfcGfcu ususu |
| 292 | 1369 | csgsgaCfcGfCfCfgucaccggaa | 1975 | usUfsccgGfuGfAfcggcGfgUfcc gsusu |
| 293 | 1370 | gsgsacCfgCfCfGfucaccggaua | 1976 | usAfsuccGfgUfGfacggCfgGfuc csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 294 | 1371 | gsasccGfcCfGfUfcaccggauca | 1977 | usGfsaucCfgGfUfgacgGfcGfgucsusu |
| 295 | 1372 | ascscgCfcGfUfCfaccggaucca | 1978 | usGfsgauCfcGfGfugacGfgCfggususu |
| 296 | 1373 | cscsgcCfgUfCfAfccggauccca | 1979 | usGfsggaUfcCfGfgugaCfgGfcggsusu |
| 297 | 1374 | csgsccGfuCfAfCfcggaucccaa | 1980 | usUfsgggAfuCfCfggugAfcGfgcgsusu |
| 298 | 1375 | gscscgUfcAfCfCfggaucccaga | 1981 | usCfsuggGfaUfCfcgguGfaCfggcsusu |
| 299 | 1376 | cscsguCfaCfCfGfgaucccagaa | 1982 | usUfscugGfgAfUfccggUfgAfcggsusu |
| 300 | 1377 | csgsucAfcCfGfGfaucccagaca | 1983 | usGfsucuGfgGfAfuccgGfuGfacgsusu |
| 301 | 1378 | gsuscaCfcGfGfAfucccagacca | 1984 | usGfsgucUfgGfGfauccGfgUfgacsusu |
| 302 | 1379 | uscsacCfgGfAfUfcccagaccga | 1985 | usCfsgguCfuGfGfgaucCfgGfugasusu |
| 303 | 1380 | csasccGfgAfUfCfccagaccgca | 1986 | usGfscggUfcUfGfggauCfcGfgugsusu |
| 304 | 1381 | ascscgGfaUfCfCfcagaccgcca | 1987 | usGfsgcgGfuCfUfgggaUfcCfggususu |
| 305 | 1382 | cscsggAfuCfCfCfagaccgccca | 1988 | usGfsggcGfgUfCfugggAfuCfcggsusu |
| 306 | 1383 | csgsgaUfcCfCfAfgaccgcccua | 1989 | usAfsgggCfgGfUfcuggGfaUfccgsusu |
| 307 | 1384 | gsgsauCfcCfAfGfaccgcccuga | 1990 | usCfsaggGfcGfGfucugGfgAfuccsusu |
| 308 | 1385 | gsasucCfcAfGfAfccgcccugca | 1991 | usGfscagGfgCfGfgucuGfgGfaucsusu |
| 309 | 1386 | asusccCfaGfAfCfcgcccugcua | 1992 | usAfsgcaGfgGfCfggucUfgGfgaususu |
| 310 | 1387 | uscsccAfgAfCfCfgcccugcuca | 1993 | usGfsagcAfgGfGfcgguCfuGfggasusu |
| 311 | 1388 | cscscaGfaCfCfGfcccugcucca | 1994 | usGfsgagCfaGfGfgcggUfcUfgggsusu |
| 312 | 1389 | cscsagAfcCfGfCfccugcuccua | 1995 | usAfsggaGfcAfGfggcgGfuCfuggsusu |
| 313 | 1390 | csasgaCfcGfCfCfcugcuccuca | 1996 | usGfsaggAfgCfAfgggcGfgUfcugsusu |
| 314 | 1391 | asgsacCfgCfCfCfugcuccucca | 1997 | usGfsgagGfaGfCfagggCfgGfucususu |
| 315 | 1392 | gsasccGfcCfCfUfgcuccuccga | 1998 | usCfsggaGfgAfGfcaggGfcGfgucsusu |
| 316 | 1393 | ascscgCfcCfUfGfcuccuccgaa | 1999 | usUfscggAfgGfAfgcagGfgCfggususu |
| 325 | 1394 | csusccUfcCfGfAfgccuuugaga | 2000 | usCfsucaAfaGfGfcucgGfaGfgagsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 328 | 1395 | csusccGfaGfCfCfuuugagaaga | 2001 | usCfsuucUfcAfAfaggcUfcGfga gsusu |
| 336 | 1396 | csusuuGfaGfAfAfggaucgcuua | 2002 | usAfsagcGfaUfCfcuucUfcAfaa gsusu |
| 337 | 1397 | ususugAfgAfAfGfgaucgcuuua | 2003 | usAfsaagCfgAfUfccuuCfuCfaa asusu |
| 338 | 1398 | ususgaGfaAfGfGfaucgcuuuca | 2004 | usGfsaaaGfcGfAfuccuUfcUfca asusu |
| 339 | 1399 | usgsagAfaGfGfAfucgcuuucca | 2005 | usGfsgaaAfgCfGfauccUfuCfuc asusu |
| 340 | 1400 | gsasgaAfgGfAfUfcgcuuuccaa | 2006 | usUfsggaAfaGfCfgaucCfuUfcu csusu |
| 341 | 1401 | asgsaaGfgAfUfCfgcuuuccaga | 2007 | usCfsuggAfaAfGfcgauCfcUfuc ususu |
| 342 | 1402 | gsasagGfaUfCfGfcuuuccagga | 2008 | usCfscugGfaAfAfgcgaUfcCfuu csusu |
| 343 | 1403 | asasggAfuCfGfCfuuuccaggca | 2009 | usGfsccuGfgAfAfagcgAfuCfcu ususu |
| 344 | 1404 | asgsgaUfcGfCfUfuuccaggcaa | 2010 | usUfsgccUfgGfAfaagcGfaUfcc ususu |
| 345 | 1405 | gsgsauCfgCfUfUfuccaggcaua | 2011 | usAfsugcCfuGfGfaaagCfgAfuc csusu |
| 346 | 1406 | gsasucGfcUfUfUfccaggcauca | 2012 | usGfsaugCfcUfGfgaaaGfcGfau csusu |
| 347 | 1407 | asuscgCfuUfUfCfcaggcaucga | 2013 | usCfsgauGfcCfUfggaaAfgCfga ususu |
| 348 | 1408 | uscsgcUfuUfCfCfaggcaucgca | 2014 | usGfscgaUfgCfCfuggaAfaGfcg asusu |
| 349 | 1409 | csgscuUfuCfCfAfggcaucgcca | 2015 | usGfsgcgAfuGfCfcuggAfaAfgc gsusu |
| 350 | 1410 | gscsuuUfcCfAfGfgcaucgccga | 2016 | usCfsggcGfaUfGfccugGfaAfag csusu |
| 351 | 1411 | csusuuCfcAfGfGfcaucgccgca | 2017 | usGfscggCfgAfUfgccuGfgAfaa gsusu |
| 352 | 1412 | ususucCfaGfGfCfaucgccgcca | 2018 | usGfsgcgGfcGfAfugccUfgGfaa asusu |
| 353 | 1413 | ususccAfgGfCfAfucgccgccca | 2019 | usGfsggcGfgCfGfaugcCfuGfga asusu |
| 369 | 1414 | cscsggGfaGfGfAfgcuggccaga | 2020 | usCfsuggCfcAfGfcuccUfcCfcg gsusu |
| 370 | 1415 | csgsggAfgGfAfGfcuggccagaa | 2021 | usUfscugGfcCfAfgcucCfuCfcc gsusu |
| 371 | 1416 | gsgsgaGfgAfGfCfuggccagaga | 2022 | usCfsucuGfgCfCfagcuCfcUfcc csusu |
| 372 | 1417 | gsgsagGfaGfCfUfggccagagaa | 2023 | usUfscucUfgGfCfcagcUfcCfuc csusu |
| 373 | 1418 | gsasggAfgCfUfGfgccagagaga | 2024 | usCfsucuCfuGfGfccagCfuCfcu csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 374 | 1419 | asgsgaGfcUfGfGfccagagagaa | 2025 | usUfscucUfcUfGfgccaGfcUfcc ususu |
| 375 | 1420 | gsgsagCfuGfGfCfcagagagaca | 2026 | usGfsucuCfuCfUfggccAfgCfuc csusu |
| 376 | 1421 | gsasgcUfgGfCfCfagagagacga | 2027 | usCfsgucUfcUfCfuggcCfaGfcu csusu |
| 377 | 1422 | asgscuGfgCfCfAfgagagacgga | 2028 | usCfscguCfuCfUfcuggCfcAfgc ususu |
| 378 | 1423 | gscsugGfcCfAfGfagagacggga | 2029 | usCfsccgUfcUfCfucugGfcCfag csusu |
| 382 | 1424 | gscscaGfaGfAfGfacgggccuca | 2030 | usGfsaggCfcCfGfucucUfcUfgg csusu |
| 383 | 1425 | cscsagAfgAfGfAfcgggccucca | 2031 | usGfsgagGfcCfCfgucuCfuCfug gsusu |
| 384 | 1426 | csasgaGfaGfAfCfgggccuccca | 2032 | usGfsggaGfgCfCfcgucUfcUfcu gsusu |
| 385 | 1427 | asgsagAfgAfCfGfggccucccga | 2033 | usCfsgggAfgGfCfccguCfuCfuc ususu |
| 394 | 1428 | gsgsccUfcCfCfGfgaguccagga | 2034 | usCfscugGfaCfUfccggGfaGfgc csusu |
| 395 | 1429 | gscscuCfcCfGfGfaguccaggaa | 2035 | usUfsccuGfgAfCfuccgGfgAfgg csusu |
| 396 | 1430 | cscsucCfcGfGfAfguccaggaua | 2036 | usAfsuccUfgGfAfcuccGfgGfag gsusu |
| 397 | 1431 | csusccCfgGfAfGfuccaggauua | 2037 | usAfsaucCfuGfGfacucCfgGfga gsusu |
| 398 | 1432 | uscsccGfgAfGfUfccaggauuca | 2038 | usGfsaauCfcUfGfgacuCfcGfgg asusu |
| 399 | 1433 | cscscgGfaGfUfCfcaggauucaa | 2039 | usUfsgaaUfcCfUfggacUfcCfgg gsusu |
| 400 | 1434 | cscsggAfgUfCfCfaggauucaga | 2040 | usCfsugaAfuCfCfuggaCfuCfcg gsusu |
| 401 | 1435 | csgsgaGfuCfCfAfggauucagaa | 2041 | usUfscugAfaUfCfcuggAfcUfcc gsusu |
| 402 | 1436 | gsgsagUfcCfAfGfgauucagaua | 2042 | usAfsucuGfaAfUfccugGfaCfuc csusu |
| 403 | 1437 | gsasguCfcAfGfGfauucagauca | 2043 | usGfsaucUfgAfAfuccuGfgAfcu csusu |
| 404 | 1438 | asgsucCfaGfGfAfuucagaucua | 2044 | usAfsgauCfuGfAfauccUfgGfac ususu |
| 408 | 1439 | csasggAfuUfCfAfgaucugguua | 2045 | usAfsaccAfgAfUfcugaAfuCfcu gsusu |
| 409 | 1440 | asgsgaUfuCfAfGfaucugguuua | 2046 | usAfsaacCfaGfAfucugAfaUfcc ususu |
| 410 | 1441 | gsgsauUfcAfGfAfucugguuuca | 2047 | usGfsaaaCfcAfGfaucuGfaAfuc csusu |
| 411 | 1442 | gsasuuCfaGfAfUfcugguuucaa | 2048 | usUfsgaaAfcCfAfgaucUfgAfau csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 412 | 1443 | asusucAfgAfUfCfugguuucaga | 2049 | usCfsugaAfaCfCfagauCfuGfaaususu |
| 420 | 1444 | csusggUfuUfCfAfgaaucgaaga | 2050 | usCfsuucGfaUfUfcugaAfaCfcagsusu |
| 421 | 1445 | usgsguUfuCfAfGfaaucgaagga | 2051 | usCfscuuCfgAfUfucugAfaAfccasusu |
| 422 | 1446 | gsgsuuUfcAfGfAfaucgaaggga | 2052 | usCfsccuUfcGfAfuucuGfaAfaccsusu |
| 423 | 1447 | gsusuuCfaGfAfAfucgaagggca | 2053 | usGfscccUfuCfGfauucUfgAfaacsusu |
| 424 | 1448 | ususucAfgAfAfUfcgaagggcca | 2054 | usGfsgccCfuUfCfgauuCfuGfaaasusu |
| 425 | 1449 | ususcaGfaAfUfCfgaagggccaa | 2055 | usUfsggcCfcUfUfcgauUfcUfgaasusu |
| 426 | 1450 | uscsagAfaUfCfGfaagggccaga | 2056 | usCfsuggCfcCfUfucgaUfuCfugasusu |
| 427 | 1451 | csasgaAfuCfGfAfagggccagga | 2057 | usCfscugGfcCfCfuucgAfuUfcugsusu |
| 428 | 1452 | asgsaaUfcGfAfAfgggccaggca | 2058 | usGfsccuGfgCfCfcuucGfaUfucususu |
| 429 | 1453 | gsasauCfgAfAfGfggccaggcaa | 2059 | usUfsgccUfgGfCfccuuCfgAfuucsusu |
| 430 | 1454 | asasucGfaAfGfGfgccaggcaca | 2060 | usGfsugcCfuGfGfcccuUfcGfauususu |
| 431 | 1455 | asuscgAfaGfGfGfccaggcacca | 2061 | usGfsgugCfcUfGfgcccUfuCfgaususu |
| 432 | 1456 | uscsgaAfgGfGfCfcaggcaccca | 2062 | usGfsgguGfcCfUfggccCfuUfcgasusu |
| 509 | 1457 | gsgsggUfcAfCfCfcugcucccua | 2063 | usAfsgggAfgCfAfggguGfaCfcccsusu |
| 510 | 1458 | gsgsguCfaCfCfCfugcucccuca | 2064 | usGfsaggGfaGfCfagggUfgAfcccsusu |
| 511 | 1459 | gsgsucAfcCfCfUfgcucccucga | 2065 | usCfsgagGfgAfGfcaggGfuGfaccsusu |
| 512 | 1460 | gsuscaCfcCfUfGfcucccucgua | 2066 | usAfscgaGfgGfAfgcagGfgUfgacsusu |
| 513 | 1461 | uscsacCfcUfGfCfucccucguga | 2067 | usCfsacgAfgGfGfagcaGfgGfugasusu |
| 514 | 1462 | csascccCfuGfCfUfcccucgugga | 2068 | usCfscacGfaGfGfgagcAfgGfgugsusu |
| 516 | 1463 | cscscuGfcUfCfCfcucgugggua | 2069 | usAfscccAfcGfAfgggaGfcAfgggsusu |
| 517 | 1464 | cscsugCfuCfCfCfucgugggguca | 2070 | usGfsaccCfaCfGfagggAfgCfaggsusu |
| 518 | 1465 | csusgcUfcCfCfUfcgugggucga | 2071 | usCfsgacCfcAfCfgaggGfaGfcagsusu |
| 519 | 1466 | usgscuCfcCfUfCfgugggucgca | 2072 | usGfscgaCfcCfAfcgagGfgAfgcasusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 520 | 1467 | gscsucCfcUfCfGfugggucgcca | 2073 | usGfsgcgAfcCfCfacgaGfgGfag csusu |
| 521 | 1468 | csusccCfuCfGfUfgggucgccua | 2074 | usAfsggcGfaCfCfcacgAfgGfga gsusu |
| 522 | 1469 | uscsccUfcGfUfGfggucgccuua | 2075 | usAfsaggCfgAfCfccacGfaGfgg asusu |
| 523 | 1470 | cscscuCfgUfGfGfgucgccuuca | 2076 | usGfsaagGfcGfAfcccaCfgAfgg gsusu |
| 524 | 1471 | cscsucGfuGfGfGfucgccuucga | 2077 | usCfsgaaGfgCfGfacccAfcGfag gsusu |
| 525 | 1472 | csuscgUfgGfGfUfcgccuucgca | 2078 | usGfscgaAfgGfCfgaccCfaCfga gsusu |
| 526 | 1473 | uscsguGfgGfUfCfgccuucgcca | 2079 | usGfsgcgAfaGfGfcgacCfcAfcg asusu |
| 530 | 1474 | gsgsguCfgCfCfUfucgcccacaa | 2080 | usUfsgugGfgCfGfaaggCfgAfcc csusu |
| 531 | 1475 | gsgsucGfcCfUfUfcgcccacaca | 2081 | usGfsuguGfgGfCfgaagGfcGfac csusu |
| 532 | 1476 | gsuscgCfcUfUfCfgcccacacca | 2082 | usGfsgugUfgGfGfcgaaGfgCfga csusu |
| 533 | 1477 | uscsgcCfuUfCfGfcccacaccga | 2083 | usCfsgguGfuGfGfgcgaAfgGfcg asusu |
| 544 | 1478 | csascaCfcGfGfCfgcguggggaa | 2084 | usUfsccccCfaCfGfcgccGfgUfgu gsusu |
| 545 | 1479 | ascsacCfgGfCfGfcguggggaaa | 2085 | usUfsuccCfcAfCfgcgcCfgGfug ususu |
| 552 | 1480 | csgscgUfgGfGfGfaacggggcua | 2086 | usAfsgccCfcGfUfucccCfaCfgc gsusu |
| 553 | 1481 | gscsguGfgGfGfAfacggggcuua | 2087 | usAfsagcCfcCfGfuuccCfcAfcg csusu |
| 566 | 1482 | gsgscuUfcCfCfGfcaccccacga | 2088 | usCfsgugGfgGfUfgcggGfaAfgc csusu |
| 567 | 1483 | gscsuuCfcCfGfCfaccccacgua | 2089 | usAfscguGfgGfGfugcgGfgAfag csusu |
| 619 | 1484 | ususcgUfgAfGfCfcaggcagcga | 2090 | usCfsgcuGfcCfUfggcuCfaCfga asusu |
| 620 | 1485 | uscsguGfaGfCfCfaggcagcgaa | 2091 | usUfscgcUfgCfCfuggcUfcAfcg asusu |
| 621 | 1486 | csgsugAfgCfCfAfggcagcgaga | 2092 | usCfsucgCfuGfCfcuggCfuCfac gsusu |
| 622 | 1487 | gsusgaGfcCfAfGfgcagcgagga | 2093 | usCfscucGfcUfGfccugGfcUfca csusu |
| 671 | 1488 | csgsccGfgCfAfGfaggggaucua | 2094 | usAfsgauCfcCfCfucugCfcGfgc gsusu |
| 672 | 1489 | gscscgGfcAfGfAfggggaucuca | 2095 | usGfsagaUfcCfCfcucuGfcCfgg csusu |
| 673 | 1490 | cscsggCfaGfAfGfgggaucucca | 2096 | usGfsgagAfuCfCfccucUfgCfcg gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 674 | 1491 | csgsgcAfgAfGfGfggaucuccca | 2097 | usGfsggaGfaUfCfcccuCfuGfcc gsusu |
| 675 | 1492 | gsgscaGfaGfGfGfgaucucccaa | 2098 | usUfsgggAfgAfUfccccUfcUfgc csusu |
| 683 | 1493 | gsgsauCfuCfCfCfaaccugccca | 2099 | usGfsggcAfgGfUfugggAfgAfuc csusu |
| 684 | 1494 | gsasucUfcCfCfAfaccugcccca | 2100 | usGfsgggCfaGfGfuuggGfaGfau csusu |
| 685 | 1495 | asuscuCfcCfAfAfccugccccga | 2101 | usCfsgggGfcAfGfguugGfgAfga ususu |
| 686 | 1496 | uscsucCfcAfAfCfcugccccgga | 2102 | usCfscggGfgCfAfgguuGfgGfag asusu |
| 706 | 1497 | csgscgGfgGfAfUfuucgccuaca | 2103 | usGfsuagGfcGfAfaaucCfcCfgc gsusu |
| 707 | 1498 | gscsggGfgAfUfUfucgccuacga | 2104 | usCfsguaGfgCfGfaaauCfcCfcg csusu |
| 708 | 1499 | csgsggGfaUfUfUfcgccuacgca | 2105 | usGfscguAfgGfCfgaaaUfcCfcc gsusu |
| 709 | 1500 | gsgsggAfuUfUfCfgccuacgcca | 2106 | usGfsgcgUfaGfGfcgaaAfuCfcc csusu |
| 710 | 1501 | gsgsgaUfuUfCfGfccuacgccga | 2107 | usCfsggcGfuAfGfgcgaAfaUfcc csusu |
| 711 | 1502 | gsgsauUfuCfGfCfcuacgccgca | 2108 | usGfscggCfgUfAfggcgAfaAfuc csusu |
| 712 | 1503 | gsasuuUfcGfCfCfuacgccgcca | 2109 | usGfsgcgGfcGfUfaggcGfaAfau csusu |
| 713 | 1504 | asusuuCfgCfCfUfacgccgccca | 2110 | usGfsggcGfgCfGfuaggCfgAfaa ususu |
| 714 | 1505 | ususucGfcCfUfAfcgccgcccca | 2111 | usGfsgggCfgGfCfguagGfcGfaa asusu |
| 746 | 1506 | gsgsgcGfcUfCfUfcccacccuca | 2112 | usGfsaggGfuGfGfgagaGfcGfcc csusu |
| 747 | 1507 | gsgscgCfuCfUfCfccacccucaa | 2113 | usUfsgagGfgUfGfggagAfgCfgc csusu |
| 748 | 1508 | gscsgcUfcUfCfCfcacccucaga | 2114 | usCfsugaGfgGfUfgggaGfaGfcg csusu |
| 749 | 1509 | csgscuCfuCfCfCfacccucagga | 2115 | usCfscugAfgGfGfugggAfgAfgc gsusu |
| 750 | 1510 | gscsucUfcCfCfAfcccucaggca | 2116 | usGfsccuGfaGfGfguggGfaGfag csusu |
| 751 | 1511 | csuscuCfcCfAfCfccucaggcua | 2117 | usAfsgccUfgAfGfggugGfgAfga gsusu |
| 752 | 1512 | uscsucCfcAfCfCfcucaggcuca | 2118 | usGfsagcCfuGfAfggguGfgGfag asusu |
| 753 | 1513 | csusccCfaCfCfCfucaggcucca | 2119 | usGfsgagCfcUfGfagggUfgGfga gsusu |
| 754 | 1514 | uscsccAfcCfCfUfcaggcuccua | 2120 | usAfsggaGfcCfUfgaggGfuGfgg asusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 755 | 1515 | cscscaCfcCfUfCfaggcuccuca | 2121 | usGfsaggAfgCfCfugagGfgUfgg gsusu |
| 756 | 1516 | cscsacCfcUfCfAfggcuccucga | 2122 | usCfsgagGfaGfCfcugaGfgGfug gsusu |
| 757 | 1517 | csasccCfuCfAfGfgcuccucgga | 2123 | usCfscgaGfgAfGfccugAfgGfgu gsusu |
| 758 | 1518 | ascsccUfcAfGfGfcuccucggua | 2124 | usAfsccgAfgGfAfgccuGfaGfgg ususu |
| 759 | 1519 | cscscuCfaGfGfCfuccucgguga | 2125 | usCfsaccGfaGfGfagccUfgAfgg gsusu |
| 760 | 1520 | cscsucAfgGfCfUfccucggugga | 2126 | usCfscacCfgAfGfgagcCfuGfag gsusu |
| 761 | 1521 | csuscaGfgCfUfCfcucgguggca | 2127 | usGfsccaCfcGfAfggagCfcUfga gsusu |
| 767 | 1522 | csusccUfcGfGfUfggccuccgca | 2128 | usGfscggAfgGfCfcaccGfaGfga gsusu |
| 768 | 1523 | uscscuCfgGfUfGfgccuccgcaa | 2129 | usUfsgcgGfaGfGfccacCfgAfgg asusu |
| 777 | 1524 | gscscuCfcGfCfAfcccgggcaaa | 2130 | usUfsugcCfcGfGfgugcGfgAfgg csusu |
| 778 | 1525 | cscsucCfgCfAfCfccgggcaaaa | 2131 | usUfsuugCfcCfGfggugCfgGfag gsusu |
| 779 | 1526 | csusccGfcAfCfCfcgggcaaaaa | 2132 | usUfsuuuGfcCfCfggguGfcGfga gsusu |
| 780 | 1527 | uscscgCfaCfCfCfgggcaaaaga | 2133 | usCfsuuuUfgCfCfcgggUfgCfgg asusu |
| 781 | 1528 | cscsgcAfcCfCfGfggcaaaagca | 2134 | usGfscuuUfuGfCfccggGfuGfcg gsusu |
| 782 | 1529 | csgscaCfcCfGfGfgcaaaagcca | 2135 | usGfsgcuUfuUfGfcccgGfgUfgc gsusu |
| 788 | 1530 | csgsggCfaAfAfAfgccgggagga | 2136 | usCfscucCfcGfGfcuuuUfgCfcc gsusu |
| 789 | 1531 | gsgsgcAfaAfAfGfccgggaggaa | 2137 | usUfsccuCfcCfGfgcuuUfuGfcc csusu |
| 790 | 1532 | gsgscaAfaAfGfCfcgggaggaca | 2138 | usGfsuccUfcCfCfggcuUfuUfgc csusu |
| 791 | 1533 | gscsaaAfaGfCfCfgggaggacca | 2139 | usGfsgucCfuCfCfcggcUfuUfug csusu |
| 840 | 1534 | csusgcGfcGfGfUfggcacagcca | 2140 | usGfsgcuGfuGfCfcaccGfcGfca gsusu |
| 841 | 1535 | usgscgCfgGfUfGfgcacagccua | 2141 | usAfsggcUfgUfGfccacCfgCfgc asusu |
| 851 | 1536 | csascaGfcCfUfGfggcccgcuca | 2142 | usGfsagcGfgGfCfccagGfcUfgu gsusu |
| 852 | 1537 | ascsagCfcUfGfGfgcccgcucaa | 2143 | usUfsgagCfgGfGfcccaGfgCfug ususu |
| 853 | 1538 | csasgcCfuGfGfGfcccgcucaaa | 2144 | usUfsugaGfcGfGfgcccAfgGfcu gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 854 | 1539 | asgsccUfgGfGfCfccgcucaaga | 2145 | usCfsuugAfgCfGfggccCfaGfgc usu su |
| 878 | 1540 | csgscaGfgGfCfCfaaggggugca | 2146 | usGfscacCfcCfUfuggcCfcUfgc gsusu |
| 879 | 1541 | gscsagGfgCfCfAfaggggugcua | 2147 | usAfsgcaCfcCfCfuuggCfcCfug csusu |
| 901 | 1542 | cscsacCfcAfCfGfucccagggga | 2148 | usCfsccccUfgGfGfacguGfgGfug gsusu |
| 902 | 1543 | csasccCfaCfGfUfcccaggggaa | 2149 | usUfsccccCfuGfGfgacgUfgGfgu gsusu |
| 903 | 1544 | ascsccAfcGfUfCfccaggggaga | 2150 | usCfsuccCfcUfGfggacGfuGfgg usu su |
| 911 | 1545 | cscscaGfgGfGfAfguccguggua | 2151 | usAfsccaCfgGfAfcuccCfcUfgg gsusu |
| 912 | 1546 | cscsagGfgGfAfGfuccguggaga | 2152 | usCfsaccAfcGfGfacucCfcCfug gsusu |
| 913 | 1547 | csasggGfgAfGfUfccguggugga | 2153 | usCfscacCfaCfGfgacuCfcCfcu gsusu |
| 914 | 1548 | asgsggGfaGfUfCfcguggugga | 2154 | usCfsccaCfcAfCfggacUfcCfcc usu su |
| 960 | 1549 | gsgscgGfcGfUfGfggaaccccaa | 2155 | usUfsgggGfuUfCfccacGfcCfgc csusu |
| 975 | 1550 | cscsaaGfcCfGfGfggcagcucca | 2156 | usGfsgagCfuGfCfcccgGfcUfug gsusu |
| 976 | 1551 | csasagCfcGfGfGfgcagcuccaa | 2157 | usUfsggaGfcUfGfccccGfgCfuu gsusu |
| 977 | 1552 | asasgcCfgGfGfGfcagcuccaca | 2158 | usGfsuggAfgCfUfgcccCfgGfcu usu su |
| 983 | 1553 | gsgsgcAfgCfUfCfcaccuccccca | 2159 | usGfsgggAfgGfUfggagCfuGfcc csusu |
| 984 | 1554 | gsgscaGfcUfCfCfaccuccccaa | 2160 | usUfsgggGfaGfGfuggaGfcUfgc csusu |
| 985 | 1555 | gscsagCfuCfCfAfccuccccaga | 2161 | usCfsuggGfgAfGfguggAfgCfug csusu |
| 986 | 1556 | csasgcUfcCfAfCfcuccccagca | 2162 | usGfscugGfgGfAfggugGfaGfcu gsusu |
| 1031 | 1557 | csgscgGfcAfGfGfggcagaugca | 2163 | usGfscauCfuGfCfccccuGfcCfgc gsusu |
| 1033 | 1558 | csgsgcAfgGfGfGfcagaugcaaa | 2164 | usUfsugcAfuCfUfgcccCfuGfcc gsusu |
| 1034 | 1559 | gsgscaGfgGfGfCfagaugcaaga | 2165 | usCfsuugCfaUfCfugccCfcUfgc csusu |
| 1035 | 1560 | gscsagGfgGfCfAfgaugcaagga | 2166 | usCfscuuGfcAfUfcugcCfcCfug csusu |
| 1036 | 1561 | csasggGfgCfAfGfaugcaaggca | 2167 | usGfsccuUfgCfAfucugCfcCfcu gsusu |
| 1037 | 1562 | asgsggGfcAfGfAfugcaaggcaa | 2168 | usUfsgccUfuGfCfaucuGfcCfcc usu su |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1046 | 1563 | usgscaAfgGfCfAfucccggcgca | 2169 | usGfscgcCfgGfGfaugcCfuUfgc asusu |
| 1048 | 1564 | csasagGfcAfUfCfccggcgccca | 2170 | usGfsggcGfcCfGfggauGfcCfuu gsusu |
| 1049 | 1565 | asasggCfaUfCfCfcggcgcccua | 2171 | usAfsgggCfgCfCfgggaUfgCfcu ususu |
| 1064 | 1566 | cscsucCfcAfGfGfcgcuccagga | 2172 | usCfscugGfaGfCfgccuGfgGfag gsusu |
| 1086 | 1567 | gsgscgCfcCfUfGfgucugcacua | 2173 | usAfsgugCfaGfAfccagGfgCfgc csusu |
| 1087 | 1568 | gscsgcCfcUfGfGfucugcacuca | 2174 | usGfsaguGfcAfGfaccaGfgGfcg csusu |
| 1088 | 1569 | csgsccCfuGfGfUfcugcacucca | 2175 | usGfsgagUfgCfAfgaccAfgGfgc gsusu |
| 1089 | 1570 | gscsccUfgGfUfCfugcacuccca | 2176 | usGfsggaGfuGfCfagacCfaGfgg csusu |
| 1090 | 1571 | cscscuGfgUfCfUfgcacucccca | 2177 | usGfsgggAfgUfGfcagaCfcAfgg gsusu |
| 1091 | 1572 | cscsugGfuCfUfGfcacuccccua | 2178 | usAfsgggGfaGfUfgcagAfcCfag gsusu |
| 1092 | 1573 | csusggUfcUfGfCfacuccccuga | 2179 | usCfsaggGfgAfGfugcaGfaCfca gsusu |
| 1093 | 1574 | usgsguCfuGfCfAfcuccccugca | 2180 | usGfscagGfgGfAfgugcAfgAfcc asusu |
| 1094 | 1575 | gsgsucUfgCfAfCfuccccugcga | 2181 | usCfsgcaGfgGfGfagugCfaGfac csusu |
| 1095 | 1576 | gsuscuGfcAfCfUfccccugcgga | 2182 | usCfscgcAfgGfGfgaguGfcAfga csusu |
| 1096 | 1577 | uscsugCfaCfUfCfcccugcggca | 2183 | usGfsccgCfaGfGfggagUfgCfag asusu |
| 1097 | 1578 | csusgcAfcUfCfCfccugcggcca | 2184 | usGfsgccGfcAfGfgggaGfuGfca gsusu |
| 1098 | 1579 | usgscaCfuCfCfCfcugcggccua | 2185 | usAfsggcCfgCfAfggggAfgUfgc asusu |
| 1100 | 1580 | csascuCfcCfCfUfgcggccugca | 2186 | usGfscagGfcCfGfcaggGfgAfgu gsusu |
| 1101 | 1581 | ascsucCfcCfUfGfcggccugcua | 2187 | usAfsgcaGfgCfCfgcagGfgGfag ususu |
| 1103 | 1582 | uscsccCfuGfCfGfgccugcugca | 2188 | usGfscagCfaGfGfccgcAfgGfgg asusu |
| 1106 | 1583 | cscsugCfgGfCfCfugcugcugga | 2189 | usCfscagCfaGfCfaggcCfgCfag gsusu |
| 1107 | 1584 | csusgcGfgCfCfUfgcugcuggaa | 2190 | usUfsccaGfcAfGfcaggCfcGfca gsusu |
| 1108 | 1585 | usgscgGfcCfUfGfcugcuggaua | 2191 | usAfsuccAfgCfAfgcagGfcCfgc asusu |
| 1109 | 1586 | gscsggCfcUfGfCfugcuggauga | 2192 | usCfsaucCfaGfCfagcaGfgCfcg csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1110 | 1587 | csgsgcCfuGfCfUfgcuggaugaa | 2193 | usUfscauCfcAfGfcagcAfgGfcc gsusu |
| 1111 | 1588 | gsgsccUfgCfUfGfcuggaugaga | 2194 | usCfsucaUfcCfAfgcagCfaGfgc csusu |
| 1112 | 1589 | gscscuGfcUfGfCfuggaugagca | 2195 | usGfscucAfuCfCfagcaGfcAfgg csusu |
| 1113 | 1590 | cscsugCfuGfCfUfggaugagcua | 2196 | usAfsgcuCfaUfCfcagcAfgCfag gsusu |
| 1114 | 1591 | csusgcUfgCfUfGfgaugagcuca | 2197 | usGfsagcUfcAfUfccagCfaGfca gsusu |
| 1115 | 1592 | usgscuGfcUfGfGfaugagcucca | 2198 | usGfsgagCfuCfAfuccaGfcAfgc asusu |
| 1116 | 1593 | gscsugCfuGfGfAfugagcuccua | 2199 | usAfsggaGfcUfCfauccAfgCfag csusu |
| 1117 | 1594 | csusgcUfgGfAfUfgagcuccuga | 2200 | usCfsaggAfgCfUfcaucCfaGfca gsusu |
| 1118 | 1595 | usgscuGfgAfUfGfagcuccugga | 2201 | usCfscagGfaGfCfucauCfcAfgc asusu |
| 1119 | 1596 | gscsugGfaUfGfAfgcuccuggca | 2202 | usGfsccaGfgAfGfcucaUfcCfag csusu |
| 1130 | 1597 | uscscuGfgCfGfAfgcccggagua | 2203 | usAfscucCfgGfGfcucgCfcAfgg asusu |
| 1131 | 1598 | cscsugGfcGfAfGfcccggaguua | 2204 | usAfsacuCfcGfGfgcucGfcCfag gsusu |
| 1132 | 1599 | csusggCfgAfGfCfccggaguuua | 2205 | usAfsaacUfcCfGfggcuCfgCfca gsusu |
| 1137 | 1600 | gsasgcCfcGfGfAfguuucugcaa | 2206 | usUfsgcaGfaAfAfcuccGfgGfcu csusu |
| 1138 | 1601 | asgsccCfgGfAfGfuuucugcaga | 2207 | usCfsugcAfgAfAfacucCfgGfgc ususu |
| 1139 | 1602 | gscsccGfgAfGfUfuucugcagca | 2208 | usGfscugCfaGfAfaacuCfcGfgg csusu |
| 1140 | 1603 | cscscgGfaGfUfUfucugcagcaa | 2209 | usUfsgcuGfcAfGfaaacUfcCfgg gsusu |
| 1141 | 1604 | cscsggAfgUfUfUfcugcagcaga | 2210 | usCfsugcUfgCfAfgaaaCfuCfcg gsusu |
| 1142 | 1605 | csgsgaGfuUfUfCfugcagcagga | 2211 | usCfscugCfuGfCfagaaAfcUfcc gsusu |
| 1143 | 1606 | gsgsagUfuUfCfUfgcagcaggca | 2212 | usGfsccuGfcUfGfcagaAfaCfuc csusu |
| 1144 | 1607 | gsasguUfuCfUfGfcagcaggcga | 2213 | usCfsgccUfgCfUfgcagAfaAfcu csusu |
| 1145 | 1608 | asgsuuUfcUfGfCfagcaggcgca | 2214 | usGfscgcCfuGfCfugcaGfaAfac ususu |
| 1146 | 1609 | gsusuuCfuGfCfAfgcaggcgcaa | 2215 | usUfsgcgCfcUfGfcugcAfgAfaa csusu |
| 1147 | 1610 | ususucUfgCfAfGfcaggcgcaaa | 2216 | usUfsugcGfcCfUfgcugCfaGfaa asusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1148 | 1611 | ususcuGfcAfGfCfaggcgcaaca | 2217 | usGfsuugCfgCfCfugcuGfcAfgaasusu |
| 1149 | 1612 | uscsugCfaGfCfAfggcgcaacca | 2218 | usGfsguuGfcGfCfcugcUfgCfagasusu |
| 1150 | 1613 | csusgcAfgCfAfGfgcgcaaccua | 2219 | usAfsgguUfgCfGfccugCfuGfcagsusu |
| 1151 | 1614 | usgscaGfcAfGfGfcgcaaccuca | 2220 | usGfsaggUfuGfCfgccuGfcUfgcasusu |
| 1152 | 1615 | gscsagCfaGfGfCfgcaaccucua | 2221 | usAfsgagGfuUfGfcgccUfgCfugcsusu |
| 1153 | 1616 | csasgcAfgGfCfGfcaaccucuca | 2222 | usGfsagaGfgUfUfgcgcCfuGfcugsusu |
| 1154 | 1617 | asgscaGfgCfGfCfaaccucucca | 2223 | usGfsgagAfgGfUfugcgCfcUfgcusus u |
| 1155 | 1618 | gscsagGfcGfCfAfaccucuccua | 2224 | usAfsggaGfaGfGfuugcGfcCfugcsusu |
| 1156 | 1619 | csasggCfgCfAfAfccucuccuaa | 2225 | usUfsaggAfgAfGfguugCfgCfcugsusu |
| 1157 | 1620 | asgsgcGfcAfAfCfcucuccuaga | 2226 | usCfsuagGfaGfAfgguuGfcGfccusus u |
| 1158 | 1621 | gsgscgCfaAfCfCfucuccuagaa | 2227 | usUfscuaGfgAfGfagguUfgCfgccsusu |
| 1159 | 1622 | gscsgcAfaCfCfUfcuccuagaaa | 2228 | usUfsucuAfgGfAfgaggUfuGfcgcsusu |
| 1160 | 1623 | csgscaAfcCfUfCfuccuagaaaa | 2229 | usUfsuucUfaGfGfagagGfuUfgcgsusu |
| 1161 | 1624 | gscsaaCfcUfCfUfccuagaaaca | 2230 | usGfsuuuCfuAfGfgagaGfgUfugcsusu |
| 1162 | 1625 | csasacCfuCfUfCfcuagaaacga | 2231 | usCfsguuUfcUfAfggagAfgGfuugsusu |
| 1163 | 1626 | asasccUfcUfCfCfuagaaacgga | 2232 | usCfscguUfuCfUfaggaGfaGfguusus u |
| 1169 | 1627 | uscscuAfgAfAfAfcggaggccca | 2233 | usGfsggcCfuCfCfguuuCfuAfggasusu |
| 1170 | 1628 | cscsuaGfaAfAfCfggaggcccca | 2234 | usGfsgggCfcUfCfcguuUfcUfaggsusu |
| 1171 | 1629 | csusagAfaAfCfGfgaggccccga | 2235 | usCfsgggGfcCfUfccguUfuCfuagsusu |
| 1428 | 1630 | cscsggUfgAfGfAfgacuccacua | 2236 | usAfsgugGfaGfUfcucuCfaCfcggsusu |
| 1429 | 1631 | csgsguGfaGfAfGfacuccacuca | 2237 | usGfsaguGfgAfGfucucUfcAfccgsusu |
| 1430 | 1632 | gsgsugAfgAfGfAfcuccacucca | 2238 | usGfsgagUfgGfAfgucuCfuCfaccsusu |
| 1570 | 1633 | cscscuUfgUfUfCfuuccgugaaa | 2239 | usUfsucaCfgGfAfagaaCfaAfgggsusu |
| 1571 | 1634 | cscsuuGfuUfCfUfuccgugaaaa | 2240 | usUfsuucAfcGfGfaagaAfcAfaggsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1572 | 1635 | csusugUfuCfUfUfccgugaaaua | 2241 | usAfsuuuCfaCfGfgaagAfaCfaagsusu |
| 1573 | 1636 | ususguUfcUfUfCfcgugaaauua | 2242 | usAfsauuUfcAfCfggaaGfaAfcaasusu |
| 1574 | 1637 | usgsuuCfuUfCfCfgugaaauuca | 2243 | usGfsaauUfuCfAfcggaAfgAfacasusu |
| 1575 | 1638 | gsusucUfuCfCfGfugaaauucua | 2244 | usAfsgaaUfuUfCfacggAfaGfaacsusu |
| 1576 | 1639 | ususcuUfcCfGfUfgaaauucuga | 2245 | usCfsagaAfuUfUfcacgGfaAfgaasusu |
| 1577 | 1640 | uscsuuCfcGfUfGfaaauucugga | 2246 | usCfscagAfaUfUfucacGfgAfagasusu |
| 1578 | 1641 | csusucCfgUfGfAfaauucuggca | 2247 | usGfsccaGfaAfUfuucaCfgGfaagsusu |
| 1589 | 1642 | ususcuGfgCfUfGfaaugucucca | 2248 | usGfsgagAfcAfUfucagCfcAfgaasusu |
| 1590 | 1643 | uscsugGfcUfGfAfaugucuccca | 2249 | usGfsggaGfaCfAfuucaGfcCfagasusu |
| 1618 | 1644 | gsascgCfuGfUfCfuaggcaaaca | 2250 | usGfsuuuGfcCfUfagacAfgCfgucsusu |
| 1619 | 1645 | ascsgcUfgUfCfUfaggcaaacca | 2251 | usGfsguuUfgCfCfuagaCfaGfcgususu |
| 1620 | 1646 | csgscuGfuCfUfAfggcaaaccua | 2252 | usAfsgguUfuGfCfcuagAfcAfgcgsusu |
| 1621 | 1647 | gscsugUfcUfAfGfgcaaaccuga | 2253 | usCfsaggUfuUfGfccuaGfaCfagcsusu |
| 1622 | 1648 | csusguCfuAfGfGfcaaaccugga | 2254 | usCfscagGfuUfUfgccuAfgAfcagsusu |
| 1623 | 1649 | usgsucUfaGfGfCfaaaccuggaa | 2255 | usUfsccaGfgUfUfugccUfaGfacasusu |
| 1624 | 1650 | gsuscuAfgGfCfAfaaccuggaua | 2256 | usAfsuccAfgGfUfuugcCfuAfgacsusu |
| 1625 | 1651 | uscsuaGfgCfAfAfaccuggauua | 2257 | usAfsaucCfaGfGfuuugCfcUfagasusu |
| 1626 | 1652 | csusagGfcAfAfAfccuggauuaa | 2258 | usUfsaauCfcAfGfguuuGfcCfuagsusu |
| 1627 | 1653 | usasggCfaAfAfCfcuggauuaga | 2259 | usCfsuaaUfcCfAfgguuUfgCfcuasusu |
| 1628 | 1654 | asgsgcAfaAfCfCfuggauuagaa | 2260 | usUfscuaAfuCfCfagguUfuGfccususu |
| 1629 | 1655 | gsgscaAfaCfCfUfggauuagaga | 2261 | usCfsucuAfaUfCfcaggUfuUfgccsusu |
| 1630 | 1656 | gscsaaAfcCfUfGfgauuagagua | 2262 | usAfscucUfaAfUfccagGfuUfugcsusu |
| 1631 | 1657 | csasaaCfcUfGfGfauuagaguua | 2263 | usAfsacuCfuAfAfuccaGfgUfuugsusu |
| 1632 | 1658 | asasacCfuGfGfAfuuagaguuaa | 2264 | usUfsaacUfcUfAfauccAfgGfuuususu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1633 | 1659 | asasccUfgGfAfUfuagaguuaca | 2265 | usGfsuaaCfuCfUfaaucCfaGfgu ususu |
| 1634 | 1660 | ascscuGfgAfUfUfagaguuacaa | 2266 | usUfsguaAfcUfCfuaauCfcAfgg ususu |
| 1635 | 1661 | cscsugGfaUfUfAfgaguuacaua | 2267 | usAfsuguAfaCfUfcuaaUfcCfag gsusu |
| 1636 | 1662 | csusggAfuUfAfGfaguuacauca | 2268 | usGfsaugUfaAfCfucuaAfuCfca gsusu |
| 1637 | 1663 | usgsgaUfuAfGfAfguuacaucua | 2269 | usAfsgauGfuAfAfcucuAfaUfcc asusu |
| 1638 | 1664 | gsgsauUfaGfAfGfuuacaucuca | 2270 | usGfsagaUfgUfAfacucUfaAfuc csusu |
| 1639 | 1665 | gsasuuAfgAfGfUfuacaucucca | 2271 | usGfsgagAfuGfUfaacuCfuAfau csusu |
| 1640 | 1666 | asusuaGfaGfUfUfacaucuccua | 2272 | usAfsggaGfaUfGfuaacUfcUfaa ususu |
| 1641 | 1667 | ususagAfgUfUfAfcaucuccuga | 2273 | usCfsaggAfgAfUfguaaCfuCfua asusu |
| 1642 | 1668 | usasgaGfuUfAfCfaucuccugga | 2274 | usCfscagGfaGfAfuguaAfcUfcu asusu |
| 1643 | 1669 | asgsagUfuAfCfAfucuccuggaa | 2275 | usUfsccaGfgAfGfauguAfaCfuc ususu |
| 1651 | 1670 | asuscuCfcUfGfGfaugauuagua | 2276 | usAfscuaAfuCfAfuccaGfgAfga ususu |
| 1652 | 1671 | uscsucCfuGfGfAfugauuaguua | 2277 | usAfsacuAfaUfCfauccAfgGfag asusu |
| 1653 | 1672 | csusccUfgGfAfUfgauuaguuca | 2278 | usGfsaacUfaAfUfcaucCfaGfga gsusu |
| 1654 | 1673 | uscscuGfgAfUfGfauuaguucaa | 2279 | usUfsgaaCfuAfAfucauCfcAfgg asusu |
| 1655 | 1674 | cscsugGfaUfGfAfuuaguucaga | 2280 | usCfsugaAfcUfAfaucaUfcCfag gsusu |
| 1656 | 1675 | csusggAfuGfAfUfuaguucagaa | 2281 | usUfscugAfaCfUfaaucAfuCfca gsusu |
| 26 | 1676 | gscsacCfcUfCfCfccgcggaaga | 2282 | usCfsuucCfgCfGfgggaGfgGfug csusu |
| 27 | 1677 | csasccCfuCfCfCfcgcggaagca | 2283 | usGfscuuCfcGfCfggggAfgGfgu gsusu |
| 28 | 1678 | ascsccUfcCfCfCfgcggaagcca | 2284 | usGfsgcuUfcCfGfcgggGfaGfgg ususu |
| 30 | 1679 | cscsucCfcCfGfCfggaagcccga | 2285 | usCfsgggCfuUfCfcgcgGfgGfag gsusu |
| 35 | 1680 | cscsgcGfgAfAfGfcccggggaca | 2286 | usGfsuccCfcGfGfgcuuCfcGfcg gsusu |
| 37 | 1681 | gscsggAfaGfCfCfcggggacgaa | 2287 | usUfscguCfcCfCfgggcUfuCfcg csusu |
| 38 | 1682 | csgsgaAfgCfCfCfggggacgaga | 2288 | usCfsucgUfcCfCfcgggCfuUfcc gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 193 | 1683 | asusuuGfgUfUfUfcagaaugaga | 2289 | usCfsucaUfuCfUfgaaaCfcAfaa ususu |
| 233 | 1684 | ascscgGfcGfGfGfaaucucggca | 2290 | usGfsccgAfgAfUfucccGfcCfgg ususu |
| 250 | 1685 | cscscuGfgCfCfCfgggagacgca | 2291 | usGfscguCfuCfCfcgggCfcAfgg gsusu |
| 251 | 1686 | cscsugGfcCfCfGfggagacgcga | 2292 | usCfsgcgUfcUfCfccggGfcCfag gsusu |
| 252 | 1687 | csusggCfcCfGfGfgagacgcgga | 2293 | usCfscgcGfuCfUfcccgGfgCfca gsusu |
| 263 | 1688 | gsascgCfgGfCfCfcgccagaaga | 2294 | usCfsuucUfgGfCfgggcCfgCfgu csusu |
| 264 | 1689 | ascsgcGfgCfCfCfgccagaagga | 2295 | usCfscuuCfuGfGfcgggCfcGfcg ususu |
| 279 | 1690 | asgsgcCfgGfCfGfaaagcggaca | 2296 | usGfsuccGfcUfUfucgcCfgGfcc ususu |
| 280 | 1691 | gsgsccGfgCfGfAfaagcggacca | 2297 | usGfsgucCfgCfUfuucgCfcGfgc csusu |
| 281 | 1692 | gscscgGfcGfAfAfagcggaccga | 2298 | usCfsgguCfcGfCfuuucGfcCfgg csusu |
| 317 | 1693 | cscsgcCfcUfGfCfuccuccgaga | 2299 | usCfsucgGfaGfGfagcaGfgGfcg gsusu |
| 355 | 1694 | cscsagGfcAfUfCfgccgcccgga | 2300 | usCfscggGfcGfGfcgauGfcCfug gsusu |
| 359 | 1695 | gscsauCfgCfCfGfcccgggagga | 2301 | usCfscucCfcGfGfgcggCfgAfug csusu |
| 360 | 1696 | csasucGfcCfGfCfccgggaggaa | 2302 | usUfsccuCfcCfGfggcgGfcGfau gsusu |
| 361 | 1697 | asuscgCfcGfCfCfcgggaggaga | 2303 | usCfsuccUfcCfCfgggcGfgCfga ususu |
| 362 | 1698 | uscsgcCfgCfCfCfgggaggagca | 2304 | usGfscucCfuCfCfcgggCfgGfcg asusu |
| 363 | 1699 | csgsccGfcCfCfGfggaggagcua | 2305 | usAfsgcuCfcUfCfccggGfcGfgc gsusu |
| 437 | 1700 | gsgsgcCfaGfGfCfacccgggaca | 2306 | usGfsuccCfgGfGfugccUfgGfcc csusu |
| 452 | 1701 | gsascaGfgGfUfGfgcagggcgca | 2307 | usGfscgcCfcUfGfccacCfcUfgu csusu |
| 453 | 1702 | ascsagGfgUfGfGfcagggcgcca | 2308 | usGfsgcgCfcCfUfgccaCfcCfug ususu |
| 455 | 1703 | asgsggUfgGfCfAfgggcgcccga | 2309 | usCfsgggCfgCfCfcugcCfaCfcc ususu |
| 456 | 1704 | gsgsguGfgCfAfGfggcgcccgca | 2310 | usGfscggGfcGfCfccugCfcAfcc csusu |
| 458 | 1705 | gsusggCfaGfGfGfcgcccgcgca | 2311 | usGfscgcGfgGfCfgcccUfgCfca csusu |
| 480 | 1706 | asgsgcGfgCfCfUfgugcagcgca | 2312 | usGfscgcUfgCfAfcaggCfcGfcc ususu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 481 | 1707 | gsgscgGfcCfUfGfugcagcgcga | 2313 | usCfsgcgCfuGfCfacagGfcCfgccsusu |
| 482 | 1708 | gscsggCfcUfGfUfgcagcgcgga | 2314 | usCfscgcGfcUfGfcacaGfgCfcgcsusu |
| 534 | 1709 | csgsccUfuCfGfCfccacaccgga | 2315 | usCfscggUfgUfGfggcgAfaGfgcgsusu |
| 546 | 1710 | csasccGfgCfGfCfguggggaaca | 2316 | usGfsuucCfcCfAfcgcgCfcGfgugsusu |
| 547 | 1711 | ascscgGfcGfCfGfuggggaacga | 2317 | usCfsguuCfcCfCfacgcGfcCfggususu |
| 548 | 1712 | cscsggCfgCfGfUfggggaacgga | 2318 | usCfscguUfcCfCfcacgCfgCfcggsusu |
| 549 | 1713 | csgsgcGfcGfUfGfgggaacggga | 2319 | usCfsccgUfuCfCfccacGfcGfccgsusu |
| 551 | 1714 | gscsgcGfuGfGfGfgaacggggca | 2320 | usGfscccCfgUfUfccccAfcGfcgcsusu |
| 565 | 1715 | gsgsgcUfuCfCfCfgcaccccaca | 2321 | usGfsuggGfgUfGfcgggAfaGfcccsusu |
| 575 | 1716 | csasccCfcAfCfGfugcccugcga | 2322 | usCfsgcaGfgGfCfacguGfgGfgugsusu |
| 577 | 1717 | cscsccAfcGfUfGfcccugcgcga | 2323 | usCfsgcgCfaGfGfgcacGfuGfgggsusu |
| 579 | 1718 | cscsacGfuGfCfCfcugcgcgcca | 2324 | usGfsgcgCfgCfAfgggcAfcGfuggsusu |
| 581 | 1719 | ascsguGfcCfCfUfgcgcgccuga | 2325 | usCfsaggCfgCfGfcaggGfcAfcgususu |
| 588 | 1720 | csusgcGfcGfCfCfuggggcucua | 2326 | usAfsgagCfcCfCfaggcGfcGfcagsusu |
| 616 | 1721 | gscsuuUfcGfUfGfagccaggcaa | 2327 | usUfsgccUfgGfCfucacGfaAfagcsusu |
| 617 | 1722 | csusuuCfgUfGfAfgccaggcaga | 2328 | usCfsugcCfuGfGfcucaCfgAfaagsusu |
| 618 | 1723 | ususucGfuGfAfGfccaggcagca | 2329 | usGfscugCfcUfGfgcucAfcGfaaasusu |
| 627 | 1724 | cscsagGfcAfGfCfgagggccgca | 2330 | usGfscggCfcCfUfcgcuGfcCfuggsusu |
| 652 | 1725 | csusgcAfgCfCfCfagccaggcca | 2331 | usGfsgccUfgGfCfugggCfuGfcagsusu |
| 654 | 1726 | gscsagCfcCfAfGfccaggccgca | 2332 | usGfscggCfcUfGfgcugGfgCfugcsusu |
| 659 | 1727 | cscsagCfcAfGfGfccgcgccgga | 2333 | usCfscggCfgCfGfgccuGfgCfuggsusu |
| 668 | 1728 | cscsgcGfcCfGfGfcagaggggaa | 2334 | usUfsccccCfuCfUfgccgGfcGfcggsusu |
| 690 | 1729 | cscsaaCfcUfGfCfcccggcgcga | 2335 | usCfsgcgCfcGfGfggcaGfgUfuggsusu |
| 692 | 1730 | asasccUfgCfCfCfcggcgcgcga | 2336 | usCfsgcgCfgCfCfggggCfaGfguususu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 705 | 1731 | gscsgcGfgGfGfAfuuucgccuaa | 2337 | usUfsaggCfgAfAfauccCfcGfcg csusu |
| 715 | 1732 | ususcgCfcUfAfCfgccgccccga | 2338 | usCfsgggGfcGfGfcguaGfgCfga asusu |
| 717 | 1733 | csgsccUfaCfGfCfcgccccggca | 2339 | usGfsccgGfgGfCfggcgUfaGfgc gsusu |
| 732 | 1734 | gsgscuCfcUfCfCfggacggggca | 2340 | usGfscccCfgUfCfcggaGfgAfgc csusu |
| 733 | 1735 | gscsucCfuCfCfGfgacggggcga | 2341 | usCfsgccCfcGfUfccggAfgGfag csusu |
| 745 | 1736 | gsgsggCfgCfUfCfucccacccua | 2342 | usAfsgggUfgGfGfagagCfgCfcc csusu |
| 802 | 1737 | gsasggAfcCfGfGfgacccgcaga | 2343 | usCfsugcGfgGfUfcccgGfuCfcu csusu |
| 809 | 1738 | gsgsgaCfcCfGfCfagcgcgacga | 2344 | usCfsgucGfcGfCfugcgGfgUfcc csusu |
| 813 | 1739 | cscscgCfaGfCfGfcgacggccua | 2345 | usAfsggcCfgUfCfgcgcUfgCfgg gsusu |
| 827 | 1740 | gscscuGfcCfGfGfgccccugcga | 2346 | usCfsgcaGfgGfGfcccgGfcAfgg csusu |
| 839 | 1741 | cscsugCfgCfGfGfuggcacagca | 2347 | usGfscugUfgCfCfaccgCfgCfag gsusu |
| 842 | 1742 | gscsgcGfgUfGfGfcacagccuga | 2348 | usCfsaggCfuGfUfgccaCfcGfcg csusu |
| 843 | 1743 | csgscgGfuGfGfCfacagccugga | 2349 | usCfscagGfcUfGfugccAfcCfgc gsusu |
| 845 | 1744 | csgsguGfgCfAfCfagccugggca | 2350 | usGfscccAfgGfCfugugCfcAfcc gsusu |
| 850 | 1745 | gscsacAfgCfCfUfgggcccgcua | 2351 | usAfsgcgGfgCfCfcaggCfuGfug csusu |
| 856 | 1746 | cscsugGfgCfCfCfgcucaagcga | 2352 | usCfsgcuUfgAfGfcgggCfcCfag gsusu |
| 877 | 1747 | cscsgcAfgGfGfCfcaaggggua | 2353 | usCfsaccCfcUfUfggccCfuGfcg gsusu |
| 892 | 1748 | gsusgcUfuGfCfGfccacccacga | 2354 | usCfsgugGfgUfGfgcgcAfaGfca csusu |
| 893 | 1749 | usgscuUfgCfGfCfcacccacgua | 2355 | usAfscguGfgGfUfggcgCfaAfgc asusu |
| 894 | 1750 | gscsuuGfcGfCfCfacccacguca | 2356 | usGfsacgUfgGfGfuggcGfcAfag csusu |
| 895 | 1751 | csusugCfgCfCfAfcccacgucca | 2357 | usGfsgacGfuGfGfguggCfgCfaa gsusu |
| 897 | 1752 | usgscgCfcAfCfCfcacgucccaa | 2358 | usUfsgggAfcGfUfggguGfgCfgc asusu |
| 919 | 1753 | asgsucCfgUfGfGfuggggcugga | 2359 | usCfscagCfcCfCfaccaCfgGfac ususu |
| 936 | 1754 | gsgsgcCfgGfGfGfuccccaggua | 2360 | usAfsccuGfgGfGfacccCfgGfcc csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 939 | 1755 | cscsggGfgUfCfCfccaggucgca | 2361 | usGfscgaCfcUfGfgggaCfcCfcg gsusu |
| 956 | 1756 | cscsggGfgCfGfGfcgugggaaca | 2362 | usGfsuucCfcAfCfgccgCfcCfcg gsusu |
| 989 | 1757 | csusccAfcCfUfCfcccagcccga | 2363 | usCfsgggCfuGfGfggagGfuGfga gsusu |
| 992 | 1758 | csasccUfcCfCfCfagcccgcgca | 2364 | usGfscgcGfgGfCfugggGfaGfgu gsusu |
| 994 | 1759 | cscsucCfcCfAfGfcccgcgccca | 2365 | usGfsggcGfcGfGfgcugGfgGfag gsusu |
| 1023 | 1760 | csgsccUfcCfGfCfgcggcaggga | 2366 | usCfsccuGfcCfGfcgcgGfaGfgc gsusu |
| 1028 | 1761 | cscsgcGfcGfGfCfaggggcagaa | 2367 | usUfscugCfcCfCfugccGfcGfcg gsusu |
| 1030 | 1762 | gscsgcGfgCfAfGfgggcagauga | 2368 | usCfsaucUfgCfCfccugCfcGfcg csusu |
| 1067 | 1763 | cscscaGfgCfGfCfuccaggagca | 2369 | usGfscucCfuGfGfagcgCfcUfgg gsusu |
| 1081 | 1764 | gsasgcCfgGfCfGfcccuggucua | 2370 | usAfsgacCfaGfGfgcgcCfgGfcu csusu |
| 1083 | 1765 | gscscgGfcGfCfCfcuggucugca | 2371 | usGfscagAfcCfAfgggcGfcCfgg csusu |
| 1084 | 1766 | cscsggCfgCfCfCfuggucugcaa | 2372 | usUfsgcaGfaCfCfagggCfgCfcg gsusu |
| 1085 | 1767 | csgsgcGfcCfCfUfggucugcaca | 2373 | usGfsugcAfgAfCfcaggGfcGfcc gsusu |
| 1102 | 1768 | csusccCfcUfGfCfggccugcuga | 2374 | usCfsagcAfgGfCfcgcaGfgGfga gsusu |
| 1120 | 1769 | csusggAfuGfAfGfcuccuggcga | 2375 | usCfsgccAfgGfAfgcucAfuCfca gsusu |
| 1189 | 1770 | gsgsggAfgCfUfGfgaggccucga | 2376 | usCfsgagGfcCfUfccagCfuCfcc csusu |
| 1192 | 1771 | gsasgcUfgGfAfGfgccucggaaa | 2377 | usUfsuccGfaGfGfccucCfaGfcu csusu |
| 1193 | 1772 | asgscuGfgAfGfGfccucggaaga | 2378 | usCfsuucCfgAfGfgccuCfcAfgc ususu |
| 1194 | 1773 | gscsugGfaGfGfCfcucggaagaa | 2379 | usUfscuuCfcGfAfggccUfcCfag csusu |
| 1212 | 1774 | gsgsccGfcCfUfCfgcuggaagca | 2380 | usGfscuuCfcAfGfcgagGfcGfgc csusu |
| 1213 | 1775 | gscscgCfcUfCfGfcuggaagcaa | 2381 | usUfsgcuUfcCfAfgcgaGfgCfgg csusu |
| 1214 | 1776 | cscsgcCfuCfGfCfuggaagcaca | 2382 | usGfsugcUfuCfCfagcgAfgGfcg gsusu |
| 1215 | 1777 | csgsccUfcGfCfUfggaagcacca | 2383 | usGfsgugCfuUfCfcagcGfaGfgc gsusu |
| 1216 | 1778 | gscscuCfgCfUfGfgaagcaccca | 2384 | usGfsgguGfcUfUfccagCfgAfgg csusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1218 | 1779 | csuscgCfuGfGfAfagcaccccua | 2385 | usAfsgggGfuGfCfuuccAfgCfga gsusu |
| 1234 | 1780 | csuscaGfcGfAfGfgaagaauaca | 2386 | usGfsuauUfcUfUfccucGfcUfga gsusu |
| 1235 | 1781 | uscsagCfgAfGfGfaagaauacca | 2387 | usGfsguaUfuCfUfuccuCfgCfug asusu |
| 1242 | 1782 | gsgsaaGfaAfUfAfccgggcucua | 2388 | usAfsgagCfcCfGfguauUfcUfuc csusu |
| 1251 | 1783 | cscsggGfcUfCfUfgcuggaggaa | 2389 | usUfsccuCfcAfGfcagaGfcCfcg gsusu |
| 1257 | 1784 | uscsugCfuGfGfAfggagcuuuaa | 2390 | usUfsaaaGfcUfCfcuccAfgCfag asusu |
| 1258 | 1785 | csusgcUfgGfAfGfgagcuuuaga | 2391 | usCfsuaaAfgCfUfccucCfaGfca gsusu |
| 1260 | 1786 | gscsugGfaGfGfAfgcuuuaggaa | 2392 | usUfsccuAfaAfGfcuccUfcCfag csusu |
| 1261 | 1787 | csusggAfgGfAfGfcuuuaggaca | 2393 | usGfsuccUfaAfAfgcucCfuCfca gsusu |
| 1265 | 1788 | asgsgaGfcUfUfUfaggacgcgga | 2394 | usCfscgcGfuCfCfuaaaGfcUfcc ususu |
| 1266 | 1789 | gsgsagCfuUfUfAfggacgcggga | 2395 | usCfsccgCfgUfCfcuaaAfgCfuc csusu |
| 1267 | 1790 | gsasgcUfuUfAfGfgacgcgggga | 2396 | usCfscccGfcGfUfccuaAfaGfcu csusu |
| 1268 | 1791 | asgscuUfuAfGfGfacgcggggua | 2397 | usAfscccCfgCfGfuccuAfaAfgc ususu |
| 1269 | 1792 | gscsuuUfaGfGfAfcgcgggguua | 2398 | usAfsaccCfcGfCfguccUfaAfag csusu |
| 1270 | 1793 | csusuuAfgGfAfCfgcgggguuga | 2399 | usCfsaacCfcCfGfcgucCfuAfaa gsusu |
| 1271 | 1794 | ususuaGfgAfCfGfcgggguugga | 2400 | usCfscaaCfcCfCfgcguCfcUfaa asusu |
| 1272 | 1795 | ususagGfaCfGfCfgggguuggga | 2401 | usCfsccaAfcCfCfcgcgUfcCfua asusu |
| 1274 | 1796 | asgsgaCfgCfGfGfgguugggaca | 2402 | usGfsuccCfaAfCfcccgCfgUfcc ususu |
| 1279 | 1797 | gscsggGfgUfUfGfggacggggua | 2403 | usAfscccCfgUfCfccaaCfcCfcg csusu |
| 1284 | 1798 | gsusugGfgAfCfGfgggucgggua | 2404 | usAfscccGfaCfCfccguCfcCfaa csusu |
| 1288 | 1799 | gsgsacGfgGfGfUfcggguguuua | 2405 | usAfsaccAfcCfCfgaccCfcGfuc csusu |
| 1389 | 1800 | gsgscuGfaCfCfGfgccugggaua | 2406 | usAfsuccCfaGfGfccggUfcAfgc csusu |
| 1390 | 1801 | gscsugAfcCfGfGfccugggauua | 2407 | usAfsaucCfcAfGfgccgGfuCfag csusu |
| 1400 | 1802 | csusggGfaUfUfCfcugccuucua | 2408 | usAfsgaaGfgCfAfggaaUfcCfca gsusu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1401 | 1803 | usgsggAfuUfCfCfugccuucuaa | 2409 | usUfsagaAfgGfCfaggaAfuCfcc asusu |
| 1419 | 1804 | gsgsucUfaGfGfCfccggugagaa | 2410 | usUfscucAfcCfGfggccUfaGfac csusu |
| 1420 | 1805 | gsuscuAfgGfCfCfcggugagaga | 2411 | usCfsucuCfaCfCfgggcCfuAfga csusu |
| 1421 | 1806 | uscsuaGfgCfCfCfggugagagaa | 2412 | usUfscucUfcAfCfcgggCfcUfag asusu |
| 1422 | 1807 | csusagGfcCfCfGfgugagagaca | 2413 | usGfsucuCfuCfAfccggGfcCfua gsusu |
| 1425 | 1808 | gsgsccCfgGfUfGfagagacucca | 2414 | usGfsgagUfcUfCfucacCfgGfgc csusu |
| 1426 | 1809 | gscsccGfgUfGfAfgagacuccaa | 2415 | usUfsggaGfuCfUfcucaCfcGfgg csusu |
| 1427 | 1810 | cscscgGfuGfAfGfagacuccaca | 2416 | usGfsuggAfgUfCfucucAfcCfgg gsusu |
| 1607 | 1811 | cscsccAfcCfUfUfccgacgcuga | 2417 | usCfsagcGfuCfGfgaagGfuGfgg gsusu |
| 1608 | 1812 | cscscaCfcUfUfCfcgacgcugua | 2418 | usAfscagCfgUfCfggaaGfgUfgg gsusu |
| 1612 | 1813 | cscsuuCfcGfAfCfgcugucuaga | 2419 | usCfsuagAfcAfGfcgucGfgAfag gsusu |
| 1613 | 1814 | csusucCfgAfCfGfcugucuagga | 2420 | usCfscuaGfaCfAfgcguCfgGfaa gsusu |
| 1614 | 1815 | ususccGfaCfGfCfugucuaggca | 2421 | usGfsccuAfgAfCfagcgUfcGfga asusu |
| 1615 | 1816 | uscscgAfcGfCfUfgucuaggcaa | 2422 | usUfsgccUfaGfAfcagcGfuCfgg asusu |
| 1616 | 1817 | cscsgaCfgCfUfGfucuaggcaaa | 2423 | usUfsugcCfuAfGfacagCfgUfcg gsusu |
| 1617 | 1818 | csgsacGfcUfGfUfcuaggcaaaa | 2424 | usUfsuugCfcUfAfgacaGfcGfuc gsusu |
| 420 | 2426 | csusGfguuUfCfAfgaAfucgaAf sgsa | 2437 | vpUsCfsuucgauucugaAfaccags usu |
| 1628 | 2427 | asgsGfcaaAfCfCfugGfauuaGf sasa | 2438 | vpUsUfscuaauccagguUfugccus usu |
| 1629 | 2428 | gsgsCfaaaCfCfUfggAfuuagAf sgsa | 2439 | vpUsCfsucuaauccaggUfuugccs usu |
| 1635 | 2429 | cscsUfggaUfUfAfgaGfuuacAf susa | 2440 | vpUsAfsuguaacucuaaUfccaggs usu |
| 1636 | 2430 | csusGfgauUfAfGfagUfuacaUf scsa | 2441 | vpUsGfsauguaacucuaAfuccags usu |
| 1652 | 2431 | uscsUfccuGfGfAfugAfuuagUf susa | 2442 | vpUsAfsacuaaucauccAfggagas usu |
| 1653 | 2432 | csusCfcugGfAfUfgaUfuaguUf scsa | 2443 | vpUsGfsaacuaaucaucCfaggags usu |
| 668 | 2433 | cscsGfcgcCfGfGfcaGfagggGf sasa | 2444 | vpUsUfsccccucugccgGfcgcggs usu |

TABLE 1B-continued provides modified siRNAs comprising modified sense strand and modified antisense strand.

| Position in transcript NM_001306068.3 | SEQ ID NO: | Sense strand | SEQ ID NO: | Antisense strand |
|---|---|---|---|---|
| 1654 | 2434 | uscsCfuggAfUfGfauUfaguuCfaa | 2445 | vpUsUfsgaacuaaucauCfcaggasusu |
| 1655 | 2435 | cscsUfggaUfGfAfuuAfguucAfga | 2446 | vpUsCfsugaacuaaucaUfccaggsusu |
| 1656 | 2436 | csusGfgauGfAfUfuaGfuucaGfaa | 2447 | vpUsUfscugaacuaaucAfuccagsusu |

Column 1 shows the beginning position of the target sequence in DUX4_human_#NM_001306068.3 (SEQ ID NO: 2425).
The target sequence is 19 nucleotide long starting from the beginning position.
For example, row 1 shows that the beginning position of the target sequence is 1, which means that the target sequence is the sequence corresponding to positions 1-19 of DUX4_human_#NM_001306068.3 (SEQ ID NO: 2425).
The sequences of the sense strands and antisense strands are shown from the 5' end to the 3' end.

TABLE 1C provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 11 | 1215 | csgsacAfcCfCfUfcggacagcaa | 1821 | usUfsgcuGfuCfCfgaggGfuGfucgsusu | 69.3 ± 4.6 |
| 13 | 1217 | ascsacCfcUfCfGfgacagcacca | 1823 | usGfsgugCfuGfUfccgaGfgGfugususu | 83.6 ± 4.4 |
| 61 | 1240 | csgsacGfgAfGfAfcucguuugga | 1846 | usCfscaaAfcGfAfgucuCfcGfucgsusu | 86.4 ± 6.3 |
| 67 | 1246 | asgsacUfcGfUfUfuggaccccga | 1852 | usCfsgggGfuCfCfaaacGfaGfucususu | 94.1 ± 6.2 |
| 109 | 1264 | usgscuUfuGfAfGfcggaacccga | 1870 | usCfsgggUfuCfCfgcucAfaAfgcasusu | 110.3 ± 5.2 |
| 115 | 1270 | gsasgcGfgAfAfCfccguacccga | 1876 | usCfsgggUfaCfGfgguuCfcGfcucsusu | 117.3 ± 15.1 |
| 124 | 1272 | cscsguAfcCfCfGfggcaucgcca | 1878 | usGfsgcgAfuGfCfccggGfuAfcggsusu | 76.3 ± 4.6 |
| 125 | 1273 | csgsuaCfcCfGfGfgcaucgccaa | 1879 | usUfsggcGfaUfGfcccgGfgUfacgsusu | 110.6 ± 6.5 |
| 131 | 1278 | csgsggCfaUfCfGfccaccagaga | 1884 | usCfsucuGfgUfGfgcgaUfgCfccgsusu | 80.8 ± 1.4 |
| 133 | 1280 | gsgscaUfcGfCfCfaccagagaaa | 1886 | usUfsucuCfuGfGfuggcGfaUfgccsusu | 80.5 ± 4 |
| 163 | 1297 | gscscaUfcGfGfCfauuccggaga | 1903 | usCfsuccGfgAfAfugccGfaUfggcsusu | 88.3 ± 7.2 |
| 164 | 1298 | cscsauCfgGfCfAfuuccggagca | 1904 | usGfscucCfgGfAfaugcCfgAfuggsusu | 88.5 ± 6.5 |
| 165 | 1299 | csasucGfgCfAfUfuccggagcca | 1905 | usGfsgcuCfcGfGfaaugCfcGfaugsusu | 90.4 ± 7.7 |
| 187 | 1313 | gsusccAfgAfUfUfugguuucaga | 1919 | usCfsugaAfaCfCfaaauCfuGfgacsusu | 60.3 ± 3.3 |
| 188 | 1314 | uscscaGfaUfUfUfgguuucagaa | 1920 | usUfscugAfaAfCfcaaaUfcUfggasusu | 73.4 ± 3.6 |
| 203 | 1327 | asgsaaUfgAfGfAfggucacgcca | 1933 | usGfsgcgUfgAfCfcucuCfaUfucususu | 127.4 ± 3.8 |

TABLE 1C-continued provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 204 | 1328 | gsasauGfaGfAfGfgucacgccaa | 1934 | usUfsggcGfuGfAfccucUfcAfuucsusu | 123.9 ± 10.8 |
| 277 | 1362 | gsasagGfcCfGfGfcgaaagcgga | 1968 | usCfscgcUfuUfCfgccgGfcCfuucsusu | 116.9 ± 9.2 |
| 292 | 1369 | csgsgaCfcGfCfCfgucaccggaa | 1975 | usUfsccgGfuGfAfcggcGfgUfccgsusu | 79.9 ± 36.3 |
| 299 | 1376 | cscsguCfaCfCfGfgaucccagaa | 1982 | usUfscugGfgAfUfccggUfgAfcggsusu | 118.8 ± 4.7 |
| 300 | 1377 | csgsucAfcCfGfGfaucccagaca | 1983 | usGfsucuGfgGfAfuccgGfuGfacgsusu | 108.1 ± 8.1 |
| 301 | 1378 | gsuscaCfcGfGfAfuccca gacca | 1984 | usGfsgucUfgGfGfauccGfgUfgacsusu | 81.3 ± 13.7 |
| 307 | 1384 | gsgsauCfcCfAfGfaccgcccuga | 1990 | usCfsaggGfcGfGfucugGfgAfuccsusu | 97.8 ± 13.6 |
| 315 | 1392 | gsasccGfcCfCfUfgcuccuccga | 1998 | usCfsggaGfgAfGfcaggGfcGfgucsusu | 108.8 ± 7.9 |
| 316 | 1393 | ascscgCfcCfUfGfcuccuccgaa | 1999 | usUfscggAfgGfAfgcagGfgCfggusus u | 104.7 ± 10 |
| 339 | 1399 | usgsagAfaGfGfAfucgcuuucca | 2005 | usGfsgaaAfgCfGfauccUfuCfucasusu | 60.6 ± 0.7 |
| 347 | 1407 | asuscgCfuUfUfCfcaggcaucga | 2013 | usCfsgauGfcCfUfggaaAfgCfgausus u | 103.4 ± 5.1 |
| 348 | 1408 | uscsgcUfuUfCfCfaggcaucgca | 2014 | usGfscgaUfgCfCfuggaAfaGfcgasusu | 75.9 ± 1.9 |
| 349 | 1409 | csgscuUfuCfCfAfggcaucgcca | 2015 | usGfsgcgAfuGfCfcuggAfaAfgcgsusu | 69.7 ± 7.3 |
| 404 | 1438 | asgsucCfaGfGfAfuucagaucua | 2044 | usAfsgauCfuGfAfauccUfgGfacusus u | 23.5 ± 7.3 |
| 412 | 1443 | asusucAfgAfUfCfugguuucaga | 2049 | usCfsugaAfaCfCfagauCfuGfaausus u | 22.1 ± 3.9 |
| 420 | 1444 | csusggUfuUfCfAfgaaucgaaga | 2050 | usCfsuucGfaUfUfcugaAfaCfcagsusu | 56.4 ± 10.9 |
| 532 | 1476 | gsuscgCfcUfUfCfgcccacacca | 2082 | usGfsgugUfgGfGfcgaaGfgCfgacsusu | 96.9 ± 3.5 |
| 533 | 1477 | uscsgcCfuUfCfGfcccacaccga | 2083 | usCfsgguGfuGfGfgcgaAfgGfcgasusu | 105 ± 4.7 |
| 619 | 1484 | ususcgUfgAfGfCfcaggcagcga | 2090 | usCfsgcuGfcCfUfggcuCfaCfgaasusu | 112.2 ± 3.4 |
| 620 | 1485 | uscsguGfaGfCfCfaggcagcgaa | 2091 | usUfscgcUfgCfCfuggcUfcAfcgasusu | 96 ± 2 |
| 621 | 1486 | csgsugAfgCfCfAfggcagcgaga | 2092 | usCfsucgCfuGfCfcuggCfuCfacgsusu | 94.4 ± 8.1 |
| 708 | 1499 | csgsggGfaUfUfUfcgccuacgca | 2105 | usGfscguAfgGfCfgaaaUfcCfccgsusu | 82.8 ± 5.8 |
| 747 | 1507 | gsgscgCfuCfUfCfccacccucaa | 2113 | usUfsgagGfgUfGfggagAfgCfgccsusu | 83.1 ± 6.3 |
| 748 | 1508 | gscsgcUfcUfCfCfcacccucaga | 2114 | usCfsugaGfgGfUfgggaGfaGfcgcsusu | 100.9 ± 5.5 |
| 749 | 1509 | csgscuCfuCfCfCfacccucagga | 2115 | usCfscugAfgGfGfugggAfgAfgcgsusu | 105.9 ± 9 |

TABLE 1C-continued provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 779 | 1526 | csusccGfcAfCfCfcgg gcaaaaa | 2132 | usUfsuuuGfcCfCfggguGfc Gfgagsusu | 147.2 ± 4.1 |
| 781 | 1528 | cscsgcAfcCfCfGfggc aaaagca | 2134 | usGfscuuUfuGfCfccggGfu Gfcggsusu | 103.5 ± 6.7 |
| 852 | 1537 | ascsagCfcUfGfGfgcc cgcucaa | 2143 | usUfsgagCfgGfGfcccaGfg Cfugusus u | 110.3 ± 6.8 |
| 1036 | 1561 | csasggGfgCfAfGfaug caaggca | 2167 | usGfsccuUfgCfAfucugCfc Cfcugsusu | 95 ± 4.8 |
| 1100 | 1580 | csascuCfcCfCfUfgcg gccugca | 2186 | usGfscagGfcCfGfcaggGfg Afgugsusu | 68.9 ± 6.8 |
| 1101 | 1581 | ascsucCfcCfUfGfcgg ccugcua | 2187 | usAfsgcaGfgCfCfgcagGfg Gfagusus u | 80.1 ± 7.3 |
| 1107 | 1584 | csusgcGfgCfCfUfgcu gcuggaa | 2190 | usUfsccaGfcAfGfcaggCfc Gfcagsusu | 90.5 ± 5.1 |
| 1109 | 1586 | gscsggCfcUfGfCfugc uggauga | 2192 | usCfsaucCfaGfCfagcaGfg Cfcgcsusu | 79.7 ± 11.1 |
| 1115 | 1592 | usgscuGfcUfGfGfaug agcucca | 2198 | usGfsgagCfuCfAfuccaGfc Afgcasusu | 84.7 ± 7.9 |
| 1131 | 1598 | cscsugGfcGfAfGfccc ggaguua | 2204 | usAfsacuCfcGfGfgcucGfc Cfaggsusu | 77.9 ± 9.6 |
| 1132 | 1599 | csusggCfgAfGfCfccg gaguuua | 2205 | usAfsaacUfcCfGfggcuCfg Cfcagsusu | 56.4 ± 1.7 |
| 1140 | 1603 | cscscgGfaGfUfUfucu gcagcaa | 2209 | usUfsgcuGfcAfGfaaacUfc Cfgggsusu | 116.1 ± 4.3 |
| 1141 | 1604 | cscsggAfgUfUfUfcug cagcaga | 2210 | usCfsugcUfgCfAfgaaaCfu Cfcggsusu | 94.4 ± 2.7 |
| 1147 | 1610 | ususucUfgCfAfGfcag gcgcaaa | 2216 | usUfsugcGfcCfUfgcugCfa Gfaaasusu | 73.3 ± 4.7 |
| 1148 | 1611 | ususcuGfcAfGfCfagg cgcaaca | 2217 | usGfsuugCfgCfCfugcuGfc Afgaasusu | 84 ± 0.8 |
| 1149 | 1612 | uscsugCfaGfCfAfggc gcaacca | 2218 | usGfsguuGfcGfCfcugcUfg Cfagasusu | 48.4 ± 4.3 |
| 1163 | 1626 | asasccUfcUfCfCfuag aaacgga | 2232 | usCfscguUfuCfUfaggaGfa Gfguusus u | 29 ± 4.5 |
| 1171 | 1629 | csusagAfaAfCfGfgag gccccga | 2235 | usCfsgggGfcCfUfccguUfu Cfuagsusu | 68.9 ± 3.7 |
| 1428 | 1630 | cscsggUfgAfGfAfgac uccacua | 2236 | usAfsgugGfaGfUfcucuCfa Cfcggsusu | 68.6 ± 2.6 |
| 1619 | 1645 | ascsgcUfgUfCfUfagg caaacca | 2251 | usGfsguuUfgCfCfuagaCfa Gfcgusus u | 27.8 ± 2.5 |
| 1628 | 1654 | asgsgcAfaAfCfCfugg auuagaa | 2260 | usUfscuaAfuCfCfagguUfu Gfccusus u | 18.1 ± 5.3 |
| 1629 | 1655 | gsgscaAfaCfCfUfgga uuagaga | 2261 | usCfsucuAfaUfCfcaggUfu Ufgccsusu | 18.1 ± 5.3 |
| 1635 | 1661 | cscsugGfaUfUfAfgag uuacaua | 2267 | usAfsuguAfaCfUfcuaaUfc Cfaggsusu | 11.5 ± 5.8 |
| 1636 | 1662 | csusggAfuUfAfGfagu uacauca | 2268 | usGfsaugUfaAfCfucuaAfu Cfcagsusu | 19.6 ± 3 |

TABLE 1C-continued provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 1637 | 1663 | usgsgaUfuAfGfAfguu acaucua | 2269 | usAfsgauGfuAfAfcucuAfa Ufccasusu | 34.8 ± 6.6 |
| 1638 | 1664 | gsgsauUfaGfAfGfuua caucuca | 2270 | usGfsagaUfgUfAfacucUfa Afuccsusu | 13.1 ± 1.7 |
| 1639 | 1665 | gsasuuAfgAfGfUfuac aucucca | 2271 | usGfsgagAfuGfUfaacuCfu Afaucsusu | 29.9 ± 6.2 |
| 1651 | 1670 | asuscuCfcUfGfGfaug auuagua | 2276 | usAfscuaAfuCfAfuccaGfg Afgausus u | 30.4 ± 7.4 |
| 1652 | 1671 | uscsucCfuGfGfAfuga uuaguua | 2277 | usAfsacuAfaUfCfauccAfg Gfagasusu | 10.1 ± 2.5 |
| 1653 | 1672 | csusccUfgGfAfUfgau uaguuca | 2278 | usGfsaacUfaAfUfcaucCfa Gfgagsusu | 24.1 ± 5.3 |
| 1654 | 1673 | uscscuGfgAfUfGfauu aguucaa | 2279 | usUfsgaaCfuAfAfucauCfc Afggasusu | 10.7 ± 1.3 |
| 1655 | 1674 | cscsugGfaUfGfAfuua guucaga | 2280 | usCfsugaAfcUfAfaucaUfc Cfaggsusu | 14 ± 14.6 |
| 1656 | 1675 | csusggAfuGfAfUfuag uucagaa | 2281 | usUfscugAfaCfUfaaucAfu Cfcagsusu | 3.2 ± 0.8 |
| 27 | 1677 | csasccCfuCfCfCfcgc ggaagca | 2283 | usGfscuuCfcGfCfggggAfg Gfgugsusu | 91.5 ± 1.7 |
| 28 | 1678 | ascsccUfcCfCfCfgcg gaagcca | 2284 | usGfsgcuUfcCfGfcgggGfa Gfggusus u | 85.6 ± 6.4 |
| 251 | 1686 | cscsugGfcCfCfGfgga gacgcga | 2292 | usCfsgcgUfcUfCfccggGfc Cfaggsusu | 125.4 ± 9.2 |
| 252 | 1687 | csusggCfcCfGfGfgag acgcgga | 2293 | usCfscgcGfuCfUfcccgGfg Cfcagsusu | 136.3 ± 23.7 |
| 317 | 1693 | cscsgcCfcUfGfCfucc uccgaga | 2299 | usCfsucgGfaGfGfagcaGfg Gfcggsusu | 80.4 ± 5.4 |
| 355 | 1694 | cscsagGfcAfUfCfgcc gcccgga | 2300 | usCfscggGfcGfGfcgauGfc Cfuggsusu | 106.5 ± 22.1 |
| 363 | 1699 | csgsccGfcCfCfGfgga ggagcua | 2305 | usAfsgcuCfcUfCfccggGfc Gfgcgsusu | 90.9 ± 5.5 |
| 437 | 1700 | gsgsgcCfaGfGfCfacc cgggaca | 2306 | usGfsuccCfgGfGfugccUfg Gfcccsusu | 151.6 ± 3.6 |
| 452 | 1701 | gsascaGfgGfUfGfgca gggcgca | 2307 | usGfscgcCfcUfGfccacCfc Ufgucsusu | 116.8 ± 6.3 |
| 453 | 1702 | ascsagGfgUfGfGfcag ggcgcca | 2308 | usGfsgcgCfcCfUfgccaCfc Cfugusus u | 111.9 ± 10.8 |
| 547 | 1711 | ascscgGfcGfCfGfugg ggaacga | 2317 | usCfsguuCfcCfCfacgcGfc Cfggusus u | 69.3 ± 9.9 |
| 548 | 1712 | cscsggCfgCfGfUfggg gaacgga | 2318 | usCfscguUfcCfCfcacgCfg Cfcggsusu | 109.4 ± 16 |
| 549 | 1713 | csgsgcGfcGfUfGfggg aacggga | 2319 | usCfsccgUfuCfCfccacGfc Gfccgsusu | 106.2 ± 17.4 |
| 565 | 1715 | gsgsgcUfuCfCfCfgca ccccaca | 2321 | usGfsuggGfgUfGfcgggAfa Gfcccsusu | 93.2 ± 12.1 |
| 579 | 1718 | cscsacGfuGfCfCfcug cgcgcca | 2324 | usGfsgcgCfgCfAfgggcAfc Gfuggsusu | 76.8 ± 14.7 |
| 581 | 1719 | ascsguGfcCfCfUfgcg cgccuga | 2325 | usCfsaggCfgCfGfcaggGfc Afcgusus u | 135.7 ± 4.9 |

TABLE 1C-continued provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 588 | 1720 | csusgcGfcGfCfCfugg ggcucua | 2326 | usAfsgagCfcCfCfaggcGfc Gfcagsusu | 153.3 ± 29.1 |
| 627 | 1724 | cscsagGfcAfGfCfgag ggccgca | 2330 | usGfscggCfcCfUfcgcuGfc Cfuggsusu | 134.6 ± 20.4 |
| 652 | 1725 | csusgcAfgCfCfCfagc caggcca | 2331 | usGfsgccUfgGfCfugggCfu Gfcagsusu | 134.7 ± 7.3 |
| 659 | 1727 | cscsagCfcAfGfGfccg cgccgga | 2333 | usCfscggCfgCfGfgccuGfg Cfuggsusu | 132.1 ± 10.9 |
| 668 | 1728 | cscsgcGfcCfGfGfcag aggggaa | 2334 | usUfscccCfuCfUfgccgGfc Gfcggsusu | 110.8 ± 2.7 |
| 692 | 1730 | asasccUfgCfCfCfcgg cgcgcga | 2336 | usCfsgcgCfgCfCfggggCfa Gfguusus u | 111.7 ± 11.1 |
| 715 | 1732 | ususcgCfcUfAfCfgcc gccccga | 2338 | usCfsgggGfcGfGfcguaGfg Cfgaasusu | 123.4 ± 14.3 |
| 717 | 1733 | csgsccUfaCfGfCfcgc cccggca | 2339 | usGfsccgGfgGfCfggcgUfa Gfgcgsusu | 146 ± 19.9 |
| 732 | 1734 | gsgscuCfcUfCfCfgga cggggca | 2340 | usGfsccccCfgUfCfcggaGfg Afgccsusu | 99.8 ± 10.3 |
| 733 | 1735 | gscsucCfuCfCfGfgac ggggcga | 2341 | usCfsgccCfcGfUfccggAfg Gfagcsusu | 115.5 ± 7.3 |
| 813 | 1739 | cscscgCfaGfCfGfcga cggccua | 2345 | usAfsggcCfgUfCfgcgcUfg Cfgggsusu | 87 ± 9.8 |
| 827 | 1740 | gscscuGfcCfGfGfgcc ccugcga | 2346 | usCfsgcaGfgGfGfcccgGfc Afggcsusu | 120.7 ± 4.5 |
| 843 | 1743 | csgscgGfuGfGfCfaca gccugga | 2349 | usCfscagGfcUfGfugccAfc Cfgcgsusu | 145.9 ± 57 |
| 845 | 1744 | csgsguGfgCfAfCfagc cugggca | 2350 | usGfscccAfgGfCfugugCfc Afccgsusu | 104.5 ± 6.2 |
| 877 | 1747 | cscsgcAfgGfGfCfcaa gggguga | 2353 | usCfsaccCfcUfUfggccCfu Gfcggsusu | 268.3 ± 2.3 |
| 892 | 1748 | gsusgcUfuGfCfGfcca cccacga | 2354 | usCfsgugGfgUfGfgcgcAfa Gfcacsusu | 184 ± 4.8 |
| 893 | 1749 | usgscuUfgCfGfCfcac ccacgua | 2355 | usAfscguGfgGfUfggcgCfa Afgcasusu | 207.9 ± 46.2 |
| 939 | 1755 | cscsggGfgUfCfCfcca ggucgca | 2361 | usGfscgaCfcUfGfgggaCfc Cfcggsusu | 134.4 ± 12.5 |
| 956 | 1756 | cscsggGfgCfGfGfcgu gggaaca | 2362 | usGfsuucCfcAfCfgccgCfc Cfcggsusu | 74.4 ± 22.1 |
| 989 | 1757 | csusccAfcCfUfCfccca gcccga | 2363 | usCfsgggCfuGfGfggagGfu Gfgagsusu | 164.5 ± 14.2 |
| 1028 | 1761 | cscsgcGfcGfGfCfagg ggcagaa | 2367 | usUfscugCfcCfCfugccGfc Gfcggsusu | 165.2 ± 13.4 |
| 1067 | 1763 | cscscaGfgCfGfCfucc aggagca | 2369 | usGfscucCfuGfGfagcgCfc Ufgggsusu | 86.3 ± 5.4 |
| 1083 | 1765 | gscscgGfcGfCfCfcug gucugca | 2371 | usGfscagAfcCfAfgggcGfc Cfggcsusu | 94.6 ± 5.2 |
| 1084 | 1766 | cscsggCfgCfCfCfugg ucugcaa | 2372 | usUfsgcaGfaCfCfagggCfg Cfcggsusu | 88.2 ± 40 |

TABLE 1C-continued provides mRNA activity of exemplary siRNAs comprising modified sense strand and modified antisense strand.

| Position in transcript | SEQ ID NO: | Sense strand | SEQ ID NO: | Antisense strand | mRNA level, % at 10 nM |
|---|---|---|---|---|---|
| 1085 | 1767 | csgsgcGfcCfCfUfggucugcaca | 2373 | usGfsugcAfgAfCfcaggGfcGfccgsusu | 409.8 ± 34.8 |
| 1212 | 1774 | gsgsccGfcCfUfCfgcuggaagca | 2380 | usGfscuuCfcAfGfcgagGfcGfgccsusu | 101.1 ± 14.1 |
| 1213 | 1775 | gscscgCfcUfCfGfcuggaagcaa | 2381 | usUfsgcuUfcCfAfgcgaGfgCfggcsusu | 25.1 ± 4.6 |
| 1235 | 1781 | uscsagCfgAfGfGfaagaauacca | 2387 | usGfsguaUfuCfUfuccuCfgCfugasusu | 43.5 ± 4.2 |
| 1251 | 1783 | cscsggGfcUfCfUfgcuggaggaa | 2389 | usUfsccuCfcAfGfcagaGfcCfcggsusu | 167.4 ± 7.4 |
| 1260 | 1786 | gscsugGfaGfGfAfgcuuuaggaa | 2392 | usUfsccuAfaAfGfcuccUfcCfagcsusu | 113.5 ± 2 |
| 1261 | 1787 | csusggAfgGfAfGfcuuuaggaca | 2393 | usGfsuccUfaAfAfgcucCfuCfcagsusu | 79.4 ± 7.7 |
| 1267 | 1790 | gsasgcUfuUfAfGfgacgcgggga | 2396 | usCfscccGfcGfUfccuaAfaGfcucsusu | 43.3 ± 2.9 |
| 1268 | 1791 | asgscuUfuAfGfGfacgcggggua | 2397 | usAfscccCfgCfGfuccuAfaAfgcusus u | 59.6 ± 10.2 |
| 1269 | 1792 | gscsuuUfaGfGfAfcgcgggguua | 2398 | usAfsaccCfcGfCfguccUfaAfagcsusu | 138 ± 17.3 |
| 1274 | 1796 | asgsgaCfgCfGfGfgguugggaca | 2402 | usGfsuccCfaAfCfcccgCfgUfccusus u | 142.5 ± 9.3 |
| 1279 | 1797 | gscsggGfgUfUfGfggacggggua | 2403 | usAfscccCfgUfCfccaaCfcCfcgcsusu | 122.7 ± 2.6 |
| 1284 | 1798 | gsusugGfgAfCfGfgggucgggua | 2404 | usAfscccGfaCfCfccguCfcCfaacsusu | 100.2 ± 9 |
| 1288 | 1799 | gsgsacGfgGfGfUfcgggugguua | 2405 | usAfsaccAfcCfCfgaccCfcGfuccsusu | 58.3 ± 6.7 |
| 1389 | 1800 | gsgscuGfaCfCfGfgccugggaua | 2406 | usAfsuccCfaGfGfccggUfcAfgccsusu | 203.5 ± 86.3 |
| 1390 | 1801 | gscsugAfcCfGfGfccugggauua | 2407 | usAfsaucCfcAfGfgccgGfuCfagcsusu | 477.1 ± 98.6 |
| 1421 | 1806 | uscsuaGfgCfCfCfggugagagaa | 2412 | usUfscucUfcAfCfcgggCfcUfagasusu | 182 ± 17.3 |
| 1427 | 1810 | cscscgGfuGfAfGfagacuccaca | 2416 | usGfsuggAfgUfCfucucAfcCfgggsusu | 79.2 ± 20 |
| 1612 | 1813 | cscsuuCfcGfAfCfgcugucuaga | 2419 | usCfsuagAfcAfGfcgucGfgAfaggsusu | 58.8 ± 7.7 |
| 1613 | 1814 | csusucCfgAfCfGfcugucuagga | 2420 | usCfscuaGfaCfAfgcguCfgGfaagsusu | 62.5 ± 5.9 |

Column 1 shows the beginning position of the target sequence in DUX4_human_#NM_001306068.3 (SEQ ID NO: 2425).

The target sequence is 19 nucleotide long starting from the beginning position.

For example, row 1 shows that the beginning position of the target sequence is 11, which means that the target sequence is the sequence corresponding to positions 11-29 of DUX4_human_#NM_001306068.3 (SEQ ID NO: 2425).

The sequences of the sense strands and antisense strands are shown from the 5' end to the 3' end.

TABLE 1D provides IC50 values of exemplary siRNAs comprising modified sense strand and modified antisense strand.

| Position in transcript | Corresponding Unmodified siRNAs SEQ ID NO of Sense strand | SEQ ID NO of Antisense strand | Modified siRNAs SEQ ID NO: | Sense strand | SEQ ID NO: | Antisense strand | IC50, pM |
|---|---|---|---|---|---|---|---|
| 61 | 28 | 634 | 1240 | csgsacGfgAfGfAfc ucguuugga | 1846 | usCfscaaAfcGfAfgucuC fcGfucgsusu | 817.2 ± 1425.6 |
| 404 | 226 | 832 | 1438 | asgsucCfaGfGfAfu ucagaucua | 2044 | usAfsgauCfuGfAfauccU fgGfacusus u | 71.4 ± 24 |
| 412 | 231 | 837 | 1443 | asusucAfgAfUfCfu gguuucaga | 2049 | usCfsugaAfaCfCfagau CfuGfaausus u | 84.1 ± 41.8 |
| 1163 | 414 | 1020 | 1626 | asasccUfcUfCfCfu agaaacgga | 2232 | usCfscguUfuCfUfagga GfaGfguusus u | 660.5 ± 269.1 |
| 1619 | 433 | 1039 | 1645 | ascsgcUfgUfCfUfa ggcaaacca | 2251 | usGfsguuUfgCfCfuaga CfaGfcgusus u | 91.7 ± 38.4 |
| 1628 | 442 | 1048 | 1654 | asgsgcAfaAfCfCfu ggauuagaa | 2260 | usUfscuaAfuCfCfaggu UfuGfccusus u | 30.5 ± 13.3 |
| 1629 | 443 | 1049 | 1655 | gsgscaAfaCfCfUfg gauuagaga | 2261 | usCfsucuAfaUfCfcaggU fuUfgccsusu | 89.8 ± 44.4 |
| 1635 | 449 | 1055 | 1661 | cscsugGfaUfUfAfg aguuacaua | 2267 | usAfsuguAfaCfUfcuaaU fcCfaggsusu | 23.6 ± 12.2 |
| 1636 | 450 | 1056 | 1662 | csusggAfuUfAfGfa guuacauca | 2268 | usGfsaugUfaAfCfucua AfuCfcagsusu | 94.3 ± 29.2 |
| 1651 | 458 | 1064 | 1670 | asuscuCfcUfGfGfa ugauuagua | 2276 | usAfscuaAfuCfAfuccaG fgAfgausus u | 26.8 ± 29.1 |
| 1652 | 459 | 1065 | 1671 | uscsucCfuGfGfAfu gauuaguua | 2277 | usAfsacuAfaUfCfauccA fgGfagasusu | 27.3 ± 11.7 |
| 1653 | 460 | 1066 | 1672 | csusccUfgGfAfUfg auuaguuca | 2278 | usGfsaacUfaAfUfcaucC faGfgagsusu | 105.4 ± 55.2 |
| 1654 | 461 | 1067 | 1673 | uscscuGfgAfUfGfa uuaguucaa | 2279 | usUfsgaaCfuAfAfucauC fcAfggasusu | 133.7 ± 57.8 |
| 1655 | 462 | 1068 | 1674 | cscsugGfaUfGfAfu uaguucaga | 2280 | usCfsugaAfcUfAfaucaU fcCfaggsusu | 32.6 ± 22.6 |
| 1656 | 463 | 1069 | 1675 | csusggAfuGfAfUfu aguucagaa | 2281 | usUfscugAfaCfUfaaucA fuCfcagsusu | 20.9 ± 14.1 |
| 1213 | 563 | 1169 | 1775 | gscscgCfcUfCfGfc uggaagcaa | 2381 | usUfsgcuUfcCfAfgcgaG fgCfggcsusu | 138.3 ± 71.8 |
| 1267 | 578 | 1184 | 1790 | gsasgcUfuUfAfGfg acgcgggga | 2396 | usCfscccGfcGfUfccuaA faGfcucsusu | 31.4 ± 45.4 |

Column 1 shows the beginning position of the target sequence in DUX4_human_#NM_001306068.3 (SEQ ID NO: 2425).
The target sequence is 19 nucleotide long starting from the beginning position.
For example, row 1 shows that the beginning position of the target sequence is 61, which means that the target sequence is the sequence corresponding to positions 61-79 of DUX4_human_#NM_001306068.3 (SEQ ID NO: 2425)

TABLE 1E provides comparison of mRNA knockdown activity of exemplary siRNAs comprising modified sense strand and modified antisense strand with different chemical modifications.

| | Corresponding Unmodified siRNAs | | Modified siRNAs | | | | | | |
|---|---|---|---|---|---|---|---|---|---|
| Position in transcript | SEQ ID NO of Sense strand | SEQ ID NO of Anti-sense strand | SEQ ID NO: | Sense strand | SEQ ID NO: | Antisense strand | mRNA level, % for 10 nM siRNA | mRNA level, % for 1 nM siRNA | mRNA level, % for 0.1 nM siRNA |
| 420 | 232 | 838 | 1444 | csusggUfuUfCfAfgaaucgaaga | 2050 | usCfsuucGfaUfUfcugaAfaCfcagsusu | 22 ± 2 | 65 ± 6 | 85 ± 12 |
| 420 | 232 | 838 | 2426 | csusGfguuUfCfAfgaAfucgaAfsgsa | 2437 | vpUsCfsuucgauucugaAfaccagsusu | 21 ± 6 | 56 ± 3 | 81 ± 22 |
| 1628 | 442 | 1048 | 1654 | asgsgcAfaAfCfCfuggauuagaa | 2260 | usUfscuaAfuCfCfagguUfuGfccusus u | 26 ± 4 | 45 ± 11 | 68 ± 3 |
| 1628 | 442 | 1048 | 2427 | asgsGfcaaAfCfCfugGfauuaGfsasa | 2438 | vpUsUfscuaauccagguUfugccusus u | 20 ± 4 | 35 ± 2 | 47 ± 5 |
| 1629 | 443 | 1049 | 1655 | gsgscaAfaCfCfUfggauuagaga | 2261 | usCfsucuAfaUfCfcaggUfuUfgccsusu | 28 ± 6 | 61 ± 12 | 92 ± 2 |
| 1629 | 443 | 1049 | 2428 | gsgsCfaaaCfCfUfggAfuuagAfsgsa | 2439 | vpUsCfsucuaauccaggUfuugccsusu | 31 ± 4 | 40 ± 4 | 67 ± 5 |
| 1635 | 449 | 1055 | 1661 | cscsugGfaUfUfAfgaguuacaua | 2267 | usAfsuguAfaCfUfcuaaUfcCfaggsusu | 18 ± 3 | 42 ± 4 | 61 ± 7 |
| 1635 | 449 | 1055 | 2429 | cscsUfggaUfUfAfgaGfuuacAfsusa | 2440 | vpUsAfsuguaacucuaaUfccaggsusu | 12 ± 2 | 28 ± 2 | 42 ± 10 |
| 1636 | 450 | 1056 | 1662 | csusggAfuUfAfGfaguuacauca | 2268 | usGfsaugUfaAfCfucuaAfuCfcagsusu | 19 ± 2 | 61 ± 7 | 84 ± 10 |
| 1636 | 450 | 1056 | 2430 | csusGfgauUfAfGfagUfuacaUfscsa | 2441 | vpUsGfsauguaacucuaAfuccagsusu | 28 ± 6 | 54 ± 12 | 84 ± 6 |
| 1652 | 459 | 1065 | 1671 | uscsucCfuGfGfAfugauuaguua | 2277 | usAfsacuAfaUfCfauccAfgGfagasusu | 20 ± 1 | 46 ± 7 | 65 ± 11 |
| 1652 | 459 | 1065 | 2431 | uscsUfccuGfGfAfugAfuuagUfsusa | 2442 | vpUsAfsacuaaucauccAfggagasusu | 17 ± 6 | 32 ± 5 | 48 ± 6 |
| 1653 | 460 | 1066 | 1672 | csusccUfgGfAfUfgauuaguuca | 2278 | usGfsaacUfaAfUfcaucCfaGfgagsusu | 37 ± 7 | 73 ± 12 | 91 ± 22 |
| 1653 | 460 | 1066 | 2432 | csusCfcugGfAfUfgaUfuaguUfscsa | 2443 | vpUsGfsaacuaaucauCcfaggagsusu | 47 ± 11 | 69 ± 11 | 81 ± 9 |
| 668 | 516 | 1122 | 1728 | cscsgcGfcCfGfGfcagaggggaa | 2334 | usUfscccCfuCfUfgccgGfcGfcggsusu | 91 ± 12 | 93 ± 25 | 99 ± 11 |
| 668 | 516 | 1122 | 2433 | cscsGfcgcCfGfGfcaGfagggGfsasa | 2444 | vpUsUfsccccucugccgGfcgcggsusu | 108 ± 8 | 111 ± 24 | 99 ± 12 |

Column 1 shows the beginning position of the target sequence in DUX4_human_#NM_001306068.3 (SEQ ID NO: 2425).

The target sequence is 19 nucleotide long starting from the beginning position.

For example, row 1 shows that the beginning position of the target sequence is 420, which means that the target sequence is the sequence corresponding to positions 420-438 of DUX4_human_#NM_001306068.3 (SEQ ID NO: 2425).

The sequences of the sense strands and antisense strands are shown from the 5' end to the 3' end.

TABLE 1F provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1 | 2448 | AUGGCCCUCCCGACACCCU | 3012 | AGGGUGUCGGGAGGGCCAU |
| 2 | 2449 | UGGCCCUCCCGACACCCUC | 3013 | GAGGGUGUCGGGAGGGCCA |
| 11 | 2450 | CGACACCCUCGGACAGCAC | 3014 | GUGCUGUCCGAGGGUGUCG |
| 12 | 2451 | GACACCCUCGGACAGCACC | 3015 | GGUGCUGUCCGAGGGUGUC |
| 13 | 2452 | ACACCCUCGGACAGCACCC | 3016 | GGGUGCUGUCCGAGGGUGU |
| 14 | 2453 | CACCCUCGGACAGCACCCU | 3017 | AGGGUGCUGUCCGAGGGUG |
| 15 | 2454 | ACCCUCGGACAGCACCCUC | 3018 | GAGGGUGCUGUCCGAGGGU |
| 16 | 2455 | CCCUCGGACAGCACCCUCC | 3019 | GGAGGGUGCUGUCCGAGGG |
| 17 | 2456 | CCUCGGACAGCACCCUCCC | 3020 | GGGAGGGUGCUGUCCGAGG |
| 18 | 2457 | CUCGGACAGCACCCUCCCC | 3021 | GGGGAGGGUGCUGUCCGAG |
| 19 | 2458 | UCGGACAGCACCCUCCCCG | 3022 | CGGGGAGGGUGCUGUCCGA |
| 23 | 2459 | ACAGCACCCUCCCCGCGGA | 3023 | UCCGCGGGGAGGGUGCUGU |
| 24 | 2460 | CAGCACCCUCCCCGCGGAA | 3024 | UUCCGCGGGGAGGGUGCUG |
| 25 | 2461 | AGCACCCUCCCCGCGGAAG | 3025 | CUUCCGCGGGGAGGGUGCU |
| 39 | 15 | GGAAGCCCGGGGACGAGGA | 3026 | UCCUCGUCCCCGGGCUUCC |
| 40 | 16 | GAAGCCCGGGGACGAGGAC | 3027 | GUCCUCGUCCCCGGGCUUC |
| 41 | 17 | AAGCCCGGGGACGAGGACG | 3028 | CGUCCUCGUCCCCGGGCUU |
| 49 | 18 | GGACGAGGACGGCGACGGA | 3029 | UCCGUCGCCGUCCUCGUCC |
| 50 | 19 | GACGAGGACGGCGACGGAG | 3030 | CUCCGUCGCCGUCCUCGUC |
| 51 | 20 | ACGAGGACGGCGACGGAGA | 3031 | UCUCCGUCGCCGUCCUCGU |
| 52 | 21 | CGAGGACGGCGACGGAGAC | 3032 | GUCUCCGUCGCCGUCCUCG |
| 53 | 2462 | GAGGACGGCGACGGAGACU | 3033 | AGUCUCCGUCGCCGUCCUC |
| 54 | 2463 | AGGACGGCGACGGAGACUC | 3034 | GAGUCUCCGUCGCCGUCCU |
| 55 | 2464 | GGACGGCGACGGAGACUCG | 3035 | CGAGUCUCCGUCGCCGUCC |
| 56 | 2465 | GACGGCGACGGAGACUCGU | 3036 | ACGAGUCUCCGUCGCCGUC |
| 57 | 2466 | ACGGCGACGGAGACUCGUU | 3037 | AACGAGUCUCCGUCGCCGU |
| 60 | 2467 | GCGACGGAGACUCGUUUGG | 3038 | CCAAACGAGUCUCCGUCGC |
| 61 | 2468 | CGACGGAGACUCGUUUGGA | 3039 | UCCAAACGAGUCUCCGUCG |
| 62 | 2469 | GACGGAGACUCGUUUGGAC | 3040 | GUCCAAACGAGUCUCCGUC |
| 63 | 2470 | ACGGAGACUCGUUUGGACC | 3041 | GGUCCAAACGAGUCUCCGU |
| 64 | 2471 | CGGAGACUCGUUUGGACCC | 3042 | GGGUCCAAACGAGUCUCCG |
| 65 | 2472 | GGAGACUCGUUUGGACCCC | 3043 | GGGGUCCAAACGAGUCUCC |
| 66 | 2473 | GAGACUCGUUUGGACCCCG | 3044 | CGGGGUCCAAACGAGUCUC |
| 67 | 2474 | AGACUCGUUUGGACCCCGA | 3045 | UCGGGGUCCAAACGAGUCU |
| 71 | 2475 | UCGUUUGGACCCCGAGCCA | 3046 | UGGCUCGGGGUCCAAACGA |
| 76 | 2476 | UGGACCCCGAGCCAAAGCG | 3047 | CGCUUUGGCUCGGGGUCCA |
| 77 | 37 | GGACCCCGAGCCAAAGCGA | 3048 | UCGCUUUGGCUCGGGGUCC |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 78 | 38 | GACCCCGAGCCAAAGCGAG | 3049 | CUCGCUUUGGCUCGGGGUC |
| 79 | 39 | ACCCCGAGCCAAAGCGAGG | 3050 | CCUCGCUUUGGCUCGGGGU |
| 80 | 40 | CCCCGAGCCAAAGCGAGGC | 3051 | GCCUCGCUUUGGCUCGGGG |
| 81 | 41 | CCCGAGCCAAAGCGAGGCC | 3052 | GGCCUCGCUUUGGCUCGGG |
| 82 | 42 | CCGAGCCAAAGCGAGGCCC | 3053 | GGGCCUCGCUUUGGCUCGG |
| 83 | 2477 | CGAGCCAAAGCGAGGCCCU | 3054 | AGGGCCUCGCUUUGGCUCG |
| 84 | 2478 | GAGCCAAAGCGAGGCCCUG | 3055 | CAGGGCCUCGCUUUGGCUC |
| 85 | 2479 | AGCCAAAGCGAGGCCCUGC | 3056 | GCAGGGCCUCGCUUUGGCU |
| 86 | 2480 | GCCAAAGCGAGGCCCUGCG | 3057 | CGCAGGGCCUCGCUUUGGC |
| 87 | 2481 | CCAAAGCGAGGCCCUGCGA | 3058 | UCGCAGGGCCUCGCUUUGG |
| 88 | 2482 | CAAAGCGAGGCCCUGCGAG | 3059 | CUCGCAGGGCCUCGCUUUG |
| 89 | 2483 | AAAGCGAGGCCCUGCGAGC | 3060 | GCUCGCAGGGCCUCGCUUU |
| 90 | 2484 | AAGCGAGGCCCUGCGAGCC | 3061 | GGCUCGCAGGGCCUCGCUU |
| 108 | 2485 | CUGCUUUGAGCGGAACCCG | 3062 | CGGGUUCCGCUCAAAGCAG |
| 109 | 2486 | UGCUUUGAGCGGAACCCGU | 3063 | ACGGGUUCCGCUCAAAGCA |
| 110 | 2487 | GCUUUGAGCGGAACCCGUA | 3064 | UACGGGUUCCGCUCAAAGC |
| 111 | 2488 | CUUUGAGCGGAACCCGUAC | 3065 | GUACGGGUUCCGCUCAAAG |
| 112 | 2489 | UUUGAGCGGAACCCGUACC | 3066 | GGUACGGGUUCCGCUCAAA |
| 113 | 2490 | UUGAGCGGAACCCGUACCC | 3067 | GGGUACGGGUUCCGCUCAA |
| 114 | 2491 | UGAGCGGAACCCGUACCCG | 3068 | CGGGUACGGGUUCCGCUCA |
| 115 | 2492 | GAGCGGAACCCGUACCCGG | 3069 | CCGGGUACGGGUUCCGCUC |
| 116 | 2493 | AGCGGAACCCGUACCCGGG | 3070 | CCCGGGUACGGGUUCCGCU |
| 124 | 2494 | CCGUACCCGGGCAUCGCCA | 3071 | UGGCGAUGCCCGGGUACGG |
| 125 | 2495 | CGUACCCGGGCAUCGCCAC | 3072 | GUGGCGAUGCCCGGGUACG |
| 126 | 2496 | GUACCCGGGCAUCGCCACC | 3073 | GGUGGCGAUGCCCGGGUAC |
| 127 | 2497 | UACCCGGGCAUCGCCACCA | 3074 | UGGUGGCGAUGCCCGGGUA |
| 129 | 2498 | CCCGGGCAUCGCCACCAGA | 3075 | UCUGGUGGCGAUGCCCGGG |
| 130 | 2499 | CCGGGCAUCGCCACCAGAG | 3076 | CUCUGGUGGCGAUGCCCGG |
| 131 | 2500 | CGGGCAUCGCCACCAGAGA | 3077 | UCUCUGGUGGCGAUGCCCG |
| 132 | 2501 | GGGCAUCGCCACCAGAGAA | 3078 | UUCUCUGGUGGCGAUGCCC |
| 133 | 2502 | GGCAUCGCCACCAGAGAAC | 3079 | GUUCUCUGGUGGCGAUGCC |
| 134 | 2503 | GCAUCGCCACCAGAGAACG | 3080 | CGUUCUCUGGUGGCGAUGC |
| 135 | 2504 | CAUCGCCACCAGAGAACGG | 3081 | CCGUUCUCUGGUGGCGAUG |
| 136 | 2505 | AUCGCCACCAGAGAACGGC | 3082 | GCCGUUCUCUGGUGGCGAU |
| 137 | 2506 | UCGCCACCAGAGAACGGCU | 3083 | AGCCGUUCUCUGGUGGCGA |
| 138 | 2507 | CGCCACCAGAGAACGGCUG | 3084 | CAGCCGUUCUCUGGUGGCG |
| 144 | 2508 | CAGAGAACGGCUGGCCCAG | 3085 | CUGGGCCAGCCGUUCUCUG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 145 | 2509 | AGAGAACGGCUGGCCCAGG | 3086 | CCUGGGCCAGCCGUUCUCU |
| 146 | 2510 | GAGAACGGCUGGCCCAGGC | 3087 | GCCUGGGCCAGCCGUUCUC |
| 147 | 2511 | AGAACGGCUGGCCCAGGCC | 3088 | GGCCUGGGCCAGCCGUUCU |
| 148 | 2512 | GAACGGCUGGCCCAGGCCA | 3089 | UGGCCUGGGCCAGCCGUUC |
| 157 | 2513 | GCCCAGGCCAUCGGCAUUC | 3090 | GAAUGCCGAUGGCCUGGGC |
| 158 | 2514 | CCCAGGCCAUCGGCAUUCC | 3091 | GGAAUGCCGAUGGCCUGGG |
| 159 | 2515 | CCAGGCCAUCGGCAUUCCG | 3092 | CGGAAUGCCGAUGGCCUGG |
| 160 | 2516 | CAGGCCAUCGGCAUUCCGG | 3093 | CCGGAAUGCCGAUGGCCUG |
| 161 | 2517 | AGGCCAUCGGCAUUCCGGA | 3094 | UCCGGAAUGCCGAUGGCCU |
| 162 | 2518 | GGCCAUCGGCAUUCCGGAG | 3095 | CUCCGGAAUGCCGAUGGCC |
| 163 | 2519 | GCCAUCGGCAUUCCGGAGC | 3096 | GCUCCGGAAUGCCGAUGGC |
| 164 | 2520 | CCAUCGGCAUUCCGGAGCC | 3097 | GGCUCCGGAAUGCCGAUGG |
| 165 | 2521 | CAUCGGCAUUCCGGAGCCC | 3098 | GGGCUCCGGAAUGCCGAUG |
| 166 | 2522 | AUCGGCAUUCCGGAGCCCA | 3099 | UGGGCUCCGGAAUGCCGAU |
| 167 | 2523 | UCGGCAUUCCGGAGCCCAG | 3100 | CUGGGCUCCGGAAUGCCGA |
| 168 | 2524 | CGGCAUUCCGGAGCCCAGG | 3101 | CCUGGGCUCCGGAAUGCCG |
| 169 | 2525 | GGCAUUCCGGAGCCCAGGG | 3102 | CCCUGGGCUCCGGAAUGCC |
| 170 | 2526 | GCAUUCCGGAGCCCAGGGU | 3103 | ACCCUGGGCUCCGGAAUGC |
| 171 | 2527 | CAUUCCGGAGCCCAGGGUC | 3104 | GACCCUGGGCUCCGGAAUG |
| 172 | 2528 | AUUCCGGAGCCCAGGGUCC | 3105 | GGACCCUGGGCUCCGGAAU |
| 173 | 2529 | UUCCGGAGCCCAGGGUCCA | 3106 | UGGACCCUGGGCUCCGGAA |
| 174 | 2530 | UCCGGAGCCCAGGGUCCAG | 3107 | CUGGACCCUGGGCUCCGGA |
| 175 | 2531 | CCGGAGCCCAGGGUCCAGA | 3108 | UCUGGACCCUGGGCUCCGG |
| 176 | 2532 | CGGAGCCCAGGGUCCAGAU | 3109 | AUCUGGACCCUGGGCUCCG |
| 177 | 2533 | GGAGCCCAGGGUCCAGAUU | 3110 | AAUCUGGACCCUGGGCUCC |
| 186 | 2534 | GGUCCAGAUUUGGUUUCAG | 3111 | CUGAAACCAAAUCUGGACC |
| 187 | 2535 | GUCCAGAUUUGGUUUCAGA | 3112 | UCUGAAACCAAAUCUGGAC |
| 188 | 2536 | UCCAGAUUUGGUUUCAGAA | 3113 | UUCUGAAACCAAAUCUGGA |
| 189 | 2537 | CCAGAUUUGGUUUCAGAAU | 3114 | AUUCUGAAACCAAAUCUGG |
| 190 | 2538 | CAGAUUUGGUUUCAGAAUG | 3115 | CAUUCUGAAACCAAAUCUG |
| 192 | 2539 | GAUUUGGUUUCAGAAUGAG | 3116 | CUCAUUCUGAAACCAAAUC |
| 194 | 2540 | UUUGGUUUCAGAAUGAGAG | 3117 | CUCUCAUUCUGAAACCAAA |
| 195 | 2541 | UUGGUUUCAGAAUGAGAGG | 3118 | CCUCUCAUUCUGAAACCAA |
| 196 | 2542 | UGGUUUCAGAAUGAGAGGU | 3119 | ACCUCUCAUUCUGAAACCA |
| 197 | 2543 | GGUUUCAGAAUGAGAGGUC | 3120 | GACCUCUCAUUCUGAAACC |
| 198 | 2544 | GUUUCAGAAUGAGAGGUCA | 3121 | UGACCUCUCAUUCUGAAAC |
| 199 | 2545 | UUUCAGAAUGAGAGGUCAC | 3122 | GUGACCUCUCAUUCUGAAA |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 200 | 2546 | UUCAGAAUGAGAGGUCACG | 3123 | CGUGACCUCUCAUUCUGAA |
| 201 | 2547 | UCAGAAUGAGAGGUCACGC | 3124 | GCGUGACCUCUCAUUCUGA |
| 202 | 2548 | CAGAAUGAGAGGUCACGCC | 3125 | GGCGUGACCUCUCAUUCUG |
| 203 | 2549 | AGAAUGAGAGGUCACGCCA | 3126 | UGGCGUGACCUCUCAUUCU |
| 204 | 2550 | GAAUGAGAGGUCACGCCAG | 3127 | CUGGCGUGACCUCUCAUUC |
| 205 | 2551 | AAUGAGAGGUCACGCCAGC | 3128 | GCUGGCGUGACCUCUCAUU |
| 206 | 2552 | AUGAGAGGUCACGCCAGCU | 3129 | AGCUGGCGUGACCUCUCAU |
| 207 | 2553 | UGAGAGGUCACGCCAGCUG | 3130 | CAGCUGGCGUGACCUCUCA |
| 208 | 2554 | GAGAGGUCACGCCAGCUGA | 3131 | UCAGCUGGCGUGACCUCUC |
| 209 | 2555 | AGAGGUCACGCCAGCUGAG | 3132 | CUCAGCUGGCGUGACCUCU |
| 210 | 2556 | GAGGUCACGCCAGCUGAGG | 3133 | CCUCAGCUGGCGUGACCUC |
| 211 | 2557 | AGGUCACGCCAGCUGAGGC | 3134 | GCCUCAGCUGGCGUGACCU |
| 212 | 2558 | GGUCACGCCAGCUGAGGCA | 3135 | UGCCUCAGCUGGCGUGACC |
| 213 | 2559 | GUCACGCCAGCUGAGGCAG | 3136 | CUGCCUCAGCUGGCGUGAC |
| 214 | 2560 | UCACGCCAGCUGAGGCAGC | 3137 | GCUGCCUCAGCUGGCGUGA |
| 215 | 2561 | CACGCCAGCUGAGGCAGCA | 3138 | UGCUGCCUCAGCUGGCGUG |
| 224 | 2562 | UGAGGCAGCACCGGCGGGA | 3139 | UCCCGCCGGUGCUGCCUCA |
| 225 | 129 | GAGGCAGCACCGGGGGGAA | 3140 | UUCCCGCCGGUGCUGCCUC |
| 226 | 2563 | AGGCAGCACCGGCGGGAAU | 3141 | AUUCCCGCCGGUGCUGCCU |
| 227 | 2564 | GGCAGCACCGGCGGGAAUC | 3142 | GAUUCCCGCCGGUGCUGCC |
| 228 | 2565 | GCAGCACCGGGGGGAAUCU | 3143 | AGAUUCCCGCCGGUGCUGC |
| 229 | 2566 | CAGCACCGGGGGGAAUCUC | 3144 | GAGAUUCCCGCCGGUGCUG |
| 230 | 2567 | AGCACCGGCGGGAAUCUCG | 3145 | CGAGAUUCCCGCCGGUGCU |
| 231 | 2568 | GCACCGGCGGGAAUCUCGG | 3146 | CCGAGAUUCCCGCCGGUGC |
| 232 | 2569 | CACCGGGGGGAAUCUCGGC | 3147 | GCCGAGAUUCCCGCCGGUG |
| 235 | 2570 | CGGCGGGAAUCUCGGCCCU | 3148 | AGGGCCGAGAUUCCCGCCG |
| 236 | 2571 | GGCGGGAAUCUCGGCCCUG | 3149 | CAGGGCCGAGAUUCCCGCC |
| 237 | 2572 | GCGGGAAUCUCGGCCCUGG | 3150 | CCAGGGCCGAGAUUCCCGC |
| 238 | 2573 | CGGGAAUCUCGGCCCUGGC | 3151 | GCCAGGGCCGAGAUUCCCG |
| 239 | 2574 | GGGAAUCUCGGCCCUGGCC | 3152 | GGCCAGGGCCGAGAUUCCC |
| 240 | 2575 | GGAAUCUCGGCCCUGGCCC | 3153 | GGGCCAGGGCCGAGAUUCC |
| 241 | 2576 | GAAUCUCGGCCCUGGCCCG | 3154 | CGGGCCAGGGCCGAGAUUC |
| 261 | 144 | GAGACGCGGCCCGCCAGAA | 3155 | UUCUGGCGGGCCGCGUCUC |
| 262 | 145 | AGACGCGGCCCGCCAGAAG | 3156 | CUUCUGGGGGGCCGCGUCU |
| 273 | 146 | GCCAGAAGGCCGGCGAAAG | 3157 | CUUUCGCCGGCCUUCUGGC |
| 274 | 147 | CCAGAAGGCCGGCGAAAGC | 3158 | GCUUUCGCCGGCCUUCUGG |
| 275 | 148 | CAGAAGGCCGGCGAAAGCG | 3159 | CGCUUUCGCCGGCCUUCUG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 276 | 149 | AGAAGGCCGGCGAAAGCGG | 3160 | CCGCUUUCGCCGGCCUUCU |
| 277 | 150 | GAAGGCCGGCGAAAGCGGA | 3161 | UCCGCUUUCGCCGGCCUUC |
| 278 | 151 | AAGGCCGGCGAAAGCGGAC | 3162 | GUCCGCUUUCGCCGGCCUU |
| 285 | 2577 | GCGAAAGCGGACCGCCGUC | 3163 | GACGGCGGUCCGCUUUCGC |
| 286 | 2578 | CGAAAGCGGACCGCCGUCA | 3164 | UGACGGCGGUCCGCUUUCG |
| 287 | 2579 | GAAAGCGGACCGCCGUCAC | 3165 | GUGACGGCGGUCCGCUUUC |
| 288 | 2580 | AAAGCGGACCGCCGUCACC | 3166 | GGUGACGGCGGUCCGCUUU |
| 289 | 2581 | AAGCGGACCGCCGUCACCG | 3167 | CGGUGACGGCGGUCCGCUU |
| 292 | 2582 | CGGACCGCCGUCACCGGAU | 3168 | AUCCGGUGACGGCGGUCCG |
| 293 | 2583 | GGACCGCCGUCACCGGAUC | 3169 | GAUCCGGUGACGGCGGUCC |
| 294 | 2584 | GACCGCCGUCACCGGAUCC | 3170 | GGAUCCGGUGACGGCGGUC |
| 295 | 2585 | ACCGCCGUCACCGGAUCCC | 3171 | GGGAUCCGGUGACGGCGGU |
| 296 | 2586 | CCGCCGUCACCGGAUCCCA | 3172 | UGGGAUCCGGUGACGGCGG |
| 297 | 2587 | CGCCGUCACCGGAUCCCAG | 3173 | CUGGGAUCCGGUGACGGCG |
| 298 | 2588 | GCCGUCACCGGAUCCCAGA | 3174 | UCUGGGAUCCGGUGACGGC |
| 299 | 2589 | CCGUCACCGGAUCCCAGAC | 3175 | GUCUGGGAUCCGGUGACGG |
| 300 | 2590 | CGUCACCGGAUCCCAGACC | 3176 | GGUCUGGGAUCCGGUGACG |
| 301 | 2591 | GUCACCGGAUCCCAGACCG | 3177 | CGGUCUGGGAUCCGGUGAC |
| 302 | 2592 | UCACCGGAUCCCAGACCGC | 3178 | GCGGUCUGGGAUCCGGUGA |
| 303 | 2593 | CACCGGAUCCCAGACCGCC | 3179 | GGCGGUCUGGGAUCCGGUG |
| 304 | 2594 | ACCGGAUCCCAGACCGCCC | 3180 | GGGCGGUCUGGGAUCCGGU |
| 305 | 2595 | CCGGAUCCCAGACCGCCCU | 3181 | AGGGCGGUCUGGGAUCCGG |
| 306 | 2596 | CGGAUCCCAGACCGCCCUG | 3182 | CAGGGCGGUCUGGGAUCCG |
| 307 | 2597 | GGAUCCCAGACCGCCCUGC | 3183 | GCAGGGCGGUCUGGGAUCC |
| 308 | 2598 | GAUCCCAGACCGCCCUGCU | 3184 | AGCAGGGCGGUCUGGGAUC |
| 309 | 2599 | AUCCCAGACCGCCCUGCUC | 3185 | GAGCAGGGCGGUCUGGGAU |
| 310 | 2600 | UCCCAGACCGCCCUGCUCC | 3186 | GGAGCAGGGCGGUCUGGGA |
| 311 | 2601 | CCCAGACCGCCCUGCUCCU | 3187 | AGGAGCAGGGCGGUCUGGG |
| 312 | 2602 | CCAGACCGCCCUGCUCCUC | 3188 | GAGGAGCAGGGCGGUCUGG |
| 313 | 2603 | CAGACCGCCCUGCUCCUCC | 3189 | GGAGGAGCAGGGCGGUCUG |
| 314 | 2604 | AGACCGCCCUGCUCCUCCG | 3190 | CGGAGGAGCAGGGCGGUCU |
| 315 | 2605 | GACCGCCCUGCUCCUCCGA | 3191 | UCGGAGGAGCAGGGCGGUC |
| 316 | 2606 | ACCGCCCUGCUCCUCCGAG | 3192 | CUCGGAGGAGCAGGGCGGU |
| 325 | 2607 | CUCCUCCGAGCCUUUGAGA | 3193 | UCUCAAAGGCUCGGAGGAG |
| 328 | 2608 | CUCCGAGCCUUUGAGAAGG | 3194 | CCUUCUCAAAGGCUCGGAG |
| 336 | 2609 | CUUUGAGAAGGAUCGCUUU | 3195 | AAAGCGAUCCUUCUCAAAG |
| 337 | 2610 | UUUGAGAAGGAUCGCUUUC | 3196 | GAAAGCGAUCCUUCUCAAA |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 338 | 2611 | UUGAGAAGGAUCGCUUUCC | 3197 | GGAAAGCGAUCCUUCUCAA |
| 339 | 2612 | UGAGAAGGAUCGCUUUCCA | 3198 | UGGAAAGCGAUCCUUCUCA |
| 340 | 2613 | GAGAAGGAUCGCUUUCCAG | 3199 | CUGGAAAGCGAUCCUUCUC |
| 341 | 2614 | AGAAGGAUCGCUUUCCAGG | 3200 | CCUGGAAAGCGAUCCUUCU |
| 342 | 2615 | GAAGGAUCGCUUUCCAGGC | 3201 | GCCUGGAAAGCGAUCCUUC |
| 343 | 2616 | AAGGAUCGCUUUCCAGGCA | 3202 | UGCCUGGAAAGCGAUCCUU |
| 344 | 2617 | AGGAUCGCUUUCCAGGCAU | 3203 | AUGCCUGGAAAGCGAUCCU |
| 345 | 2618 | GGAUCGCUUUCCAGGCAUC | 3204 | GAUGCCUGGAAAGCGAUCC |
| 346 | 2619 | GAUCGCUUUCCAGGCAUCG | 3205 | CGAUGCCUGGAAAGCGAUC |
| 347 | 2620 | AUCGCUUUCCAGGCAUCGC | 3206 | GCGAUGCCUGGAAAGCGAU |
| 348 | 2621 | UCGCUUUCCAGGCAUCGCC | 3207 | GGCGAUGCCUGGAAAGCGA |
| 349 | 2622 | CGCUUUCCAGGCAUCGCCG | 3208 | CGGCGAUGCCUGGAAAGCG |
| 350 | 2623 | GCUUUCCAGGCAUCGCCGC | 3209 | GCGGCGAUGCCUGGAAAGC |
| 351 | 2624 | CUUUCCAGGCAUCGCCGCC | 3210 | GGCGGCGAUGCCUGGAAAG |
| 352 | 2625 | UUUCCAGGCAUCGCCGCCC | 3211 | GGGCGGCGAUGCCUGGAAA |
| 353 | 2626 | UUCCAGGCAUCGCCGCCCG | 3212 | CGGGCGGCGAUGCCUGGAA |
| 369 | 2627 | CCGGGAGGAGCUGGCCAGA | 3213 | UCUGGCCAGCUCCUCCCGG |
| 370 | 2628 | CGGGAGGAGCUGGCCAGAG | 3214 | CUCUGGCCAGCUCCUCCCG |
| 371 | 2629 | GGGAGGAGCUGGCCAGAGA | 3215 | UCUCUGGCCAGCUCCUCCC |
| 372 | 2630 | GGAGGAGCUGGCCAGAGAG | 3216 | CUCUCUGGCCAGCUCCUCC |
| 373 | 2631 | GAGGAGCUGGCCAGAGAGA | 3217 | UCUCUCUGGCCAGCUCCUC |
| 374 | 2632 | AGGAGCUGGCCAGAGAGAC | 3218 | GUCUCUCUGGCCAGCUCCU |
| 375 | 2633 | GGAGCUGGCCAGAGAGACG | 3219 | CGUCUCUCUGGCCAGCUCC |
| 376 | 2634 | GAGCUGGCCAGAGAGACGG | 3220 | CCGUCUCUCUGGCCAGCUC |
| 377 | 2635 | AGCUGGCCAGAGAGACGGG | 3221 | CCCGUCUCUCUGGCCAGCU |
| 378 | 2636 | GCUGGCCAGAGAGACGGGC | 3222 | GCCCGUCUCUCUGGCCAGC |
| 382 | 2637 | GCCAGAGAGACGGGCCUCC | 3223 | GGAGGCCCGUCUCUCUGGC |
| 383 | 2638 | CCAGAGAGACGGGCCUCCC | 3224 | GGGAGGCCCGUCUCUCUGG |
| 384 | 2639 | CAGAGAGACGGGCCUCCCG | 3225 | CGGGAGGCCCGUCUCUCUG |
| 385 | 2640 | AGAGAGACGGGCCUCCCGG | 3226 | CCGGGAGGCCCGUCUCUCU |
| 394 | 2641 | GGCCUCCCGGAGUCCAGGA | 3227 | UCCUGGACUCCGGGAGGCC |
| 395 | 2642 | GCCUCCCGGAGUCCAGGAU | 3228 | AUCCUGGACUCCGGGAGGC |
| 396 | 2643 | CCUCCCGGAGUCCAGGAUU | 3229 | AAUCCUGGACUCCGGGAGG |
| 397 | 2644 | CUCCCGGAGUCCAGGAUUC | 3230 | GAAUCCUGGACUCCGGGAG |
| 398 | 2645 | UCCCGGAGUCCAGGAUUCA | 3231 | UGAAUCCUGGACUCCGGGA |
| 399 | 2646 | CCCGGAGUCCAGGAUUCAG | 3232 | CUGAAUCCUGGACUCCGGG |
| 400 | 2647 | CCGGAGUCCAGGAUUCAGA | 3233 | UCUGAAUCCUGGACUCCGG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 401 | 2648 | CGGAGUCCAGGAUUCAGAU | 3234 | AUCUGAAUCCUGGACUCCG |
| 402 | 2649 | GGAGUCCAGGAUUCAGAUC | 3235 | GAUCUGAAUCCUGGACUCC |
| 403 | 2650 | GAGUCCAGGAUUCAGAUCU | 3236 | AGAUCUGAAUCCUGGACUC |
| 404 | 2651 | AGUCCAGGAUUCAGAUCUG | 3237 | CAGAUCUGAAUCCUGGACU |
| 408 | 2652 | CAGGAUUCAGAUCUGGUUU | 3238 | AAACCAGAUCUGAAUCCUG |
| 409 | 2653 | AGGAUUCAGAUCUGGUUUC | 3239 | GAAACCAGAUCUGAAUCCU |
| 410 | 2654 | GGAUUCAGAUCUGGUUUCA | 3240 | UGAAACCAGAUCUGAAUCC |
| 411 | 2655 | GAUUCAGAUCUGGUUUCAG | 3241 | CUGAAACCAGAUCUGAAUC |
| 412 | 2656 | AUUCAGAUCUGGUUUCAGA | 3242 | UCUGAAACCAGAUCUGAAU |
| 420 | 2657 | CUGGUUUCAGAAUCGAAGG | 3243 | CCUUCGAUUCUGAAACCAG |
| 421 | 2658 | UGGUUUCAGAAUCGAAGGG | 3244 | CCCUUCGAUUCUGAAACCA |
| 422 | 2659 | GGUUUCAGAAUCGAAGGGC | 3245 | GCCCUUCGAUUCUGAAACC |
| 423 | 2660 | GUUUCAGAAUCGAAGGGCC | 3246 | GGCCCUUCGAUUCUGAAAC |
| 424 | 2661 | UUUCAGAAUCGAAGGGCCA | 3247 | UGGCCCUUCGAUUCUGAAA |
| 425 | 2662 | UUCAGAAUCGAAGGGCCAG | 3248 | CUGGCCCUUCGAUUCUGAA |
| 426 | 2663 | UCAGAAUCGAAGGGCCAGG | 3249 | CCUGGCCCUUCGAUUCUGA |
| 427 | 2664 | CAGAAUCGAAGGGCCAGGC | 3250 | GCCUGGCCCUUCGAUUCUG |
| 428 | 2665 | AGAAUCGAAGGGCCAGGCA | 3251 | UGCCUGGCCCUUCGAUUCU |
| 429 | 2666 | GAAUCGAAGGGCCAGGCAC | 3252 | GUGCCUGGCCCUUCGAUUC |
| 430 | 2667 | AAUCGAAGGGCCAGGCACC | 3253 | GGUGCCUGGCCCUUCGAUU |
| 431 | 2668 | AUCGAAGGGCCAGGCACCC | 3254 | GGGUGCCUGGCCCUUCGAU |
| 432 | 2669 | UCGAAGGGCCAGGCACCCG | 3255 | CGGGUGCCUGGCCCUUCGA |
| 509 | 2670 | GGGGUCACCCUGCUCCCUC | 3256 | GAGGGAGCAGGGUGACCCC |
| 510 | 2671 | GGGUCACCCUGCUCCCUCG | 3257 | CGAGGGAGCAGGGUGACCC |
| 511 | 2672 | GGUCACCCUGCUCCCUCGU | 3258 | ACGAGGGAGCAGGGUGACC |
| 512 | 2673 | GUCACCCUGCUCCCUCGUG | 3259 | CACGAGGGAGCAGGGUGAC |
| 513 | 2674 | UCACCCUGCUCCCUCGUGG | 3260 | CCACGAGGGAGCAGGGUGA |
| 514 | 2675 | CACCCUGCUCCCUCGUGGG | 3261 | CCCACGAGGGAGCAGGGUG |
| 516 | 2676 | CCCUGCUCCCUCGUGGGUC | 857 | GACCCACGAGGGAGCAGGG |
| 517 | 2677 | CCUGCUCCCUCGUGGGUCG | 858 | CGACCCACGAGGGAGCAGG |
| 518 | 2678 | CUGCUCCCUCGUGGGUCGC | 859 | GCGACCCACGAGGGAGCAG |
| 519 | 2679 | UGCUCCCUCGUGGGUCGCC | 860 | GGCGACCCACGAGGGAGCA |
| 520 | 2680 | GCUCCCUCGUGGGUCGCCU | 861 | AGGCGACCCACGAGGGAGC |
| 521 | 2681 | CUCCCUCGUGGGUCGCCUU | 862 | AAGGCGACCCACGAGGGAG |
| 522 | 2682 | UCCCUCGUGGGUCGCCUUC | 863 | GAAGGCGACCCACGAGGGA |
| 523 | 2683 | CCCUCGUGGGUCGCCUUCG | 864 | CGAAGGCGACCCACGAGGG |
| 524 | 2684 | CCUCGUGGGUCGCCUUCGC | 865 | GCGAAGGCGACCCACGAGG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 525 | 2685 | CUCGUGGGUCGCCUUCGCC | 866 | GGCGAAGGCGACCCACGAG |
| 526 | 2686 | UCGUGGGUCGCCUUCGCCC | 867 | GGGCGAAGGCGACCCACGA |
| 530 | 2687 | GGGUCGCCUUCGCCCACAC | 3262 | GUGUGGGCGAAGGCGACCC |
| 531 | 2688 | GGUCGCCUUCGCCCACACC | 3263 | GGUGUGGGCGAAGGCGACC |
| 532 | 2689 | GUCGCCUUCGCCCACACCG | 3264 | CGGUGUGGGCGAAGGCGAC |
| 533 | 2690 | UCGCCUUCGCCCACACCGG | 3265 | CCGGUGUGGGCGAAGGCGA |
| 544 | 2691 | CACACCGGCGCGUGGGGAA | 3266 | UUCCCCACGCGCCGGUGUG |
| 545 | 2692 | ACACCGGCGCGUGGGGAAC | 3267 | GUUCCCCACGCGCCGGUGU |
| 552 | 2693 | CGCGUGGGGAACGGGGCUU | 3268 | AAGCCCCGUUCCCCACGCG |
| 553 | 2694 | GCGUGGGGAACGGGGCUUC | 3269 | GAAGCCCCGUUCCCCACGC |
| 566 | 2695 | GGCUUCCCGCACCCCACGU | 3270 | ACGUGGGGUGCGGGAAGCC |
| 567 | 2696 | GCUUCCCGCACCCCACGUG | 3271 | CACGUGGGGUGCGGGAAGC |
| 619 | 2697 | UUCGUGAGCCAGGCAGCGA | 3272 | UCGCUGCCUGGCUCACGAA |
| 620 | 2698 | UCGUGAGCCAGGCAGCGAG | 3273 | CUCGCUGCCUGGCUCACGA |
| 621 | 2699 | CGUGAGCCAGGCAGCGAGG | 3274 | CCUCGCUGCCUGGCUCACG |
| 622 | 2700 | GUGAGCCAGGCAGCGAGGG | 3275 | CCCUCGCUGCCUGGCUCAC |
| 671 | 2701 | CGCCGGCAGAGGGGAUCUC | 3276 | GAGAUCCCCUCUGCCGGCG |
| 672 | 2702 | GCCGGCAGAGGGGAUCUCC | 3277 | GGAGAUCCCCUCUGCCGGC |
| 673 | 2703 | CCGGCAGAGGGGAUCUCCC | 3278 | GGGAGAUCCCCUCUGCCGG |
| 674 | 2704 | CGGCAGAGGGGAUCUCCCA | 3279 | UGGGAGAUCCCCUCUGCCG |
| 675 | 2705 | GGCAGAGGGGAUCUCCCAA | 3280 | UUGGGAGAUCCCCUCUGCC |
| 683 | 2706 | GGAUCUCCCAACCUGCCCC | 3281 | GGGGCAGGUUGGGAGAUCC |
| 684 | 2707 | GAUCUCCCAACCUGCCCCG | 3282 | CGGGGCAGGUUGGGAGAUC |
| 685 | 2708 | AUCUCCCAACCUGCCCCGG | 3283 | CCGGGGCAGGUUGGGAGAU |
| 686 | 2709 | UCUCCCAACCUGCCCCGGC | 3284 | GCCGGGGCAGGUUGGGAGA |
| 706 | 2710 | CGCGGGGAUUUCGCCUACG | 3285 | CGUAGGCGAAAUCCCCGCG |
| 707 | 2711 | GCGGGGAUUUCGCCUACGC | 3286 | GCGUAGGCGAAAUCCCCGC |
| 708 | 2712 | CGGGGAUUUCGCCUACGCC | 3287 | GGCGUAGGCGAAAUCCCCG |
| 709 | 2713 | GGGGAUUUCGCCUACGCCG | 3288 | CGGCGUAGGCGAAAUCCCC |
| 710 | 2714 | GGGAUUUCGCCUACGCCGC | 3289 | GCGGCGUAGGCGAAAUCCC |
| 711 | 2715 | GGAUUUCGCCUACGCCGCC | 3290 | GGCGGCGUAGGCGAAAUCC |
| 712 | 2716 | GAUUUCGCCUACGCCGCCC | 3291 | GGGCGGCGUAGGCGAAAUC |
| 713 | 2717 | AUUUCGCCUACGCCGCCCC | 3292 | GGGGCGGCGUAGGCGAAAU |
| 714 | 2718 | UUUCGCCUACGCCGCCCCG | 3293 | CGGGGCGGCGUAGGCGAAA |
| 746 | 2719 | GGGCGCUCUCCCACCCUCA | 3294 | UGAGGGUGGGAGAGCGCCC |
| 747 | 2720 | GGCGCUCUCCCACCCUCAG | 3295 | CUGAGGGUGGGAGAGCGCC |
| 748 | 2721 | GCGCUCUCCCACCCUCAGG | 3296 | CCUGAGGGUGGGAGAGCGC |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 749 | 2722 | CGCUCUCCCACCCUCAGGC | 3297 | GCCUGAGGGUGGGAGAGCG |
| 750 | 2723 | GCUCUCCCACCCUCAGGCU | 3298 | AGCCUGAGGGUGGGAGAGC |
| 751 | 2724 | CUCUCCCACCCUCAGGCUC | 3299 | GAGCCUGAGGGUGGGAGAG |
| 752 | 2725 | UCUCCCACCCUCAGGCUCC | 3300 | GGAGCCUGAGGGUGGGAGA |
| 753 | 2726 | CUCCCACCCUCAGGCUCCU | 3301 | AGGAGCCUGAGGGUGGGAG |
| 754 | 2727 | UCCCACCCUCAGGCUCCUC | 3302 | GAGGAGCCUGAGGGUGGGA |
| 755 | 2728 | CCCACCCUCAGGCUCCUCG | 3303 | CGAGGAGCCUGAGGGUGGG |
| 756 | 2729 | CCACCCUCAGGCUCCUCGG | 3304 | CCGAGGAGCCUGAGGGUGG |
| 757 | 2730 | CACCCUCAGGCUCCUCGGU | 3305 | ACCGAGGAGCCUGAGGGUG |
| 758 | 2731 | ACCCUCAGGCUCCUCGGUG | 3306 | CACCGAGGAGCCUGAGGGU |
| 759 | 2732 | CCCUCAGGCUCCUCGGUGG | 3307 | CCACCGAGGAGCCUGAGGG |
| 760 | 2733 | CCUCAGGCUCCUCGGUGGC | 3308 | GCCACCGAGGAGCCUGAGG |
| 761 | 2734 | CUCAGGCUCCUCGGUGGCC | 3309 | GGCCACCGAGGAGCCUGAG |
| 767 | 2735 | CUCCUCGGUGGCCUCCGCA | 3310 | UGCGGAGGCCACCGAGGAG |
| 768 | 2736 | UCCUCGGUGGCCUCCGCAC | 3311 | GUGCGGAGGCCACCGAGGA |
| 777 | 2737 | GCCUCCGCACCCGGGCAAA | 3312 | UUUGCCCGGGUGCGGAGGC |
| 778 | 2738 | CCUCCGCACCCGGGCAAAA | 3313 | UUUUGCCCGGGUGCGGAGG |
| 779 | 2739 | CUCCGCACCCGGGCAAAAG | 3314 | CUUUUGCCCGGGUGCGGAG |
| 780 | 2740 | UCCGCACCCGGGCAAAAGC | 3315 | GCUUUUGCCCGGGUGCGGA |
| 781 | 316 | CCGCACCCGGGCAAAAGCC | 3316 | GGCUUUUGCCCGGGUGCGG |
| 782 | 317 | CGCACCCGGGCAAAAGCCG | 3317 | CGGCUUUUGCCCGGGUGCG |
| 788 | 318 | CGGGCAAAAGCCGGGAGGA | 3318 | UCCUCCCGGCUUUUGCCCG |
| 789 | 319 | GGGCAAAAGCCGGGAGGAC | 3319 | GUCCUCCCGGCUUUUGCCC |
| 790 | 320 | GGCAAAAGCCGGGAGGACC | 3320 | GGUCCUCCCGGCUUUUGCC |
| 791 | 321 | GCAAAAGCCGGGAGGACCG | 3321 | CGGUCCUCCCGGCUUUUGC |
| 840 | 2741 | CUGCGCGGUGGCACAGCCU | 3322 | AGGCUGUGCCACCGCGCAG |
| 841 | 2742 | UGCGCGGUGGCACAGCCUG | 3323 | CAGGCUGUGCCACCGCGCA |
| 851 | 2743 | CACAGCCUGGGCCCGCUCA | 3324 | UGAGCGGGCCCAGGCUGUG |
| 852 | 2744 | ACAGCCUGGGCCCGCUCAA | 3325 | UUGAGCGGGCCCAGGCUGU |
| 853 | 2745 | CAGCCUGGGCCCGCUCAAG | 3326 | CUUGAGCGGGCCCAGGCUG |
| 854 | 2746 | AGCCUGGGCCCGCUCAAGC | 3327 | GCUUGAGCGGGCCCAGGCU |
| 878 | 2747 | CGCAGGGCCAAGGGGUGCU | 3328 | AGCACCCCUUGGCCCUGCG |
| 879 | 2748 | GCAGGGCCAAGGGGUGCUU | 3329 | AAGCACCCCUUGGCCCUGC |
| 901 | 2749 | CCACCCACGUCCCAGGGGA | 3330 | UCCCCUGGGACGUGGGUGG |
| 902 | 2750 | CACCCACGUCCCAGGGGAG | 3331 | CUCCCCUGGGACGUGGGUG |
| 903 | 2751 | ACCCACGUCCCAGGGGAGU | 3332 | ACUCCCCUGGGACGUGGGU |
| 911 | 2752 | CCCAGGGGAGUCCGUGGUG | 3333 | CACCACGGACUCCCCUGGG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 912 | 2753 | CCAGGGGAGUCCGUGGUGG | 3334 | CCACCACGGACUCCCCUGG |
| 913 | 2754 | CAGGGGAGUCCGUGGUGGG | 3335 | CCCACCACGGACUCCCCUG |
| 914 | 2755 | AGGGGAGUCCGUGGUGGGG | 3336 | CCCCACCACGGACUCCCCU |
| 960 | 2756 | GGCGGCGUGGGAACCCCAA | 3337 | UUGGGGUUCCCACGCCGCC |
| 975 | 2757 | CCAAGCCGGGGCAGCUCCA | 3338 | UGGAGCUGCCCCGGCUUGG |
| 976 | 2758 | CAAGCCGGGGCAGCUCCAC | 3339 | GUGGAGCUGCCCCGGCUUG |
| 977 | 2759 | AAGCCGGGGCAGCUCCACC | 3340 | GGUGGAGCUGCCCCGGCUU |
| 983 | 2760 | GGGCAGCUCCACCUCCCCA | 3341 | UGGGGAGGUGGAGCUGCCC |
| 984 | 2761 | GGCAGCUCCACCUCCCCAG | 3342 | CUGGGGAGGUGGAGCUGCC |
| 985 | 2762 | GCAGCUCCACCUCCCCAGC | 3343 | GCUGGGGAGGUGGAGCUGC |
| 986 | 2763 | CAGCUCCACCUCCCCAGCC | 3344 | GGCUGGGGAGGUGGAGCUG |
| 1031 | 2764 | CGCGGCAGGGGCAGAUGCA | 3345 | UGCAUCUGCCCCUGCCGCG |
| 1033 | 2765 | CGGCAGGGGCAGAUGCAAG | 3346 | CUUGCAUCUGCCCCUGCCG |
| 1034 | 2766 | GGCAGGGGCAGAUGCAAGG | 3347 | CCUUGCAUCUGCCCCUGCC |
| 1035 | 2767 | GCAGGGGCAGAUGCAAGGC | 3348 | GCCUUGCAUCUGCCCCUGC |
| 1036 | 2768 | CAGGGGCAGAUGCAAGGCA | 3349 | UGCCUUGCAUCUGCCCCUG |
| 1037 | 2769 | AGGGGCAGAUGCAAGGCAU | 3350 | AUGCCUUGCAUCUGCCCCU |
| 1046 | 2770 | UGCAAGGCAUCCCGGCGCC | 3351 | GGCGCCGGGAUGCCUUGCA |
| 1048 | 2771 | CAAGGCAUCCCGGCGCCCU | 3352 | AGGGCGCCGGGAUGCCUUG |
| 1049 | 2772 | AAGGCAUCCCGGCGCCCUC | 3353 | GAGGGCGCCGGGAUGCCUU |
| 1064 | 2773 | CCUCCCAGGCGCUCCAGGA | 3354 | UCCUGGAGCGCCUGGGAGG |
| 1086 | 2774 | GGCGCCCUGGUCUGCACUC | 3355 | GAGUGCAGACCAGGGCGCC |
| 1087 | 2775 | GCGCCCUGGUCUGCACUCC | 3356 | GGAGUGCAGACCAGGGCGC |
| 1088 | 2776 | CGCCCUGGUCUGCACUCCC | 3357 | GGGAGUGCAGACCAGGGCG |
| 1089 | 2777 | GCCCUGGUCUGCACUCCCC | 3358 | GGGGAGUGCAGACCAGGGC |
| 1090 | 2778 | CCCUGGUCUGCACUCCCCU | 3359 | AGGGGAGUGCAGACCAGGG |
| 1091 | 2779 | CCUGGUCUGCACUCCCCUG | 3360 | CAGGGGAGUGCAGACCAGG |
| 1092 | 2780 | CUGGUCUGCACUCCCCUGC | 3361 | GCAGGGGAGUGCAGACCAG |
| 1093 | 2781 | UGGUCUGCACUCCCCUGCG | 3362 | CGCAGGGGAGUGCAGACCA |
| 1094 | 2782 | GGUCUGCACUCCCCUGCGG | 3363 | CCGCAGGGGAGUGCAGACC |
| 1095 | 2783 | GUCUGCACUCCCCUGCGGC | 3364 | GCCGCAGGGGAGUGCAGAC |
| 1096 | 2784 | UCUGCACUCCCCUGCGGCC | 3365 | GGCCGCAGGGGAGUGCAGA |
| 1097 | 2785 | CUGCACUCCCCUGCGGCCU | 3366 | AGGCCGCAGGGGAGUGCAG |
| 1098 | 2786 | UGCACUCCCCUGCGGCCUG | 3367 | CAGGCCGCAGGGGAGUGCA |
| 1100 | 2787 | CACUCCCCUGCGGCCUGCU | 3368 | AGCAGGCCGCAGGGGAGUG |
| 1101 | 2788 | ACUCCCCUGCGGCCUGCUG | 3369 | CAGCAGGCCGCAGGGGAGU |
| 1103 | 2789 | UCCCCUGCGGCCUGCUGCU | 976 | AGCAGCAGGCCGCAGGGGA |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1106 | 2790 | CCUGCGGCCUGCUGCUGGA | 3370 | UCCAGCAGCAGGCCGCAGG |
| 1107 | 2791 | CUGCGGCCUGCUGCUGGAU | 3371 | AUCCAGCAGCAGGCCGCAG |
| 1108 | 2792 | UGCGGCCUGCUGCUGGAUG | 3372 | CAUCCAGCAGCAGGCCGCA |
| 1109 | 2793 | GCGGCCUGCUGCUGGAUGA | 3373 | UCAUCCAGCAGCAGGCCGC |
| 1110 | 2794 | CGGCCUGCUGCUGGAUGAG | 3374 | CUCAUCCAGCAGCAGGCCG |
| 1111 | 2795 | GGCCUGCUGCUGGAUGAGC | 3375 | GCUCAUCCAGCAGCAGGCC |
| 1112 | 2796 | GCCUGCUGCUGGAUGAGCU | 3376 | AGCUCAUCCAGCAGCAGGC |
| 1113 | 2797 | CCUGCUGCUGGAUGAGCUC | 3377 | GAGCUCAUCCAGCAGCAGG |
| 1114 | 2798 | CUGCUGCUGGAUGAGCUCC | 3378 | GGAGCUCAUCCAGCAGCAG |
| 1115 | 2799 | UGCUGCUGGAUGAGCUCCU | 3379 | AGGAGCUCAUCCAGCAGCA |
| 1116 | 2800 | GCUGCUGGAUGAGCUCCUG | 3380 | CAGGAGCUCAUCCAGCAGC |
| 1117 | 2801 | CUGCUGGAUGAGCUCCUGG | 3381 | CCAGGAGCUCAUCCAGCAG |
| 1118 | 2802 | UGCUGGAUGAGCUCCUGGC | 3382 | GCCAGGAGCUCAUCCAGCA |
| 1119 | 2803 | GCUGGAUGAGCUCCUGGCG | 3383 | CGCCAGGAGCUCAUCCAGC |
| 1130 | 2804 | UCCUGGCGAGCCCGGAGUU | 3384 | AACUCCGGGCUCGCCAGGA |
| 1131 | 2805 | CCUGGCGAGCCCGGAGUUU | 3385 | AAACUCCGGGCUCGCCAGG |
| 1132 | 2806 | CUGGCGAGCCCGGAGUUUC | 3386 | GAAACUCCGGGCUCGCCAG |
| 1137 | 2807 | GAGCCCGGAGUUUCUGCAG | 3387 | CUGCAGAAACUCCGGGCUC |
| 1138 | 2808 | AGCCCGGAGUUUCUGCAGC | 3388 | GCUGCAGAAACUCCGGGCU |
| 1139 | 2809 | GCCCGGAGUUUCUGCAGCA | 3389 | UGCUGCAGAAACUCCGGGC |
| 1140 | 2810 | CCCGGAGUUUCUGCAGCAG | 3390 | CUGCUGCAGAAACUCCGGG |
| 1141 | 2811 | CCGGAGUUUCUGCAGCAGG | 3391 | CCUGCUGCAGAAACUCCGG |
| 1142 | 2812 | CGGAGUUUCUGCAGCAGGC | 3392 | GCCUGCUGCAGAAACUCCG |
| 1143 | 2813 | GGAGUUUCUGCAGCAGGCG | 3393 | CGCCUGCUGCAGAAACUCC |
| 1144 | 2814 | GAGUUUCUGCAGCAGGCGC | 3394 | GCGCCUGCUGCAGAAACUC |
| 1145 | 2815 | AGUUUCUGCAGCAGGCGCA | 3395 | UGCGCCUGCUGCAGAAACU |
| 1146 | 2816 | GUUUCUGCAGCAGGCGCAA | 3396 | UUGCGCCUGCUGCAGAAAC |
| 1147 | 2817 | UUUCUGCAGCAGGCGCAAC | 3397 | GUUGCGCCUGCUGCAGAAA |
| 1148 | 2818 | UUCUGCAGCAGGCGCAACC | 3398 | GGUUGCGCCUGCUGCAGAA |
| 1149 | 2819 | UCUGCAGCAGGCGCAACCU | 3399 | AGGUUGCGCCUGCUGCAGA |
| 1150 | 2820 | CUGCAGCAGGCGCAACCUC | 3400 | GAGGUUGCGCCUGCUGCAG |
| 1151 | 2821 | UGCAGCAGGCGCAACCUCU | 3401 | AGAGGUUGCGCCUGCUGCA |
| 1152 | 2822 | GCAGCAGGCGCAACCUCUC | 3402 | GAGAGGUUGCGCCUGCUGC |
| 1153 | 2823 | CAGCAGGCGCAACCUCUCC | 3403 | GGAGAGGUUGCGCCUGCUG |
| 1154 | 2824 | AGCAGGCGCAACCUCUCCU | 3404 | AGGAGAGGUUGCGCCUGCU |
| 1155 | 2825 | GCAGGCGCAACCUCUCCUA | 3405 | UAGGAGAGGUUGCGCCUGC |
| 1156 | 2826 | CAGGCGCAACCUCUCCUAG | 3406 | CUAGGAGAGGUUGCGCCUG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1157 | 2827 | AGGCGCAACCUCUCCUAGA | 3407 | UCUAGGAGAGGUUGCGCCU |
| 1158 | 2828 | GGCGCAACCUCUCCUAGAA | 3408 | UUCUAGGAGAGGUUGCGCC |
| 1159 | 2829 | GCGCAACCUCUCCUAGAAA | 3409 | UUUCUAGGAGAGGUUGCGC |
| 1160 | 2830 | CGCAACCUCUCCUAGAAAC | 3410 | GUUUCUAGGAGAGGUUGCG |
| 1161 | 2831 | GCAACCUCUCCUAGAAACG | 3411 | CGUUUCUAGGAGAGGUUGC |
| 1162 | 2832 | CAACCUCUCCUAGAAACGG | 3412 | CCGUUUCUAGGAGAGGUUG |
| 1163 | 2833 | AACCUCUCCUAGAAACGGA | 3413 | UCCGUUUCUAGGAGAGGUU |
| 1169 | 2834 | UCCUAGAAACGGAGGCCCC | 3414 | GGGGCCUCCGUUUCUAGGA |
| 1170 | 2835 | CCUAGAAACGGAGGCCCCG | 3415 | CGGGGCCUCCGUUUCUAGG |
| 1171 | 2836 | CUAGAAACGGAGGCCCCGG | 3416 | CCGGGGCCUCCGUUUCUAG |
| 1428 | 2837 | CCGGUGAGAGACUCCACUC | 3417 | GAGUGGAGUCUCUCACCGG |
| 1429 | 2838 | CGGUGAGAGACUCCACUCC | 3418 | GGAGUGGAGUCUCUCACCG |
| 1430 | 2839 | GGUGAGAGACUCCACUCCG | 3419 | CGGAGUGGAGUCUCUCACC |
| 1570 | 2840 | CCCUUGUUCUUCCGUGAAA | 3420 | UUUCACGGAAGAACAAGGG |
| 1571 | 2841 | CCUUGUUCUUCCGUGAAAU | 3421 | AUUUCACGGAAGAACAAGG |
| 1572 | 2842 | CUUGUUCUUCCGUGAAAUU | 3422 | AAUUUCACGGAAGAACAAG |
| 1573 | 2843 | UUGUUCUUCCGUGAAAUUC | 3423 | GAAUUUCACGGAAGAACAA |
| 1574 | 2844 | UGUUCUUCCGUGAAAUUCU | 3424 | AGAAUUUCACGGAAGAACA |
| 1575 | 2845 | GUUCUUCCGUGAAAUUCUG | 3425 | CAGAAUUUCACGGAAGAAC |
| 1576 | 2846 | UUCUUCCGUGAAAUUCUGG | 3426 | CCAGAAUUUCACGGAAGAA |
| 1577 | 2847 | UCUUCCGUGAAAUUCUGGC | 3427 | GCCAGAAUUUCACGGAAGA |
| 1578 | 2848 | CUUCCGUGAAAUUCUGGCU | 3428 | AGCCAGAAUUUCACGGAAG |
| 1589 | 2849 | UUCUGGCUGAAUGUCUCCC | 3429 | GGGAGACAUUCAGCCAGAA |
| 1590 | 2850 | UCUGGCUGAAUGUCUCCCC | 3430 | GGGGAGACAUUCAGCCAGA |
| 1618 | 2851 | GACGCUGUCUAGGCAAACC | 3431 | GGUUUGCCUAGACAGCGUC |
| 1619 | 2852 | ACGCUGUCUAGGCAAACCU | 3432 | AGGUUUGCCUAGACAGCGU |
| 1620 | 2853 | CGCUGUCUAGGCAAACCUG | 3433 | CAGGUUUGCCUAGACAGCG |
| 1621 | 2854 | GCUGUCUAGGCAAACCUGG | 3434 | CCAGGUUUGCCUAGACAGC |
| 1622 | 2855 | CUGUCUAGGCAAACCUGGA | 3435 | UCCAGGUUUGCCUAGACAG |
| 1623 | 2856 | UGUCUAGGCAAACCUGGAU | 3436 | AUCCAGGUUUGCCUAGACA |
| 1624 | 2857 | GUCUAGGCAAACCUGGAUU | 3437 | AAUCCAGGUUUGCCUAGAC |
| 1625 | 2858 | UCUAGGCAAACCUGGAUUA | 3438 | UAAUCCAGGUUUGCCUAGA |
| 1626 | 2859 | CUAGGCAAACCUGGAUUAG | 3439 | CUAAUCCAGGUUUGCCUAG |
| 1627 | 2860 | UAGGCAAACCUGGAUUAGA | 3440 | UCUAAUCCAGGUUUGCCUA |
| 1628 | 2861 | AGGCAAACCUGGAUUAGAG | 3441 | CUCUAAUCCAGGUUUGCCU |
| 1629 | 2862 | GGCAAACCUGGAUUAGAGU | 3442 | ACUCUAAUCCAGGUUUGCC |
| 1630 | 2863 | GCAAACCUGGAUUAGAGUU | 3443 | AACUCUAAUCCAGGUUUGC |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1631 | 2864 | CAAACCUGGAUUAGAGUUA | 3444 | UAACUCUAAUCCAGGUUUG |
| 1632 | 2865 | AAACCUGGAUUAGAGUUAC | 3445 | GUAACUCUAAUCCAGGUUU |
| 1633 | 2866 | AACCUGGAUUAGAGUUACA | 3446 | UGUAACUCUAAUCCAGGUU |
| 1634 | 2867 | ACCUGGAUUAGAGUUACAU | 3447 | AUGUAACUCUAAUCCAGGU |
| 1635 | 2868 | CCUGGAUUAGAGUUACAUC | 3448 | GAUGUAACUCUAAUCCAGG |
| 1636 | 2869 | CUGGAUUAGAGUUACAUCU | 3449 | AGAUGUAACUCUAAUCCAG |
| 1637 | 2870 | UGGAUUAGAGUUACAUCUC | 3450 | GAGAUGUAACUCUAAUCCA |
| 1638 | 2871 | GGAUUAGAGUUACAUCUCC | 3451 | GGAGAUGUAACUCUAAUCC |
| 1639 | 2872 | GAUUAGAGUUACAUCUCCU | 3452 | AGGAGAUGUAACUCUAAUC |
| 1640 | 2873 | AUUAGAGUUACAUCUCCUG | 3453 | CAGGAGAUGUAACUCUAAU |
| 1641 | 2874 | UUAGAGUUACAUCUCCUGG | 3454 | CCAGGAGAUGUAACUCUAA |
| 1642 | 2875 | UAGAGUUACAUCUCCUGGA | 3455 | UCCAGGAGAUGUAACUCUA |
| 1643 | 2876 | AGAGUUACAUCUCCUGGAU | 3456 | AUCCAGGAGAUGUAACUCU |
| 1651 | 2877 | AUCUCCUGGAUGAUUAGUU | 3457 | AACUAAUCAUCCAGGAGAU |
| 1652 | 2878 | UCUCCUGGAUGAUUAGUUC | 3458 | GAACUAAUCAUCCAGGAGA |
| 1653 | 2879 | CUCCUGGAUGAUUAGUUCA | 3459 | UGAACUAAUCAUCCAGGAG |
| 1654 | 2880 | UCCUGGAUGAUUAGUUCAG | 3460 | CUGAACUAAUCAUCCAGGA |
| 1655 | 2881 | CCUGGAUGAUUAGUUCAGA | 3461 | UCUGAACUAAUCAUCCAGG |
| 1656 | 2882 | CUGGAUGAUUAGUUCAGAG | 3462 | CUCUGAACUAAUCAUCCAG |
| 26 | 2883 | GCACCCUCCCCGCGGAAGC | 3463 | GCUUCCGCGGGGAGGGUGC |
| 27 | 2884 | CACCCUCCCCGCGGAAGCC | 3464 | GGCUUCCGCGGGGAGGGUG |
| 28 | 2885 | ACCCUCCCCGCGGAAGCCC | 3465 | GGGCUUCCGCGGGGAGGGU |
| 30 | 2886 | CCUCCCCGCGGAAGCCCGG | 3466 | CCGGGCUUCCGCGGGGAGG |
| 35 | 468 | CCGCGGAAGCCCGGGGACG | 3467 | CGUCCCCGGGCUUCCGCGG |
| 37 | 469 | GCGGAAGCCCGGGGACGAG | 3468 | CUCGUCCCCGGGCUUCCGC |
| 38 | 470 | CGGAAGCCCGGGGACGAGG | 3469 | CCUCGUCCCCGGGCUUCCG |
| 193 | 2887 | AUUUGGUUUCAGAAUGAGA | 3470 | UCUCAUUCUGAAACCAAAU |
| 233 | 2888 | ACCGGCGGGAAUCUCGGCC | 3471 | GGCCGAGAUUCCCGCCGGU |
| 250 | 2889 | CCCUGGCCCGGGAGACGCG | 3472 | CGCGUCUCCCGGGCCAGGG |
| 251 | 2890 | CCUGGCCCGGGAGACGCGG | 3473 | CCGCGUCUCCCGGGCCAGG |
| 252 | 2891 | CUGGCCCGGGAGACGCGGC | 3474 | GCCGCGUCUCCCGGGCCAG |
| 263 | 476 | GACGCGGCCCGCCAGAAGG | 3475 | CCUUCUGGCGGGCCGCGUC |
| 264 | 477 | ACGCGGCCCGCCAGAAGGC | 3476 | GCCUUCUGGCGGGCCGCGU |
| 279 | 478 | AGGCCGGCGAAAGCGGACC | 3477 | GGUCCGCUUUCGCCGGCCU |
| 280 | 479 | GGCCGGCGAAAGCGGACCG | 3478 | CGGUCCGCUUUCGCCGGCC |
| 281 | 480 | GCCGGCGAAAGCGGACCGC | 3479 | GCGGUCCGCUUUCGCCGGC |
| 317 | 2892 | CCGCCCUGCUCCUCCGAGC | 3480 | GCUCGGAGGAGCAGGGCGG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 355 | 2893 | CCAGGCAUCGCCGCCCGGG | 3481 | CCCGGGCGGCGAUGCCUGG |
| 359 | 2894 | GCAUCGCCGCCCGGGAGGA | 3482 | UCCUCCCGGGCGGCGAUGC |
| 360 | 2895 | CAUCGCCGCCCGGGAGGAG | 3483 | CUCCUCCCGGGGGCGAUG |
| 361 | 2896 | AUCGCCGCCCGGGAGGAGC | 3484 | GCUCCUCCCGGGCGGCGAU |
| 362 | 2897 | UCGCCGCCCGGGAGGAGCU | 3485 | AGCUCCUCCCGGGCGGCGA |
| 363 | 2898 | CGCCGCCCGGGAGGAGCUG | 3486 | CAGCUCCUCCCGGGCGGCG |
| 437 | 488 | GGGCCAGGCACCCGGGACA | 3487 | UGUCCCGGGUGCCUGGCCC |
| 452 | 2899 | GACAGGGUGGCAGGGCGCC | 3488 | GGCGCCCUGCCACCCUGUC |
| 453 | 2900 | ACAGGGUGGCAGGGCGCCC | 3489 | GGGCGCCCUGCCACCCUGU |
| 455 | 2901 | AGGGUGGCAGGGCGCCCGC | 3490 | GCGGGCGCCCUGCCACCCU |
| 456 | 2902 | GGGUGGCAGGGCGCCCGCG | 3491 | CGCGGGCGCCCUGCCACCC |
| 458 | 2903 | GUGGCAGGGCGCCCGCGCA | 3492 | UGCGCGGGCGCCCUGCCAC |
| 480 | 2904 | AGGCGGCCUGUGCAGCGCG | 3493 | CGCGCUGCACAGGCCGCCU |
| 481 | 2905 | GGCGGCCUGUGCAGCGCGG | 3494 | CCGCGCUGCACAGGCCGCC |
| 482 | 2906 | GCGGCCUGUGCAGCGCGGC | 3495 | GCCGCGCUGCACAGGCCGC |
| 534 | 2907 | CGCCUUCGCCCACACCGGC | 3496 | GCCGGUGUGGGCGAAGGCG |
| 546 | 2908 | CACCGGCGCGUGGGGAACG | 3497 | CGUUCCCCACGCGCCGGUG |
| 547 | 2909 | ACCGGCGCGUGGGGAACGG | 3498 | CCGUUCCCCACGCGCCGGU |
| 548 | 2910 | CCGGCGCGUGGGGAACGGG | 3499 | CCCGUUCCCCACGCGCCGG |
| 549 | 2911 | CGGCGCGUGGGGAACGGGG | 3500 | CCCCGUUCCCCACGCGCCG |
| 551 | 2912 | GCGCGUGGGGAACGGGGCU | 3501 | AGCCCCGUUCCCCACGCGC |
| 565 | 2913 | GGGCUUCCCGCACCCCACG | 3502 | CGUGGGGUGCGGGAAGCCC |
| 575 | 2914 | CACCCCACGUGCCCUGCGC | 3503 | GCGCAGGGCACGUGGGGUG |
| 577 | 2915 | CCCCACGUGCCCUGCGCGC | 3504 | GCGCGCAGGGCACGUGGGG |
| 579 | 2916 | CCACGUGCCCUGCGCGCCU | 3505 | AGGCGCGCAGGGCACGUGG |
| 581 | 2917 | ACGUGCCCUGCGCGCCUGG | 3506 | CCAGGCGCGCAGGGCACGU |
| 588 | 2918 | CUGCGCGCCUGGGGCUCUC | 1114 | GAGAGCCCCAGGCGCGCAG |
| 616 | 2919 | GCUUUCGUGAGCCAGGCAG | 3507 | CUGCCUGGCUCACGAAAGC |
| 617 | 2920 | CUUUCGUGAGCCAGGCAGC | 3508 | GCUGCCUGGCUCACGAAAG |
| 618 | 2921 | UUUCGUGAGCCAGGCAGCG | 3509 | CGCUGCCUGGCUCACGAAA |
| 627 | 512 | CCAGGCAGCGAGGGCCGCC | 3510 | GGCGGCCCUCGCUGCCUGG |
| 652 | 2922 | CUGCAGCCCAGCCAGGCCG | 3511 | CGGCCUGGCUGGGCUGCAG |
| 654 | 514 | GCAGCCCAGCCAGGCCGCG | 3512 | CGCGGCCUGGCUGGGCUGC |
| 659 | 515 | CCAGCCAGGCCGCGCCGGC | 3513 | GCCGGCGCGGCCUGGCUGG |
| 668 | 2923 | CCGCGCCGGCAGAGGGGAU | 3514 | AUCCCCUCUGCCGGCGCGG |
| 690 | 2924 | CCAACCUGCCCCGGCGCGC | 3515 | GCGCGCCGGGGCAGGUUGG |
| 692 | 2925 | AACCUGCCCCGGCGCGCGG | 3516 | CCGCGCGCCGGGGCAGGUU |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 705 | 2926 | GCGCGGGGAUUUCGCCUAC | 3517 | GUAGGCGAAAUCCCCGCGC |
| 715 | 2927 | UUCGCCUACGCCGCCCCGG | 3518 | CCGGGGCGGCGUAGGCGAA |
| 717 | 2928 | CGCCUACGCCGCCCCGGCU | 3519 | AGCCGGGGCGGCGUAGGCG |
| 732 | 2929 | GGCUCCUCCGGACGGGGCG | 3520 | CGCCCCGUCCGGAGGAGCC |
| 733 | 2930 | GCUCCUCCGGACGGGGCGC | 3521 | GCGCCCCGUCCGGAGGAGC |
| 745 | 2931 | GGGGCGCUCUCCCACCCUC | 3522 | GAGGGUGGGAGAGCGCCCC |
| 802 | 525 | GAGGACCGGGACCCGCAGC | 3523 | GCUGCGGGUCCCGGUCCUC |
| 809 | 526 | GGGACCCGCAGCGCGACGG | 3524 | CCGUCGCGCUGCGGGUCCC |
| 813 | 2932 | CCCGCAGCGCGACGGCCUG | 3525 | CAGGCCGUCGCGCUGCGGG |
| 827 | 2933 | GCCUGCCGGGCCCCUGCGC | 1134 | GCGCAGGGGCCCGGCAGGC |
| 839 | 2934 | CCUGCGCGGUGGCACAGCC | 3526 | GGCUGUGCCACCGCGCAGG |
| 842 | 2935 | GCGCGGUGGCACAGCCUGG | 3527 | CCAGGCUGUGCCACCGCGC |
| 843 | 2936 | CGCGGUGGCACAGCCUGGG | 3528 | CCCAGGCUGUGCCACCGCG |
| 845 | 2937 | CGGUGGCACAGCCUGGGCC | 3529 | GGCCCAGGCUGUGCCACCG |
| 850 | 2938 | GCACAGCCUGGGCCCGCUC | 3530 | GAGCGGGCCCAGGCUGUGC |
| 856 | 2939 | CCUGGGCCCGCUCAAGCGG | 3531 | CCGCUUGAGCGGGCCCAGG |
| 877 | 2940 | CCGCAGGGCCAAGGGGUGC | 3532 | GCACCCCUUGGCCCUGCGG |
| 892 | 2941 | GUGCUUGCGCCACCCACGU | 3533 | ACGUGGGUGGCGCAAGCAC |
| 893 | 2942 | UGCUUGCGCCACCCACGUC | 3534 | GACGUGGGUGGCGCAAGCA |
| 894 | 2943 | GCUUGCGCCACCCACGUCC | 3535 | GGACGUGGGUGGCGCAAGC |
| 895 | 2944 | CUUGCGCCACCCACGUCCC | 3536 | GGGACGUGGGUGGCGCAAG |
| 897 | 2945 | UGCGCCACCCACGUCCCAG | 3537 | CUGGGACGUGGGUGGCGCA |
| 919 | 2946 | AGUCCGUGGUGGGGCUGGG | 3538 | CCCAGCCCCACCACGGACU |
| 936 | 2947 | GGGCCGGGGUCCCCAGGUC | 3539 | GACCUGGGGACCCCGGCCC |
| 939 | 2948 | CCGGGGUCCCCAGGUCGCC | 3540 | GGCGACCUGGGGACCCCGG |
| 956 | 2949 | CCGGGGCGGCGUGGGAACC | 3541 | GGUUCCCACGCCGCCCCGG |
| 989 | 2950 | CUCCACCUCCCCAGCCCGC | 3542 | GCGGGCUGGGGAGGUGGAG |
| 992 | 2951 | CACCUCCCCAGCCCGCGCC | 3543 | GGCGCGGGCUGGGGAGGUG |
| 994 | 2952 | CCUCCCCAGCCCGCGCCCC | 3544 | GGGGCGCGGGCUGGGGAGG |
| 1023 | 2953 | CGCCUCCGCGCGGCAGGGG | 3545 | CCCCUGCCGCGCGGAGGCG |
| 1028 | 2954 | CCGCGCGGCAGGGGCAGAU | 3546 | AUCUGCCCCUGCCGCGCGG |
| 1030 | 2955 | GCGCGGCAGGGGCAGAUGC | 3547 | GCAUCUGCCCCUGCCGCGC |
| 1067 | 2956 | CCCAGGCGCUCCAGGAGCC | 3548 | GGCUCCUGGAGCGCCUGGG |
| 1081 | 2957 | GAGCCGGCGCCCUGGUCUG | 3549 | CAGACCAGGGCGCCGGCUC |
| 1083 | 2958 | GCCGGCGCCCUGGUCUGCA | 3550 | UGCAGACCAGGGCGCCGGC |
| 1084 | 2959 | CCGGCGCCCUGGUCUGCAC | 3551 | GUGCAGACCAGGGCGCCGG |
| 1085 | 2960 | CGGCGCCCUGGUCUGCACU | 3552 | AGUGCAGACCAGGGCGCCG |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1102 | 2961 | CUCCCCUGCGGCCUGCUGC | 1162 | GCAGCAGGCCGCAGGGGAG |
| 1120 | 2962 | CUGGAUGAGCUCCUGGCGA | 3553 | UCGCCAGGAGCUCAUCCAG |
| 1189 | 2963 | GGGGAGCUGGAGGCCUCGG | 3554 | CCGAGGCCUCCAGCUCCCC |
| 1192 | 2964 | GAGCUGGAGGCCUCGGAAG | 3555 | CUUCCGAGGCCUCCAGCUC |
| 1193 | 2965 | AGCUGGAGGCCUCGGAAGA | 3556 | UCUUCCGAGGCCUCCAGCU |
| 1194 | 2966 | GCUGGAGGCCUCGGAAGAG | 3557 | CUCUUCCGAGGCCUCCAGC |
| 1212 | 2967 | GGCCGCCUCGCUGGAAGCA | 3558 | UGCUUCCAGCGAGGCGGCC |
| 1213 | 2968 | GCCGCCUCGCUGGAAGCAC | 3559 | GUGCUUCCAGCGAGGCGGC |
| 1214 | 2969 | CCGCCUCGCUGGAAGCACC | 3560 | GGUGCUUCCAGCGAGGCGG |
| 1215 | 2970 | CGCCUCGCUGGAAGCACCC | 3561 | GGGUGCUUCCAGCGAGGCG |
| 1216 | 2971 | GCCUCGCUGGAAGCACCCC | 3562 | GGGGUGCUUCCAGCGAGGC |
| 1218 | 2972 | CUCGCUGGAAGCACCCCUC | 3563 | GAGGGGUGCUUCCAGCGAG |
| 1234 | 2973 | CUCAGCGAGGAAGAAUACC | 3564 | GGUAUUCUUCCUCGCUGAG |
| 1235 | 2974 | UCAGCGAGGAAGAAUACCG | 3565 | CGGUAUUCUUCCUCGCUGA |
| 1242 | 2975 | GGAAGAAUACCGGGCUCUG | 3566 | CAGAGCCCGGUAUUCUUCC |
| 1251 | 2976 | CCGGGCUCUGCUGGAGGAG | 3567 | CUCCUCCAGCAGAGCCCGG |
| 1257 | 2977 | UCUGCUGGAGGAGCUUUAG | 3568 | CUAAAGCUCCUCCAGCAGA |
| 1258 | 2978 | CUGCUGGAGGAGCUUUAGG | 3569 | CCUAAAGCUCCUCCAGCAG |
| 1260 | 2979 | GCUGGAGGAGCUUUAGGAC | 3570 | GUCCUAAAGCUCCUCCAGC |
| 1261 | 2980 | CUGGAGGAGCUUUAGGACG | 3571 | CGUCCUAAAGCUCCUCCAG |
| 1265 | 2981 | AGGAGCUUUAGGACGCGGG | 3572 | CCCGCGUCCUAAAGCUCCU |
| 1266 | 2982 | GGAGCUUUAGGACGCGGGG | 3573 | CCCCGCGUCCUAAAGCUCC |
| 1267 | 2983 | GAGCUUUAGGACGCGGGGU | 3574 | ACCCCGCGUCCUAAAGCUC |
| 1268 | 2984 | AGCUUUAGGACGCGGGGUU | 3575 | AACCCCGCGUCCUAAAGCU |
| 1269 | 2985 | GCUUUAGGACGCGGGGUUG | 3576 | CAACCCCGCGUCCUAAAGC |
| 1270 | 2986 | CUUUAGGACGCGGGGUUGG | 3577 | CCAACCCCGCGUCCUAAAG |
| 1271 | 2987 | UUUAGGACGCGGGGUUGGG | 3578 | CCCAACCCCGCGUCCUAAA |
| 1272 | 2988 | UUAGGACGCGGGGUUGGGA | 3579 | UCCCAACCCCGCGUCCUAA |
| 1274 | 2989 | AGGACGCGGGGUUGGGACG | 3580 | CGUCCCAACCCCGCGUCCU |
| 1279 | 2990 | GCGGGGUUGGGACGGGGUC | 3581 | GACCCCGUCCCAACCCCGC |
| 1284 | 2991 | GUUGGGACGGGGUCGGGUG | 3582 | CACCCGACCCCGUCCCAAC |
| 1288 | 2992 | GGACGGGGUCGGGUGGUUC | 3583 | GAACCACCCGACCCCGUCC |
| 1389 | 2993 | GGCUGACCGGCCUGGGAUU | 3584 | AAUCCCAGGCCGGUCAGCC |
| 1390 | 2994 | GCUGACCGGCCUGGGAUUC | 3585 | GAAUCCCAGGCCGGUCAGC |
| 1400 | 2995 | CUGGGAUUCCUGCCUUCUA | 3586 | UAGAAGGCAGGAAUCCCAG |
| 1401 | 2996 | UGGGAUUCCUGCCUUCUAG | 3587 | CUAGAAGGCAGGAAUCCCA |
| 1419 | 2997 | GGUCUAGGCCCGGUGAGAG | 3588 | CUCUCACCGGGCCUAGACC |

TABLE 1F-continued provides exemplary unmodified siRNAs with the sequences of the sense strand and the antisense strand.

| Position in transcript | SEQ ID NO: | Sense strand | SEQ ID NO: | Antisense strand |
|---|---|---|---|---|
| 1420 | 2998 | GUCUAGGCCCGGUGAGAGA | 3589 | UCUCUCACCGGGCCUAGAC |
| 1421 | 2999 | UCUAGGCCCGGUGAGAGAC | 3590 | GUCUCUCACCGGGCCUAGA |
| 1422 | 3000 | CUAGGCCCGGUGAGAGACU | 3591 | AGUCUCUCACCGGGCCUAG |
| 1425 | 3001 | GGCCCGGUGAGAGACUCCA | 3592 | UGGAGUCUCUCACCGGGCC |
| 1426 | 3002 | GCCCGGUGAGAGACUCCAC | 3593 | GUGGAGUCUCUCACCGGGC |
| 1427 | 3003 | CCCGGUGAGAGACUCCACU | 3594 | AGUGGAGUCUCUCACCGGG |
| 1607 | 3004 | CCCCACCUUCCGACGCUGU | 3595 | ACAGCGUCGGAAGGUGGGG |
| 1608 | 3005 | CCCACCUUCCGACGCUGUC | 3596 | GACAGCGUCGGAAGGUGGG |
| 1612 | 3006 | CCUUCCGACGCUGUCUAGG | 3597 | CCUAGACAGCGUCGGAAGG |
| 1613 | 3007 | CUUCCGACGCUGUCUAGGC | 3598 | GCCUAGACAGCGUCGGAAG |
| 1614 | 3008 | UUCCGACGCUGUCUAGGCA | 3599 | UGCCUAGACAGCGUCGGAA |
| 1615 | 3009 | UCCGACGCUGUCUAGGCAA | 3600 | UUGCCUAGACAGCGUCGGA |
| 1616 | 3010 | CCGACGCUGUCUAGGCAAA | 3601 | UUUGCCUAGACAGCGUCGG |
| 1617 | 3011 | CGACGCUGUCUAGGCAAAC | 3602 | GUUUGCCUAGACAGCGUCG |

Column 1 shows the beginning position of the target sequence in DUX4_human_#NM_001306068.3 (SEQ ID NO: 2425).
The target sequence is 19 nucleotide long starting from the beginning position.
For example, row 1 shows that the beginning position of the target sequence is 1, which means that the target sequence is the sequence corresponding to positions 1-19 of DUX4_human_#NM_001306068.3 (SEQ ID NO: 2425).
As the nucleotide "T" in the unmodified siRNAs in Table 1A represents RNA uridine, the siRNAs in Table 1F may be used interchangeably with the siRNAs in Table 1A targeting the same positions.
The sequences of the sense strands and antisense strands are shown from the 5' end to the 3' end.

TABLE 2

List of abbreviations of nucleotides in the nucleic acid sequences disclosed herein, e.g., in Tables 1B-1E

| Abbreviation | Nucleotide(s) |
|---|---|
| A | adenosine-3'-phosphate |
| Af | 2'-deoxy-2'-fluoro-adenosine-3'-phosphate |
| Afs | 2'-deoxy-2'-fluoro-adenosine-3'-phosphorothioate |
| As | adenosine-3'-phosphorothioate |
| C | cytidine-3'-phosphate |
| Cf | 2'-deoxy-2'-fluoro-cytidine-3'-phosphate |
| Cfs | 2'-deoxy-2'-fluoro-cytidine-3'-phosphorothioate |
| Cs | cytidine-3'-phosphorothioate |
| G | Guanosine-3'-phosphate |
| Gf | 2'-deoxy-2'-fluoro-guanosine-3'-phosphate |
| Gfs | 2'-deoxy-2'-fluoro-guanosine-3'-phosphorothioate |
| Gs | guanosine-3'-phosphorothioate |
| U | uridine-3'-phosphate |
| Uf | 2'-deoxy-2'-fluoro-uridine-3'-phosphate |

TABLE 2-continued

List of abbreviations of nucleotides in the nucleic acid sequences disclosed herein, e.g., in Tables 1B-1E

| Abbreviation | Nucleotide(s) |
|---|---|
| Ufs | 2'-deoxy-2'-fluoro-uridine-3'-phosphorothioate |
| Us | uridine-3'-phosphorothioate |
| a | 2'-O-methyl-adenosine-3'-phosphate |
| as | 2'-O-methyl-adenosine-3'-phosphorothioate |
| c | 2'-O-methyl-cytidine-3'-phosphate |
| cs | 2'-O-methyl-cytidine-3'-phosphorothioate |
| g | 2'-O-methyl-guanosine-3'-phosphate |
| gs | 2'-O-methyl-guanosine-3'-phosphorothioate |
| u | 2'-O-methyl-uridine-3'-phosphate |
| us | 2'-O-methyl-uridine-3'-phosphorothioate |
| T | deoxythymidine-3'-phosphate |
| vpUs | 5'-vinylphosphonate-2'-O-methyl-uridine-3'-phosphorothioate |

TABLE 3

Exemplary sequences of DUX4 mRNA transcript

| SEQ ID NO | Sequence |
|---|---|
| 2425 | NM_001306068.3 *Homo sapiens* double homeobox 4 (DUX4), transcript variant 1, mRNA:<br>ATGGCCCTCCCGACACCCTCGGACAGCACCCTCCCCGCGGAAGCCCGGGGACGAGG<br>ACGGCGACGGAGACTCGTTTGGACCCCGAGCCAAAGCGAGGCCCTGCGAGCCTGCT<br>TTGAGCGGAACCCGTACCCGGGCATCGCCACCAGAGAACGGCTGGCCCAGGCCATC<br>GGCATTCCGGAGCCCAGGGTCCAGATTTGGTTTCAGAATGAGAGGTCACGCCAGCTG |

TABLE 3-continued

Exemplary sequences of DUX4 mRNA transcript

| SEQ ID NO | Sequence |
|---|---|
| | AGGCAGCACCGGCGGGAATCTCGGCCCTGGCCCGGGAGACGCGGCCCGCCAGAAG<br>GCCGGCGAAAGCGGACCGCCGTCACCGGATCCCAGACCGCCCTGCTCCTCCGAGCC<br>TTTGAGAAGGATCGCTTTCCAGGCATCGCCGCCCGGGAGGAGCTGGCCAGAGAGAC<br>GGGCCTCCCGGAGTCCAGGATTCAGATCTGGTTTCAGAATCGAAGGGCCAGGCACCC<br>GGGACAGGGTGGCAGGGCGCCCGCGCAGGCAGGCGGCCTGTGCAGCGCGGCCCC<br>CGGCGGGGGTCACCCTGCTCCCTCGTGGGTCGCCTTCGCCCACACCGGCGCGTGGG<br>GAACGGGGCTTCCCGCACCCCACGTGCCCTGCGCGCCTGGGGCTCTCCCACAGGGG<br>GCTTTCGTGAGCCAGGCAGCGAGGGCCGCCCCCGCGCTGCAGCCCAGCCAGGCCG<br>CGCCGGCAGAGGGGATCTCCCAACCTGCCCCGGCGCGCGGGGATTTCGCCTACGCC<br>GCCCCGGCTCCTCCGGACGGGGCGCTCTCCCACCCTCAGGCTCCTCGGTGGCCTCC<br>GCACCCGGGCAAAAGCCGGGAGGACCGGGACCCGCAGCGCGACGGCCTGCCGGGC<br>CCCTGCGCGGTGGCACAGCCTGGGCCCGCTCAAGCGGGGCCGCAGGGCCAAGGGG<br>TGCTTGCGCCACCCACGTCCCAGGGGAGTCCGTGGTGGGGCTGGGGCCGGGGTCC<br>CCAGGTCGCCGGGGGGCGTGGGAACCCCAAGCCGGGGCAGCTCCACCTCCCCAG<br>CCCGCGCCCCCGGACGCCTCCGCCTCCGCGCGGCAGGGGCAGATGCAAGGCATCC<br>CGGCGCCCTCCCAGGCGCTCCAGGAGCCGGCGCCCTGGTCTGCACTCCCCTGCGGC<br>CTGCTGCTGGATGAGCTCCTGGCGAGCCCGGAGTTTCTGCAGCAGGCGCAACCTCTC<br>CTAGAAACGGAGGCCCCGGGGGAGCTGGAGGCCTCGGAAGAGGCCGCCTCGCTGG<br>AAGCACCCCTCAGCGAGGAAGAATACCGGGCTCTGCTGGAGGAGCTTTAGGACGCG<br>GGGTTGGGACGGGGTCGGGTGGTTCGGGGCAGGGCGGTGGCCTCTCTTTCGCGGG<br>GAACACCTGGCTGGCTACGGAGGGGCGTGTCTCCGCCCCGCCCCCTCCACCGGGCT<br>GACCGGCCTGGGATTCCTGCCTTCTAGGTCTAGGCCCGGTGAGAGACTCCACTCCGC<br>GGAGAACTGCCTTTCTTTCCTGGGCATCCCGGGGATCCCAGAGCCGGCCCAGGTACC<br>AGCAGACCTGCGCGCAGTGCGCACCCCGGCTGACGTGCAAGGGAGCTCGCTGGCCT<br>CTCTGTGCCCTTGTTCTTCCGTGAAATTCTGGCTGAATGTCTCCCCCCACCTTCCGAC<br>GCTGTCTAGGCAAACCTGGATTAGAGTTACATCTCCTGGATGATTAGTTCAGAGATATA<br>TTAAAATGCCCCCTCCCTGTGGATCCTATAG |

Table 4 provides targeting positions with SEQ ID NO: 2425 (NM 001306068.3) for an oligonucleotide of the present disclosure. In some embodiments, an oligonucleotide targets a sequence corresponding to positions selected from Table 4.

TABLE 4

| Targeting positions |
|---|
| 1-19 |
| 2-20 |
| 11-29 |
| 12-30 |
| 13-31 |
| 14-32 |
| 15-33 |
| 16-34 |
| 17-35 |
| 18-36 |
| 19-37 |
| 23-41 |
| 24-42 |
| 25-43 |
| 26-44 |
| 27-45 |
| 28-46 |
| 30-48 |
| 35-53 |
| 37-55 |
| 38-56 |
| 39-57 |
| 40-58 |
| 41-59 |
| 49-67 |
| 50-68 |
| 51-69 |
| 52-70 |
| 53-71 |
| 54-72 |
| 55-73 |
| 56-74 |
| 57-75 |

TABLE 4-continued

| Targeting positions |
|---|
| 60-78 |
| 61-79 |
| 62-80 |
| 63-81 |
| 64-82 |
| 65-83 |
| 66-84 |
| 67-85 |
| 71-89 |
| 76-94 |
| 77-95 |
| 78-96 |
| 79-97 |
| 80-98 |
| 81-99 |
| 82-100 |
| 83-101 |
| 84-102 |
| 85-103 |
| 86-104 |
| 87-105 |
| 88-106 |
| 89-107 |
| 90-108 |
| 108-126 |
| 109-127 |
| 110-128 |
| 111-129 |
| 112-130 |
| 113-131 |
| 114-132 |
| 115-133 |
| 116-134 |
| 124-142 |
| 125-143 |
| 126-144 |
| 127-145 |
| 129-147 |
| 130-148 |
| 131-149 |

TABLE 4-continued

| Targeting positions |
|---|
| 132-150 |
| 133-151 |
| 134-152 |
| 135-153 |
| 136-154 |
| 137-155 |
| 138-156 |
| 144-162 |
| 145-163 |
| 146-164 |
| 147-165 |
| 148-166 |
| 157-175 |
| 158-176 |
| 159-177 |
| 160-178 |
| 161-179 |
| 162-180 |
| 163-181 |
| 164-182 |
| 165-183 |
| 166-184 |
| 167-185 |
| 168-186 |
| 169-187 |
| 170-188 |
| 171-189 |
| 172-190 |
| 173-191 |
| 174-192 |
| 175-193 |
| 176-194 |
| 177-195 |
| 186-204 |
| 187-205 |
| 188-206 |
| 189-207 |
| 190-208 |
| 192-210 |
| 193-211 |
| 194-212 |
| 195-213 |
| 196-214 |
| 197-215 |
| 198-216 |
| 199-217 |
| 200-218 |
| 201-219 |
| 202-220 |
| 203-221 |
| 204-222 |
| 205-223 |
| 206-224 |
| 207-225 |
| 208-226 |
| 209-227 |
| 210-228 |
| 211-229 |
| 212-230 |
| 213-231 |
| 214-232 |
| 215-233 |
| 224-242 |
| 225-243 |
| 226-244 |
| 227-245 |
| 228-246 |
| 229-247 |
| 230-248 |
| 231-249 |
| 232-250 |
| 233-251 |
| 235-253 |
| 236-254 |
| 237-255 |
| 238-256 |
| 239-257 |
| 240-258 |

TABLE 4-continued

| Targeting positions |
|---|
| 241-259 |
| 250-268 |
| 251-269 |
| 252-270 |
| 261-279 |
| 262-280 |
| 263-281 |
| 264-282 |
| 273-291 |
| 274-292 |
| 275-293 |
| 276-294 |
| 277-295 |
| 278-296 |
| 279-297 |
| 280-298 |
| 281-299 |
| 285-303 |
| 286-304 |
| 287-305 |
| 288-306 |
| 289-307 |
| 292-310 |
| 293-311 |
| 294-312 |
| 295-313 |
| 296-314 |
| 297-315 |
| 298-316 |
| 299-317 |
| 300-318 |
| 301-319 |
| 302-320 |
| 303-321 |
| 304-322 |
| 305-323 |
| 306-324 |
| 307-325 |
| 308-326 |
| 309-327 |
| 310-328 |
| 311-329 |
| 312-330 |
| 313-331 |
| 314-332 |
| 315-333 |
| 316-334 |
| 317-335 |
| 325-343 |
| 328-346 |
| 336-354 |
| 337-355 |
| 338-356 |
| 339-357 |
| 340-358 |
| 341-359 |
| 342-360 |
| 343-361 |
| 344-362 |
| 345-363 |
| 346-364 |
| 347-365 |
| 348-366 |
| 349-367 |
| 350-368 |
| 351-369 |
| 352-370 |
| 353-371 |
| 355-373 |
| 359-377 |
| 360-378 |
| 361-379 |
| 362-380 |
| 363-381 |
| 369-387 |
| 370-388 |
| 371-389 |
| 372-390 |

TABLE 4-continued

| Targeting positions |
|---|
| 373-391 |
| 374-392 |
| 375-393 |
| 376-394 |
| 377-395 |
| 378-396 |
| 382-400 |
| 383-401 |
| 384-402 |
| 385-403 |
| 394-412 |
| 395-413 |
| 396-414 |
| 397-415 |
| 398-416 |
| 399-417 |
| 400-418 |
| 401-419 |
| 402-420 |
| 403-421 |
| 404-422 |
| 408-426 |
| 409-427 |
| 410-428 |
| 411-429 |
| 412-430 |
| 420-438 |
| 421-439 |
| 422-440 |
| 423-441 |
| 424-442 |
| 425-443 |
| 426-444 |
| 427-445 |
| 428-446 |
| 429-447 |
| 430-448 |
| 431-449 |
| 432-450 |
| 437-455 |
| 452-470 |
| 453-471 |
| 455-473 |
| 456-474 |
| 458-476 |
| 480-498 |
| 481-499 |
| 482-500 |
| 509-527 |
| 510-528 |
| 511-529 |
| 512-530 |
| 513-531 |
| 514-532 |
| 516-534 |
| 517-535 |
| 518-536 |
| 519-537 |
| 520-538 |
| 521-539 |
| 522-540 |
| 523-541 |
| 524-542 |
| 525-543 |
| 526-544 |
| 530-548 |
| 531-549 |
| 532-550 |
| 533-551 |
| 534-552 |
| 544-562 |
| 545-563 |
| 546-564 |
| 547-565 |
| 548-566 |
| 549-567 |
| 551-569 |
| 552-570 |

TABLE 4-continued

| Targeting positions |
|---|
| 553-571 |
| 565-583 |
| 566-584 |
| 567-585 |
| 575-593 |
| 577-595 |
| 579-597 |
| 581-599 |
| 588-606 |
| 616-634 |
| 617-635 |
| 618-636 |
| 619-637 |
| 620-638 |
| 621-639 |
| 622-640 |
| 627-645 |
| 652-670 |
| 654-672 |
| 659-677 |
| 668-686 |
| 671-689 |
| 672-690 |
| 673-691 |
| 674-692 |
| 675-693 |
| 683-701 |
| 684-702 |
| 685-703 |
| 686-704 |
| 690-708 |
| 692-710 |
| 705-723 |
| 706-724 |
| 707-725 |
| 708-726 |
| 709-727 |
| 710-728 |
| 711-729 |
| 712-730 |
| 713-731 |
| 714-732 |
| 715-733 |
| 717-735 |
| 732-750 |
| 733-751 |
| 745-763 |
| 746-764 |
| 747-765 |
| 748-766 |
| 749-767 |
| 750-768 |
| 751-769 |
| 752-770 |
| 753-771 |
| 754-772 |
| 755-773 |
| 756-774 |
| 757-775 |
| 758-776 |
| 759-777 |
| 760-778 |
| 761-779 |
| 767-785 |
| 768-786 |
| 777-795 |
| 778-796 |
| 779-797 |
| 780-798 |
| 781-799 |
| 782-800 |
| 788-806 |
| 789-807 |
| 790-808 |
| 791-809 |
| 802-820 |
| 809-827 |
| 813-831 |

TABLE 4-continued

| Targeting positions |
|---|
| 827-845 |
| 839-857 |
| 840-858 |
| 841-859 |
| 842-860 |
| 843-861 |
| 845-863 |
| 850-868 |
| 851-869 |
| 852-870 |
| 853-871 |
| 854-872 |
| 856-874 |
| 877-895 |
| 878-896 |
| 879-897 |
| 892-910 |
| 893-911 |
| 894-912 |
| 895-913 |
| 897-915 |
| 901-919 |
| 902-920 |
| 903-921 |
| 911-929 |
| 912-930 |
| 913-931 |
| 914-932 |
| 919-937 |
| 936-954 |
| 939-957 |
| 956-974 |
| 960-978 |
| 975-993 |
| 976-994 |
| 977-995 |
| 983-1001 |
| 984-1002 |
| 985-1003 |
| 986-1004 |
| 989-1007 |
| 992-1010 |
| 994-1012 |
| 1023-1041 |
| 1028-1046 |
| 1030-1048 |
| 1031-1049 |
| 1033-1051 |
| 1034-1052 |
| 1035-1053 |
| 1036-1054 |
| 1037-1055 |
| 1046-1064 |
| 1048-1066 |
| 1049-1067 |
| 1064-1082 |
| 1067-1085 |
| 1081-1099 |
| 1083-1101 |
| 1084-1102 |
| 1085-1103 |
| 1086-1104 |
| 1087-1105 |
| 1088-1106 |
| 1089-1107 |
| 1090-1108 |
| 1091-1109 |
| 1092-1110 |
| 1093-1111 |
| 1094-1112 |
| 1095-1113 |
| 1096-1114 |
| 1097-1115 |
| 1098-1116 |
| 1100-1118 |
| 1101-1119 |
| 1102-1120 |
| 1103-1121 |

TABLE 4-continued

| Targeting positions |
|---|
| 1106-1124 |
| 1107-1125 |
| 1108-1126 |
| 1109-1127 |
| 1110-1128 |
| 1111-1129 |
| 1112-1130 |
| 1113-1131 |
| 1114-1132 |
| 1115-1133 |
| 1116-1134 |
| 1117-1135 |
| 1118-1136 |
| 1119-1137 |
| 1120-1138 |
| 1130-1148 |
| 1131-1149 |
| 1132-1150 |
| 1137-1155 |
| 1138-1156 |
| 1139-1157 |
| 1140-1158 |
| 1141-1159 |
| 1142-1160 |
| 1143-1161 |
| 1144-1162 |
| 1145-1163 |
| 1146-1164 |
| 1147-1165 |
| 1148-1166 |
| 1149-1167 |
| 1150-1168 |
| 1151-1169 |
| 1152-1170 |
| 1153-1171 |
| 1154-1172 |
| 1155-1173 |
| 1156-1174 |
| 1157-1175 |
| 1158-1176 |
| 1159-1177 |
| 1160-1178 |
| 1161-1179 |
| 1162-1180 |
| 1163-1181 |
| 1169-1187 |
| 1170-1188 |
| 1171-1189 |
| 1189-1207 |
| 1192-1210 |
| 1193-1211 |
| 1194-1212 |
| 1212-1230 |
| 1213-1231 |
| 1214-1232 |
| 1215-1233 |
| 1216-1234 |
| 1218-1236 |
| 1234-1252 |
| 1235-1253 |
| 1242-1260 |
| 1251-1269 |
| 1257-1275 |
| 1258-1276 |
| 1260-1278 |
| 1261-1279 |
| 1265-1283 |
| 1266-1284 |
| 1267-1285 |
| 1268-1286 |
| 1269-1287 |
| 1270-1288 |
| 1271-1289 |
| 1272-1290 |
| 1274-1292 |
| 1279-1297 |
| 1284-1302 |
| 1288-1306 |

TABLE 4-continued

| Targeting positions |
|---|
| 1389-1407 |
| 1390-1408 |
| 1400-1418 |
| 1401-1419 |
| 1419-1437 |
| 1420-1438 |
| 1421-1439 |
| 1422-1440 |
| 1425-1443 |
| 1426-1444 |
| 1427-1445 |
| 1428-1446 |
| 1429-1447 |
| 1430-1448 |
| 1570-1588 |
| 1571-1589 |
| 1572-1590 |
| 1573-1591 |
| 1574-1592 |
| 1575-1593 |
| 1576-1594 |
| 1577-1595 |
| 1578-1596 |
| 1589-1607 |
| 1590-1608 |
| 1607-1625 |
| 1608-1626 |
| 1612-1630 |
| 1613-1631 |
| 1614-1632 |
| 1615-1633 |
| 1616-1634 |
| 1617-1635 |
| 1618-1636 |
| 1619-1637 |
| 1620-1638 |
| 1621-1639 |
| 1622-1640 |
| 1623-1641 |
| 1624-1642 |

TABLE 4-continued

| Targeting positions |
|---|
| 1625-1643 |
| 1626-1644 |
| 1627-1645 |
| 1628-1646 |
| 1629-1647 |
| 1630-1648 |
| 1631-1649 |
| 1632-1650 |
| 1633-1651 |
| 1634-1652 |
| 1635-1653 |
| 1636-1654 |
| 1637-1655 |
| 1638-1656 |
| 1639-1657 |
| 1640-1658 |
| 1641-1659 |
| 1642-1660 |
| 1643-1661 |
| 1651-1669 |
| 1652-1670 |
| 1653-1671 |
| 1654-1672 |
| 1655-1673 |
| 1656-1674 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

SEQUENCE LISTING

The patent contains a lengthy sequence listing. A copy of the sequence listing is available in electronic form from the USPTO web site (https://seqdata.uspto.gov/docdetail?docId=US12781225B2). An electronic copy of the sequence listing will also be available from the USPTO upon request and payment of the fee set forth in 37 CFR 1.19(b)(3).

What is claimed is:

1. An RNAi oligonucleotide comprising a sense strand and an antisense strand, wherein the sense strand and the antisense strand form a duplex, wherein the sense strand and antisense strands are selected from the group consisting of:

| SEQ ID NO: | Sense strand |
|---|---|
| 1240 | csgsacGfgAfGfAfcucguuugga |
| 1438 | asgsucCfaGfGfAfuucagaucua |
| 1443 | asusucAfgAfUfCfugguuucaga |
| 1626 | asasccUfcUfCfCfuagaaacgga |
| 1645 | ascsgcUfgUfCfUfaggcaaacca |
| 1654 | asgsgcAfaAfCfCfuggauuagaa |
| 1655 | gsgscaAfaCfCfUfggauuagaga |
| 1661 | cscsugGfaUfUfAfgaguuacaua |
| 1662 | csusggAfuUfAfGfaguuacauca |

-continued

| | |
|---|---|
| 1670 | asuscuCfcUfGfGfaugauuagua |
| 1671 | uscsucCfuGfGfAfugauuaguua |
| 1672 | csusccUfgGfAfUfgauuaguuca |
| 1673 | uscscuGfgAfUfGfauuaguucaa |
| 1674 | cscsugGfaUfGfAfuuaguucaga |
| 1675 | csusggAfuGfAfUfuaguucagaa |
| 1775 | gscscgCfcUfCfGfcuggaagcaa |
| 1790 | gsasgcUfuUfAfGfgacgcgggga |
| 1444 | csusggUfuUfCfAfgaaucgaaga |
| 2426 | csusGfguuUfCfAfgaAfucgaAfsgsa |
| 2427 | asgsGfcaaAfCfCfugGfauuaGfsasa |
| 2428 | gsgsCfaaaCfCfUfggAfuuagAfsgsa |
| 2429 | cscsUfggaUfUfAfgaGfuuacAfsusa |
| 2430 | csusGfgauUfAfGfagUfuacaUfscsa |
| 2431 | uscsUfccuGfGfAfugAfuuagUfsusa |
| 2432 | csusCfcugGfAfUfgaUfuaguUfscsa |
| 1728 | cscsgcGfcCfGfGfcagaggggaa |
| 2433 | cscsGfcgcCfGfGfcaGfagggGfsasa |

-continued

| | |
|---|---|
| 2434 | uscsCfuggAfUfGfauUfaguuCfaa |
| 2435 | cscsUfggaUfGfAfuuAfguucAfga |
| 2436 | csusGfgauGfAfUfuaGfuucaGfaa |

| SEQ ID NO: | Antisense strand |
|---|---|
| 1846 | usCfscaaAfcGfAfgucuCfcGfucgsusu |
| 2044 | usAfsgauCfuGfAfauccUfgGfacususu |
| 2049 | usCfsugaAfaCfCfagauCfuGfaaususu |
| 2232 | usCfscguUfuCfUfaggaGfaGfguusesu |
| 2251 | usGfsguuUfgCfCfuagaCfaGfcgususu |
| 2260 | usUfscuaAfuCfCfagguUfuGfccususu |
| 2261 | usCfsucuAfaUfCfcaggUfuUfgccsusu |
| 2267 | usAfsuguAfaCfUfcuaaUfcCfaggsusu |
| 2268 | usGfsaugUfaAfCfucuaAfuCfcagsusu |
| 2276 | usAfscuaAfuCfAfuccaGfgAfgaususu |
| 2277 | usAfsacuAfaUfCfauccAfgGfagasusu |
| 2278 | usGfsaacUfaAfUfcaucCfaGfgagsusu |
| 2279 | usUfsgaaCfuAfAfucauCfcAfggasusu |
| 2280 | usCfsugaAfcUfAfaucaUfcCfaggsusu |
| 2281 | usUfscugAfaCfUfaaucAfuCfcagsusu |
| 2381 | usUfsgcuUfcCfAfgcgaGfgCfggcsusu |
| 2396 | usCfscccGfcGfUfccuaAfaGfcucsusu |
| 2050 | usCfsuucGfaUfUfcugaAfaCfcagsusu |
| 2437 | vpUsCfsuucgauucugaAfaccagsusu |
| 2438 | vpUsUfscuaauccagguUfugccususu |
| 2439 | vpUsCfsucuaauccaggUfuugccsusu |
| 2440 | vpUsAfsuguaacucuaaUfccaggsusu |
| 2441 | vpUsGfsauguaacucuaAfuccagsusu |
| 2442 | vpUsAfsacuaaucauccAfggagasusu |
| 2443 | vpUsGfsaacuaaucaucCfaggagsusu |
| 2334 | usUfscccCfuCfUfgccgGfcGfcggsusu |
| 2444 | vpUsUfsccccucugccgGfcgcggsusu |
| 2445 | vpUsUfsgaacuaaucauCfcaggasusu |
| 2446 | vpUsCfsugaacuaaucaUfccaggsusu |
| 2447 | vpUsUfscugaacuaaucAfuccagsusu |

wherein:

Af represents 2'-deoxy-2'-fluoro-adenosine-3'-phosphate;

Afs represents 2'-deoxy-2'-fluoro-adenosine-3'-phosphorothioate;

Cf represents 2'-deoxy-2'-fluoro-cytidine-3'-phosphate;

Cfs represents 2'-deoxy-2'-fluoro-cytidine-3'-phosphorothioate;

Gf represents 2'-deoxy-2'-fluoro-guanosine-3'-phosphate;

Gfs represents 2'-deoxy-2'-fluoro-guanosine-3'-phosphorothioate;

Uf represents 2'-deoxy-2'-fluoro-uridine-3'-phosphate;

Ufs represents 2'-deoxy-2'-fluoro-uridine-3'-phosphorothioate;

a represents 2'-O-methyl-adenosine-3'-phosphate;

as represents 2'-O-methyl-adenosine-3'-phosphorothioate;

c represents 2'-O-methyl-cytidine-3'-phosphate;

cs represents 2'-O-methyl-cytidine-3'-phosphorothioate;

g represents 2'-O-methyl-guanosine-3'-phosphate;

gs represents 2'-O-methyl-guanosine-3'-phosphorothioate;

u represents 2'-O-methyl-uridine-3'-phosphate;

us represents 2'-O-methyl-uridine-3'-phosphorothioate; and vpUs represents 5'-vinylphosphonate-2'-O-methyl-uridine-3'-phosphorothioate.

2. The RNAi oligonucleotide of claim 1, wherein (i) the sense strand is csgsacGfgAfGfAfcucguuugga (SEQ ID NO: 1240), and the antisense strand is usCfscaaAfcGfAfgucuCfcGfucgsusu (SEQ ID NO: 1846); or (ii) the sense strand is asasccUfcUfCfCfuagaaacgga (SEQ ID NO: 1626), and the antisense strand is usCfscguUfuCfUfaggaGfaGfguususu (SEQ ID NO: 2232); or (iii) the sense strand is gscscgCfcUfCfGfcuggaagcaa (SEQ ID NO: 1775), and the antisense strand is usUfsgcuUfcCfAfgcgaGfgCfggcsusu (SEQ ID NO: 2381).

3. The RNAi oligonucleotide of claim 1, wherein the sense strand is asgsucCfaGfGfAfuucagaucua (SEQ ID NO: 1438), and the antisense strand is usAfsgauCfuGfAfauccUfgGfacususu (SEQ ID NO: 2044).

4. The RNAi oligonucleotide of claim 1, wherein the sense strand is asusucAfgAfUfCfugguuucaga (SEQ ID NO: 1443), and the antisense strand is usCfsugaAfaCfCfagauCfuGfaaususu (SEQ ID NO: 2049).

5. The RNAi oligonucleotide of claim 1, wherein the sense strand is ascsgcUfgUfCfUfaggcaaacca (SEQ ID NO: 1645), and the antisense strand is usGfsguuUfgCfCfuagaCfaGfcgususu (SEQ ID NO: 2251).

6. The RNAi oligonucleotide of claim 1, wherein the sense strand is asgsgcAfaAfCfCfuggauuagaa (SEQ ID NO: 1654), and the antisense strand is usUfscuaAfuCfCfagguUfuGfccususu (SEQ ID NO: 2260).

7. The RNAi oligonucleotide of claim 1, wherein the sense strand is gsgscaAfaCfCfUfggauuagaga (SEQ ID NO: 1655), and the antisense strand is usCfsucuAfaUfCfcaggUfuUfgccsusu (SEQ ID NO: 2261).

8. The RNAi oligonucleotide of claim 1, wherein the sense strand is cscsugGfaUfUfAfgaguuacaua (SEQ ID NO: 1661), and the antisense strand is usAfsuguAfaCfUfcuaaUfcCfaggsusu (SEQ ID NO: 2267).

9. The RNAi oligonucleotide of claim 1, wherein the sense strand is csusggAfuUfAfGfaguuacauca (SEQ ID NO: 1662), and the antisense strand is usGfsaugUfaAfCfucuaAfuCfcagsusu (SEQ ID NO: 2268).

10. The RNAi oligonucleotide of claim 1, wherein the sense strand is asuscuCfcUfGfGfaugauuagua (SEQ ID NO: 1670), and the antisense strand is usAfscuaAfuCfAfuccaGfgAfgaususu (SEQ ID NO: 2276).

11. The RNAi oligonucleotide of claim 1, wherein the sense strand is uscsucCfuGfGfAfugauuaguua (SEQ ID NO: 1671), and the antisense strand is usAfsacuAfaUfCfauccAfgGfagasusu (SEQ ID NO: 2277).

12. The RNAi oligonucleotide of claim 1, wherein the sense strand is csusccUfgGfAfUfgauuaguuca (SEQ ID NO: 1672), and the antisense strand is usGfsaacUfaAfUfcaucCfaGfgagsusu (SEQ ID NO: 2278).

13. The RNAi oligonucleotide of claim 1, wherein the sense strand is uscscuGfgAfUfGfauuaguucaa (SEQ ID NO: 1673), and the antisense strand is usUfsgaaCfuAfAfucauCfcAfggasusu (SEQ ID NO: 2279).

14. The RNAi oligonucleotide of claim 1, wherein the sense strand is cscsugGfaUfGfAfuuaguucaga (SEQ ID NO: 1674), and the antisense strand is usCfsugaAfcUfAfaucaUfcCfaggsusu (SEQ ID NO: 2280).

15. The RNAi oligonucleotide of claim 1, wherein the sense strand is csusggAfuGfAfUfuaguucagaa (SEQ ID NO: 1675), and the antisense strand is usUfscugAfaCfUfaaucAfuCfcagsusu (SEQ ID NO: 2281).

16. The RNAi oligonucleotide of claim 1, wherein the sense strand is gsasgcUfuUfAfGfgacgggga (SEQ ID NO: 1790), and the antisense strand is usCfscccGfcGfUfccuaAfaGfcucsusu (SEQ ID NO: 2396).

17. The RNAi oligonucleotide of claim 1, wherein the sense strand is csusggUfuUfCfAfgaaucgaaga (SEQ ID NO: 1444), and the antisense strand is usCfsuucGfaUfUfcugaAfaCfcagsusu (SEQ ID NO: 2050).

18. The RNAi oligonucleotide of claim 1, wherein the sense strand is csusGfguuUfCfAfgaAfucgaAfsgsa (SEQ ID NO: 2426), and the antisense strand is vpUsCfsuucgauucugaAfaccagsusu (SEQ ID NO: 2437).

19. The RNAi oligonucleotide of claim 1, wherein the sense strand is asgsGfcaaAfCfCfugGfauuaGfsasa (SEQ ID NO: 2427), and the antisense strand is vpUsUfscuaauccagguUfugccususu (SEQ ID NO: 2438).

20. The RNAi oligonucleotide of claim 1, wherein the sense strand is gsgsCfaaaCfCfUfggAfuuagAfsgsa (SEQ ID NO: 2428), and the antisense strand is vpUsCfsucuaauccaggUfuugccsusu (SEQ ID NO: 2439).

21. The RNAi oligonucleotide of claim 1, wherein the sense strand is cscsUfggaUfUfAfgaGfuuacAfsusa (SEQ ID NO: 2429), and the antisense strand is vpUsAfsuguaacucuaaUfccaggsusu (SEQ ID NO: 2440).

22. The RNAi oligonucleotide of claim 1, wherein the sense strand is csusGfgauUfAfGfagUfuacaUfscsa (SEQ ID NO: 2430), and the antisense strand is vpUsGfsauguaacucuaAfuccagsusu (SEQ ID NO: 2441).

23. The RNAi oligonucleotide of claim 1, wherein the sense strand is uscsUfccuGfGfAfugAfuuagUfsusa (SEQ ID NO: 2431), and the antisense strand is vpUsAfsacuaaucauccAfggagasusu (SEQ ID NO: 2442).

24. The RNAi oligonucleotide of claim 1, wherein the sense strand is csusCfcugGfAfUfgaUfuaguUfscsa (SEQ ID NO: 2432), and the antisense strand is vpUsGfsaacuaaucaucCfaggagsusu (SEQ ID NO: 2443).

25. The RNAi oligonucleotide of claim 1, wherein the sense strand is cscsgcGfcCfGfGfcagaggggaa (SEQ ID NO: 1728), and the antisense strand is usUfscccCfuCfUfgccgGfcGfcggsusu (SEQ ID NO: 2334).

26. The RNAi oligonucleotide of claim 1, wherein the sense strand is cscsGfcgcCfGfGfcaGfagggGfsasa (SEQ ID NO: 2433), and the antisense strand is vpUsUfsccccucugccgGfcgcggsusu (SEQ ID NO: 2444).

27. The RNAi oligonucleotide of claim 1, wherein the sense strand is uscsCfuggAfUfGfauUfaguuCfaa (SEQ ID NO: 2434), and the antisense strand is vpUsUfsgaacuaaucauCfcaggasusu (SEQ ID NO: 2445).

28. The RNAi oligonucleotide of claim 1, wherein the sense strand is cscsUfggaUfGfAfuuAfguucAfga (SEQ ID NO: 2435), and the antisense strand is vpUsCfsugaacuaaucaUfccaggsusu (SEQ ID NO: 2446).

29. The RNAi oligonucleotide of claim 1, wherein the sense strand is csusGfgauGfAfUfuaGfuucaGfaa (SEQ ID NO: 2436), and the antisense strand is vpUsUfscugaacuaaucAfuccagsusu (SEQ ID NO: 2447).

30. A pharmaceutical composition comprising the RNAi oligonucleotide of claim 1, or a pharmaceutically acceptable salt thereof, and a pharmaceutically acceptable carrier or excipient.

* * * * *